(12) United States Patent
Beelen et al.

(10) Patent No.: US 12,364,697 B2
(45) Date of Patent: *Jul. 22, 2025

(54) G1T38 SUPERIOR DOSAGE REGIMES

(71) Applicant: Pharmacosmos Holding A/S, Holbaek (DK)

(72) Inventors: Andrew Beelen, Research Triangle Park, NC (US); Jay Copeland Strum, Hillsborough, NC (US)

(73) Assignee: Pharmacosmos Holding A/S, Holbaek (DK)

(*) Notice: Subject to any disclaimer, the term of this patent is extended or adjusted under 35 U.S.C. 154(b) by 0 days.

This patent is subject to a terminal disclaimer.

(21) Appl. No.: 17/839,215

(22) Filed: Jun. 13, 2022

(65) Prior Publication Data

US 2023/0149406 A1 May 18, 2023

Related U.S. Application Data

(63) Continuation of application No. 16/924,033, filed on Jul. 8, 2020, now Pat. No. 11,357,779, which is a continuation of application No. PCT/US2019/012720, filed on Jan. 8, 2019.

(60) Provisional application No. 62/614,952, filed on Jan. 8, 2018, provisional application No. 62/679,575, filed on Jun. 1, 2018, provisional application No. 62/788,017, filed on Jan. 3, 2019.

(51) Int. Cl.
*A61K 31/519* (2006.01)
*A61K 31/506* (2006.01)

(52) U.S. Cl.
CPC .......... *A61K 31/519* (2013.01); *A61K 31/506* (2013.01)

(58) Field of Classification Search
CPC ............................. A61K 31/519; A61K 31/506
See application file for complete search history.

(56) References Cited

U.S. PATENT DOCUMENTS

| | | |
|---|---|---|
| 7,855,211 B2 | 12/2010 | Coates et al. |
| 8,415,355 B2 | 4/2013 | Brain et al. |
| 8,598,186 B2 | 12/2013 | Tavares et al. |
| 8,598,197 B2 | 12/2013 | Tavares et al. |
| 8,691,830 B2 | 4/2014 | Tavares et al. |
| 8,822,683 B2 | 9/2014 | Tavares et al. |
| 8,829,012 B2 | 9/2014 | Tavares et al. |
| 9,102,682 B2 | 8/2015 | Tavares et al. |
| 9,260,442 B2 | 1/2016 | Tavares et al. |
| 9,259,399 B2 | 2/2016 | Chen-Kiang et al. |
| 9,464,092 B2 | 10/2016 | Strum et al. |
| 9,481,691 B2 | 11/2016 | Tavares et al. |
| 9,487,530 B2 | 11/2016 | Strum et al. |
| 9,499,564 B2 | 11/2016 | Tavares et al. |
| 9,527,857 B2 | 12/2016 | Strum et al. |
| 9,700,557 B2 | 7/2017 | Caponigro et al. |
| 9,717,735 B2 | 8/2017 | Strum et al. |
| 9,745,316 B2 | 8/2017 | Tavares |
| 9,856,268 B2 | 1/2018 | Tavares et al. |
| 9,931,345 B2 | 4/2018 | Strum et al. |
| 9,957,276 B2 | 5/2018 | Tavares et al. |
| 10,076,523 B2 | 9/2018 | Strum et al. |
| 10,085,992 B2 | 10/2018 | Strum et al. |
| 10,189,849 B2 | 1/2019 | Tavares et al. |
| 10,189,850 B2 | 1/2019 | Tavares et al. |
| 10,189,851 B2 | 1/2019 | Tavares et al. |
| 10,231,969 B2 | 3/2019 | Strum et al. |
| 11,357,779 B2 * | 6/2022 | Beelen ................ A61K 31/519 |
| 2010/0105653 A1 | 4/2010 | Besong et al. |
| 2011/0224221 A1 | 9/2011 | Sharpless et al. |
| 2011/0224227 A1 | 9/2011 | Sharpless et al. |
| 2012/0100100 A1 | 4/2012 | Sharpless et al. |
| 2014/0037622 A1 | 2/2014 | Boshoff et al. |
| 2014/0107114 A1 | 4/2014 | Kim et al. |
| 2014/0274896 A1 | 9/2014 | Strum et al. |
| 2016/0220569 A1 | 8/2016 | Strum et al. |
| 2016/0310499 A1 | 10/2016 | Strum et al. |
| 2016/0332989 A1 | 11/2016 | Wu et al. |
| 2017/0209574 A1 | 7/2017 | Cao et al. |
| 2017/0224819 A1 | 8/2017 | Hamdy et al. |
| 2017/0296659 A1 | 10/2017 | Lebwohl et al. |
| 2017/0368036 A1 | 12/2017 | Hattersley et al. |
| 2018/0221378 A1 | 8/2018 | Strum et al. |
| 2018/0243304 A1 | 8/2018 | Caponigro et al. |
| 2018/0318305 A1 | 11/2018 | Harris et al. |
| 2018/0360840 A1 | 12/2018 | Strum et al. |
| 2018/0360841 A1 | 12/2018 | Strum et al. |
| 2019/0030034 A1 | 1/2019 | Strum et al. |

(Continued)

FOREIGN PATENT DOCUMENTS

| | | |
|---|---|---|
| CN | 106065016 A1 | 11/2016 |
| JP | 2013/519698 | 8/2011 |

(Continued)

OTHER PUBLICATIONS

Byrn, S. et al. Pharmaceutical Solids: A Strategic Approach to Regulatory Considerations. Pharmaceutical Research. 12(7):945-954(Jul. 1, 1995).
Kawaguchi et al. Drug and crystal polymorphism. Journal of Human Environmental Engineering, 4(2):310-317(2002). (Translation).
Oshima, H. Crystallization of Polymorphs and Pseudo-polymorphs and Its Control. Transition to Stability. Pharm Stage. 6(10):48-53(2007). (Translation).
Establishment of Specifications and Test Methods for New Drugs. Pharmaceutical Affairs Bureau. 568(May 1, 2001). (Translation).
Takada, N. API form screening and selection in drug discovery stage. Pharm Stage. 6(10):20-25(2007). (Translation).
Yamano, M. Approach to Crystal Polymorph in Process Research of New Drug. Journal of Synthetic Organic Chemistry. 65:907-913(2007). (Translation).

(Continued)

*Primary Examiner* — Erich A Leeser
(74) *Attorney, Agent, or Firm* — Knowles Intellectual Property Strategies, LLC

(57) ABSTRACT

A G1T38 human oral dosage regime that provides a (mean AUC(0-24),ss (h*ng/mL))/(dose (mg)) ratio of less than 5 and/or a (mean AUC(0-24),ss (h*ng/mL))/(Absolute Neutrophil Count (cells/mm3)) ratio on day 22 of dosing of not greater than 1.25.

18 Claims, 41 Drawing Sheets

(56) References Cited

U.S. PATENT DOCUMENTS

| | | | |
|---|---|---|---|
| 2019/0119292 A1 | 4/2019 | Tavares et al. | |
| 2019/0151311 A1 | 5/2019 | Strum et al. | |
| 2019/0175598 A1 | 6/2019 | Selvaraj et al. | |
| 2019/0275049 A1 | 9/2019 | Goldberg et al. | |

FOREIGN PATENT DOCUMENTS

| | | | |
|---|---|---|---|
| TW | | 200633693 A | 10/2006 |
| TW | | 201618774 A | 6/2016 |
| WO | WO 2005/094830 A1 | | 10/2005 |
| WO | WO 2006/061712 A2 | | 6/2006 |
| WO | WO 2008/079933 A2 | | 7/2008 |
| WO | WO 2009/085185 A1 | | 7/2009 |
| WO | WO 2010/012777 A1 | | 2/2010 |
| WO | WO 2010/020675 A1 | | 2/2010 |
| WO | WO 2011/101277 A1 | | 8/2011 |
| WO | WO 2011/101409 A1 | | 8/2011 |
| WO | WO 2011/101417 A1 | | 8/2011 |
| WO | WO 2012/068381 A2 | | 5/2012 |
| WO | WO 2012/129344 A1 | | 9/2012 |
| WO | WO 2013/014448 A1 | | 9/2013 |
| WO | WO 2013/148748 A1 | | 10/2013 |
| WO | WO 2014/128588 A1 | | 8/2014 |
| WO | WO 2015/061407 A1 | | 4/2015 |
| WO | WO 2015/084892 A1 | | 6/2015 |
| WO | WO 2015/095840 A1 | | 6/2015 |
| WO | WO 2015/161285 A1 | | 10/2015 |
| WO | WO 2015/161287 A1 | | 10/2015 |
| WO | WO 2015/161288 A1 | | 10/2015 |
| WO | WO 2016/024227 A1 | | 2/2016 |
| WO | WO 2016/025650 A1 | | 2/2016 |
| WO | WO 2017/160568 A1 | | 9/2017 |
| WO | WO 2017/193141 A1 | | 11/2017 |
| WO | WO 2018/089518 A1 | | 5/2018 |
| WO | WO 2018/106729 A1 | | 6/2018 |
| WO | WO 2018/156812 A1 | | 8/2018 |
| WO | WO 2018/170447 A1 | | 9/2018 |
| WO | WO 2018/183479 A1 | | 10/2018 |
| WO | WO 2018/218633 A1 | | 12/2018 |
| WO | WO 2018/223022 A1 | | 12/2018 |
| WO | WO 2018/228990 A1 | | 12/2018 |
| WO | WO 2018/231859 A1 | | 12/2018 |
| WO | WO 2018/233620 A1 | | 12/2018 |
| WO | WO 2018/237158 A1 | | 12/2018 |
| WO | WO 2019/006393 A1 | | 1/2019 |
| WO | WO 2019/026006 A1 | | 2/2019 |
| WO | WO 2019/108589 A1 | | 6/2019 |

OTHER PUBLICATIONS

Wang, Zhijie et al. Phase II clinical study of platinum-containing regimen combined with Celebrex for first-line treatment of advanced non-small cell lung cancer; Chinese Journal of Lung Cancer, Issue 03, Jun. 20, 2008.
Aldrich. Kras Mutant Cell lines. (Jul. 10, 2018). https://www.cancer.gov/research/key-initiatives/ras/outreach/reference-reagents/cell-lines.
Barginear, M.F. & Budman, D.R. Trastuzumab-DM1: A review of the novel immuno-conjugate for HER2-overexpressing breast cancer. The Open Breast Cancer Journal, 2009; 1: 25-30.
Baughn, L.B. et al. A novel orally active small molecule potently induces G1 arrest in primary myeloma cells and prevents tumor growth by specific inhibition of cyclin-dependent kinase 4/6. Cancer Res, Aug. 1, 2006; 66(15): 7661-7667.
Bisi, J.E. et al. Preclinical Characterization of G1T28: A Novel CDK4/6 Inhibitor for Reduction of Chemotherapy-Induced Myelosuppression. Mol. Cancer Therap. (15)5: 783-793, Jan. 29, 2016.
Bisi, J.E. et al. Preclinical development of G1T38: A novel, potent and selective inhibitor of cyclin dependent kinases 4/6 for use as an oral antineoplastic in patients with CDK4/6 sensitive tumor, Oncotarget. 8(26), 42343-42358, 16216, 2017.
Blachly et al. Emerging Drug Profile: Cyclin-Dependent Kinase Inhibitors. Leuk Lymphoma. Oct. 2013; 54(10): 2133-2143. doi:10.3109/10428194.2013.783911.
Bonelli, M.A. et al. Combined inhibition of CDK 4/6 and PI3K/AKT/mTOR pathways induces a synergistic anti-tumor effect in malignant pleural mesothelioma cells. Neoplasia, 2017, 19(8), 637-648.
Bose et al. Cyclin-dependent kinase inhibitor therapy for hematologic malignancies. Expert Opin Investigating Drugs. Jun. 2013; 22(6): 723-738. doi:10.1517/13543784.2013.7.
Boss, D.S. et al. Safety, tolerability, pharmacokinetics and pharmacodynamics of the oral cyclin-dependent kinase inhibitor AZD5438 when administered at intermittent and continuous dosing schedules in patients with advanced solid tumours. Ann. Oncol. 2010; 21: 884-894. Published online Oct. 13, 2009.
Bucher, N. & Britten, C.D. G2 checkpoint abrogation and checkpoint kinase-1 targeting in the treatment of cancer. Br J Cancer, Feb. 12, 2008; 98(3): 523-528.
Bulat, I. et al. G1T38, an oral CDK4/6 inhibitor, dosed continuously in combination with Fulvestrant for HR+breast cancer: Preliminary Phase 1b Results. Journals of Clinical Oncology 36, No. 15 suppl, 1061-1061, 4 pages, 2018.
Bulat, I. et al. G1T38, An Oral Cdk4/6 Inhibitor, Dosed Continuously in Combination with Fulvestrant for Hr+ breast cancer: Preliminary Phase 1b Results. Abstract #1061 (G1 Therapeutics Presentation).
Chou, A. et al. Tailored first-line and second-line CDK4-targeting treatment combinations in mouse models of pancreatic cancer. Gut, 2017; 0:1-14. Published online Oct. 28, 2017 doi:10.1136.gutjnl-2017-315144.
Menu, E. et al. A novel therapeutic combination using PD 0332991 and bortezomib: study in the 5T33MM myeloma model. Cancer Res, Jul. 15, 2008; 68(14): 5519-5523.
Mino, R.C. Crystalline Polymorphism of Organic Compounds. opics in Current Chemistry, Springer, berlin, DE, 1998, 198, 163-208; ISSN: 0340-1022; DOI: 10.1007/3-540-69178-2.
Mita, M.M. et al. Randomized Phase II trial of the cyclin-dependent kinase inhibitor dinaciclib (MK-7965) versus capecitabine in patients with advanced breast cancer. Clin. Breast Cancer, 2014; 14:169-176.
NCT01958021—Study of Efficacy and Safety of LEE011 in Postmenopausal Women With Advanced Breast Cancer. (Monaleesa-2), First posted Oct. 8, 2013.
NCT02079636—A Study of Abemaciclib (LY2835219) in Combination with Another Anticancer Drug in Participants with Lung Cancer (NSCLC); Mar. 6, 2014.
NCT02779751—A Study of Abemaciclib (LY2835219) in Participants with Non-Small Cell Lung Cancer or Breast Cancer; May 20, 2016.
NCT03041311—Carboplatin, Etoposide, and Atezolizumab with or without Trilaciclib; Jul. 26, 2019.
NCT03294694—Ribociclib + PDR001 in Breast Cancer and Ovarian Cancer; Sep. 27, 2017.
NCT02983071—G1T38, a CDK 4/6 Inhibitor, in Combination With Fulvestrant in Hormone Receptor-Positive, HER2-Negative Locally Advanced or Metastatic Breast Cancer.
NCT03455829—G1T38, a CDK 4/6 Inhibitor, in Combination With Osimertinib in EGFR-Mutant Non-Small Cell Lung Cancer.
O'Dwyer, et al. phase I dose escalation trial of a daily oral CDK 4/6 inhibitor PD-0332991. J Clin Oncol, 2007; 25(18S): 3550. [Abstract].
Ottensmeier, et al. A Novel Phase II Trial of Ipilimumab, Carboplatin and Etoposide (ICE) for the First Line Treatment of Extensive Stage Small Cell Lung Cancer (SCLC). Annals of Oncology 25 (Supplement 4): iv511-iv516, 2014.
Rader et al. Dual CDK4/CDK6 Inhibition Induces Cell Cycle Arrest and Senescence in Neuroblastoma. Clin Cancer Res., 2013, 19(22): 6173-82.
Roberts et al. Multiple Roles of Cyclin-Dependent Kinase 4/6 Inhibitors in Cancer Therapy. JNCI, 2012; 104(6):476-487.
Rocha Lima, C.M.S. et al. G1T28, a cyclin dependent kinase 4/6 inhibitor, in combination with etoposide and carboplatin for extensive stage small cell lung cancer (ES-SCLC): preliminary results. Cancer Research, 2016, 76(14), CT151, XP002799585; & 107th

(56) References Cited

OTHER PUBLICATIONS

Annual Meeting of the American Association of Cancer Research (AACR), New Orleans, LA Apr. 16-20, 2016.
Schwartz, G.K. et al. Phase I study of PD 0332991, a cyclin-dependent kinase inhibitor, administered in 3-week cycles (Schedule 2/1). Br J Cancer, Jun. 7, 2011; 104(12): 1862-1868.
Smith, B. et al. Single oral dose acute and subacute toxicity of a c-MET tyrosine kinase inhibitor and CDK 4/6 inhibitor combination drug therapy. Am J. Cancer Res., 2018, 8(1), 183-191.
Sorrentino, J.A. et al. G1T28, a novel CDK 4/6 inhibitor, protects murine hematopoietic stem and progenitor cells from cytotoxic chemotherapy. Cancer Research, 2015, 75(15), 941, XP002799586; & 106th Annual Meeting of the American Association for Cancer Research (AACR), Philadelphia, PA, Apr. 18-22, 2015.
Sorrentino, J.A. et al. Trilaciclib (G1T28), a CDK 4/6 inhibitor, enhances the efficacy of combination therapy and immune checkpoint inhibitor treatment in preclinical models. Cancer Research, 2017, 77(13), Supplement 1, XP002799587.
Sorrentino, J.A. et al. Abstract 2824: G1T38, a novel, oral, potent and selective CDK 4/6 inhibitor for the treatment of Rb competent tumors. Cancer Research. 2016, 1-2; Apr. 16, 2016 (14_Supplement). Poster Presentation Jul. 15, 2016.
Stice, J.P. et al. CDK4/6 Therapeutic Intervention and viable alternative to taxane in CRPC. Molecular Cancer Research, 2017, 15(6), 660-669, XP55457140.
Tan et al. Trilaciclib plus chemotherapy versus chemotherapy alone in patients with metastatic triple-negative breast cancer; a multicenter, randomized, open-label, phase 2 trial. Lancet Oncol., 2019; 209(11), 1587-1601.
Weiss et al. Myelopreservation with the CDK4/6 inhibitor Trilaciclib in patients with small-cell lung cancer receiving first-line chemotherapy: a phase Ib/randomized phase II trial. Annals of Oncology, 2019, 30: 1613-1621.
Wood, A.C. et al. Dual ALK and CDK 4/6 inhibition demonstrates synergy against neuroblastoma. Clin. Cancer Res., 2017, 23(11), 2856-2868.
Zhou, J. et al. Palbociclib, a selective CDK 4/6 inhibitor, enhances the effect of selumetinib in RAS-driven non-small cell lung cancer. Cancer Letters, 2017, 408, 130-137.
US, 2023/0043305, A1, U.S. Appl. No. 17/683,146, Smith et al., Feb. 9, 2023.
U.S. Appl. No. 18/117,983, Strum, filed Mar. 6, 2023.
Singhal, D. et al. Drug polymorphism and dosage form design: a practical perspective, Advanced Drug Delivery Reviews. 56:33(2004).
U.S. Pat. No. 8,598,186, B2, U.S. Appl. No. 13/869,520, Tavares et al., Dec. 3, 2013.
U.S. Pat. No. 8,598,197, B2, U.S. Appl. No. 13/869,576, Tavares et al., Dec. 3, 2013.
U.S. Pat. No. 8,691,830, B2, U.S. Appl. No. 13/869,594, Tavares et al., Apr. 8, 2014.
U.S. Pat. No. 8,822,683, B2, U.S. Appl. No. 14/162,637, Tavares et al., Sep. 2, 2014.
U.S. Pat. No. 8,829,012, B2, U.S. Appl. No. 14/162,649, Tavares et al., Sep. 9, 2014.
U.S. Pat. No. 9,102,682, B2, U.S. Appl. No. 14/452,296, Tavares et al., Aug. 11, 2015.
U.S. Pat. No. 9,260,442, B2, U.S. Appl. No. 14/498,796, Tavares, Jan. 27, 2016.
U.S. Pat. No. 9,464,092, B2, U.S. Appl. No. 14/212,911, Strum et al., Oct. 11, 2016.
U.S. Pat. No. 9,481,691, B2, U.S. Appl. No. 14/712,630, Tavares et al., Nov. 1, 2016.
U.S. Pat. No. 9,487,530, B2, U.S. Appl. No. 14/212,430, Strum et al., Nov. 8, 2016.
U.S. Pat. No. 9,499,564, B2, U.S. Appl. No. 14/712,582, Tavares et al., Nov. 22, 2016.
U.S. Pat. No. 9,527,857, B2, U.S. Appl. No. 14/214,048, Strum et al., Dec. 27, 2016.
U.S. Pat. No. 9,717,735, B2, U.S. Appl. No. 14/690,180, Strum et al., Aug. 1, 2017.
U.S. Pat. No. 9,745,316, B2, U.S. Appl. No. 14/982,443, Tavares, Aug. 29, 2017.
U.S. Pat. No. 9,856,268, B2, U.S. Appl. No. 15/348,862, Tavares, Jan. 2, 2018.
U.S. Pat. No. 9,931,345, B2, U.S. Appl. No. 15/288,878, Strum et al., Apr. 3, 2018.
U.S. Pat. No. 9,957,276, B2, U.S. Appl. No. 15/348,770, Tavares et al., May 1, 2018.
U.S. Pat. No. 10,076,523, B2, U.S. Appl. No. 15/387,083, Strum et al., Sep. 18, 2018.
U.S. Pat. No. 10,085,992, B2, U.S. Appl. No. 15/342,990, Strum et al., Oct. 2, 2018.
U.S. Pat. No. 10,189,849, B2, U.S. Appl. No. 15/918,834, Tavares et al., Jan. 29, 2019.
U.S. Pat. No. 10,189,850, B2, U.S. Appl. No. 15/918,852, Tavares et al., Jan. 29, 2019.
U.S. Pat. No. 10,189,851, B2, U.S. Appl. No. 15/918,877, Tavares et al., Jan. 29, 2019.
U.S. Pat. No. 10,231,969, B2, U.S. Appl. No. 15/457,699, Strum, et al., Mar. 29, 2019.
U.S. Pat. No. 10,376,519, B2, U.S. Appl. No. 15/665,071, Strum, et al., Aug. 13, 2019
U.S. Pat. No. 10,413,547, B2, U.S. Appl. No. 16/142,574, Strum, et al., Sep. 17, 2019.
U.S. Pat. No. 10,434,104, B2, U.S. Appl. No. 16/112,362, Strum, et al., Oct. 8, 2019.
U.S. Pat. No. 10,464,940, B2, U.S. Appl. No. 15/860,483, Tavares et al., Nov. 5, 2019.
U.S. Pat. No. 10,618,905, B2, U.S. Appl. No. 16/230,412, Strum, et al., Apr. 14, 2020.
U.S. Pat. No. 10,633,362, B2, U.S. Appl. No. 16/221,201, Strum, et al., Apr. 28, 2020.
U.S. Pat. No. 10,660,896, B2, U.S. Appl. No. 15/943,278, Strum, et al., May 26, 2020.
U.S. Pat. No. 10,654,831, B2, U.S. Appl. No. 16/230,388, Strum, et al., May 19, 2020.
U.S. Pat. No. 10,696,682, B2, U.S. Appl. No. 16/226,430, Tavares et al., Jun. 30, 2020.
U.S. Pat. No. 10,709,711, B2, U.S. Appl. No. 16/228,308, Strum et al., Jul. 14, 2020.
U.S. Pat. No. 10,829,490, B2, U.S. Appl. No. 16/230,396, Strum et al., Nov. 10, 2020.
U.S. Pat. No. 10,865,210, B2 , U.S. Appl. No. 16/230,381, Smith et al., Dec. 15, 2020.
U.S. Pat. No. 10,925,878, B2, U.S. Appl. No. 16/178,419, Strum et al., Feb. 23, 2021.
U.S. Pat. No. 10,927,120, B2, U.S. Appl. No. 16/721,631, Smith et al., Feb. 23, 2021.
U.S. Pat. No. 10,966,984, B2, U.S. Appl. No. 16/112,360, Strum et al., Apr. 6, 2021.
U.S. Pat. No. 10,981,887, B2, U.S. Appl. No. 16/824,290, Strum et al., Apr. 20, 2021.
U.S. Pat. No. 10,988,479, B2, U.S. Appl. No. 17/097,854, Schneider, Apr. 27, 2021.
U.S. Pat. No. 11,040,042, B2, U.S. Appl. No. 16/886,309, Strum et al., Jun. 22, 2021.
U.S. Pat. No. 11,090,306, A1, U.S. Appl. No. 16/572,418, Strum, et al., Aug. 17, 2021.
U.S. Pat. No. 11,261,193, A1, U.S. Appl. No. 16/721,631, Smith et al., Mar. 1, 2022.
U.S. Pat. No. 11,357,779, A1, U.S. Appl. No. 16/924,033, Beelen et al., Jun. 14, 2022.
U.S. Pat. No. 11,364,222, A1, U.S. Appl. No. 16/460,502, Strum et al., Jun. 21, 2022.
U.S. Pat. No. 11,395,821, A1, U.S. Appl. No. 16/547,342, Sorrentino, et al., Jul. 26, 2022.
U.S. Pat. No. 11,446,295, A1, U.S. Appl. No. 16/254,364, Strum, et al., Sep. 20, 2022.
U.S. Pat. No. 11,529,352, A1, U.S. Appl. No. 16/432,244, Sorrentino, et al., Dec. 20, 2022.
US, 2019/0167691, A1, U.S. Appl. No. 16/268,317, Strum, et al., Jun. 6, 2019.

(56) References Cited

OTHER PUBLICATIONS

US, 2020/0239486, A1, U.S. Appl. No. 16/847,426, Strum, et al., Jul. 30, 2020.
US, 2020/0283406, A1, U.S. Appl. No. 16/877,249, Strum, et al., Sep. 10, 2020.
US, 2020/0331925, A1, U.S. Appl. No. 16/918,985, Strum, et al., Oct. 22, 2020.
US, 2020/0345743, A1, U.S. Appl. No. 16/926,035, Strum, et al., Nov. 5, 2020.
US, 2021/0030758, A1, U.S. Appl. No. 17/067,549, Strum, et al., Feb. 4, 2021.
US, 2021/0047328, A1, U.S. Appl. No. 17/088,298, Strum, et al., Feb. 18, 2021.
US, 2021/0077498, A1, U.S. Appl. No. 17/102,311, Strum, et al., Mar. 18, 2021.
US, 2021/0122755, A1, U.S. Appl. No. 17/121,392, Smith et al., Apr. 29, 2021.
US, 2021/0213022, A1, U.S. Appl. No. 17/181,638, Strum, et al., Jul. 15, 2021.
US, 2021/0171554, A1, U.S. Appl. No. 17/176,962, Strum, et al., Jun. 10, 2021.
US, 2021/0179567, A1, U.S. Appl. No. 17/184,354, Schneider et al., Jun. 17, 2021.
US, 2021/0267986, A1, U.S. Appl. No. 17/315,011, Sorrentino et al., Sep. 2, 2021.
US, 2021/0387993, A1, U.S. Appl. No. 17/236,687, Schneider et al., Dec. 16, 2021.
US, 2021/0299130, A1, U.S. Appl. No. 17/222,873, Strum, et al., Sep. 30, 2021.
U.S. Appl. No. 17/683,146, Smith et al., filed Feb. 28, 2022.
U.S. Appl. No. 17/890,130, Strum et al., filed Aug. 17, 2022.
U.S. Appl. No. 17/854,755, Sorrentino et al., filed Jun. 30, 2022.
U.S. Appl. No. 17/898,196, Strum et al., filed Aug. 29, 2022.
U.S. Appl. No. 18/072,963, Sorrentino et al., filed Dec. 1, 2022.
US, 2023/0146638, A1, U.S. Appl. No. 17/854,755, Sorrentino et al., May 11, 2023.
U.S. Appl. No. 18/120,806, Tavares et al., filed Mar. 13, 2023.
Morissette, S.L. et al. High-through put crystallization: polymorphs, salts, cocrystals and solvates of pharmaceutical solids. Advanced Drug Delivery Reviews. 56:275-300(2004).
Shaw, A.T. et al. Alectinib in ALK-positive, crizotinib-resistant, non-small-cell lung cancer: a single-group, multicentre, phase 2 trial. Lancet Oncol. 17(2):234-242(Feb. 2016). Epub Dec. 19, 2015 (abstract).
Bisi, J.E. et al. Preclinical Characterization of G1T28: A Novel CDK4/6 Inhibitor for Reduction of Chemotherapy-Induced Myelosuppression. Mol. Cancer Therap. (2016) (15)5: 783-793.
Bisi, J.E. et al. Preclinical development of G1T38: A novel, potent and selective inhibitor of cyclin dependent kinases 4/6 for use as an oral antineoplastic in patients with CDK4/6 sensitive tumors. Oncotarget. 2017, 8(26), 42343-42358 doi:10.18632/oncotarget.16216.
Cross et al. AZD9291, an irreversible EGFR TKI, overcomes T790M-mediated resistance to EGFR inhibitors in lung cancer. Cancer Discov. Sep. 2014; 4 (9): 1046-1061. doi:10.1158/2159-8290.CD-14-0337.
Deep, G. et al. New Combination Therapies with Cell Cycle Agents. Current Opinion in Investigational Drugs, 2008; 9(6), 591-605.
Deng et al. CDK4/6 Inhibition Augments Antitumor Immunity by Enhancing T-cell Activation. Cancer Discovery Feb. 2018. Published online Nov. 3, 2017; doi: 10.1158/2159-8290.CD-17-0915.
Dickson, M. et al. Phase II Trial of the CDK4 Inhibitor PD0332991 in Patients with Advanced CDK4-Amplified Well-Differentiated or Dedifferentiated Liposarcoma. J Clin Oncol. Jun. 1, 2013; 31(16): 2024-2028.
Finn et al. PD 0332991, a selective cyclin D kinase 4/6 inhibitor, preferentially inhibits proliferation of luminal estrogen receptor-positive human breast cancer cell lines in vitro. Breast Cancer Research, Oct. 29, 2009; 11(5): R77.
Finn et al. Results of a randomized phase 2 study of PD 0332991, a cyclin-dependent kinase (CDK) 4/6 inhibitor, in combination with letrozole vs letrozole alone for first-line treatment of ER+/HER2-advanced breast cancer (BC). Cancer Res, 2012; 72(24 Suppl): Abstract nr S1-6.
Fry, D.W. et al. Specific inhibition of cyclin-dependent kinase 4/6 by PD 0332991 and associated antitumor activity in human tumor xenografts. Mol Cancer Ther., Nov. 2004; 3(11): 1427-1438.
Goel S. et al. Overcoming therapeutic resistance in HER2-positive breast cancers with CDK 4/6 inhibitors. Cancer Cell, 2016, 29, 255-269.
Goel, S. et al. CDK4/6 Inhibition Triggers Anti-Tumour Immunity. Nature, 2017, 548 (7668), 471-475. doi: 10.1038/nature23465. Epub Aug. 16, 2017.
Gojo, I. et al. Phase II study of the cyclin-dependent kinase (CDK) inhibitor dinaciclib (SCH 727965) in patients with advanced acute leukemias. ASH Annual Meeting Abstracts. 2010; 116: 3287.
Hamilton et al. Synergism of Cyclin-Dependent Kinase Inhibitors with Camptothecin Derivatives in Small Cell Lung Cancer Cell Lines. Molecules (2014), 19(2): 2077-2088.
Hamilton et al. Synergistic Anticancer Activity of Topotecan—Cyclin-Dependent Kinase Inhibitor Combinations against Drug-Resistant Small Cell Lung Cancer (SCLC) Cell Lines. Journal of Cancer Therapy (2013) 4: 47-53.
He et al. Transient CDK4/6 inhibition protects hematopoietic stem cells from chemotherapy-induced exhaustion. Science Translational Medicine, 2017, 9, eaal3986.
Janne et al. AZD9291 in EGFR Inhibitor-Resistant Non-Small-Cell Lung Cancer. N Engl J Med 2015; 372: 1689-99. DOI: 10.1056/NEJMoa1411817.
Johnson et al. Cyclin-dependent kinases (cdks) and the DNA damage response: rationale for cdk inhibitor-chemotherapy combinations as an anticancer strategy for solid tumors. Expert Opin Ther Targets, 2010, 14(11): 1199-1212.
Johnson, N. & Shapiro, G. Cyclin-dependent kinase 4/6 inhibition in cancer therapy. Cell Cycle, Nov. 1, 2012; 11(21): 3913-3918.
Kim, S. et al. The potent and selective cyclin-dependent kinases 4 and 6 inhibitor ribociclib (LEE011) is a versatile combination partner in preclinical cancer models. Oncotarget, 2018, 9(81), 35226-35240.
Liu et al. PD 0332991, a selective cyclin D kinase 4/6 inhibitor, sensitizes lung cancer cells to treatment with epidermal growth factor receptor tyrosine kinase inhibitors. Oncotarget, 2016, 7(51), pp. 84951-84964.
Caira, M.R. Crystalline Polymorphism of Organic Compounds. Topics in Current Chemistry. Design of Organic Solids. *Springer*, Berlin, DE, 1998, 198, 163-208; ISSN: 0340-1022; DOI: 10.1007/3-540-69178-2.
U.S. Pat. No. 11,395,821, U.S. Appl. No. 16/547,342, Sorrentino et al., Jul. 26, 2022.
U.S. Pat. No. 11,629,150, B2, U.S. Appl. No. 17/121,392, Smith et al., Apr. 18, 2023.
U.S. Pat. No. 11,654,148, B2, U.S. Appl. No. 17/181,638, Strum et al., May 23, 2023.
U.S. Pat. No. 11,708,337, B2, U.S. Appl. No. 17/184,354, Schneider et al., Jul. 25, 2023.
U.S. Pat. No. 11,717,523, B2, U.S. Appl. No. 17/222,873, Strum et al., Aug. 8, 2023.
US, 2023/0241059, A1, U.S. Appl. No. 17/898,196, Strum et al., Aug. 3, 2023.
US, 2023/0248733, A1, U.S. Appl. No. 17/890,130, Strum et al., Aug. 10, 2023.
US, 2023/0302001, A1, U.S. Appl. No. 18/072,963, Sorrentino et al., Sep. 28, 2023.
US, 2023/0364098, A1, U.S. Appl. No. 18/117,983, Strum et al., Nov. 16, 2023.
US, 2023/0381189, A1, U.S. Appl. No. 18/231,091, Strum et al., Nov. 30, 2023.
US, 2024/0109906, A1, U.S. Appl. No. 18/120,806, Tavares et al., Apr. 4, 2024.
U.S. Appl. No. 18/225,537, Schneider et al., filed Jul. 24, 2023.
U.S. Pat. No. 12,139,494, B2, U.S. Appl. No. 17/683,146, Smith et al., Nov. 12, 2024.
U.S. Pat. No. 12,168,666, B2, U.S. Appl. No. 17/236,687, Schneider et al., Dec. 17, 2024.

(56) References Cited

OTHER PUBLICATIONS

US, 2022/0175780, A1, U.S. Appl. No. 17/403,577, Strum et al., Jun. 9, 2022.
US, 2022/0175787, A1, U.S. Appl. No. 17/554,940, Roberts et al., Jun. 9, 2022.
US, 2022/0241275, A1, U.S. Appl. No. 17/718,052, Strum et al., Aug. 4, 2022.
US, 2024/0139196, A1, U.S. Appl. No. 18/394,512, Beelen et al., May 2, 2024.
US, 2024/0199556, A1, U.S. Appl. No. 18/225,537, Schneider et al., Jul. 24, 2023.
U.S. Appl. No. 18/943,701, Smith et al., filed Nov. 11, 2024.
U.S. Appl. No. 18/957,373, Tavares et al., filed Nov. 22, 2024.
U.S. Appl. No. 18/973,646, Schneider et al., filed Dec. 9, 2024.
Xu, Binghe et al. "Lerociclib plus fulvestrant in patients with HR+/HER2-locally advanced or metastatic breast cancer who have progressed on prior endocrine therapy: Leonarda-1 a phase III randomized trial." Nature Communications 16.1, 716, Jan. 16, 2025.

\* cited by examiner

G1T38 SUPERIOR DOSAGE REGIMES

CROSS-REFERENCE TO RELATED APPLICATIONS

This application is a continuation of U.S. patent application Ser. No. 16/924,033, filed on Jul. 8, 2020, which is a continuation of International Patent Application No. PCT/US2019/012720, filed in the U.S. Receiving Office on Jan. 8, 2019, which claims the benefit of U.S. Provisional Application No. 62/614,952, filed Jan. 8, 2018, U.S. Provisional Application No. 62/679,575, filed Jun. 1, 2018, and U.S. Provisional Application No. 62/788,017, filed Jan. 3, 2019. The entirety of each these applications is hereby incorporated by reference herein for all purposes.

FIELD OF THE INVENTION

This invention is an advantageous dosage regime for administration of the selective CDK 4/6 inhibitor known as G1T38, which is 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one, based on human clinical trials.

BACKGROUND

The regulation of the cell cycle is governed and controlled by specific proteins, which are activated and deactivated mainly through phosphorylation/dephosphorylation processes in a precisely timed manner. The key proteins that coordinate the initiation, progression, and completion of cell-cycle program are cyclin dependent kinases (CDKs). Cyclin-dependent kinases belong to the serine-threonine protein kinase family. They are heterodimeric complexes composed of a catalytic kinase subunit and a regulatory cyclin subunit. CDK activity is controlled by association with their corresponding regulatory subunits (cyclins) and CDK inhibitor proteins (Cip & Kip proteins, INK4s), by their phosphorylation state, and by ubiquitin-mediated proteolytic degradation (see D. G. Johnson, C. L. Walker, Annu. Rev. Pharmacol. Toxicol 39 (1999) 295-312; D. O. Morgan, Annu. Rev. Cell Dev. Biol. 13 (1997) 261-291; C. J. Sherr, Science 274 (1996) 1672-1677; T. Shimamura et al., Bioorg. Med. Chem. Lett. 16 (2006) 3751-3754).

There are four CDKs that are significantly involved in cellular proliferation: CDK1, which predominantly regulates the transition from G2 to M phase, and CDK2, CDK4, and CDK6, which regulate the transition from G1 to S phase (Malumbres M, Barbacid M. Cell cycle, CDKs and cancer: a changing paradigm. Nat. Rev. Cancer 2009; 9(3):153-166). In early to mid G1 phase, when the cell is responsive to mitogenic stimuli, activation of CDK4-cyclin D and CDK6-cyclin D induces phosphorylation of the retinoblastoma protein (pRb). Phosphorylation of pRb releases the transcription factor E2F, which enters the nucleus to activate transcription of other cyclins which promote further progression of the cell cycle (see J. A. Diehl, Cancer Biol. Ther. 1 (2002) 226-231; C. J. Sherr, Cell 73 (1993) 1059-1065). CDK4 and CDK6 are closely related proteins with basically indistinguishable biochemical properties (see M. Malumbres, M. Barbacid, Trends Biochem. Sci. 30 (2005) 630-641).

A number of CDK 4/6 inhibitors have been identified for use to treat CDK4/6 replication dependent cancer. For example, WO 03/062236 identifies a series of 2-(pyridin-2-ylamino-pyrido[2,3]pyrimidin-7-ones for the treatment of Rb positive cancers that show selectivity for CDK4/6, including 6-acetyl-8-cyclopentyl-5-methyl-2-(5-piperazin-1-yl-pyridin-2-ylammino)-8H-pyrido-[2,3-d]-pyrimidin-7-one (IBRANCE/palbociclib: Pfizer). The clinical trial studies have reported rates of Grade 3/4 neutropenia and leukopenia with the use of palbociclib, resulting in 71% of patients requiring a dose interruption and 35% requiring a dose reduction; and adverse events leading to 10% of the discontinuations (see Finn, Abstract S1-6, SABCS 2012). These side effects may be caused by the undesirable pharmacokinetics of palbociclib, which has a relatively long $T_{1/2}$ of roughly 26.7 hours and a median accumulation ratio of 2.4, resulting in an accumulative concentration build-up of the CDK4/6 inhibitor and a persistent quiescence of HPSC replication. Due to these effects, the approved dosing regime for palbociclib requires a 7-day holiday after 21-days of once daily dosing.

U.S. Pat. No. 7,855,211 is directed to protein kinase inhibitors and includes the chemical structure of 2-pyrimidinamine, N-[5-[(4-ethyl-1-piperazinyl)methyl]-2-pyridinyl]-5-fluoro-4-[4-fluoro-2-methyl-1-(1-methylethyl)-1H-benzimidazol-6-yl]-(VERZENIO™/abemaciclib: Eli Lilly & Co.). Abemaciclib is indicated in combination with fulvestrant for the treatment of women with hormone receptor (HR)-positive, human epidermal growth factor 2 (HER2)-negative advanced or metastatic breast cancer with disease progression following endocrine therapy and as a monotherapy for the treatment of adult patients with HR-positive, HER2-negative advanced or metastatic breast cancer with disease progression following endocrine therapy and prior chemotherapy in the metastatic setting. The clinical trial studies (MONARCH 1 (monotherapy) and MONARCH 2 (abemaciclib plus fulvestrant)) have reported a significant incidence of diarrhea, as well as neutropenia attributable to abemaciclib. Diarrhea occurred in 86% of patients receiving abemaciclib plus fulvestrant in MONARCH 2 and 90% of patients receiving abemaciclib alone in MONARCH 1. Grade 3 diarrhea occurred in 13% of patients receiving abemaciclib plus fulvestrant in MONARCH 2 and in 20% of patients receiving abemaciclib alone in MONARCH 1. Neutropenia occurred in 46% of patients receiving abemaciclib plus fulvestrant in MONARCH 2 and 37% of patients receiving abemaciclib alone in MONARCH 1. A Grade ≥3 decrease in neutrophil count (based on laboratory findings) occurred in 32% of patients receiving abemaciclib plus fulvestrant in MONARCH 2 and in 27% of patients receiving abemaciclib in MONARCH 1. 22% of patients with diarrhea required dose omission and 22% required a dose reduction. Supportive care was also required. These side effects may be caused by the undesirable pharmacokinetics of abemaciclib, which has a relatively long $T_{1/2}$ of roughly 18.3 hours. The estimated geometric mean accumulation ratio was 2.3 (50% CV) and 3.2 (59% CV) based on Cmax and AUC, respectively, resulting in an accumulative concentration build-up of the CDK4/6 inhibitor and a persistent quiescence of HPSC replication.

U.S. Pat. No. 8,415,355 describes pyrrolopyrimidine compounds and their uses and includes 7-cyclopentyl-N,N-dimethyl-2-((5-(piperazin-1-yl)pyridin-2-yl)amino)-7H-pyrrolo[2,3-d]pyrimidine-6-carboxamide (KISQALI™/ribociclib: Novartis). Ribociclib is indicated in combination with an aromatase inhibitor (letrozole) as initial endocrine-based therapy for the treatment of postmenopausal women with hormone receptor (HR)-positive, human epidermal growth factor receptor 2 (HER2)-negative advanced or metastatic breast cancer. The clinical trial study (MONA-LEESA-2) has reported that neutropenia was the most frequently reported adverse reaction (AR) (75%), and a grade 3/4 decrease in neutrophil count (based on laboratory findings) was reported in 60% of patients receiving ribociclib+letrozole. Dose reductions due to adverse reactions (ARs) occurred in 45% of patients receiving ribociclib plus letrozole. Permanent discontinuations due to ARs were reported in 7% of patients receiving ribociclib plus letrozole. These side effects may be caused by the undesirable pharmacokinetics of ribociclib, which has a relatively long $T_{1/2}$ of roughly 32 hours with a geometric mean accumulation ratio of 2.51 (range: 0.972 to 6.40), resulting in an accumulative concentration build-up of the CDK4/6 inhibitor and a persistent quiescence of HPSC replication. Due to these effects, the approved dosing regime for ribociclib requires a 7-day holiday after 21-days of once daily dosing.

Recently, G1 Therapeutics, Inc. has identified a selective CDK4/6 inhibitor for human clinical use: 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one (G1T38) with the structure

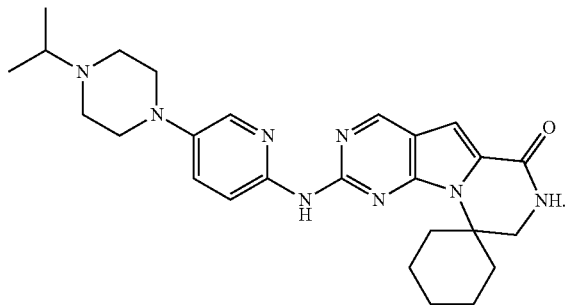

While selective CDK4/6 inhibitors are generally designed to target CDK4/6-replication dependent cancers, the very fact that they inhibit CDK4/6 activity may also result in deleterious effects to CDK4/6-dependent healthy cells, for example their growth inhibition. CDK4/6 activity is necessary for the production of healthy blood cells by the bone marrow, as healthy hematopoietic stem and progenitor cells (HSPCs) require the activity of CDK4/6 for proliferation (see Roberts et al. Multiple Roles of Cyclin-Dependent Kinase 4/6 Inhibitors in Cancer Therapy. JNCI 2012; 104 (6):476-487). Healthy hematopoietic stem cells give rise to progenitor cells which in turn give rise to all the differentiated components of blood (e.g., lymphocytes, erythrocytes, platelets, granulocytes, monocytes). Healthy hematopoietic cells display a gradient dependency on CDK4/6 activity for proliferation during myeloid/erythroid differentiation (see Johnson et al. Mitigation of hematological radiation toxicity in mice through pharmacological quiescence induced by CDK4/6 inhibition. J Clin. Invest. 2010; 120(7): 2528-2536). Accordingly, the least differentiated cells (e.g., healthy hematopoietic stem cells (HSCs), multi-potent progenitors (MPPs), and common myeloid progenitors (CMP)) appear to be the most dependent on CDK4/6 activity for proliferation, and therefore the most deleteriously affected by the use of a CDK4/6 inhibitor to treat a CDK4/6 replication dependent cancer or other proliferative disorder.

Accordingly, there is an ongoing need for improved dosage regimes useful in treating patients with select Rb-positive cancers and abnormal cellular proliferative disorders while minimizing the treatment's effect on healthy cells such as HSPCs.

It is an object of the present invention to provide a guided dosage regime for G1T38 to achieve a superior balance during administration of activity and toxicity which is sustainable over an extended period.

SUMMARY OF THE INVENTION

As a result of human clinical trials, a dosage regime has been surprisingly identified that can guide the safe and effective long-term administration of the selective CDK 4/6 inhibitor G1T38 or a pharmaceutically acceptable salt thereof in a human. It was not possible to confirm this dosage regime prior to human administration.

Thus, it has been determined that:
(i) A solid dosage regime of G1T38 for oral delivery that provides a (mean steady state $AUC_{(0\text{-}24ss)}$ (h*ng/mL))/mg dose ratio of not greater than 5;
or
(ii) A solid dosage regime of G1T38 for oral delivery that provides on Day 22 after first dosing a mean steady state $AUC_{(0\text{-}24\ ss)}$ (h*ng/mL))/Absolute Neutrophil Count (cells/mm$^3$) ratio of not greater than 1.25;
provides superior results for the treatment of humans with an Rb-positive neoplastic disorder. These dosage regimes have been identified in Phase Ib/2a human clinical trials in the United States with the U.S. Food and Drug Administration for the treatment of estrogen positive, HER2-negative breast cancer after endocrine therapy failure.

Prior to human clinical studies, preclinical studies in mice were carried out (Bisi, et al., Preclinical development of G1T38: A novel, potent and selective inhibitor of cyclin dependent kinases 4/6 for use as an oral antineoplastic in patients with CDK 4/6 sensitive tumors," *Oncotarget*, Mar. 15, 2017; provided to the U.S. FDA in the Investigational New Drug submission). The *Oncotarget* article disclosed that in mice, G1T38 concentrates in the tumor after a single dosage of 100 mg/kg. However, given the difference in metabolism, actual mass, and surface area of the mouse and the human, direct correlations with human absorption and compartmentalization are not predictable in advance, even though preclinical data is submitted to and required by the FDA. See also U.S. Pat. No. 9,527,857. The rate of drug distribution is determined by blood flow and the rate of diffusion and/or transport to the target cells. Because circulation time and blood flow scale allometrically with increased body size, smaller animals would be expected to distribute drugs to their targets faster. Also, because of the increased blood flow to the liver and kidneys, smaller animals would be expected to eliminate the drugs faster. However, again, the trajectory for different drugs is variable, and the only way to determine whether and what a superior dosage regime is for a drug to treat cancer is by administering the drug to humans.

The volume of distribution is considered (the total amount of drug in the body)/(drug blood plasma concentration) at time zero. The total amount of drug in the body is the dose for an intravenously (IV) administered drug and the plasma concentration is at time zero. Time zero is the instant after all the drug has been administered. This is most straight forward for IV drugs given rapidly (e.g., over 30-60 seconds). It is significantly more complicated for oral drugs because the amount of drug in the body is unknown unless absolute bioavailability ($F_{abs}$ or simply F) has been measured. When the drug is given orally, then F remains unknown and $V_d$ cannot be determined. This is the expression $V_d/F$ where F is an unknown constant. $V_d/F$ is referred to as "apparent volume of distribution." There are no assumptions made for the value of F. $V_d/F$ is determined using the terminal elimination rate constant ($k_e$), which is derived mathematically from the concentration vs time curve. Once $k_e$ is known, a value for the plasma concentration at time zero is extrapolated (because oral drugs are absorbed slowly, plasma concentration at time zero cannot be physically measured). Volume of distribution for oral drugs is always expressed as $V_d/F$ or $V_z/F$, where "z" indicates that the volume was derived using the terminal elimination rate constant ($k_e$).

It has been surprisingly discovered that a dosage regime of the G1T38 can be achieved that exhibits an $(AUC_{(0-24),ss}$ of less than 1200 h*ng/ml), a $C_{max}$ less than about 75 ng/mL, and/or a $V_d/F$ of greater than 10,000 L. This is unexpected because the three other commercial selective CDK 4/6 inhibitors, palbociclib, ribociclib. and abemaciclib, have significantly lower $V_d/F$ and cannot achieve this dosing regime. The present dosage regime provides surprising efficacy against CDK4/6-replication dependent cancers while significantly reducing therapy-limiting side effects such as neutropenia and gastrointestinal complications associated with other CDK4/6 inhibitors. This dosage regime for administration in a human are particularly useful in therapeutic regimens for the long-term treatment of, for example, estrogen receptor positive, HER2 negative (ER⁺/HER2⁻) breast cancer, prostate cancer, and non-small cell lung carcinoma, while minimizing the effect of CDK4/6 inhibitory toxicity on CDK4/6 replication dependent healthy cells, such as hematopoietic stem cells and hematopoietic progenitor cells (together referred to as HSPCs), and allow for continuous, daily dosing for extended periods of time, for example greater than 24 months. In one embodiment, G1T38 or its pharmaceutically acceptable salt is orally administered once daily. In one embodiment, G1T38 or its pharmaceutically acceptable salt is orally administered twice daily.

In some aspects, the CDK4/6 inhibitor administered in an oral dosage regime to a human is 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one (G1T38) having the structure (Compound I)

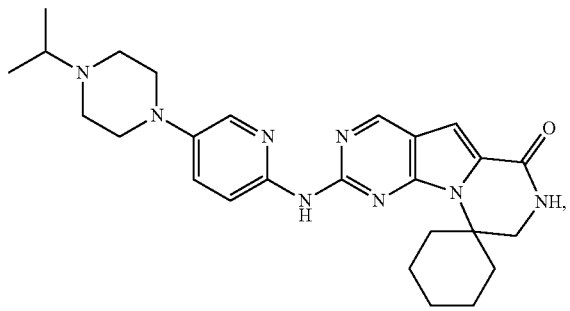 [SMILES: CC(C)N1CCN(c2ccc(Nc3ncc4cc5n(c4n3)C3(CCCCC3)CNC5=O)nc2)CC1]

or a pharmaceutically acceptable composition, salt or isotopic analog thereof.

In one embodiment, G1T38 is administered as a hydrochloride salt of 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one, such as the mono- or dihydrochloride salt. In one embodiment, the compound administered has the structure (Compound II)

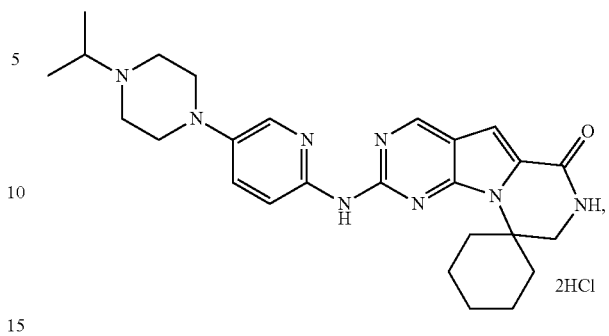

or a pharmaceutically acceptable composition or isotopic analog thereof. In one embodiment, Compound II is an isolated morphic form referred to herein as Form B.

In another embodiment, the CDK4/6 inhibitor administered is 2'-((5-(piperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one (Compound III)

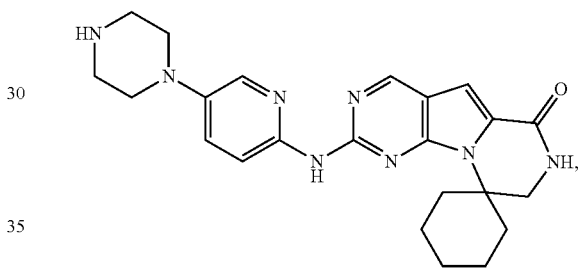

or a pharmaceutically acceptable composition, salt, or isotopic analog thereof.

In yet another aspect, an oral dosage regime for administration to a human comprising G1T38, or a pharmaceutical salt thereof, for example Form B of Compound II, provides a mean $AUC_{(0-24),ss}$ (h*ng/mL) of less than about 1000 h*ng/mL. In one embodiment, the mean $AUC_{(0-24),ss}$ (h*ng/mL) is less than about 900 h*ng/mL, 800 h*ng/mL, 700 h*ng/mL, or 600 h*ng/mL. In one embodiment, the mean $AUC_{(0-24),ss}$ (h*ng/mL) is between about 600 h*ng/mL and 1200 h*ng/mL. In one embodiment, the mean $AUC_{(0-24),ss}$ (h*ng/mL) is between about 800 h*ng/mL and 1000 h*ng/mL. In one embodiment, the mean $AUC_{(0-24),ss}$ (h*ng/mL) is measured for serum Compound I.

In one aspect, an oral dosage regime for administration to a human comprises G1T38 or its pharmaceutically acceptable salt, for example Form B of Compound II, that results in an Absolute Neutrophil Count (ANC) of greater than about 1000 cells/mm³ as measured at Day 22 from initial dosing. In one embodiment, the Absolute Neutrophil Count (ANC) is greater than about 800 cells/mm³, 1000 cells/mm³, 1200 cells/mm³, 1400 cells/mm³, 1600 cells/mm³, 1800 cells/mm³, or 2000 cells/mm³ as measured at day 22 from initial dosing.

In one aspect, an oral dosage regime for administration to a human comprising G1T38 or its pharmaceutically acceptable salt, for example Form B of Compound II, that achieves a mean $C_{max}$ (ng/mL) measured at day 29 of dosing of less than about 75 ng/mL. In one embodiment, the mean $C_{max}$ (ng/mL) measured at day 29 of dosing of less than about 70 ng/mL. In one embodiment, the mean $C_{max}$ (ng/mL) measured at day 29 of dosing of less than about 65 ng/mL. In one embodiment, the $C_{max}$ (ng/mL) is measured for serum Compound I.

In one aspect, an oral dosage regime for administration to a human comprises G1T38 or its pharmaceutically acceptable salt, for example Form B of Compound II, that achieves a mean $V_d/F$ (L) of greater than about 10,000 L; 11,000 L; 12,000 L; 14,000 L or 15,000 L. In one embodiment, the $V_d/F$ is measured for Compound I.

In one aspect, an oral dosage regime for administration to a human comprising G1T38 or its pharmaceutically acceptable salt, for example Form B of Compound II, that provides a Dose Normalized $AUC_{(0-24),ss}$ (mean $AUC_{(0-24),ss}$ (h*ng/mL))/(dose (mg)) ratio of less than 5. In one embodiment, the (mean $AUC_{(0-24),ss}$ (h*ng/mL))/(dose (mg)) ratio is less than about 4.5, 4, 3.5, 3, 2.5 or 2. In one embodiment, the mean $AUC_{(0-24),ss}$ is measured for serum Compound I.

In one aspect, an oral dosage regime for administration to a human comprises G1T38 or its pharmaceutically acceptable salt, for example Form B of Compound II, that achieves a (mean $AUC_{(0-24),ss}$ (h*ng/mL))/(dose (mg)) ratio of less than 10. In one embodiment, the (mean $AUC_{(0-24),ss}$ (h*ng/mL))/(dose (mg)) ratio is less than about 9.5, 9.0, 8.5, 8.0, 7.5, 7.0, 6.5, 6.0, 5.5, 5.0, 4.5, 4.0, 3.5, 3, or 2.5. In one embodiment, the mean $AUC_{(0-24),ss}$ is measured for serum Compound I.

In one aspect, an oral dosage regime for administration to a human comprises G1T38 or a pharmaceutically acceptable salt thereof, for example Form B of Compound II, that achieves a (mean $AUC_{(0-24),ss}$ (h*ng/mL))/(Absolute Neutrophil Count (cells/mm$^3$)) ratio on day 22 of dosing of not greater than 1.25. In one embodiment, the (mean $AUC_{(0-24),ss}$ (h*ng/mL))/(Absolute Neutrophil Count (cells/mm$^3$)) ratio on day 22 of dosing is not greater than 1.2; 1.1; 1.0; 0.9; 0.8; 0.7; 0.6 or 0.5. In one embodiment, the mean $AUC_{(0-24),ss}$ is measured for serum Compound I.

In one embodiment, 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one, or its pharmaceutically acceptable salt, is provided in an oral dosage regime that is dosed once a day. In one embodiment, 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one, or its pharmaceutically acceptable salt, is provided in an oral dosage regime that is dosed two times a day, optionally spaced about 12 hours apart. In one embodiment, 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one, or its dihydrochloride salt, is provided in an oral dosage regime that is dosed once a day. In one embodiment, 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one, or its dihydrochloride salt, is provided in an oral dosage regime that is dosed once a day. 2'-((5-(piperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one, or its pharmaceutically acceptable salt, is provided in an oral dosage regime that is dosed two times a day, optionally spaced about 12 hours apart. 2'-((5-(piperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one, or its pharmaceutically acceptable salt, is provided in an oral dosage regime that is dosed two times a day, optionally spaced about 12 hours apart.

In one embodiment, the oral dosing regime comprises about 200 mg, 300 mg, 400 mg, 500 mg, or 650 mg of Compound II that is dosed once a day. In one embodiment, the oral dosing regime comprises about 100 mg, 150 mg, or 200 mg of Compound II that is dosed twice a day, optionally spaced about 12 hours apart. In one embodiment, Compound II is dosed as isolated morphic Form B.

The dosing regime described herein may be dosed continuously, for example at least one time a day for a period of at least, for example, 24 days, 28 days, 35 days, 42 days, 8 weeks, 12 weeks, 16 weeks, 24 weeks, 48 weeks, 12 months, 16 months, 18 months, 24 months or longer.

In an aspect of the present invention, the G1T38 oral dosage regime described herein is administered to a subject having a CDK4/6-replication dependent cancer so that a blood PK and or PD profile as described herein is maintained in the subject during treatment.

In an aspect of the present invention, the G1T38 oral dosage regime described herein is administered to a subject having a CDK4/6-replication dependent cancer in combination with an anti-estrogen compound such as selective estrogen receptor modulators (SERMs), selective estrogen receptor downregulators (SERDs), aromatase inhibitors, and luteinizing hormone releasing agents so that a blood PK and or PD profile as described herein is maintained in the subject during treatment.

In an aspect of the present invention, the G1T38 oral dosage regime described herein is administered to a subject having a CDK4/6-replication dependent cancer selected from Hr+/HER2− breast cancer, HR−/HER2+ breast cancer, EGFR mutant non-small cell carcinoma, KRAS mutant non small cell lung carcinoma, castrate resistant prostate cancer, mantle cell lymphoma, marginal zone lymphoma, chronic lymphocytic leukemia, follicular lymphoma, diffuse large B-cell lymphoma, BRAF mutant melanoma, Ras mutant colorectal cancer, RAS mutant pancreatic cancer, Ras mutant cholangiocarcinoma, and gastrointestinal stromal tumor (GIST).

In an aspect of the present invention, the G1T38 oral dosage regime described herein is administered to a subject having a CDK4/6-replication dependent cancer in combination with a monoclonal antibody directed to human epidermal growth factor receptor 2 (HER2), a human epidermal growth factor receptor 1 (HER1) and/or human epidermal growth factor receptor 2 (HER2) inhibitor, an epidermal growth factor receptor (EGFR) inhibitor, an anaplastic lymphoma kinase (ALK) inhibitor, an androgen receptor (AR) blocker, a Rapidly Accelerated Fibrosarcoma (RAF) inhibitor, a vascular endothelial growth factor receptor 2 (VEGFR2) and tyrosine-protein kinase receptor (TIE2) inhibitor, a Bruton's tyrosine kinase (BTK) inhibitor, a CYP17 inhibitor, an extracellular signal-regulated kinase (ERK) inhibitor, a gonadotropin releasing hormone superagonist (GnRH agonist), a luteinizing hormone-releasing hormone (LH-RH) agonist, a luteinizing hormone-releasing hormone (LH-RH) antagonist, a mechanistic target of rapamycin (mTOR) inhibitor, a mitogen-activated protein kinase (MEK) inhibitor, a nucleoside or nucleotide analogue or prodrug, a phosphatidylinositol 3-kinase (PI3K) pathway inhibitor, a rapidly accelerated fibrosarcoma (RAF) kinase inhibitor, a renin-angiotensin system (RAS) inhibitor, a selective estrogen receptor degrader (SERD), a selective estrogen receptor modulator (SERM), a serine-threonine protein kinase B (Akt) inhibitor, or a topoisomerase inhibitor. In one embodiment, the one or more additional therapeutic agents are selected from letrozole, anastrozole, fulvestrant, tamoxifen, etoposide, enzalutamide, pictilisib, exemestane, or a combination thereof.

DETAILED DESCRIPTION OF THE INVENTION

Definitions

Figure 1:
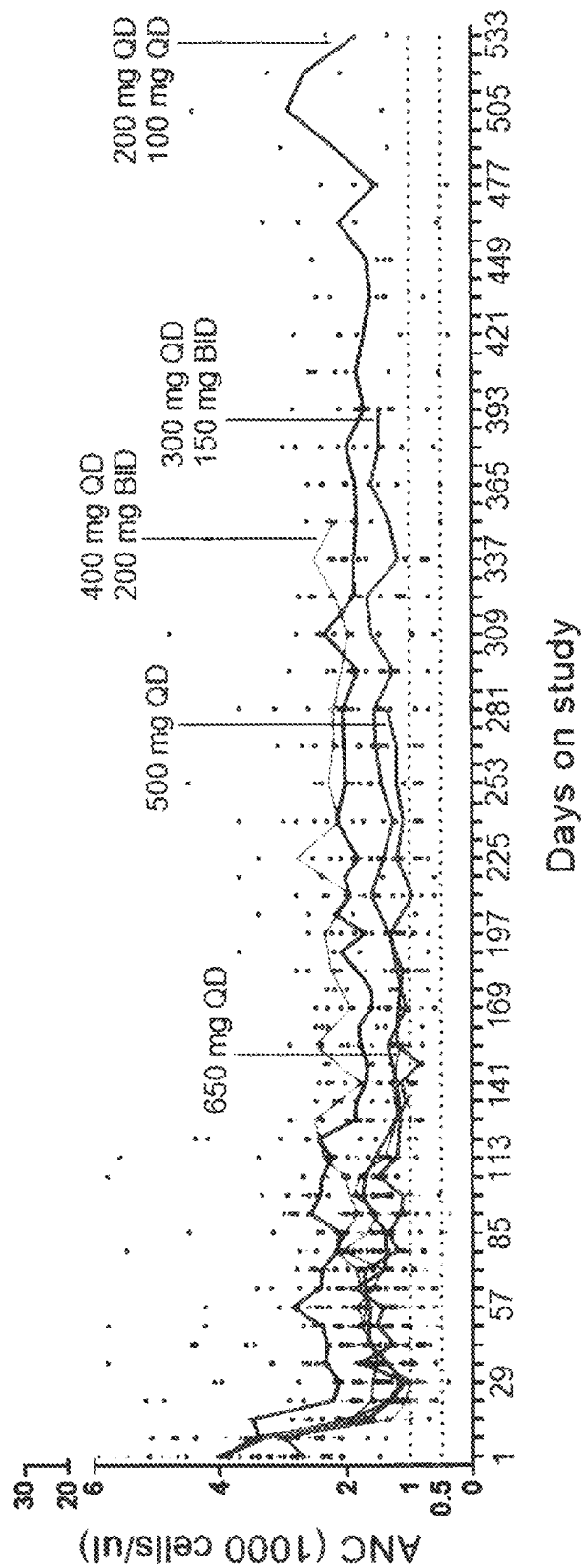
FIG. 1 is a graph of the mean absolute neutrophil count (ANC) in blood samples obtained from cohorts dosed at 200 mg once a day (QD), 100 twice a day (BID), 300 mg QD, 150 mg bid, 400 mg QD, 200 mg BID, 500 mg QD, and 650 QD as measured on selected days of the study (Example 5). Cohorts that were dosed at 200 mg QD and 100 mg BID were combined in the graph. Cohorts that were dosed at 300 QD and 150 mg BID were combined in the graph. Cohorts that were dosed as 400 QD and 200 BID were combined in the graph. The x axis is time measured in days and the y axis is mean ANC measured in 1000 cells/μL.

Absolute Neutrophil Count (ANC) as used herein means the number of neutrophilgranulocytes (also known as polymorphonuclear cells, PMNs, polys, granulocytes, segmented neutrophils or segs) present in the blood.

"AUC" (Amount*time/volume) as used herein means the area under the plasma concentration-time curve.

"$AUC_{(0-24)}$" (Amount*time/volume) as used herein means the area under the plasma concentration time curve from time zero to 24 hours after dosing.

"$AUC_{(0-24),ss}$" (Amount*time/volume) at steady state as used herein means the area under the plasma concentration time curve from time zero to 24 hours after dosing at steady state. Steady state refers to the situation where the overall intake of a drug is fairly in dynamic equilibrium with its elimination. In practice, it is generally considered that steady state is reached when a time of 4 to 5 times the half-life for a drug after regular dosing is started.

"Dose Normalized AUC" as used herein refers to AUC as described above divided by the dose of the compound given in milligrams. For example, if a 200 milligram dose of drug produces a 400 (h*ng/mL) $AUC_{(0-24),ss}$ then the dose normalized $AUC_{(0-24),ss}$ is 2.

"$C_{max}$" (Amount/volume) as used herein means the maximum (peak) plasma drug concentration.

"$t_{max}$" (Time) as used herein means time to reach maximum (peak) plasma concentration following drug administration.

"$V_d/F$" (Liters) as used herein means the theoretical volume that would be necessary to contain the total amount of an administered drug at the same concentration that it is observed in the blood plasma. It is generally defined as the distribution of a medication between plasma and the rest of the body after oral or parenteral dosing. "$V_d/F$" as used herein is calculated by using the terminal elimination rate constant, which is derived mathematically from the concentration vs time curve to extrapolate a value of plasma concentration at time zero. Volume of distribution for oral drugs is normally expressed as $V_d/F$ or $V_z/F$. The skilled artisan is familiar with calculating $V_d/F$ or $V_z/F$.

"PD" as used herein means pharmacodynamic.

"PK" as used herein means pharmacokinetic.

"QD" as used herein means once daily.

"BID" as used herein means twice daily.

"SAE" as used herein means serious adverse event.

The term "carrier" applied to pharmaceutical compositions/combinations of the invention refers to a diluent, excipient, or vehicle with which a CDK4/6 inhibitor described herein is provided.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like.

By "hematological deficiency" is meant reduced hematological cell lineage counts or the insufficient production of blood cells (i.e., myelodysplasia) and/or lymphocytes (i.e., lymphopenia, the reduction in the number of circulating lymphocytes, such as B- and T-cells). Hematological deficiency can be observed, for example, as myelosuppression in form of anemia, reduction in platelet count (i.e., thrombocytopenia), reduction in white blood cell count (i.e., leukopenia), or the reduction in granulocytes (e.g., neutropenia).

By "off-cycle" or "drug holiday" is meant a time period during which the subject is not administered or exposed to a chemotherapeutic. For example, in a treatment regime wherein the subject is administered the chemotherapeutic in a repeated 21-day cycle, and is not administered the chemotherapeutic at the start of the next 21-day cycle due to hematologic deficiencies, the delayed period of non-administration is considered the "off-cycle" or "drug holiday." Off-target and drug holiday may also refer to an interruption in a treatment regime wherein the subject is not administered the chemotherapeutic for a time due to a deleterious side effect, for example, myelosuppression or other hematological deficiencies.

In some embodiments, the term "CDK4/6-replication dependent cancer" refers to a cancer or cellular proliferation disorder that requires the activity of CDK4/6 for replication or proliferation, or which may be growth inhibited through the activity of a selective CDK4/6 inhibitor. Cancers and disorders of such type can be characterized by (e.g., that has cells that exhibit) the presence of a functional Retinoblastoma protein. Such cancers and disorders are classified as being Rb-positive. Rb-positive abnormal cellular proliferation disorders, and variations of this term as used herein, refer to disorders or diseases caused by uncontrolled or abnormal cellular division which are characterized by the presence of a functional Retinoblastoma protein, which can include cancers. In one aspect of the present invention, the compounds and methods described herein can be used to treat a non-cancerous Rb-positive abnormal cellular proliferation disorder. Examples of such disorders may include non-malignant lymphoproliferation, non-malignant breast neoplasms, psoriasis, arthritis, dermatitis, pre-cancerous colon lesions or pulps, angiogenesis disorders, immune mediated and non-immune mediated inflammatory diseases, arthritis, age-related macular degeneration, diabetes, and other non-cancerous or benign cellular proliferation disorders.

The term "selective CDK4/6 inhibitor" used in the context of the compounds described herein includes compounds that inhibit CDK4 activity, CDK6 activity, or both CDK4 and CDK6 activity at an $IC_{50}$ molar concentration at least about 100, 200, 300, 400, or 500 times less (or in alternative embodiments, at least 750, 1000, 1500 or 2000 times less) than the IC50 molar concentration necessary to inhibit to the same degree of CDK2 activity in a standard phosphorylation assay.

The term "pharmaceutically acceptable salt" as used herein refers to those salts which are, within the scope of sound medical judgment, suitable for use in contact with subjects (e.g., human subjects) without undue toxicity, irritation, allergic response, and the like, commensurate with a reasonable benefit/risk ratio, and effective for their intended use, as well as the zwitterionic forms, where possible, of the compounds of the presently disclosed subject matter.

Thus, the term "salt" refers to the relatively non-toxic, inorganic and organic acid addition salts of compounds of the presently disclosed subject matter. These salts can be prepared in situ during the final isolation and purification of the compounds or by separately reacting the purified compound in its free base form with a suitable organic or inorganic acid and isolating the salt thus formed. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

"Pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

In one embodiment, G1T38 includes desired isotopic substitutions of atoms, at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2$H) and tritium ($^3$H) may be used anywhere in described structures. Alternatively, or in addition, isotopes of carbon, e.g., $^{13}$C and $^{14}$C, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect).

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom may be present, the hydrogen atom can be any isotope of hydrogen, including protium ($^1$H), deuterium ($^2$H) and tritium ($^3$H). Thus, reference herein to a compound encompasses all potential isotopic forms unless the context clearly dictates otherwise.

The term "isotopically-labeled" analog refers to an analog that is a "deuterated analog", a "$^{13}$C-labeled analog," or a "deuterated/$^{13}$C-labeled analog." The term "deuterated analog" means a compound described herein, whereby a H-isotope, i.e., hydrogen/protium (H), is substituted by a H-isotope, i.e., deuterium ($^2$H). Deuterium substitution can be partial or complete. Partial deuterium substitution means that at least one hydrogen is substituted by at least one deuterium. In certain embodiments, the isotope is 90%, 95%, or 99% or more enriched in an isotope at any location of interest. In some embodiments it is deuterium that is 90%, 95%, or 99% enriched at a desired location.

In the description below and herein generally, whenever any of the terms referring to 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one, or its di-HCl salt, or 2'-((5-(piperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one are used, it should be understood that pharmaceutically acceptable salts or compositions are considered included, unless otherwise stated or inconsistent with the text.

As contemplated herein and for purposes of the disclosed ranges herein, all ranges described herein include any and all numerical values occurring within the identified ranges. For example, a range of 1 to 10, or between 1 and 10, as contemplated herein, would include the numerical values 1, 2, 3, 4, 5, 6, 7, 8, 9, 10, as well as fractions thereof.

Isolated Morphic Form B of Compound II

Form B of Compound II is an unexpected, highly stable, highly crystalline form of solid Compound II, which is beneficial for therapeutic efficacy and for the manufacture of pharmaceutical formulations. Form B and other crystalline forms of solid Compound II are described in International Patent Publication No. WO 2019/006393. As discussed in Example 4, Form B is stable under thermal stress of 60° C. for 7 days. Additionally, a long-term stability study at 25° C. and 60% relative humidity revealed that isolated Compound II Form B is stable for at least 1 year (Example 15). In one embodiment isolated Compound II Form B is stable for at least about 6, 7, 8, 9, 10, 11, 12, 14, 16, 18, 20, 22, or 24 months.

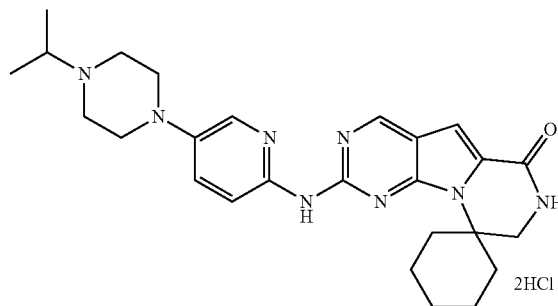

Compound II

A number of crystallization and slurry experiments were conducted (Example 10, Tables 97-100) by varying temperature, cooling procedure, and isolation procedure. From these experiments, eleven unique forms of Compound II were discovered, but only Form A, Form B, and Form D were appropriate for evaluation. The other forms resulted in weak crystalline forms, solvates, unstable hydrates, or anhydrates. Of the three solid forms, Form B was discovered to be an unexpectedly superior highly crystalline stable material for therapeutic dosage forms. In the dynamic vapor sorption experiment, Compound II remained in Form B after exposure to 90% relative humidity (Example 11).

Form B has advantageous properties for use as an active pharmaceutical ingredient in a solid dosage form and may have increased efficacy in such a formulation. In one embodiment, Form B is produced by recrystallization from HCl and acetone, as described in more detail below. In one embodiment, Form B is characterized by an XRPD pattern substantially similar to that set forth in FIG. 15. In one embodiment, Form B is characterized by an XRPD pattern comprising at least three 2theta values selected from 6.5°±0.2, 9.5±0.2°, 14.0±0.2°, 14.4±0.2°, 18.1±0.2°, 19.7±0.2°, and 22.4±0.2°. In one embodiment, Form B is characterized by an XRPD pattern comprising at least the 2theta values of 9.5±0.2°. In some embodiments isolated Compound II, Form B is characterized by the absence of at least one of the peaks at 4.6±0.2° 2theta. In some embodiments isolated Compound II, Form B is characterized by the absence of a peak at 5.0±0.2° 2theta. In one embodiment, isolated Form B is characterized as having a 7.5% weight loss between 31 and 120° C. in a thermogravimetric infrared (TG-IR) analysis. In one embodiment, isolated Form B is characterized as having differential scanning calorimetry (DSC) onset endotherms at about 105±20° C., about 220±20° C., and about 350±20° C., for example at 105° C., 220° C., and 350° C. or 92° C., 219° C., and 341° C.

Compound II Form B can be produced, for example, by recrystallizing Compound I in concentrated HCl and acetone. In one embodiment, Compound I is dissolved in concentrated HCl and heated. This is followed by the addition of acetone and isolation of the product by cooling and filtration.

In one embodiment, Compound II Form B is produced by the recrystallization of Compound II Form D. In an alternative embodiment, Compound II Form B is produced by repeated recrystallizations. In one embodiment, pure Compound II Form B is purified from impure Compound II Form B by a water:acetone (1:2) (v/v) slurry followed by vacuum drying.

Compound II Form A has less stability than Form B. Form A was produced when MeOH, EtOH, and 1-BuOH were used as solvents in the single solvent crystallizations and it was also produced in the binary solvent crystallizations using water and MeOH as the primary solvent. Slurry experiments using n-heptane and c-hexane produced Form A as well.

Compound II Form D has less stability than Form B. In one embodiment, Form D is produced by stirring a slurry of Compound II in acetonitrile at room temperature. In another embodiment, Form D is produced by dissolving Compound I in concentrated HCl before heating. Then the solution is allowed to cool and acetone is only added after crystallization begins to drive the precipitation to completion. The precipitate is then isolated via filtration. In an alternative embodiment, Form D is produced by dissolving Compound I in concentrated HCl before heating. Then the solution is allowed to cool and acetone is only added once crystallization has occurred and all solids are collected via filtration.

In alternative embodiments, a combination of two or more Forms of Compound II is provided, such as Forms B and D; Forms B and A; or Forms A and D. In an alternative embodiment, an isolated combination of three forms is provided, for example, Forms A, B, and D.

Dosing Regime of 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one The invention provides particular dosing regimes which provide blood profile ranges of the selective CDK4/6 inhibitor 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one 2'-((5-(4-isopropylpiperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one or its pharmaceutically acceptable salt, 2'-((5-(piperazin-1-yl)pyridin-2-yl)amino)-7',8'-dihydro-6'H-spiro[cyclohexane-1,9'-pyrazino[1',2':1,5]pyrrolo[2,3-d]pyrimidin]-6'-one or its pharmaceutically acceptable salt, or a selective CDK4/6 inhibitor, and methods using said dosing regimes for treating a subject having a CDK4/6-dependent cancer, for example estrogen receptor positive, HER2 negative (ER+/HER2−) breast cancer, prostate cancer, B cell leukemia, lymphoma, Ph1+ leukemia, and carcinoma, or other disorder as further described herein.

In one embodiment, the G1T38 dosing regime provides a (mean $AUC_{(0-24),ss}$ (h*ng/mL))/(dose (mg)) ratio of less than 5 and/or a (mean $AUC_{(0-24),ss}$ (h*ng/mL))/(Absolute Neutrophil Count (cells/mm$^3$)) ratio on day 22 of dosing of not greater than 1.25 is attained. In one embodiment, G1T38 is dosed as Form B of Compound II.

In one embodiment, the G1T38 dosing regime provides a $C_{max}$ of less than 100 ng/mL. In one embodiment, the G1T38 dosing regime provides a $C_{max}$ of less than 95 ng/mL. In one embodiment, the G1T38 dosing regime provides a $C_{max}$ of less than 90 ng/mL. In one embodiment, the G1T38 dosing regime provides a $C_{max}$ of less than 85 ng/mL. In one embodiment, the G1T38 dosing regime provides a $C_{max}$ of less than 80 ng/mL. In one embodiment, the G1T38 dosing regime provides a $C_{max}$ of less than 75 ng/mL. In one embodiment, the G1T38 dosing regime provides a $C_{max}$ of less than 70 ng/mL. In one embodiment, the G1T38 dosing regime provides a $C_{max}$ of less than 65 ng/mL. In one embodiment, the G1T38 dosing regime provides a $C_{max}$ of less than 60 ng/mL. In one embodiment, the G1T38 dosing regime provides a $C_{max}$ of less than 55 ng/mL. In one embodiment, the G1T38 dosing regime provides a $C_{max}$ of less than 50 ng/mL. In one embodiment, the G1T38 dosing regime provides a $C_{max}$ of less than 45 ng/mL. In one embodiment, the G1T38 dosing regime provides a $C_{max}$ of less than 40 ng/mL. In one embodiment, the G1T38 dosing regime provides a $C_{max}$ of less than 35 ng/mL. In one embodiment, the G1T38 dosing regime provides a $C_{max}$ of less than 30 ng/mL. In one embodiment, the G1T38 dosing regime provides a $C_{max}$ of less than 25 ng/mL. In one embodiment, the G1T38 dosing regime provides a $C_{max}$ of less than 20 ng/mL. In one embodiment, the G1T38 dosing regime provides a $C_{max}$ of less than 15 ng/mL. In one embodiment, G1T38 is dosed as Form B of Compound II. In one embodiment, $C_{max}$ is measured for serum Compound I.

In one embodiment, the (mean $AUC_{(0-24),ss}$ (h*ng/mL))/(Absolute Neutrophil Count (cells/mm$^3$)) ratio on day 22 of dosing is less than 1.25. In one embodiment, the (mean $AUC_{(0-24),ss}$ (h*ng/mL))/(Absolute Neutrophil Count (cells/mm$^3$)) ratio on day 22 of dosing is less than 1.15. In one embodiment, the (mean $AUC_{(0-24),ss}$ (h*ng/mL))/(Absolute Neutrophil Count (cells/mm$^3$)) ratio on day 22 of dosing is less than 1.05. In one embodiment, the (mean $AUC_{(0-24),ss}$ (h*ng/mL))/(Absolute Neutrophil Count (cells/mm$^3$)) ratio on day 22 of dosing is less than 0.95. In one embodiment, the (mean $AUC_{(0-24),ss}$ (h*ng/mL))/(Absolute Neutrophil Count (cells/mm$^3$)) ratio on day 22 of dosing is less than 0.85. In one embodiment, the (mean $AUC_{(0-24),ss}$ (h*ng/mL))/(Absolute Neutrophil Count (cells/mm$^3$)) ratio on day 22 of dosing is less than 0.75. In one embodiment, the (mean $AUC_{(0-24),ss}$ (h*ng/mL))/(Absolute Neutrophil Count (cells/mm$^3$)) ratio on day 22 of dosing is less than 0.65. In one embodiment, the (mean $AUC_{(0-24),ss}$ (h*ng/mL))/(Absolute Neutrophil Count (cells/mm$^3$)) ratio on day 22 of dosing is less than 0.55. In one embodiment, the (mean $AUC_{(0-24),ss}$ (h*ng/mL))/(Absolute Neutrophil Count (cells/mm$^3$)) ratio on day 22 of dosing is less than 0.45. In one embodiment, the (mean $AUC_{(0-24),ss}$ (h*ng/mL))/(Absolute Neutrophil Count (cells/mm$^3$)) ratio on day 22 of dosing is less than 0.35. In one embodiment, the (mean $AUC_{(0-24),ss}$ (h*ng/mL))/(Absolute Neutrophil Count (cells/mm$^3$)) ratio on day 22 of dosing is less than 0.25. In one embodiment, the (mean $AUC_{(0-24),ss}$ (h*ng/mL))/(Absolute Neutrophil Count (cells/mm$^3$)) ratio on day 22 of dosing is less than 0.15. In one embodiment, G1T38 is dosed as Form B of Compound II. In one embodiment, mean $AUC_{(0-24),ss}$ is measured for serum Compound I.

In one embodiment, the dose normalized $AUC_{(0-24),ss}$ is less than 5. In one embodiment, the dose normalized $AUC_{(0-24),ss}$ is less than 4.75. In one embodiment, the dose normalized $AUC_{(0-24),ss}$ is less than 4.5. In one embodiment, the dose normalized $AUC_{(0-24),ss}$ is less than 4.25. In one embodiment, the dose normalized $AUC_{(0-24),ss}$ is less than 4.0. In one embodiment, the dose normalized $AUC_{(0-24),ss}$ is less than 3.75. In one embodiment, the dose normalized $AUC_{(0-24),ss}$ is less than 3.5. In one embodiment, the dose normalized $AUC_{(0-24),ss}$ is less than 3.25. In one embodiment, the dose normalized $AUC_{(0-24),ss}$ is less than 3.0. In one embodiment, the dose normalized $AUC_{(0-24),ss}$ is less than 3.75. In one embodiment, the dose normalized $AUC_{(0-24),ss}$ is less than 3.5. In one embodiment, the dose normalized $AUC_{(0-24),ss}$ is less than 3.25. In one embodiment, the dose normalized $AUC_{(0-24),ss}$ is less than 3.0. In one embodiment, the dose normalized $AUC_{(0-24),ss}$ is less than 2.75. In one embodiment, the dose normalized $AUC_{(0-24),ss}$ is less than 2.5. In one embodiment, the dose normalized $AUC_{(0-24),ss}$ is less than 2.25. In one embodiment, the dose normalized $AUC_{(0-24),ss}$ is less than 2.0. In one embodiment, the dose normalized $AUC_{(0-24),ss}$ is less than 1.75. In one embodiment, the dose normalized $AUC_{(0-24),ss}$ is less than 1.5. In one embodiment, the dose normalized $AUC_{(0-24),ss}$ is less than 1.25. In one embodiment the dose normalized $AUC_{(0-24),ss}$ is less than 1.0. In one embodiment, G1T38 is dosed as Form B of Compound II. In one embodiment, dose normalized $AUC_{(0-24),ss}$ is measured for serum Compound I.

In one embodiment, the dose normalized $AUC_{(0-24),ss}$ is less than 4.75 and the (mean $AUC_{(0-24),ss}$ (h*ng/mL))/(Absolute Neutrophil Count (cells/mm$^3$)) ratio on day 22 of dosing is less than 1.25. In one embodiment, the dose normalized $AUC_{(0-24),ss}$ is less than 4.5 and the (mean $AUC_{(0-24),ss}$ (h*ng/mL))/(Absolute Neutrophil Count (cells/mm$^3$)) ratio on day 22 of dosing is less than 1.25. In one embodiment, the dose normalized $AUC_{(0-24),ss}$ is less than 4.25 and the (mean $AUC_{(0-24),ss}$ (h*ng/mL))/(Absolute Neutrophil Count (cells/mm$^3$)) ratio on day 22 of dosing is less than 1.25. In one embodiment, the dose normalized $AUC_{(0-24),ss}$ is less than 4.0 and the (mean $AUC_{(0-24),ss}$ (h*ng/mL))/(Absolute Neutrophil Count (cells/mm$^3$)) ratio on day 22 of dosing is less than 1.25. In one embodiment, the dose normalized $AUC_{(0-24),ss}$ is less than 3.75 and the (mean $AUC_{(0-24),ss}$ (h*ng/mL))/(Absolute Neutrophil Count (cells/mm$^3$)) ratio on day 22 of dosing is less than 1.25. In one embodiment, the dose normalized $AUC_{(0-24),ss}$ is less than 3.5 and the (mean $AUC_{(0-24),ss}$ (h*ng/mL))/(Absolute Neutrophil Count (cells/mm$^3$)) ratio on day 22 of dosing is less than 1.25. In one embodiment, the dose normalized $AUC_{(0-24),ss}$ is less than 3.25 and the (mean $AUC_{(0-24),ss}$ (h*ng/mL))/(Absolute Neutrophil Count (cells/mm$^3$)) ratio on day 22 of dosing is less than 1.25. In one embodiment, the dose normalized $AUC_{(0-24),ss}$ is less than 3.0 and the (mean $AUC_{(0-24),ss}$ (h*ng/mL))/(Absolute Neutrophil Count (cells/mm$^3$)) ratio on day 22 of dosing is less than 1.25. In one embodiment, the dose normalized $AUC_{(0-24),ss}$ is less than 2.75 and the (mean $AUC_{(0-24),ss}$ (h*ng/mL))/(Absolute Neutrophil Count (cells/mm$^3$)) ratio on day 22 of dosing is less than 1.25. In one embodiment, the dose normalized $AUC_{(0-24),ss}$ is less than 2.5 and the (mean $AUC_{(0-24),ss}$ (h*ng/mL))/(Absolute Neutrophil Count (cells/mm$^3$)) ratio on day 22 of dosing is less than 1.25. In one embodiment, the dose normalized $AUC_{(0-24),ss}$ is less than 2.25 and the (mean $AUC_{(0-24),ss}$ (h*ng/mL))/(Absolute Neutrophil Count (cells/mm$^3$)) ratio on day 22 of dosing is less than 1.25. In one embodiment, the dose normalized $AUC_{(0-24),ss}$ is less than 2.0 and the (mean $AUC_{(0-24),ss}$ (h*ng/mL))/(Absolute Neutrophil Count (cells/mm$^3$)) ratio on day 22 of dosing is less than 1.25. In one embodiment, G1T38 is dosed as Form B of Compound II. In one embodiment, mean $AUC_{(0-24),ss}$ is measured for serum Compound I.

In one embodiment, the $C_{max}$ is less than 75 ng/mL and the (mean $AUC_{(0-24),ss}$ (h*ng/mL))/(Absolute Neutrophil Count (cells/mm$^3$)) ratio on day 22 of dosing is less than 1.25. In one embodiment, the $C_{max}$ is less than 75 ng/mL and the (mean $AUC_{(0-24),ss}$ (h*ng/mL))/(Absolute Neutrophil Count (cells/mm$^3$)) ratio on day 22 of dosing is less than 1.15. In one embodiment, the $C_{max}$ is less than 75 ng/mL and the (mean $AUC_{(0-24),ss}$ (h*ng/mL))/(Absolute Neutrophil Count (cells/mm$^3$)) ratio on day 22 of dosing is less than 1.05. In one embodiment, the $C_{max}$ is less than 75 ng/mL and the (mean $AUC_{(0-24),ss}$ (h*ng/mL))/(Absolute Neutrophil Count (cells/mm$^3$)) ratio on day 22 of dosing is less than 0.95. In one embodiment, the $C_{max}$ is less than 75 ng/mL and the (mean $AUC_{(0-24),ss}$ (h*ng/mL))/(Absolute Neutrophil Count (cells/mm$^3$)) ratio on day 22 of dosing is less than 0.85. In one embodiment, the $C_{max}$ is less than 75 ng/mL and the (mean $AUC_{(0-24),ss}$ (h*ng/mL))/(Absolute Neutrophil Count (cells/mm$^3$)) ratio on day 22 of dosing is less than 0.75. In one embodiment, the $C_{max}$ is less than 75 ng/mL and the (mean $AUC_{(0-24),ss}$ (h*ng/mL))/(Absolute Neutrophil Count (cells/mm$^3$)) ratio on day 22 of dosing is less than 0.65. In one embodiment, the $C_{max}$ is less than 75 ng/mL and the (mean $AUC_{(0-24),ss}$ (h*ng/mL))/(Absolute Neutrophil Count (cells/mm$^3$)) ratio on day 22 of dosing is less than 0.55. In one embodiment, the $C_{max}$ is less than 75 ng/mL and the (mean $AUC_{(0-24),ss}$ (h*ng/mL))/(Absolute Neutrophil Count (cells/mm$^3$)) ratio on day 22 of dosing is less than 0.45. In one embodiment, the $C_{max}$ is less than 75 ng/mL and the (mean $AUC_{(0-24),ss}$ (h*ng/mL))/(Absolute Neutrophil Count (cells/mm$^3$)) ratio on day 22 of dosing is less than 0.35. In one embodiment, the $C_{max}$ is less than 75 ng/mL and the (mean $AUC_{(0-24),ss}$ (h*ng/mL))/(Absolute Neutrophil Count (cells/mm$^3$)) ratio on day 22 of dosing is less than 0.25. In any of the embodiments above, the $C_{max}$ is less than 70 ng/mL. In any of the embodiments above, the $C_{max}$ is less than 65 ng/mL. In one embodiment, G1T38 is dosed as Form B of Compound II. In one embodiment, mean $AUC_{(0-24),ss}$ is measured for serum Compound I.

In one embodiment, the dose normalized $AUC_{(0-24),ss}$ is less than 5 and the (mean $AUC_{(0-24),ss}$ (h*ng/mL))/(Absolute Neutrophil Count (cells/mm$^3$)) ratio on day 22 of dosing is less than 1.25. In one embodiment, the dose normalized $AUC_{(0-24),ss}$ is less than 5 and the (mean $AUC_{(0-24),ss}$ (h*ng/mL))/(Absolute Neutrophil Count (cells/mm$^3$)) ratio on day 22 of dosing is less than 1.15. In one embodiment, the dose normalized $AUC_{(0-24),ss}$ is less than 5 and the (mean $AUC_{(0-24),ss}$ (h*ng/mL))/(Absolute Neutrophil Count (cells/ mm$^3$)) ratio on day 22 of dosing is less than 1.05. In one embodiment, the dose normalized AUC$_{(0-24),ss}$ is less than 5 and the (mean AUC$_{(0-24),ss}$ (h*ng/mL))/(Absolute Neutrophil Count (cells/mm$^3$)) ratio on day 22 of dosing is less than 0.95. In one embodiment, the dose normalized AUC$_{(0-24),ss}$ is less than 5 and the (mean AUC$_{(0-24),ss}$ (h*ng/mL))/(Absolute Neutrophil Count (cells/mm$^3$)) ratio on day 22 of dosing is less than 0.85. In one embodiment, the dose normalized AUC$_{(0-24),ss}$ is less than 5 and the (mean AUC$_{(0-24),ss}$ (h*ng/mL))/(Absolute Neutrophil Count (cells/mm$^3$)) ratio on day 22 of dosing is less than 0.75. In one embodiment, the dose normalized AUC$_{(0-24),ss}$ is less than 5 and the (mean AUC$_{(0-24),ss}$ (h*ng/mL))/(Absolute Neutrophil Count (cells/mm$^3$)) ratio on day 22 of dosing is less than 0.65. In one embodiment, the dose normalized AUC$_{(0-24),ss}$ is less than 5 and the (mean AUC$_{(0-24),ss}$ (h*ng/mL))/(Absolute Neutrophil Count (cells/mm$^3$)) ratio on day 22 of dosing is less than 0.55. In one embodiment, the dose normalized AUC$_{(0-24),ss}$ is less than 5 and the (mean AUC$_{(0-24),ss}$ (h*ng/mL))/(Absolute Neutrophil Count (cells/mm$^3$)) ratio on day 22 of dosing is less than 0.45. In one embodiment, the dose normalized AUC$_{(0-24),ss}$ is less than 5 and the (mean AUC$_{(0-24),ss}$ (h*ng/mL))/(Absolute Neutrophil Count (cells/mm$^3$)) ratio on day 22 of dosing is less than 0.35. In one embodiment, the dose normalized AUC$_{(0-24),ss}$ is less than 5 and the (mean AUC$_{(0-24),ss}$ (h*ng/mL))/(Absolute Neutrophil Count (cells/mm$^3$)) ratio on day 22 of dosing is less than 0.25. In one embodiment, G1T38 is dosed as Form B of Compound II. In one embodiment, the dose normalized AUC$_{(0-24),ss}$ is measured for serum Compound I. In one embodiment, mean AUC$_{(0-24),ss}$ is measured for serum Compound I.

In one embodiment, the dose normalized AUC$_{(0-24),ss}$ is less than 4.75 and the (mean AUC$_{(0-24),ss}$ (h*ng/mL))/(Absolute Neutrophil Count (cells/mm$^3$)) ratio on day 22 of dosing is less than 1.25. In one embodiment, the dose normalized AUC$_{(0-24),ss}$ is less than 4.5 and the (mean AUC$_{(0-24),ss}$ (h*ng/mL))/(Absolute Neutrophil Count (cells/mm$^3$)) ratio on day 22 of dosing is less than 1.25. In one embodiment, the dose normalized AUC$_{(0-24),ss}$ is less than 4.25 and the (mean AUC$_{(0-24),ss}$ (h*ng/mL))/(Absolute Neutrophil Count (cells/mm$^3$)) ratio on day 22 of dosing is less than 1.25. In one embodiment, the dose normalized AUC$_{(0-24),ss}$ is less than 4.0 and the (mean AUC$_{(0-24),ss}$ (h*ng/mL))/(Absolute Neutrophil Count (cells/mm$^3$)) ratio on day 22 of dosing is less than 1.25. In one embodiment, the dose normalized AUC$_{(0-24),ss}$ is less than 3.75 and the (mean AUC$_{(0-24),ss}$ (h*ng/mL))/(Absolute Neutrophil Count (cells/mm$^3$)) ratio on day 22 of dosing is less than 1.25. In one embodiment, the dose normalized AUC$_{(0-24),ss}$ is less than 3.5 and the (mean AUC$_{(0-24),ss}$ (h*ng/mL))/(Absolute Neutrophil Count (cells/mm$^3$)) ratio on day 22 of dosing is less than 1.25. In one embodiment, the dose normalized AUC$_{(0-24),ss}$ is less than 3.25 and the (mean AUC$_{(0-24),ss}$ (h*ng/mL))/(Absolute Neutrophil Count (cells/mm$^3$)) ratio on day 22 of dosing is less than 1.25. In one embodiment, the dose normalized AUC$_{(0-24),ss}$ is less than 3.0 and the (mean AUC$_{(0-24),ss}$ (h*ng/mL))/(Absolute Neutrophil Count (cells/mm$^3$)) ratio on day 22 of dosing is less than 1.25. In one embodiment, the dose normalized AUC$_{(0-24),ss}$ is less than 2.75 and the (mean AUC$_{(0-24),ss}$ (h*ng/mL))/(Absolute Neutrophil Count (cells/mm$^3$)) ratio on day 22 of dosing is less than 1.25. In one embodiment, the dose normalized AUC$_{(0-24),ss}$ is less than 2.5 and the (mean AUC$_{(0-24),ss}$ (h*ng/mL))/(Absolute Neutrophil Count (cells/mm$^3$)) ratio on day 22 of dosing is less than 1.25. In one embodiment, the dose normalized AUC$_{(0-24),ss}$ is less than 2.25 and the (mean AUC$_{(0-24),ss}$ (h*ng/mL))/(Absolute Neutrophil Count (cells/mm$^3$)) ratio on day 22 of dosing is less than 1.25. In one embodiment, the dose normalized AUC$_{(0-24),ss}$ is less than 2.0 and the (mean AUC$_{(0-24),ss}$ (h*ng/mL))/(Absolute Neutrophil Count (cells/mm$^3$)) ratio on day 22 of dosing is less than 1.25. In one embodiment, G1T38 is dosed as Form B of Compound II. In one embodiment, the dose normalized AUC$_{(0-24),ss}$ is measured for serum Compound I. In one embodiment, mean AUC$_{(0-24),ss}$ is measured for serum Compound I.

In one embodiment, the mean V$_d$/F is greater than about 10,000 L. In one embodiment, the V$_d$/F is greater than about 11,000 L. In one embodiment, the V$_d$/F is greater than about 12,000 L. In one embodiment, the V$_d$/F is greater than 14,000 L. In one embodiment, the V$_d$/F is greater than about 15,0000 L. In one embodiment, G1T38 is dosed as Form B of Compound II. In one embodiment, V$_d$/F is measured for Compound I.

In one embodiment, the mean V$_z$/F is greater than about 10,000 L. In one embodiment, the V$_z$/F is greater than about 11,000 L. In one embodiment, the V$_z$/F is greater than about 12,000 L. In one embodiment, the V$_z$/F is greater than 14,000 L. In one embodiment, the V$_z$/F is greater than about 15,000 L. In one embodiment, G1T38 is dosed as Form B of Compound II. In one embodiment, V$_z$/F is measured for Compound I.

In one embodiment, the dose is about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg, of the Compound I. In one embodiment, the dose is about 310 mg, about 320 mg, about 330 mg, about 340 mg, about 350 mg, about 360 mg, about 370 mg, about 380 mg, about 390 mg, or about 400 mg, of the Compound I. In one embodiment, the dose is about 410 mg, about 420 mg, about 430 mg, about 440 mg, about 450 mg, about 460 mg, about 470 mg, about 480 mg, about 490 mg, or about 500 mg, of the Compound I. In one embodiment, the dose is about 510 mg, about 520 mg, about 530 mg, about 540 mg, about 550 mg, about 560 mg, about 570 mg, about 580 mg, about 590 mg, or about 600 mg, of the Compound I. In one embodiment, the dose is about 610 mg, about 620 mg, about 630 mg, about 640 mg, about 650 mg, about 660 mg, about 670 mg, about 680 mg, about 690 mg, or about 700 mg, of the Compound I. In one embodiment, the dose is about 710 mg, about 720 mg, about 730 mg, about 740 mg, about 750 mg, about 760 mg, about 770 mg, about 780 mg, about 790 mg, or about 800 mg, of the Compound I.

In one embodiment, the dose is about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg, of the Compound II. In one embodiment, the dose is about 310 mg, about 320 mg, about 330 mg, about 340 mg, about 350 mg, about 360 mg, about 370 mg, about 380 mg, about 390 mg, or about 400 mg, of the Compound II. In one embodiment, the dose is about 410 mg, about 420 mg, about 430 mg, about 440 mg, about 450 mg, about 460 mg, about 470 mg, about 480 mg, about 490 mg, or about 500 mg, of the Compound II. In one embodiment, the dose is about 510 mg, about 520 mg, about 530 mg, about 540 mg, about 550 mg, about 560 mg, about 570 mg, about 580 mg, about 590 mg, or about 600 mg, of the Compound II. In one embodiment, the dose is about 610 mg, about 620 mg, about 630 mg, about 640 mg, about 650 mg, about 660 mg, about 670 mg, about 680 mg, about 690 mg, or about 700 mg, of the Compound II. In one embodiment, the dose is about 710 mg, about 720 mg, about 730 mg, about 740 mg, about 750 mg, about 760 mg, about 770 mg, about 780 mg, about 790 mg, or about 800 mg, of the Compound II. In one embodiment, Compound II is dosed as Form B.

In one embodiment, the dose is about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, or about 300 mg, of the Compound III. In one embodiment, the dose is about 310 mg, about 320 mg, about 330 mg, about 340 mg, about 350 mg, about 360 mg, about 370 mg, about 380 mg, about 390 mg, or about 400 mg, of the Compound III. In one embodiment, the dose is about 410 mg, about 420 mg, about 430 mg, about 440 mg, about 450 mg, about 460 mg, about 470 mg, about 480 mg, about 490 mg, or about 500 mg, of the Compound III. In one embodiment, the dose is about 510 mg, about 520 mg, about 530 mg, about 540 mg, about 550 mg, about 560 mg, about 570 mg, about 580 mg, about 590 mg, or about 600 mg, of the Compound III. In one embodiment, the dose is about 610 mg, about 620 mg, about 630 mg, about 640 mg, about 650 mg, about 660 mg, about 670 mg, about 680 mg, about 690 mg, or about 700 mg, of the Compound III. In one embodiment, the dose is about 710 mg, about 720 mg, about 730 mg, about 740 mg, about 750 mg, about 760 mg, about 770 mg, about 780 mg, about 790 mg, or about 800 mg, of the Compound III.

In one embodiment, the dosing regimen comprises about 200 mg of Compound II administered once a day. In one embodiment, the dosing regimen comprises about 300 mg of Compound II administered once a day. In one embodiment, the dosing regimen comprises about 400 mg of Compound II administered once a day. In one embodiment, the dosing regimen comprises about 500 mg of Compound II administered once a day. In one embodiment, the dosing regimen comprises about 650 mg of Compound II administered once a day. In one embodiment, the dosing regimen comprises about 100 mg of Compound II administered twice a day optionally spaced about 12 hours apart. In one embodiment, the dosing regimen comprises about 150 mg of Compound II administered twice a day optionally spaced about 12 hours apart. In one embodiment, the dosing regimen comprises about 200 mg of Compound II administered twice a day optionally spaced about 12 hours apart. In one embodiment, Compound II is dosed as form B.

Pharmaceutical Preparations

G1T38 can be administered as the neat chemical, or as its pharmaceutically acceptable salt, as described herein. Accordingly, the disclosure provides pharmaceutical compositions utilized in a dosing regime for G1T38, or its pharmaceutically acceptable salt, described herein in an amount of compound or pharmaceutically acceptable salt together with at least one pharmaceutically acceptable carrier to achieve the PK and PD ranges described herein. The pharmaceutical composition may contain a compound or salt as the only active agent, or, in an alternative embodiment, the compound and at least one additional active agent. The pharmaceutical composition may also include a molar ratio of the active compound and an additional active agent.

G1T38, or a pharmaceutically acceptable salt thereof, are administered in an oral dosage form.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the CDK4/6 inhibitor is sufficient to provide a practical quantity of material for administration per unit dose of the compound.

The carrier can be inert or it can possess pharmaceutical benefits of its own. The amount of carrier employed in conjunction with the compound is sufficient to provide a practical quantity of material for administration per unit dose of the compound. Classes of carriers include, but are not limited to, binders, buffering agents, coloring agents, diluents, disintegrants, emulsifiers, fillers, flavorants, glidents, lubricants, pH modifiers, preservatives, stabilizers, surfactants, solubilizers, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, colloidal silicon dioxide, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. Optional other active agents may be included in a pharmaceutical composition, which do not substantially interfere with the activity of the compound of the present invention.

The pharmaceutical compositions can be formulated for oral administration. These compositions can contain any amount of active compound that achieves the desired result, for example between 0.1 and 99 weight % (wt. %) of the compound and usually at least about 5 wt. % of the compound. Some embodiments contain at least about 10%, 15%, 20%, 25 wt. % to about 50 wt. % or from about 5 wt. % to about 75 wt. % of the compound.

Methods of Treatment

As contemplated herein, a dosing regime providing PK and/or PD blood profiles as described herein can be used to treat a CDK4/6-replication dependent cancers.

In one embodiment, the dosing regime is used to treat breast cancer. In one embodiment the breast cancer is HR+ and HER2−. In one embodiment the breast cancer is HR− and HER2+.

In one embodiment, the dosing regime is used to treat non-small cell lung cancer (NSCLC). In one embodiment the NSCLC has an EGFR mutation. In one embodiment the NSCLC has a KRAS mutation.

In one embodiment, the dosing regime described herein is used to treat prostate cancer. In one embodiment the prostate cancer is castration resistant. In one embodiment a prior chemotherapeutic agent already failed (e.g. 2nd line therapy).

In one embodiment, a dosing regime described herein is used to treat lymphoma. In one embodiment the lymphoma is mantle cell lymphoma (MCL), marginal zone lymphoma (MZL), chronic lymphocytic leukemia (CLL), follicular lymphoma (FL), or diffuse large B-cell lymphoma (DLBCL). In one embodiment a prior chemotherapeutic agent already failed (e.g. 2nd line therapy).

In one embodiment, a dosing regime described herein is used to treat melanoma. In one embodiment the melanoma has a BRAF mutation.

In one embodiment, a dosing regime described herein is used to treat RAS mutated cancer. In one embodiment the RAS mutated cancer is colon cancer (CLC). In one embodiment the RAS mutated cancer is pancreatic cancer. In one embodiment the RAS mutated cancer is cholangiocarcinoma.

In one embodiment, a dosing regime described herein is used to treat a gastrointestinal stromal tumor (GIST). In one embodiment the treatment with imatinib or sunitinib already failed (e.g. 2nd line therapy).

Exemplary proliferative disorders which may be treated using the dosing regime described herein include, but are not limited to, benign growths, neoplasms, tumors, cancer (Rb positive or Rb negative), autoimmune disorders, inflammatory disorders graft-versus-host rejection, and fibrotic disorders.

Non-limiting examples of cancers that can be treated according to the present invention include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL)—also known as acute lymphoblastic leukemia or acute lymphoid leukemia (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CVL), chronic neutrophilic leukemia (CNL), hypereosinophilic syndrome (HES)), neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In another embodiment, the disorder is myelodysplastic syndrome (MDS).

In certain embodiments, the cancer is a hematopoietic cancer. In certain embodiments, the hematopoietic cancer is a lymphoma. In certain embodiments, the hematopoietic cancer is a leukemia. In certain embodiments, the leukemia is acute myelocytic leukemia (AML).

In certain embodiments, the proliferative disorder is a myeloproliferative neoplasm. In certain embodiments, the myeloproliferative neoplasm (MPN) is primary myelofibrosis (PMF).

In certain embodiments, the cancer is a solid tumor. A solid tumor, as used herein, refers to an abnormal mass of tissue that usually does not contain cysts or liquid areas. Different types of solid tumors are named for the type of cells that form them. Examples of classes of solid tumors include, but are not limited to, sarcomas, carcinomas, and lymphomas, as described above herein.

Additional examples of solid tumors include, but are not limited to, squamous cell carcinoma, colon cancer, breast cancer, prostate cancer, lung cancer, liver cancer, pancreatic cancer, and melanoma.

In certain embodiments, the condition treated is a disorder related to abnormal cellular proliferation.

Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis.

Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

The term "neoplasia" or "cancer" is used throughout the specification to refer to the pathological process that results in the formation and growth of a cancerous or malignant neoplasm, i.e., abnormal tissue (solid) or cells (non-solid) that grow by cellular proliferation, often more rapidly than normal and continues to grow after the stimuli that initiated the new growth cease. Malignant neoplasms show partial or complete lack of structural organization and functional coordination with the normal tissue and most invade surrounding tissues, can metastasize to several sites, are likely to recur after attempted removal and may cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated with the G1T38 dosing regime described herein either alone or in combination with at least one additional anticancer agent include squamous-cell carcinoma, basal cell carcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using Compound I include, for example, acute granulocytic leukemia, acute lymphocytic leukemia (ALL), acute myelogenous leukemia (AML), adenosarcoma, adrenal cancer, adrenocortical carcinoma, anaplastic astrocytoma, angiosarcoma, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), ependymoma, epithelioid sarcoma, esophageal cancer, ewing sarcoma, extrahepatic bile duct cancer, fallopian tube cancer, fibrosarcoma, gallbladder cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

Combination Therapy

In one embodiment, the dosing regime may include at least one additional therapeutic agent, for example, for treatment of a disorder listed herein. In one embodiment, the G1T38 dosing regime achieves a specific PK and/or PD blood profile as described herein in combination or alternation with at least one additional inhibitor of the CDK4/6 pathway or a second active compound with a different biological mechanism of action.

In one embodiment, the present invention provides a method of treating Rb-positive CDK4/6-dependent cancer by administering to a subject in need thereof G1T38 as described in combination or alternation with an additional therapeutic agent.

In one embodiment, the dosing regime described herein is used to treat breast cancer. In one embodiment the breast cancer is HR+ and HER2−. In one embodiment the breast cancer is HR− and HER2+. In one embodiment, the CDK4/6 inhibitor is used in combination with one or more additional therapeutic agents. In one embodiment the additional therapeutic agent is trastuzumab. In one embodiment the additional therapeutic agent is lapatinib. In one embodiment, the additional therapeutic agents are lapatinib and trastuzumab. In another embodiment, the additional therapeutic agent is fulvestrant. In one embodiment the additional therapeutic agent is goserelin.

In one embodiment, the G1T38 dosing regime is used to treat non-small cell lung cancer (NSCLC). In one embodiment the NSCLC has an EGFR mutation. In one embodiment, G1T38 dosing regime is used in combination with one or more additional therapeutic agents. In one embodiment the NSCLC has an EGFR mutation and an EGFR inhibitor failed (e.g. 2nd line therapy). In one embodiment the additional therapeutic agent is osimertinib. In one embodiment the additional therapeutic agent is alectinib.

In one embodiment the NSCLC has a KRAS mutation. In one embodiment, the G1T38 dosing regime is used in combination with one or more additional therapeutic agents. In one embodiment the additional therapeutic agent is a MEK inhibitor.

In one embodiment, the G1T38 dosing regime described herein is used to treat prostate cancer. In one embodiment the prostate cancer is castration resistant. In one embodiment, the G1T38 dosing regime is used in combination with one or more additional therapeutic agents. In one embodiment the additional therapeutic agent is an androgen receptor-blocker. In one embodiment a prior chemotherapeutic agent already failed (e.g. 2nd line therapy).

In one embodiment, a G1T38 dosing regime described herein is used to treat lymphoma. In one embodiment the lymphoma is mantle cell lymphoma (MCL), marginal zone lymphoma (MZL), chronic lymphocytic leukemia (CLL), follicular lymphoma (FL), or diffuse large B-cell lymphoma (DLBCL). In one embodiment, a G1T38 dosing regime described herein is used in combination with one or more additional therapeutic agents. In one embodiment the additional therapeutic agent is a BTK inhibitor. In one embodiment a prior chemotherapeutic agent already failed (e.g. 2nd line therapy).

In one embodiment, a G1T38 dosing regime described herein is used to treat melanoma. In one embodiment the melanoma has a BRAF mutation. In one embodiment, the CDK4/6 inhibitor is used in combination with one or more additional therapeutic agents. In one embodiment the additional therapeutic agents are a MEK inhibitor and a RAF inhibitor.

In one embodiment, G1T38 dosing regime described herein is used to treat RAS mutated cancer. In one embodiment the RAS mutated cancer is colon cancer (CLC). In one embodiment the RAS mutated cancer is pancreatic cancer. In one embodiment the RAS mutated cancer is cholangiocarcinoma. In one embodiment, the G1T38 dosing regime described herein is used in combination with one or more additional therapeutic agents. In one embodiment the additional therapeutic agent is a RAF inhibitor.

In one embodiment, G1T38 dosing regime described herein is used to treat a gastrointestinal stromal tumor (GIST). In one embodiment, the G1T38 dosing regime described herein is used in combination with one or more additional therapeutic agents. In one embodiment, the additional therapeutic agent is regorafenib. In one embodiment the treatment with imatinib or sunitinib already failed (e.g. 2nd line therapy).

G1T38, or a pharmaceutically acceptable salt thereof, are administered in an oral dosage form alone or in combination with another compound or another bioactive agent to treat a human with a disorder as described herein.

The term "bioactive agent" or "therapeutic agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping $C_{max}$, $T_{max}$, AUC or other pharmacokinetic parameter. In another embodiment, the compound of the present invention and the bioactive agent are administered to a host in need thereof that do not have overlapping pharmacokinetic parameter, however, one has a therapeutic impact on the therapeutic efficacy of the other.

In one aspect of this embodiment, the bioactive agent is a chemotherapeutic.

In another aspect of this embodiment, the bioactive agent is a growth factor.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

Immune checkpoint inhibitors for use in the methods described herein include, but are not limited to PD-1 inhibitors, PD-L1 inhibitors, PD-L2 inhibitors, CTLA-4 inhibitors, LAG-3 inhibitors, TIM-3 inhibitors, and V-domain Ig suppressor of T-cell activation (VISTA) inhibitors, or combinations thereof.

In one embodiment, the immune checkpoint inhibitor is a PD-1 inhibitor that blocks the interaction of PD-1 and PD-L1 by binding to the PD-1 receptor, and in turn inhibits immune suppression. In one embodiment, the immune checkpoint inhibitor is a PD-1 immune checkpoint inhibitor selected from nivolumab (Opdivo®), pembrolizumab (Keytruda®), pidilizumab, AMP-224 (AstraZeneca and MedImmune), PF-06801591 (Pfizer), MEDIO680 (AstraZeneca), PDR001 (Novartis), REGN2810 (Regeneron), MGA012 (MacroGenics), BGB-A317 (BeiGene) SHR-12-1 (Jiangsu Hengrui Medicine Company and Incyte Corporation), TSR-042 (Tesaro), and the PD-L1/VISTA inhibitor CA-170 (Curis Inc.).

In one embodiment, the immune checkpoint inhibitor is the PD-1 immune checkpoint inhibitor nivolumab (Opdivo®) administered in an effective amount for the treatment of Hodgkin lymphoma, melanoma, non-small cell lung cancer, hepatocellular carcinoma, or ovarian cancer. Nivolumab has been approved by the FDA for the use of metastatic melanoma, non-small cell lung cancer, and renal cell carcinoma. In another aspect of this embodiment, the immune checkpoint inhibitor is the PD-1 immune checkpoint inhibitor pembrolizumab (Keytruda®) administered in an effective amount for the treatment of melanoma, non-small cell lung cancer, small cell lung cancer, head and neck cancer, or urothelial cancer. In an additional aspect of this embodiment, the immune checkpoint inhibitor is the PD-1 immune checkpoint inhibitor pidilizumab (Medivation) administered in an effective amount for refractory diffuse large B-cell lymphoma (DLBCL) or metastatic melanoma.

In one embodiment, the immune checkpoint inhibitor is a PD-L1 inhibitor that blocks the interaction of PD-1 and PD-L1 by binding to the PD-L1 receptor, and in turn inhibits immune suppression. PD-L1 inhibitors include, but are not limited to, atezolizumab, durvalumab, KN035CA-170 (Curis Inc.), and LY3300054 (Eli Lilly). In one embodiment, the PD-L1 inhibitor is atezolizumab. In one embodiment, the PD-L1 inhibitor blocks the interaction between PD-L1 and CD80 to inhibit immune suppression.

In one embodiment, the immune checkpoint inhibitor is the PD-L1 immune checkpoint inhibitor atezolizumab (Tecentriq®) administered in an effective amount for the treatment of metastatic bladder cancer, metastatic melanoma, metastatic non-small cell lung cancer, or metastatic renal cell carcinoma. In another aspect of this embodiment, the immune checkpoint inhibitor is durvalumab (AstraZeneca and MedImmune) administered in an effective amount for the treatment of non-small cell lung cancer or bladder cancer. In yet another aspect of the embodiment, the immune checkpoint inhibitor is KN035 (Alphamab) administered in an effective amount for the treatment of PD-L1 positive solid tumors. An additional example of a PD-L1 immune checkpoint inhibitor is BMS-936559 (Bristol-Myers Squibb), although clinical trials with this inhibitor have been suspended as of 2015.

In one aspect of this embodiment, the immune checkpoint inhibitor is a CTLA-4 immune checkpoint inhibitor that binds to CTLA-4 and inhibits immune suppression. CTLA-4 inhibitors include, but are not limited to, ipilimumab, tremelimumab (AstraZeneca and MedImmune), AGEN1884 and AGEN2041 (Agenus).

In one embodiment, the CTLA-4 immune checkpoint inhibitor is ipilimumab (Yervoy®) administered in an effective amount for the treatment of metastatic melanoma, adjuvant melanoma, or non-small cell lung cancer.

In another embodiment, the immune checkpoint inhibitor is a LAG-3 immune checkpoint inhibitor. Examples of LAG-3 immune checkpoint inhibitors include, but are not limited to, BMS-986016 (Bristol-Myers Squibb), GSK2831781 (GlaxoSmithKline), EMIP321 (Prima BioMed), LAG525 (Novartis), and the dual PD-1 and LAG-3 inhibitor MGD013 (MacroGenics). In yet another aspect of this embodiment, the immune checkpoint inhibitor is a TIM-3 immune checkpoint inhibitor. A specific TIM-3 inhibitor includes, but is not limited to, TSR-022 (Tesaro).

Other immune checkpoint inhibitors for use in the invention described herein include, but are not limited to, B7-H3/CD276 immune checkpoint inhibitors such as MGA217, indoleamine 2,3-dioxygenase (IDO) immune checkpoint inhibitors such as Indoximod and INCB024360, killer immunoglobulin-like receptors (KIRs) immune checkpoint inhibitors such as Lirilumab (BMS-986015), carcinoembryonic antigen cell adhesion molecule (CEACAM) inhibitors (e.g., CEACAM-1, -3 and/or -5). Exemplary anti-CEACAM-1 antibodies are described in WO 2010/125571, WO 2013/082366 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In other embodiments, the anti-CEACAM antibody binds to CEACAM-5 as described in, e.g., Zheng et al. PLoS One. 2010 Sep. 2; 5(9). pii: e12529 (DOI:10:1371/journal.pone.0021146), or cross-reacts with CEACAM-1 and CEACAM-5 as described in, e.g., WO 2013/054331 and US 2014/0271618. Still other checkpoint inhibitors can be molecules directed to B and T lymphocyte attenuator molecule (BTLA), for example as described in Zhang et al., Monoclonal antibodies to B and T lymphocyte attenuator (BTLA) have no effect on in vitro B cell proliferation and act to inhibit in vitro T cell proliferation when presented in a cis, but not trans, format relative to the activating stimulus, Clin Exp Immunol. 2011 January; 163(1): 77-87.

As contemplated herein, G1T38, or a pharmaceutically acceptable salt thereof, is administered in an oral dosage form and can be in combination with any standard chemotherapeutic agent treatment modality, in further combination with an immune checkpoint inhibitor.

In one embodiment, the chemotherapeutic agent is toxic to immune effector cells. In one embodiment the chemotherapeutic agent inhibits cell growth. In one embodiment, the cytotoxic chemotherapeutic agent administered is a DNA damaging chemotherapeutic agent. In one embodiment, the chemotherapeutic agent is a protein synthesis inhibitor, a DNA-damaging chemotherapeutic, an alkylating agent, a topoisomerase inhibitor, an RNA synthesis inhibitor, a DNA complex binder, a thiolate alkylating agent, a guanine alkylating agent, a tubulin binder, DNA polymerase inhibitor, an anticancer enzyme, RAC1 inhibitor, thymidylate synthase inhibitor, oxazophosphorine compound, integrin inhibitor such as cilengitide, camptothecin or homocamptothecin, antifolate or a folate antimetabolite.

In one embodiment the additional therapeutic agent is trastuzumab. In one embodiment the additional therapeutic agent is lapatinib. In one embodiment the compound of the present invention is dosed with 2, 3, or 4 additional therapeutic agents. In one embodiment there are 2 additional therapeutic agents. In one embodiment the two additional therapeutic agents are lapatinib and trastuzumab.

In one embodiment the additional therapeutic agent is osimertinib.

In one embodiment the additional therapeutic agent is alectinib.

In one embodiment the additional therapeutic agent is a MEK inhibitor.

In one embodiment the additional therapeutic agent is an Androgen Receptor ligand.

In one embodiment the additional therapeutic agent is a BTK inhibitor.

In one embodiment the additional therapeutic agents are a MEK inhibitor and a RAF inhibitor In one embodiment the additional therapeutic agent is a RAF inhibitor.

In one embodiment the additional therapeutic agent is regorafenib.

In one embodiment the MEK inhibitor is Binimetinib, Selumetinib, Cl-040, PD-325901, PD035901, or TAK-733. In another embodiment the MEK inhibitor is Tramatenib, U0126-EtOH, PD98059, Pimasertib, BIX 02188, AZD8330, PD318088, SL-327, Refametinib, Myricetin, BI-847325, Cobimetinib, APS-2-79 HCl, or GDC-0623.

In one embodiment the RAF inhibitor is PLX-4720, Dabrafenib, GDC-0879, Lifrafenib, CCT196969, RAF265, AZ 628, NVP-BHG712, SB590885, ZM 336372, Sorafenib, GW5074, TAK-632, CEP-32496, Encorafenib, PLX7904, LY3009120, RO5126766, or MLN2480.

In one embodiment the BTK inhibitor is CC-292, CNX-774, RN486, LFM-A13, ONO-4059, Acalabrutinib, or CGI746.

In one embodiment the Androgen Receptor ligand is MK-2866, Apalutamide, Andarine, Boldenone, testosterone enanthate, dihydrotestosterone, Galertone, dehydroepiandrosterone, cyproterone acetate, megestrol acetate, epiandrosterone, AZD3514, spironolactone, chloromadinone acetate, ODM-201, EPI-001.

In one embodiment the EGFR inhibitor is Lapatinib, Afatinib, Neratinib, Catertinib, AG-490, CP-724714, Dacomitnib, WZ4002, Sapitinib, CUDC-101, AG-1478, PD153035 HCl, Pelitinib, AC480, AEE788, AP26113, OSI-420, WZ3146, WZ8040, AST-1306, Rociletinib, Genisten, Varlitinib, Icotinib, TAK-285, WHI-P154, Daphnetin, PD168393, Tyrphostin 9, CNX-2006, AG-18, Cetuximab, Nazartinib, NSC228155, AZ5104, Poziotnib, AZD3759, Lifirafenib, Olmutinib, Erlotinib, Naquotinib, EAI045, or CL-387785.

Cytotoxic, DNA-damaging chemotherapeutic agents tend to be non-specific and, particularly at high doses, toxic to normal, rapidly dividing cells such as HSPC and immune effector cells. As used herein the term "DNA-damaging" chemotherapy or chemotherapeutic agent refers to treatment with a cytostatic or cytotoxic agent (i.e., a compound) to reduce or eliminate the growth or proliferation of undesirable cells, for example cancer cells, wherein the cytotoxic effect of the agent can be the result of one or more of nucleic acid intercalation or binding, DNA or RNA alkylation, inhibition of RNA or DNA synthesis, the inhibition of another nucleic acid-related activity (e.g., protein synthesis), or any other cytotoxic effect. Such compounds include, but are not limited to, DNA damaging compounds that can kill cells. "DNA damaging" chemotherapeutic agents include, but are not limited to, alkylating agents, DNA intercalators, protein synthesis inhibitors, inhibitors of DNA or RNA synthesis, DNA base analogs, topoisomerase inhibitors, telomerase inhibitors, and telomeric DNA binding compounds. For example, alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylol melamine; nitrogen mustards such as chlorambucil, chlornaphazine, cyclophosphamide, estramustine, mechlorethamine, mechlorethamine oxide hydrochloride, melphalan, novembichine, phenesterine, prednimustine, trofosfamide, and uracil mustard; and nitroso ureas, such as carmustine, chlorozotocin, fotemustine, lomustine, nimustine, and ranimustine. Other DNA-damaging chemotherapeutic agents include daunorubicin, doxorubicin, idarubicin, epirubicin, mitomycin, and streptozocin. Chemotherapeutic antimetabolites include gemcitabine, mercaptopurine, thioguanine, cladribine, fludarabine phosphate, fluorouracil (5-FU), floxuridine, cytarabine, pentostatin, methotrexate, azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim.

Inhibitors of DNA synthesis, include alkylating agents such as dimethyl sulfate, nitrogen and sulfur mustards; intercalating agents, such as acridine dyes, actinomycins, anthracenes, benzopyrene, ethidium bromide, propidium diiodide-intertwining; and other agents, such as distamycin and netropsin. Topoisomerase inhibitors, such as irinotecan, teniposide, coumermycin, nalidixic acid, novobiocin, and oxolinic acid; inhibitors of cell division, including colcemide, mitoxantrone, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be used as the DNA damaging compound.

In one embodiment the chemotherapeutic agent is a DNA complex binder such as camptothecin, or etoposide; a thiolate alkylating agent such as nitrosourea, BCNU, CCNU, ACNU, or fotesmustine; a guanine alkylating agent such as temozolomide, a tubulin binder such as vinblastine, vincristine, vinorelbine, vinflunine, cryptophycin 52, halichondrins, such as halichondrin B, dolastatins, such as dolastatin 10 and dolastatin 15, hemiasterlins, such as hemiasterlin A and hemiasterlin B, colchicine, combrestatins, 2-methoxyestradiol, E7010, paclitaxel, docetaxel, epothilone, discodermolide; a DNA polymerase inhibitor such as cytarabine; an anticancer enzyme such as asparaginase; a Rac1 inhibitor such as 6-thioguanine; a thymidylate synthase inhibitor such as capecitabine or 5-FU; a oxazophosphorine compound such as Cytoxan; a integrin inhibitor such as cilengitide; an antifolate such as pralatrexate; a folate antimetabolite such as pemetrexed; or a camptothecin or homocamptothecin such as diflomotecan.

In one embodiment the topoisomerase inhibitor is a type I inhibitor. In another embodiment the topoisomerase inhibitor is a type II inhibitor.

Other DNA-damaging chemotherapeutic agents whose toxic effects can be mitigated by the presently disclosed selective CDK4/6 inhibitors include, but are not limited to, cisplatin, hydrogen peroxide, carboplatin, procarbazine, ifosfamide, bleomycin, plicamycin, taxol, transplatinum, thiotepa, oxaliplatin, and the like, and similar acting-type agents. In one embodiment, the DNA damaging chemotherapeutic agent is selected from the group consisting of cisplatin, carboplatin, camptothecin, and etoposide.

Other suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®), liposomal vincristine (Marqibo®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Prednisone, and Dexamethasone (Decadron). Examples of additional suitable chemotherapeutic agents include but are not limited to 5-fluorouracil, dacarbazine, alkylating agents, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), bleomycin sulfate, calicheamicin, cytochalasin B, dactinomycin (formerly actinomycin), daunorubicin HCl, daunorubicin citrate, denileukin diftitox, dihydroxy anthracin dione, Docetaxel, doxorubicin HCl, E. coli L-asparaginase, Erwinia L-asparaginase, etoposide citrovorum factor, etoposide phosphate, gemcitabine HCl, idarubicin HCl, interferon α-2b, irinotecan HCl, maytansinoid, mechlorethamine HCl, melphalan HCl, mithramycin, mitomycin C, mitotane, polifeprosan 20 with carmustine implant, procarbazine HCl, streptozotocin, teniposide, thiotepa, topotecan HCl, valrubicin, vinblastine sulfate, vincristine sulfate, and vinorelbine tartrate.

Additional cytotoxic chemotherapeutic agents for use with the present invention include: epirubicin, abraxane, taxotere, epothilone, tafluposide, vismodegib, azacytidine, doxifluridine, vindesine, and vinorelbine.

In one embodiment, the chemotherapeutic agent is not an aromatase inhibitor. In one embodiment, the chemotherapeutic agent is not a steroid. In one embodiment, the chemotherapeutic agent is not a BCR-ABL inhibitor.

In one embodiment, the chemotherapeutic agent is a DNA complex binder. In one embodiment, the chemotherapeutic agent is a tubulin binder. In one embodiment, the chemotherapeutic agent is an alkylating agent. In one embodiment, the chemotherapeutic agent is a thiolate alkylating agent.

Additional chemotherapeutic agents that may be used as described herein may include 2-methoxyestradiol or 2ME2, finasunate, etaracizumab (MEDI-522), HLL1, huN901-DM1, atiprimod, saquinavir mesylate, ritonavir, nelfinavir mesylate, indinavir sulfate, plitidepsin, P276-00, tipifarnib, lenalidomide, thalidomide, pomalidomide, simvastatin, and celecoxib. Chemotherapeutic agents useful in the present invention include, but are not limited to, Trastuzumab (Herceptin®), Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Targretin®), Alitretinoin (Panretin®), Tretinoin (Vesanoid®), Carfilzomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

Additional chemotherapeutic agents contemplated include, but are not limited to, a calcineurin inhibitor, e.g. a cyclosporin or an ascomycin, e.g. Cyclosporin A (Neoral®), FK506 (tacrolimus), pimecrolimus, a mTOR inhibitor, e.g. rapamycin or a derivative thereof, e.g. Sirolimus (Rapamune®), Everolimus (Certican®), temsirolimus, zotarolimus, biolimus-7, biolimus-9, a rapalog, e.g. ridaforolimus, campath 1H, a SIP receptor modulator, a dual mTORC1 and mTORC2 inhibitor, eg. Vistusertib (AZD2014), e.g. fingolimod or an analogue thereof, an anti IL-8 antibody, mycophenolic acid or a salt thereof, e.g. sodium salt, or a prodrug thereof, e.g. Mycophenolate Mofetil (CellCept®), OKT3 (Orthoclone OKT3®), Prednisone, ATGAM®, Thymoglobulin®, Brequinar Sodium, OKT4, T10B9.A-3A, 33B3.1, 15-deoxyspergualin, tresperimus, Leflunomide Arava®, anti-CD25, anti-IL2R, Basiliximab (Simulect®), Daclizumab (Zenapax®), mizoribine, dexamethasone, ISAtx-247, SDZ ASM 981 (pimecrolimus, Elidel®), Abatacept, belatacept, LFA3lg, etanercept (sold as Enbrel® by ImmuneXcite), adalimumab (Humira®), infliximab (Remicade®), an anti-LFA-1 antibody, natalizumab (Antegren®), Enlimomab, gavilimomab, Golimumab, antithymocyte immunoglobulin, siplizumab, Alefacept, efalizumab, Pentasa, mesalazine, asacol, codeine phosphate, benorylate, fenbufen, naprosyn, diclofenac, etodolac, indomethacin, dasatinib (Sprycel®) nilotinib (Tasigna®), bosutinib (Bosulif®), Imatinib mesylate (Gleevec®) and ponatinib (Iclusig™) amifostine, dolasetron mesylate, dronabinol, epoetin-α, etidronate, filgrastim, fluconazole, goserelin acetate, gramicidin D, granisetron, leucovorin calcium, lidocaine, Mesna, ondansetron HCl, pilocarpine HCl, porfimer sodium, vatalanib, 1-dehydrotestosterone, allopurinol sodium, Betamethasone, sodium phosphate and betamethasone acetate, calcium leucovorin, conjugated estrogens, Dexrazoxane, Dibromomannitol, esterified estrogens, estradiol, estramustine phosphate sodium, ethinyl estradiol, flutamide, folinic acid, glucocorticoids, leuprolide acetate, levamisole HCl, medroxyprogesterone acetate, megestrol acetate, methyltestosterone, nilutamide, octreotide acetate, pamidronate disodium, procaine, propranolol, testolactone, tetracaine, toremifene citrate, and sargramostim.

In one embodiment, the chemotherapeutic agent is an estrogen receptor ligands such as tamoxifen, raloxifene, fulvestrant, anordrin, bazedoxifene, broparestriol, chlorotrianisene, clomiphene citrate, cyclofenil, lasofoxifene, ormeloxifene, or toremifene; an androgen receptor ligand such as bicalutamide, enzalutamide, apalutamide, cyproterone acetate, chlormadinone acetate, spironolactone, canrenone, drospirenone, ketoconazole, topilutamide, abiraterone acetate, or cimetidine; an aromatase inhibitor such as letrozole, anastrozole, or exemestane; an anti-inflammatory such as prednisone; an oxidase inhibitor such as allopurinol; an anticancer antibody; an anticancer monoclonal antibody; an antibody against CD40 such as lucatumumab or dacetuzumab; an antibody against CD20 such as rituximab; an antibody that binds CD52 such as alemtuzumab; an antibody that binds integrin such as volociximab or natalizumab; an antibody against interleukin-6 receptor such as tocilizumab; an interleukin-2 memetic such as aldesleukin; an antibody that targets IGF1 like figitumumab; an antibody that targets DR4 such as mapatumumab; an antibody that targets TRAIL-R2 such as lexatumumab or dulanermin; a fusion protein such as atacicept; a B cell inhibitor such as atacicept; a proteasome inhibitor such as carfilzomib, bortezomib, or marizomib; a HSP90 inhibitor such as tanespimycin; a HDAC inhibitor such as vorinostat, belinostat or panobinostat; a MAPK ligand such as talmapimod; a PKC inhibitor such as enzastaurin; a HER2 receptor ligand such as trastuzumab, lapatinib, or pertuzumab; an EGFR inhibitor such as gefitinib, erlotinib, cetuximab, panitumumab, or vandetanib; a natural product such as romidepsin; a retinoid such as bexarotene, tretinoin, or alitretinoin; a receptor tyrosine kinase (RTK) inhibitor such as sunitinib, regorafenib, or pazopanib; or a VEGF inhibitor such as ziv-aflibercept, bevacizumab or dovitinib.

In one embodiment, G1T38 is further combined with the use of hematopoietic growth factors including, but not limited to, granulocyte colony stimulating factor (G-CSF, for example, sold as Neupogen® (filgrastim), Neulasta® (peg-filgrastim), or lenograstim), granulocyte-macrophage colony stimulating factor (GM-CSF, for example sold as molgramostim and sargramostim (Leukine®)), M-CSF (macrophage colony stimulating factor), Thrombopoietin (megakaryocyte growth development factor (MGDF), for example sold as Romiplostim® and Eltrombopag®) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbepoetin, Epocept, Nanokine, Epofit, Epogen, Eprex, and Procrit; epoetin-β sold as for example NeoRecormon, Recormon and Micera), epoetin-delta (sold as for example Dynepo), epoetin-omega (sold as for example Epomax), epoetin zeta (sold as for example Silapo and Retacrit) as well as for example Epocept, Epotrust, Erypro Safe, Repoitin, Vintor, Epofit, Erykine, Wepox, Espogen, Relipoietin, Shanpoietin, Zyrop and EPIAO).

Additional chemotherapeutic agents contemplated herein, particularly in the treatment of abnormal tissue of the female reproductive system such as breast, ovarian, endometrial, or uterine cancer include an estrogen inhibitor including but not limited to a SERM (selective estrogen receptor modulator), a SERD (selective estrogen receptor degrader), a complete estrogen receptor degrader, or another form of partial or complete estrogen antagonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703,810, as well as US 2015/0005286, WO 2014/205136, and WO 2014/205138. Additional non-limiting examples of anti-estrogen compounds include: SERMS such as anordrin, bazedoxifene, broparestriol, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, delmadinone acetate, dydrogesterone, medroxyprogesterone acetate, megestrol acetate, nomegestrol acetate, norethisterone acetate, progesterone, and spironolactone.

Additional chemotherapeutic agents contemplated herein, particularly in the treatment of abnormal tissue of the male reproductive system such as prostate or testicular cancer, include, but are not limited to, an androgen (such as testosterone) inhibitor including but not limited to a selective androgen receptor modulator, a selective androgen receptor degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos.

8,455,534 and 8,299,112. Additional non-limiting examples of anti-androgen compounds include: chlormadinone acetate, spironolactone, canrenone, drospirenone, ketoconazole, topilutamide, abiraterone acetate, and cimetidine.

The chemotherapeutic agent may include a kinase inhibitor, including but not limited to a phosphoinositide 3-kinase (PI3K) inhibitor, a Bruton's tyrosine kinase (BTK) inhibitor, or a spleen tyrosine kinase (Syk) inhibitor, or a combination thereof.

PI3k inhibitors are well known. Examples of PI3 kinase inhibitors include but are not limited to Wortmannin, demethoxyviridin, perifosine, idelalisib, pictilisib, Palomid 529, ZSTK474, PWT33597, CUDC-907, and AEZS-136, duvelisib, GS-9820, GDC-0032 (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl) thieno[3,2-d]pyrimidine), GDC-0980 ((S)-1-(4-((2-(2-aminopyrimidin-5-yl)-7-methyl-4-morpholinothieno[3,2-d] pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-10-yl] acetate (also known as sonolisib)), and the structure described in WO2014/071109.

BTK inhibitors are well known. Examples of BTK inhibitors include ibrutinib (also known as PCI-32765)(Imbruvica™) (1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy) phenyl)amino)pyrimidin-4-yl)amino)phenyl)acrylamide) (Avila Therapeutics) (see US Patent Publication No 2011/0117073, incorporated herein in its entirety), dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino) imidazo[1,2-a]pyrazin-6-yl)phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl) phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo [h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), BGB-3111, and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors are well known, and include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl) amino)-2,2-dimethyl-3-oxo-2H-pyrido[3,2-b][1,4]oxazin-4 (3H)-yl)methyl phosphate), BAY 61-3606 (2-(7-(3,4-Dimethoxyphenyl)-imidazo[1,2-c]pyrimidin-5-ylamino)-nicotinamide HCl), R09021 (6-[(1R,2S)-2-Aminocyclohexylamino]-4-(5,6-dimethyl-pyridin-2-ylamino)-pyridazine-3-carboxylic acid amide), imatinib (Gleevec; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino) pyrimidine-5-carboxamide), PRT-062607 (4-((3-(2H-1,2,3- triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

The chemotherapeutic agent can also be a B-cell lymphoma 2 (Bcl-2) protein inhibitor. BCL-2 inhibitors are known in the art, and include, for example, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl] amino]-3-nitrophenyl]sulfonylbenzamide), ABT-263 ((R)-4-(4-((4'-chloro-4,4-dimethyl-3,4,5,6-tetrahydro-[1, 1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), or G3139 (Oblimersen).

Additional chemotherapeutic agents for use in the methods contemplated herein include, but are not limited to, midazolam, MEK inhibitors, RAS inhibitors, ERK inhibitors, ALK inhibitors, HSP inhibitors (for example, HSP70 and HSP 90 inhibitors, or a combination thereof), RAF inhibitors, apoptotic compounds, topoisomerase inhibitors, AKT inhibitors, including but not limited to, MK-2206, GSK690693, Perifosine, (KRX-0401), GDC-0068, Triciribine, AZD5363, Honokiol, PF-04691502, and Miltefosine, or FLT-3 inhibitors, including but not limited to, P406, Dovitinib, Quizartinib (AC220), Amuvatinib (MP-470), Tandutinib (MLN518), ENMD-2076, and KW-2449, or combinations thereof. Examples of MEK inhibitors include but are not limited to trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl] azetidin-3-ol), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7 (3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide). Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol.

Known ERK inhibitors include SCH772984 (Merck/Schering-Plough), VTX-11e (Vertex), DEL-22379, Ulixertinib (BVD-523, VRT752271), GDC-0994, FR 180204, XMD8-92, and ERK5-IN-1.

Raf inhibitors are well known, and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide;4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2, 3-c]azepine-4,8-dione), Raf Kinase Inhibitor IV (2-chloro-5-(2-phenyl-5-(pyridin-4-yl)-1H-imidazol-4-yl)phenol), and Sorafenib N-Oxide (4-[4-[[[[4-Chloro-3(trifluoroMethyl)phenyl]aMino]carbonyl]aMino]phenoxy]-N-Methyl-2pyridinecarboxaMide 1-Oxide).

Known topoisomerase I inhibitors useful in the present invention include (S)-10-[(dimethylamino)methyl]-4-ethyl-4,9-dihydroxy-1H-pyrano[3',4':6,7]indolizino[1,2-b]quinoline-3,14(4H,12H)-dione monohydrochloride (topotecan), (S)-4-ethyl-4-hydroxy-1H-pyrano[3',4':6,7]indolizino[1,2-b]quinoline-3,14-(4H,12H)-dione (camptothecin), (1S,9S)-1-Amino-9-ethyl-5-fluoro-1,2,3,9,12,15-hexahydro-9-hydroxy-4-methyl-10H,13H-benzo(de)pyrano(3',4':6,7)indolizino(1,2-b)quinoline-10,13-dione (exatecan), (7-(4-methylpiperazinomethylene)-10,11-ethylenedioxy-20(S)-camptothecin (lurtotecan), or (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate (irinotecan), (R)-5-ethyl-9,10-difluoro-5-hydroxy-4,5-dihydrooxepino[3',4':6,7]indolizino[1,2-b]quinoline-3,15(1H,13H)-dione (diflomotecan), (4S)-11-((E)-((1,1-Dimethylethoxy)imino)methyl)-4-ethyl-4-hydroxy-1,12-dihydro-14H-pyrano(3',4':6,7)indolizino(1,2-b)quinoline-3,14(4H)-dione (gimatecan), (S)-8-ethyl-8-hydroxy-15-((4-methylpiperazin-1-yl)methyl)-11,14-dihydro-2H-[1,4]dioxino[2,3-g]pyrano[3',4':6,7]indolizino [1,2-b]quinoline-9,12(3H,8H)-dione (lurtotecan), (4S)-4-Ethyl-4-hydroxy-11-[2-[(1-methylethyl)amino]ethyl]-1H-pyrano[3?,4?:6,7]indolizino[1,2-b]quinoline-3,14(4H,12H)-dione (belotecan), 6-((1,3-dihydroxypropan-2-yl)amino)-2,10-dihydroxy-12-((2R,3R,4S,5S,6R)-3,4,5-trihydroxy-6-(hydroxymethyl)tetrahydro-2H-pyran-2-yl)-12,13-dihydro-5H-indolo[2,3-a]pyrrolo[3,4-c]carbazole-5,7(6H)-dione (edotecarin), 8,9-dimethoxy-5-(2-N,N-dimethylaminoethyl)-2,3-methylenedioxy-5H-dibenzo(c,h)(1,6)naphthyridin-6-one (topovale), benzo[6,7]indolizino[1,2-b]quinolin-11(13H)-one (rosettacin), (S)-4-ethyl-4-hydroxy-11-(2-(trimethylsilyl)ethyl)-1H-pyrano[3',4':6,7]indolizino[1,2-b] quinoline-3,14(4H,12H)-dione (cositecan), tetrakis{(4S)-9-[([1,4'-bipiperidinyl]-1'-carbonyl)oxy]-4,11-diethyl-3,14-dioxo-3,4,12,14-tetrahydro-1H-pyrano[3',4':6,7]indolizino [1,2-b]quinolin-4-yl} N,N',N'',N'''-{methanetetrayltetrakis [methylenepoly(oxyethylene)oxy(1-oxoethylene)]}tetraglycinate tetrahydrochloride (etirinotecan pegol), 10-hydroxy-camptothecin (HOCPT), 9-nitrocamptothecin (rubitecan), SN38 (7-ethyl-10-hydroxycamptothecin), and 10-hydroxy-9-nitrocamptothecin (CPT109), (R)-9-chloro-5-ethyl-5-hydroxy-10-methyl-12-((4-methylpiperidin-1-yl) methyl)-4,5-dihydrooxepino[3',4':6,7]indolizino[1,2-b]quinoline-3,15(1H,13H)-dione (elmotecan).

In one embodiment, the chemotherapeutic agent is not an aromatase inhibitor. In one embodiment, the chemotherapeutic agent is not an estrogen or androgen receptor agonist or antagonist.

In one embodiment, G1T38, or a pharmaceutical salt thereof, is administered in an oral dosage form and further combined with the use of hematopoietic growth factors including, but not limited to, granulocyte colony stimulating factor (G-CSF, for example, sold as Neupogen (filgrastim), Neulasta (peg-filgrastim), or lenograstim), granulocyte-macrophage colony stimulating factor (GM-CSF, for example sold as molgramostim and sargramostim (Leukine)), M-CSF (macrophage colony stimulating factor), Thrombopoietin (megakaryocyte growth development factor (MGDF), for example sold as Romiplostim and Eltrombopag) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbepoetin, Epocept, Nanokine, Epofit, Epogen, Eprex, and Procrit; epoetin-β sold as for example NeoRecormon, Recormon and Micera), epoetin-delta (sold as for example Dynepo), epoetin-omega (sold as for example Epomax), epoetin zeta (sold as for example Silapo and Retacrit) as well as for example Epocept, Epotrust, Erypro Safe, Repoitin, Vintor, Epofit, Erykine, Wepox, Espogen, Relipoietin, Shanpoietin, Zyrop and EPIAO).

In one embodiment, G1T38, or a pharmaceutical salt thereof, is administered in an oral dosage form and further combined with a CDK7 inhibitor.

In one embodiment, an effective amount of Compound II Form B is administered in combination with an effective amount of abiraterone acetate (Zytiga) for the treatment of abnormal tissue of the male reproductive system, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of abiraterone acetate (Zytiga) for the treatment of abnormal tissue of the male reproductive system, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of abiraterone acetate (Zytiga) for the treatment of prostate cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of abiraterone acetate (Zytiga) for the treatment of prostate cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of enzalutamide for the treatment of prostate cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of enzalutamide for the treatment of prostate cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of afatinib dimaleate (Gilotrif) for the treatment of non-small cell lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of afatinib dimaleate (Gilotrif) for the treatment of non-small cell lung cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of alectinib (Alecensa) for the treatment of non-small cell lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of alectinib (Alecensa) for the treatment of non-small cell lung cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of ceritinib (Zykadia) for the treatment of non-small cell lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of ceritinib (Zykadia) for the treatment of non-small cell lung cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of crizotinib (Xalkori) for the treatment of non-small cell lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of crizotinib (Xalkori) for the treatment of non-small cell lung cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of osimertinib (Tagrisso) for the treatment of non-small cell lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of osimertinib (Tagrisso) for the treatment of non-small cell lung cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of brigatinib (Alunbrig) for the treatment of non-small cell lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of brigatinib (Alunbrig) for the treatment of non-small cell lung cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of lorlatinib for the treatment of non-small cell lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of lorlatinib for the treatment of non-small cell lung cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of lapatinib ditosylate for the treatment of breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of lapatinib ditosylate for the treatment of breast cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of lapatinib ditosylate for the treatment of HER2+ breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of lapatinib ditosylate for the treatment of HER2+ breast cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of PF7775 for the treatment of non-small cell lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of PF7775 for the treatment of non-small cell lung cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of alpelisib for the treatment of solid tumors, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of alpelisib for the treatment of solid tumors, wherein the administration of Compound II Form B provides on Day 22 after first dosing a mean steady state $AUC_{(0-24\ ss)}$(h*ng/mL)/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of alpelisib for the treatment of abnormal tissue of the female reproductive system, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of alpelisib for the treatment of abnormal tissue of the female reproductive system, wherein the administration of Compound II Form B provides on Day 22 after first dosing a mean steady state $AUC_{(0-24\ ss)}$(h*ng/mL)/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of alpelisib for the treatment of breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of alpelisib for the treatment of breast cancer, wherein the administration of Compound II Form B provides on Day 22 after first dosing a mean steady state $AUC_{(0-24\ ss)}$(h*ng/mL)/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of copanlisib hydrochloride (Aligopa) for the treatment of lymphoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of copanlisib hydrochloride (Aligopa) for the treatment of lymphoma, wherein the administration of Compound II Form B provides on Day 22 after first dosing a mean steady state $AUC_{(0-24\ ss)}$(h*ng/mL)/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of copanlisib hydrochloride (Aligopa) for the treatment of follicular lymphoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of copanlisib hydrochloride (Aligopa) for the treatment of follicular lymphoma, wherein the administration of Compound II Form B provides on Day 22 after first dosing a mean steady state $AUC_{(0-24\ ss)}$(h*ng/mL)/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of idelalisib (Zydelig) for the treatment of chronic lymphocytic leukemia, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of idelalisib (Zydelig) for the treatment of chronic lymphocytic leukemia, wherein the administration of Compound II Form B provides on Day 22 after first dosing a mean steady state $AUC_{(0-24\ ss)}$(h*ng/mL)/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of idelalisib (Zydelig) for the treatment of Non-Hodgkin lymphoma, including follicular B-cell non-Hodgkin lymphoma or small lymphocytic lymphoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of idelalisib (Zydelig) for the treatment of Non-Hodgkin lymphoma, including follicular B-cell non-Hodgkin lymphoma or small lymphocytic lymphoma, wherein the administration of Compound II Form B provides on Day 22 after first dosing a mean steady state $AUC_{(0-24\ ss)}$(h*ng/mL)/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of ibrutinib (Imbruvica) for the treatment of chronic lymphocytic leukemia, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of ibrutinib (Imbruvica) for the treatment of chronic lymphocytic leukemia, wherein the administration of Compound II Form B provides on Day 22 after first dosing a mean steady state $AUC_{(0-24\ ss)}$(h*ng/mL)/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of ibrutinib (Imbruvica) for the treatment of lymphoma, including small lymphocytic lymphoma, mantle cell lymphoma, marginal zone lymphoma, or Waldenström macroglobulinemia, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of ibrutinib (Imbruvica) for the treatment of lymphoma, including small lymphocytic lymphoma, mantle cell lymphoma, marginal zone lymphoma, or Waldenström macroglobulinemia, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of binimetinib for the treatment of melanoma, including BRAF-mutant melanoma and NRAS-mutant melanoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of binimetinib for the treatment of melanoma, including BRAF-mutant melanoma and NRAS-mutant melanoma, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of cobimetinib (Cotellic) for the treatment of melanoma, including BRAF-mutant melanoma and NRAS-mutant melanoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of cobimetinib (Cotellic) for the treatment of melanoma, including BRAF-mutant melanoma and NRAS-mutant melanoma, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of binimetinib for the treatment of ovarian cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of binimetinib for the treatment of ovarian cancer, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of selumetinib for the treatment of non-small cell lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of selumetinib for the treatment of non-small cell lung cancer, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of selumetinib for the treatment of thyroid cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of selumetinib for the treatment of thyroid cancer, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of trametinib (Mekinist) for the treatment of thyroid cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of trametinib (Mekinist) for the treatment of thyroid cancer, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of trametinib (Mekinist) for the treatment of melanoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of trametinib (Mekinist) for the treatment of melanoma, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of trametinib (Mekinist) for the treatment of non-small cell lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of trametinib (Mekinist) for the treatment of non-small cell lung cancer, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of dabrafenib (Tafinlar) for the treatment of thyroid cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of dabrafenib (Tafinlar) for the treatment of thyroid cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of dabrafenib (Tafinlar) for the treatment of melanoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of dabrafenib (Tafinlar) for the treatment of melanoma, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of dabrafenib (Tafinlar) for the treatment of non-small cell lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of dabrafenib (Tafinlar) for the treatment of non-small cell lung cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of encorafenib for the treatment of melanoma, including BRAF-mutant melanoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of encorafenib for the treatment of melanoma, including BRAF-mutant melanoma, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of ipatasertib for the treatment of breast cancer, including triple negative breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of ipatasertib for the treatment of breast cancer, including triple negative breast cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of niraparib tosylate monohydrate (Zejula) for the treatment of abnormal tissue of the female reproductive system, including ovarian epithelial cancer or fallopian tube cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of niraparib tosylate monohydrate (Zejula) for the treatment of abnormal tissue of the female reproductive system, including ovarian epithelial cancer or fallopian tube cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of niraparib tosylate monohydrate (Zejula) for the treatment of peritoneal cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of niraparib tosylate monohydrate (Zejula) for the treatment of peritoneal cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of olaparib (Lynparza) for the treatment of abnormal tissue of the female reproductive system, including breast cancer, ovarian cancer, ovarian epithelial cancer or fallopian tube cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of olaparib (Lynparza) for the treatment of abnormal tissue of the female reproductive system, including breast cancer, ovarian cancer, ovarian epithelial cancer or fallopian tube cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of olaparib (Lynparza) for the treatment of BRAC1 or BRAC2-mutated breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of olaparib (Lynparza) for the treatment of BRAC1 or BRAC2-mutated breast cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of olaparib (Lynparza) for the treatment of HER2− breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of olaparib (Lynparza) for the treatment of HER2- breast cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of olaparib (Lynparza) for the treatment of peritoneal cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of olaparib (Lynparza) for the treatment of peritoneal cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of rucaparib camsylate (Rubraca) for the treatment of abnormal tissue of the female reproductive system, including breast cancer, ovarian cancer, ovarian epithelial cancer or fallopian tube cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of rucaparib camsylate (Rubraca) for the treatment of abnormal tissue of the female reproductive system, including breast cancer, ovarian cancer, ovarian epithelial cancer or fallopian tube cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of rucaparib camsylate (Rubraca) for the treatment of peritoneal cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of rucaparib camsylate (Rubraca) for the treatment of peritoneal cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of talazoparib for the treatment of abnormal tissue of the female reproductive system, including breast cancer, ovarian cancer, ovarian epithelial cancer or fallopian tube cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of talazoparib for the treatment of abnormal tissue of the female reproductive system, including breast cancer, ovarian cancer, ovarian epithelial cancer or fallopian tube cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of talazoparib for the treatment of BRAC1 or BRAC2-mutated breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of talazoparib for the treatment of BRAC1 or BRAC2-mutated breast cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of olaratumab for the treatment of soft tissue sarcoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of olaratumab for the treatment of soft tissue sarcoma, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of savolitinib for the treatment of adenocarcinoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of savolitinib for the treatment of adenocarcinoma, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of savolitinib for the treatment of non-small cell lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of savolitinib for the treatment of non-small cell lung cancer, wherein the administration of Compound II Form B provides on Day 22 after first dosing a mean steady state $AUC_{(0-24\ ss)}$(h*ng/mL))/Absolute Neutrophil Count (cells/ mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of savolitinib for the treatment of renal cell carcinoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of savolitinib for the treatment of renal cell carcinoma, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of vistusertib for the treatment of advanced breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of vistusertib for the treatment of advanced breast cancer, wherein the administration of Compound II Form B provides on Day 22 after first dosing a mean steady state $AUC_{(0-24\ ss)}$(h*ng/mL))/ Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of vistusertib for the treatment of advanced breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of vistusertib for the treatment of advanced breast cancer, wherein the administration of Compound II Form B provides on Day 22 after first dosing a mean steady state $AUC_{(0-24\ ss)}$(h*ng/mL))/ Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of abemaciclib (Versenio) for the treatment of breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of abemaciclib (Versenio) for the treatment of breast cancer, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of abemaciclib (Versenio) for the treatment of HR+ HER2– breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of abemaciclib (Versenio) for the treatment of HR+ HER2– breast cancer, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of palbociclib (Ibrance) for the treatment of breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of palbociclib (Ibrance) for the treatment of breast cancer, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of palbociclib (Ibrance) for the treatment of HR+ HER2-breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of palbociclib (Ibrance) for the treatment of HR+ HER2– breast cancer, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of palbociclib (Ibrance) for the treatment of breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of palbociclib (Ibrance) for the treatment of breast cancer, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of palbociclib (Ibrance) for the treatment of metastatic triple negative breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of palbociclib (Ibrance) for the treatment of metastatic triple negative breast cancer, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of palbociclib (Ibrance) for the treatment of small cell lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of palbociclib (Ibrance) for the treatment of small cell lung cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of cabozantinib S-malate (Cometriq™) for the treatment of thyroid cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of cabozantinib S-malate (Cometriq™) for the treatment of thyroid cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of cabozantinib S-maleate (Cometriq™) for the treatment of renal cell carcinoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of cabozantinib S-maleate (Cometriq™) for the treatment of renal cell carcinoma, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of dasatinib (Sprycel) for the treatment of leukemia, including acute lymphoblastic leukemia or chronic myelogenous leukemia, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of dasatinib (Sprycel) for the treatment of leukemia, including acute lymphoblastic leukemia or chronic myelogenous leukemia, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of dasatinib (Sprycel) for the treatment of prostate cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of dasatinib (Sprycel) for the treatment of prostate cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of Erlotinib (Tarceva®) for the treatment of prostate cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of Erlotinib (Tarceva®) for the treatment of prostate cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of Gefitinib (Iressa®) for the treatment of prostate cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of Gefitinib (Iressa®) for the treatment of prostate cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of imatinib mesylate (Gleevec) for the treatment of leukemia, including acute lymphoblastic leukemia, chronic eosinophilic leukemia, hypereosinophilic syndrome, or chronic myelogenous leukemia, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of imatinib mesylate (Gleevec) for the treatment of leukemia, including acute lymphoblastic leukemia, chronic eosinophilic leukemia, hypereosinophilic syndrome, or chronic myelogenous leukemia, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of trastuzumab (Herceptin) for the treatment of adenocarcinoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of trastuzumab (Herceptin) for the treatment of adenocarcinoma, wherein the administration of Compound II Form B provides on Day 22 after first dosing a mean steady state $AUC_{(0-24\ ss)}$(h*ng/mL))/Absolute Neutrophil Count (cells/ mm³) ratio of not greater than 1.25. In one embodiment, the mean steady state AUC$_{(0-24ss)}$ is measured for serum Compound I.

In one embodiment, an effective amount of Compound II Form B is administered in combination with an effective amount of trastuzumab (Herceptin) for the treatment of breast cancer, including HER2+ breast cancer, wherein the administration of Compound II Form B provides a (mean steady state AUC$_{(0-24ss)}$ (h*ng/mL))/mg dose ratio of not greater than 5. In one embodiment, an effective amount of Compound II Form B is administered in combination with an effective amount of trastuzumab (Herceptin) for the treatment of breast cancer, including HER2+ breast cancer, wherein the administration of Compound II Form B provides on Day 22 after first dosing a mean steady state AUC$_{(0-24\ ss)}$(h*ng/mL))/Absolute Neutrophil Count (cells/mm³) ratio of not greater than 1.25. In one embodiment, the mean steady state AUC$_{(0-24ss)}$ is measured for serum Compound I.

In one embodiment, an effective amount of Compound II Form B is administered in combination with an effective amount of imatinib mesylate (Gleevec) for the treatment of tumors, including but not limited to dermatofibrosarcoma protuberans and gastrointestinal stromal tumors, wherein the administration of Compound II Form B provides a (mean steady state AUC$_{(0-24ss)}$ (h*ng/mL))/mg dose ratio of not greater than 5. In one embodiment, an effective amount of Compound II Form B is administered in combination with an effective amount of imatinib mesylate (Gleevec) for the treatment of tumors, including but not limited to dermatofibrosarcoma protuberans and gastrointestinal stromal tumors, wherein the administration of Compound II Form B provides on Day 22 after first dosing a mean steady state AUC$_{(0-24\ ss)}$(h*ng/mL))/Absolute Neutrophil Count (cells/mm³) ratio of not greater than 1.25. In one embodiment, the mean steady state AUC$_{(0-24ss)}$ is measured for serum Compound I.

In one embodiment, an effective amount of Compound II Form B is administered in combination with an effective amount of imatinib mesylate (Gleevec) for the treatment of myelodysplastic/myeloproliferative neoplasms, wherein the administration of Compound II Form B provides a (mean steady state AUC$_{(0-24ss)}$ (h*ng/mL))/mg dose ratio of not greater than 5. In one embodiment, an effective amount of Compound II Form B is administered in combination with an effective amount of imatinib mesylate (Gleevec) for the treatment of myelodysplastic/myeloproliferative neoplasms, wherein the administration of Compound II Form B provides on Day 22 after first dosing a mean steady state AUC$_{(0-24\ ss)}$(h*ng/mL))/Absolute Neutrophil Count (cells/mm³) ratio of not greater than 1.25. In one embodiment, the mean steady state AUC$_{(0-24ss)}$ is measured for serum Compound I.

In one embodiment, an effective amount of Compound II Form B is administered in combination with an effective amount of imatinib mesylate (Gleevec) for the treatment of systemic mastocytosis, wherein the administration of Compound II Form B provides a (mean steady state AUC$_{(0-24ss)}$ (h*ng/mL))/mg dose ratio of not greater than 5. In one embodiment, an effective amount of Compound II Form B is administered in combination with an effective amount of imatinib mesylate (Gleevec) for the treatment of systemic mastocytosis, wherein the administration of Compound II Form B provides on Day 22 after first dosing a mean steady state AUC$_{(0-24\ ss)}$(h*ng/mL))/Absolute Neutrophil Count (cells/mm³) ratio of not greater than 1.25. In one embodiment, the mean steady state AUC$_{(0-24ss)}$ is measured for serum Compound I.

In one embodiment, an effective amount of Compound II Form B is administered in combination with an effective amount of nilotinib (Tasigna) for the treatment of chronic myelogenous leukemia, including Philadelphia chromosome positive chronic myeloid leukemia (Ph+ CML), wherein the administration of Compound II Form B provides a (mean steady state AUC$_{(0-24ss)}$ (h*ng/mL))/mg dose ratio of not greater than 5. In one embodiment, an effective amount of Compound II Form B is administered in combination with an effective amount of nilotinib (Tasigna) for the treatment of chronic myelogenous leukemia, including Philadelphia chromosome positive chronic myeloid leukemia (Ph+ CVL), wherein the administration of Compound II Form B provides on Day 22 after first dosing a mean steady state AUC$_{(0-24\ ss)}$(h*ng/mL))/Absolute Neutrophil Count (cells/mm³) ratio of not greater than 1.25. In one embodiment, the mean steady state AUC$_{(0-24ss)}$ is measured for serum Compound I.

In one embodiment, an effective amount of Compound II Form B is administered in combination with an effective amount of pazopanib hydrochloride (Votrient) for the treatment of renal cell carcinoma, wherein the administration of Compound II Form B provides a (mean steady state AUC$_{(0-24ss)}$ (h*ng/mL))/mg dose ratio of not greater than 5. In one embodiment, an effective amount of Compound II Form B is administered in combination with an effective amount of pazopanib hydrochloride (Votrient) for the treatment of renal cell carcinoma, wherein the administration of Compound II Form B provides on Day 22 after first dosing a mean steady state AUC$_{(0-24\ ss)}$(h*ng/mL))/Absolute Neutrophil Count (cells/mm³) ratio of not greater than 1.25. In one embodiment, the mean steady state AUC$_{(0-24ss)}$ is measured for serum Compound I.

In one embodiment, an effective amount of Compound II Form B is administered in combination with an effective amount of pazopanib hydrochloride (Votrient) for the treatment of soft tissue sarcoma, wherein the administration of Compound II Form B provides a (mean steady state AUC$_{(0-24ss)}$ (h*ng/mL))/mg dose ratio of not greater than 5. In one embodiment, an effective amount of Compound II Form B is administered in combination with an effective amount of pazopanib hydrochloride (Votrient) for the treatment of soft tissue sarcoma, wherein the administration of Compound II Form B provides on Day 22 after first dosing a mean steady state AUC$_{(0-24\ ss)}$(h*ng/mL))/Absolute Neutrophil Count (cells/mm³) ratio of not greater than 1.25. In one embodiment, the mean steady state AUC$_{(0-24ss)}$ is measured for serum Compound I.

In one embodiment, an effective amount of Compound II Form B is administered in combination with an effective amount of regorafenib (Stivarga) for the treatment of colorectal cancer, wherein the administration of Compound II Form B provides a (mean steady state AUC$_{(0-24ss)}$ (h*ng/mL))/mg dose ratio of not greater than 5. In one embodiment, an effective amount of Compound II Form B is administered in combination with an effective amount of regorafenib (Stivarga) for the treatment of colorectal cancer, wherein the administration of Compound II Form B provides on Day 22 after first dosing a mean steady state AUC$_{(0-24\ ss)}$(h*ng/mL))/Absolute Neutrophil Count (cells/mm³) ratio of not greater than 1.25. In one embodiment, the mean steady state AUC$_{(0-24ss)}$ is measured for serum Compound I.

In one embodiment, an effective amount of Compound II Form B is administered in combination with an effective amount of regorafenib (Stivarga) for the treatment of gastrointestinal stromal tumor, wherein the administration of Compound II Form B provides a (mean steady state $\text{AUC}_{(0\text{-}24ss)}$ (h*ng/mL))/mg dose ratio of not greater than 5. In one embodiment, an effective amount of Compound II Form B is administered in combination with an effective amount of regorafenib (Stivarga) for the treatment of gastrointestinal stromal tumor, wherein the administration of Compound II Form B provides on Day 22 after first dosing a mean steady state $\text{AUC}_{(0\text{-}24\ ss)}$(h*ng/mL))/Absolute Neutrophil Count (cells/mm$^3$) ratio of not greater than 1.25. In one embodiment, the mean steady state $\text{AUC}_{(0\text{-}24ss)}$ is measured for serum Compound I.

In one embodiment, an effective amount of Compound II Form B is administered in combination with an effective amount of regorafenib (Stivarga) for the treatment of hepatocellular carcinoma, wherein the administration of Compound II Form B provides a (mean steady state $\text{AUC}_{(0\text{-}24ss)}$ (h*ng/mL))/mg dose ratio of not greater than 5. In one embodiment, an effective amount of Compound II Form B is administered in combination with an effective amount of regorafenib (Stivarga) for the treatment of hepatocellular carcinoma, wherein the administration of Compound II Form B provides on Day 22 after first dosing a mean steady state $\text{AUC}_{(0\text{-}24\ ss)}$(h*ng/mL))/Absolute Neutrophil Count (cells/mm$^3$) ratio of not greater than 1.25. In one embodiment, the mean steady state $\text{AUC}_{(0\text{-}24ss)}$ is measured for serum Compound I.

In one embodiment, an effective amount of Compound II Form B is administered in combination with an effective amount of sorafenib Tosylate (Nexavar) for the treatment of carcinoma, including hepatocellular carcinoma or renal cell carcinoma, wherein the administration of Compound II Form B provides a (mean steady state $\text{AUC}_{(0\text{-}24ss)}$ (h*ng/mL))/mg dose ratio of not greater than 5. In one embodiment, an effective amount of Compound II Form B is administered in combination with an effective amount of sorafenib Tosylate (Nexavar) for the treatment of carcinoma, including hepatocellular carcinoma or renal cell carcinoma, wherein the administration of Compound II Form B provides on Day 22 after first dosing a mean steady state $\text{AUC}_{(0\text{-}24\ ss)}$(h*ng/mL))/Absolute Neutrophil Count (cells/mm$^3$) ratio of not greater than 1.25. In one embodiment, the mean steady state $\text{AUC}_{(0\text{-}24ss)}$ is measured for serum Compound I.

In one embodiment, an effective amount of Compound II Form B is administered in combination with an effective amount of sunitinib malate (Sutent) for the treatment of gastrointestinal stromal tumor, wherein the administration of Compound II Form B provides a (mean steady state $\text{AUC}_{(0\text{-}24ss)}$ (h*ng/mL))/mg dose ratio of not greater than 5. In one embodiment, an effective amount of Compound II Form B is administered in combination with an effective amount of sunitinib malate (Sutent) for the treatment of gastrointestinal stromal tumor, wherein the administration of Compound II Form B provides on Day 22 after first dosing a mean steady state $\text{AUC}_{(0\text{-}24\ ss)}$(h*ng/mL))/Absolute Neutrophil Count (cells/mm$^3$) ratio of not greater than 1.25. In one embodiment, the mean steady state $\text{AUC}_{(0\text{-}24ss)}$ is measured for serum Compound I.

In one embodiment, an effective amount of Compound II Form B is administered in combination with an effective amount of sunitinib malate (Sutent) for the treatment of pancreatic cancer, wherein the administration of Compound II Form B provides a (mean steady state $\text{AUC}_{(0\text{-}24ss)}$ (h*ng/mL))/mg dose ratio of not greater than 5. In one embodiment, an effective amount of Compound II Form B is administered in combination with an effective amount of sunitinib malate (Sutent) for the treatment of pancreatic cancer, wherein the administration of Compound II Form B provides on Day 22 after first dosing a mean steady state $\text{AUC}_{(0\text{-}24\ ss)}$(h*ng/mL))/Absolute Neutrophil Count (cells/mm$^3$) ratio of not greater than 1.25. In one embodiment, the mean steady state $\text{AUC}_{(0\text{-}24ss)}$ is measured for serum Compound I.

In one embodiment, an effective amount of Compound II Form B is administered in combination with an effective amount of sunitinib malate (Sutent) for the treatment of renal cell carcinoma, wherein the administration of Compound II Form B provides a (mean steady state $\text{AUC}_{(0\text{-}24ss)}$ (h*ng/mL))/mg dose ratio of not greater than 5. In one embodiment, an effective amount of Compound II Form B is administered in combination with an effective amount of sunitinib malate (Sutent) for the treatment of renal cell carcinoma, wherein the administration of Compound II Form B provides on Day 22 after first dosing a mean steady state $\text{AUC}_{(0\text{-}24\ ss)}$(h*ng/mL))/Absolute Neutrophil Count (cells/mm$^3$) ratio of not greater than 1.25. In one embodiment, the mean steady state $\text{AUC}_{(0\text{-}24ss)}$ is measured for serum Compound I.

In one embodiment, an effective amount of Compound II Form B is administered in combination with an effective amount of vemurafenib (Zelboraf) for the treatment of Erdheim-Chester disease, wherein the administration provides a (mean steady state $\text{AUC}_{(0\text{-}24ss)}$ (h*ng/mL))/mg dose ratio of not greater than 5. In one embodiment, an effective amount of Compound II Form B is administered in combination with an effective amount of vemurafenib (Zelboraf) for the treatment of Erdheim-Chester disease, wherein the administration of Compound II Form B provides on Day 22 after first dosing a mean steady state $\text{AUC}_{(0\text{-}24\ ss)}$(h*ng/mL))/Absolute Neutrophil Count (cells/mm$^3$) ratio of not greater than 1.25. In one embodiment, the mean steady state $\text{AUC}_{(0\text{-}24ss)}$ is measured for serum Compound I.

In one embodiment, an effective amount of Compound II Form B is administered in combination with an effective amount of vemurafenib (Zelboraf) for the treatment of melanoma, wherein the administration of Compound II Form B provides a (mean steady state $\text{AUC}_{(0\text{-}24ss)}$ (h*ng/mL))/mg dose ratio of not greater than 5. In one embodiment, an effective amount of Compound II Form B is administered in combination with an effective amount of vemurafenib (Zelboraf) for the treatment of melanoma, wherein the administration of Compound II Form B provides on Day 22 after first dosing a mean steady state $\text{AUC}_{(0\text{-}24\ ss)}$(h*ng/mL))/Absolute Neutrophil Count (cells/mm$^3$) ratio of not greater than 1.25. In one embodiment, the mean steady state $\text{AUC}_{(0\text{-}24ss)}$ is measured for serum Compound I.

In one embodiment, an effective amount of Compound II Form B is administered in combination with an effective amount of bosutinib (Bosulif®) for the treatment of chronic myelogenous leukemia (CML), wherein the administration of Compound II Form B provides a (mean steady state $\text{AUC}_{(0\text{-}24ss)}$ (h*ng/mL))/mg dose ratio of not greater than 5. In one embodiment, an effective amount of Compound II Form B is administered in combination with an effective amount of bosutinib (Bosulif®) for the treatment of chronic myelogenous leukemia (CML), wherein the administration of Compound II Form B provides on Day 22 after first dosing a mean steady state $\text{AUC}_{(0\text{-}24\ ss)}$(h*ng/mL))/Absolute Neutrophil Count (cells/mm$^3$) ratio of not greater than 1.25.

In one embodiment, the mean steady state $AUC_{(0-24ss)}$ is measured for serum Compound I.

In one embodiment, an effective amount of Compound II Form B is administered in combination with an effective amount of ponatinib hydrochloride (Iclusig) for the treatment of leukemia, including acute lymphoblastic leukemia and chronic myelogenous leukemia, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of ponatinib hydrochloride (Iclusig) for the treatment of leukemia, including acute lymphoblastic leukemia and chronic myelogenous leukemia, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of everolimus (Afinitor) for the treatment of breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of everolimus (Afinitor) for the treatment of breast cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of everolimus (Afinitor) for the treatment of HR+, HER2− breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of everolimus (Afinitor) for the treatment of HR+, HER2− breast cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of everolimus (Afinitor) for the treatment of pancreatic cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of everolimus (Afinitor) for the treatment of pancreatic cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of everolimus (Afinitor) for the treatment of gastrointestinal cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of everolimus (Afinitor) for the treatment of gastrointestinal cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of everolimus (Afinitor) for the treatment of lung cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of everolimus (Afinitor) for the treatment of lung cancer, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of everolimus (Afinitor) for the treatment of renal cell carcinoma, wherein the administration of Compound II Form B provides a (mean steady state $AUC_{(0-24ss)}$(h*ng/mL))/mg dose ratio of not greater than 5. In one embodiment, an effective amount of Compound II Form B is administered in combination with an effective amount of everolimus (Afinitor) for the treatment of renal cell carcinoma, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of everolimus (Afinitor) for the treatment of astrocytoma, including subependymal giant cell astrocytoma, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of everolimus (Afinitor) for the treatment of astrocytoma, including subependymal giant cell astrocytoma, wherein the administration of Compound II Form B provides on Day 22 after first dosing a mean steady state $AUC_{(0-24\ ss)}$(h*ng/mL))/Absolute Neutrophil Count (cells/mm$^3$) ratio of not greater than 1.25. In one embodiment, the mean steady state $AUC_{(0-24ss)}$ is measured for serum Compound I.

In one embodiment, an effective amount of Compound II Form B is administered in combination with an effective amount of fulvestrant (Faslodex) for the treatment of breast cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of fulvestrant (Faslodex) for the treatment of breast cancer, wherein the administration of Compound II Form B provides on Day 22 after first dosing a mean steady state $AUC_{(0-24\ ss)}$(h*ng/mL))/

Absolute Neutrophil Count (cells/mm$^3$) ratio of not greater than 1.25. In one embodiment, the mean steady state $AUC_{(0\text{-}24ss)}$ is measured for serum Compound I.

In one embodiment, an effective amount of Compound II Form B is administered in combination with an effective amount of fulvestrant (Faslodex) for the treatment of HR+, HER2− breast cancer, wherein the administration of Compound II Form B provides a (mean steady state $AUC_{(0\text{-}24ss)}$ (h*ng/mL))/mg dose ratio of not greater than 5. In one embodiment, an effective amount of Compound II Form B is administered in combination with an effective amount of fulvestrant (Faslodex) for the treatment of HR+, HER2− breast cancer, wherein the administration of Compound II Form B provides on Day 22 after first dosing a mean steady state $AUC_{(0\text{-}24\ ss)}$(h*ng/mL))/Absolute Neutrophil Count (cells/mm$^3$) ratio of not greater than 1.25. In one embodiment, the mean steady state $AUC_{(0\text{-}24ss)}$ is measured for serum Compound I.

In one embodiment, an effective amount of Compound II Form B is administered in combination with an effective amount of ramucirumab for the treatment of adenocarcinoma, wherein the administration of Compound II Form B provides a (mean steady state $AUC_{(0\text{-}24ss)}$ (h*ng/mL))/mg dose ratio of not greater than 5. In one embodiment, an effective amount of Compound II Form B is administered in combination with an effective amount of ramucirumab for the treatment of adenocarcinoma, wherein the administration of Compound II Form B provides on Day 22 after first dosing a mean steady state $AUC_{(0\text{-}24\ ss)}$(h*ng/mL))/Absolute Neutrophil Count (cells/mm$^3$) ratio of not greater than 1.25. In one embodiment, the mean steady state $AUC_{(0\text{-}24ss)}$ is measured for serum Compound I.

In one embodiment, an effective amount of Compound II Form B is administered in combination with an effective amount of ramucirumab for the treatment of non-small cell lung cancer, wherein the administration of Compound II Form B provides a (mean steady state $AUC_{(0\text{-}24ss)}$ (h*ng/mL))/mg dose ratio of not greater than 5. In one embodiment, an effective amount of Compound II Form B is administered in combination with an effective amount of ramucirumab for the treatment of non-small cell lung cancer, wherein the administration of Compound II Form B provides on Day 22 after first dosing a mean steady state $AUC_{(0\text{-}24\ ss)}$(h*ng/mL))/Absolute Neutrophil Count (cells/mm$^3$) ratio of not greater than 1.25. In one embodiment, the mean steady state $AUC_{(0\text{-}24ss)}$ is measured for serum Compound I.

In one embodiment, an effective amount of Compound II Form B is administered in combination with an effective amount of ramucirumab for the treatment of colorectal cancer, wherein the administration of Compound II Form B provides a (mean steady state $AUC_{(0\text{-}24ss)}$ (h*ng/mL))/mg dose ratio of not greater than 5. In one embodiment, an effective amount of Compound II Form B is administered in combination with an effective amount of ramucirumab for the treatment of colorectal cancer, wherein the administration of Compound II Form B provides on Day 22 after first dosing a mean steady state $AUC_{(0\text{-}24\ ss)}$(h*ng/mL))/Absolute Neutrophil Count (cells/mm$^3$) ratio of not greater than 1.25. In one embodiment, the mean steady state $AUC_{(0\text{-}24ss)}$ is measured for serum Compound I.

In one embodiment, an effective amount of Compound II Form B is administered in combination with an effective amount of ribociclib (Kisqali) for the treatment of breast cancer, wherein the administration of Compound II Form B provides a (mean steady state $AUC_{(0\text{-}24ss)}$ (h*ng/mL))/mg dose ratio of not greater than 5. In one embodiment, an effective amount of Compound II Form B is administered in combination with an effective amount of ribociclib (Kisqali) for the treatment of breast cancer, wherein the administration of Compound II Form B provides on Day 22 after first dosing a mean steady state $AUC_{(0\text{-}24\ ss)}$(h*ng/mL))/Absolute Neutrophil Count (cells/mm$^3$) ratio of not greater than 1.25. In one embodiment, the mean steady state $AUC_{(0\text{-}24ss)}$ is measured for serum Compound I.

In one embodiment, an effective amount of Compound II Form B is administered in combination with an effective amount of ribociclib (Kisqali) for the treatment of HR+ and HER2− breast cancer, wherein the administration of Compound II Form B provides a (mean steady state $AUC_{(0\text{-}24ss)}$ (h*ng/mL))/mg dose ratio of not greater than 5. In one embodiment, an effective amount of Compound II Form B is administered in combination with an effective amount of ribociclib (Kisqali) for the treatment of HR+ and HER2− breast cancer, wherein the administration of Compound II Form B provides on Day 22 after first dosing a mean steady state $AUC_{(0\text{-}24\ ss)}$(h*ng/mL))/Absolute Neutrophil Count (cells/mm$^3$) ratio of not greater than 1.25. In one embodiment, the mean steady state $AUC_{(0\text{-}24ss)}$ is measured for serum Compound I.

In one embodiment, an effective amount of Compound II Form B is administered in combination with an effective amount of enasidenib mesylate (Idhifa) for the treatment of acute myeloid leukemia, wherein the administration of Compound II Form B provides a (mean steady state $AUC_{(0\text{-}24ss)}$ (h*ng/mL))/mg dose ratio of not greater than 5. In one embodiment, an effective amount of Compound II Form B is administered in combination with an effective amount of enasidenib mesylate (Idhifa) for the treatment of acute myeloid leukemia, wherein the administration of Compound II Form B provides on Day 22 after first dosing a mean steady state $AUC_{(0\text{-}24\ ss)}$(h*ng/mL))/Absolute Neutrophil Count (cells/mm$^3$) ratio of not greater than 1.25. In one embodiment, the mean steady state $AUC_{(0\text{-}24ss)}$ is measured for serum Compound I.

In one embodiment, an effective amount of Compound II Form B is administered in combination with an effective amount of SCH772984 for the treatment of melanoma, including BRAF-mutant melanoma or NRAS-mutant melanoma, wherein the administration of Compound II Form B provides a (mean steady state $AUC_{(0\text{-}24ss)}$ (h*ng/mL))/mg dose ratio of not greater than 5. In one embodiment, an effective amount of Compound II Form B is administered in combination with an effective amount of SCH772984 for the treatment of melanoma, including BRAF-mutant melanoma or NRAS-mutant melanoma, wherein the administration of Compound II Form B provides on Day 22 after first dosing a mean steady state $AUC_{(0\text{-}24\ ss)}$(h*ng/mL))/Absolute Neutrophil Count (cells/mm$^3$) ratio of not greater than 1.25. In one embodiment, the mean steady state $AUC_{(0\text{-}24ss)}$ is measured for serum Compound I.

In one embodiment, an effective amount of Compound II Form B is administered in combination with an effective amount of ulixertinib for the treatment of melanoma, including uveal melanoma, wherein the administration of Compound II Form B provides a (mean steady state $AUC_{(0\text{-}24ss)}$ (h*ng/mL))/mg dose ratio of not greater than 5. In one embodiment, an effective amount of Compound II Form B is administered in combination with an effective amount of ulixertinib for the treatment of melanoma, including uveal melanoma, wherein the administration of Compound II Form B provides on Day 22 after first dosing a mean steady state $AUC_{(0\text{-}24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of ulixertinib for the treatment of pancreatic cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of ulixertinib for the treatment of pancreatic cancer, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

In one embodiment, an effective amount of Compound II Form B is administered in combination with an effective amount of erdafitinib for the treatment of urothelial cancer, including metastatic urothelial cancer, wherein the administration of Compound II Form B provides a (mean steady state $AUC_{(0-24ss)}$ (h*ng/mL))/mg dose ratio of not greater than 5. In one embodiment, an effective amount of Compound II Form B is administered in combination with an effective amount of erdafitinib for the treatment of urothelial cancer, including metastatic urothelial cancer, wherein the administration of Compound II Form B provides on Day 22 after first dosing a mean steady state $AUC_{(0-24\ ss)}$(h*ng/mL))/Absolute Neutrophil Count (cells/mm³) ratio of not greater than 1.25. In one embodiment, the mean steady state $AUC_{(0-24ss)}$ is measured for serum Compound I.

EXAMPLES

Example 1. Collection of Compound I and Compound III Plasma Concentration Versus Time Data for Once a Day (QD) and Twice a Day (BID) Dosing Cohorts of Form B of Compound II Patients were enrolled into 1 of 2 parallel, independently operating, dose-escalation dosing cohorts with Form B of Compound II administered continuously either once daily (QD) or twice daily (BID) with food with fixed-dose fulvestrant (intramuscularly every 14 days for the first three injections and then every 28 days). Pre- or perimenopausal patients also received goserelin for the duration of study treatment. A LHR2 agonist was started at least 28 days before the first dose of Form B, and those patients who were taking another LHRH agonist were switched to goserelin on Day 1. Patients were split into six cohorts providing once a day (QD) dosing of 200 mg, 300 mg, 400 mg, 500 mg, or 650 mg of Form B, or twice a day (BID) dosing of 100 mg, 150 mg, or 200 mg of Form B. The second dose in BID cohorts was not administered in the evening until at least 12 hours after the initial morning dose of Form B. The dosing cohorts for Form B of Compound II are provided in Table 1.

TABLE 1

Compound II Dosing Cohorts of Form B of Compound II

| Cohort | Number of Subjects (N) | Dosage |
|---|---|---|
| 1 | 6 | 200 mg QD |
| 2 | 3 | 300 mg QD |
| 3 | 3 | 400 mg QD |
| 4 | 3 | 500 mg QD |
| 5 | 3 | 650 mg QD |
| 6 | 6 | 100 mg BID |
| 7 | 3 | 150 mg BID |
| 8 | 3 | 200 mg BID |

Blood samples were collected at the following time points relative to the morning dose of Form B at Day 1 and at Day 29: pre-dose (0 hour) and 1, 2, 3, 4, 6, 8, 10, 12 (prior to the evening dose in the BID cohorts), and 24 (prior to the next day's morning dose) hours after dosing. A ±5-minute time window was allowed for samples collected between the predose and 3 hours after Form B dosing. A ±15-minute window was allowed for samples collected between 4 to 12 hours after Form B dosing. A ±1-hour window was allowed for the sample collected 24 hours after Form B dosing. Blood samples for Compound I PK trough levels were collected pre-dose at Day 8, Day 15, and Day 22 prior to the morning administration of Compound I. Plasma concentrations of Compound I and its metabolite, Compound III, were measured using validated methods.

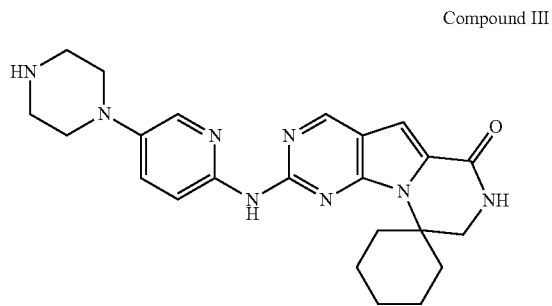 [SMILES: O=C1NCC2(CCCCC2)n2c1cc1cnc(Nc3ccc(N4CCNCC4)cn3)nc12]

Compound III

Analysis of plasma concentration versus time data for calculation of standard pharmacokinetic (PK) parameters following oral administration was conducted using Phoenix WinNonlin version 6.3 using actual blood sampling times.

The Day 1 Concentration-Time Data of Compound I for all cohorts is provided in Tables 2 to 9.

TABLE 2

Compound I Concentration (ng/mL) Summary for Cohort 1
(200 mg QD of Form B) on Day 1.

| Compound I | | | 0.0 | 1.0 | 2.0 | 3.0 | 4.0 | 6.0 | 8.0 | 10.0 | 12.0 | 24.0 |
|---|---|---|---|---|---|---|---|---|---|---|---|---|
| | | | | | | | Time (h) | | | | | |
| Day 1 | 200 mg QD | N = 6 | | | | | Concentration (ng/mL) | | | | | |
| | Mean | | 0.00 | 8.42 | 13.6 | 20.2 | 25.0 | 16.8 | 11.6 | 8.28 | 6.29 | 3.61 |
| | SD | | 0.00 | 9.94 | 12.0 | 12.4 | 11.7 | 6.98 | 4.23 | 2.68 | 2.15 | 1.89 |

TABLE 2-continued

Compound I Concentration (ng/mL) Summary for Cohort 1
(200 mg QD of Form B) on Day 1.

| Compound I | | | Time (h) | | | | | | | |
|---|---|---|---|---|---|---|---|---|---|---|
| | | 0.0 | 1.0 | 2.0 | 3.0 | 4.0 | 6.0 | 8.0 | 10.0 | 12.0 | 24.0 |
| Day 1  200 mg QD  N = 6 | | | | | | Concentration (ng/mL) | | | | | |
| | Min | 0.00 | 0.828 | 0.896 | 4.34 | 5.47 | 8.26 | 5.96 | 4.59 | 3.47 | 1.71 |
| | Median | 0.00 | 3.65 | 12.3 | 18.1 | 27.0 | 17.7 | 12.2 | 9.13 | 6.43 | 3.24 |
| | Max | 0.00 | 26.0 | 36.0 | 40.0 | 39.7 | 24.8 | 17.2 | 11.0 | 8.88 | 6.67 |
| | CV % | | 118.1 | 87.9 | 61.4 | 46.7 | 41.5 | 36.6 | 32.4 | 34.2 | 52.2 |

TABLE 3

Compound I Concentration (ng/mL) Summary for Cohort 2
(300 mg QD of Form B) on Day 1.

| Compound I | | | Time (h) | | | | | | | |
|---|---|---|---|---|---|---|---|---|---|---|
| | | 0.0 | 1.0 | 2.0 | 3.0 | 4.0 | 6.0 | 8.0 | 10.0 | 12.0 | 24.0 |
| Day 1  300 mg QD  N = 3 | | | | | | Concentration (ng/mL) | | | | | |
| | Mean | 0.00 | 22.9 | 16.9 | 27.1 | 32.0 | 31.6 | 22.7 | 19.9 | 15.5 | 8.09 |
| | SD | 0.00 | 35.7 | 19.0 | 29.3 | 29.8 | 21.0 | 15.3 | 16.0 | 12.1 | 6.21 |
| | Min | 0.00 | 0.834 | 5.84 | 7.16 | 10.2 | 7.41 | 5.51 | 4.83 | 4.48 | 1.69 |
| | Median | 0.00 | 3.73 | 5.96 | 13.4 | 19.8 | 43.1 | 28.1 | 18.1 | 13.5 | 8.48 |
| | Max | 0.00 | 64.1 | 38.8 | 60.8 | 66.0 | 44.3 | 34.6 | 36.7 | 28.4 | 14.1 |
| | CV % | | 156.1 | 112.6 | 108.2 | 93.2 | 66.3 | 67.2 | 80.5 | 78.1 | 76.8 |

TABLE 4

Compound I Concentration (ng/mL) Summary for Cohort 3
(400 mg QD of Form B) on Day 1.

| Compound I | | | Time (h) | | | | | | | |
|---|---|---|---|---|---|---|---|---|---|---|
| | | 0.0 | 1.0 | 2.0 | 3.0 | 4.0 | 6.0 | 8.0 | 10.0 | 12.0 | 24.0 |
| Day 1  400 mg QD  N = 3 | | | | | | Concentration (ng/mL) | | | | | |
| | Mean | 0.00 | 5.32 | 5.67 | 9.21 | 14.0 | 20.1 | 15.5 | 10.6 | 7.69 | 3.27 |
| | SD | 0.00 | 6.43 | 3.72 | 5.78 | 3.29 | 5.16 | 3.87 | 1.85 | 1.95 | 0.851 |
| | Min | 0.00 | 0.990 | 2.45 | 3.35 | 11.2 | 14.4 | 11.4 | 9.45 | 5.55 | 2.40 |
| | Median | 0.00 | 2.26 | 4.83 | 9.38 | 13.1 | 21.6 | 16.0 | 9.56 | 8.13 | 3.31 |
| | Max | 0.00 | 12.7 | 9.74 | 14.9 | 17.6 | 24.4 | 19.1 | 12.7 | 9.38 | 4.10 |
| | CV % | | 120.9 | 65.5 | 62.7 | 23.5 | 25.6 | 25.0 | 17.5 | 25.4 | 26.0 |

TABLE 5

Compound I Concentration (ng/mL) Summary for Cohort 4
(500 mg QD of Form B) on Day 1.

| Compound I | | | Time (h) | | | | | | | |
|---|---|---|---|---|---|---|---|---|---|---|
| | | 0.0 | 1.0 | 2.0 | 3.0 | 4.0 | 6.0 | 8.0 | 10.0 | 12.0 | 24.0 |
| Day 1  500 mg QD  N = 4 | | | | | | Concentration (ng/mL) | | | | | |
| | Mean | 0.00 | 10.4 | 18.5 | 34.3 | 35.4 | 46.5 | 40.6 | 32.2 | 27.8 | 8.93 |
| | SD | 0.00 | 6.22 | 6.43 | 15.7 | 6.94 | 17.6 | 9.53 | 6.59 | 7.63 | 4.07 |
| | Min | 0.00 | 3.84 | 11.6 | 24.8 | 27.7 | 26.3 | 27.7 | 23.3 | 18.9 | 6.38 |
| | Median | 0.00 | 10.2 | 18.1 | 27.4 | 35.3 | 45.6 | 42.3 | 33.4 | 28.3 | 7.17 |
| | Max | 0.00 | 17.2 | 26.3 | 57.7 | 43.4 | 68.7 | 50.2 | 38.7 | 35.7 | 15.0 |
| | CV % | | 59.9 | 34.7 | 45.6 | 19.6 | 37.7 | 23.5 | 20.5 | 27.5 | 45.6 |

TABLE 6

Compound I Concentration (ng/mL) Summary for Cohort 5
(650 mg QD of Form B) on Day 1.

| Compound I | | Time (h) | | | | | | | | |
|---|---|---|---|---|---|---|---|---|---|---|
| | | 0.0 | 1.0 | 2.0 | 3.0 | 4.0 | 6.0 | 8.0 | 10.0 | 12.0 | 24.0 |
| Day 1 650 mg QD | N = 6 | Concentration (ng/mL) | | | | | | | | | |
| | Mean | 0.00 | 12.7 | 24.8 | 30.9 | 43.7 | 52.7 | 59.6 | 48.4 | 37.4 | 17.1 |
| | SD | 0.00 | 10.7 | 19.1 | 12.4 | 15.6 | 14.3 | 17.3 | 21.8 | 13.5 | 7.37 |
| | Min | 0.00 | 2.83 | 8.99 | 14.1 | 20.8 | 35.2 | 38.2 | 20.6 | 23.9 | 8.76 |
| | Median | 0.00 | 9.68 | 19.1 | 31.6 | 43.5 | 49.8 | 60.3 | 47.9 | 37.3 | 16.0 |
| | Max | 0.00 | 33.2 | 57.6 | 50.1 | 66.3 | 70.3 | 80.7 | 78.5 | 53.6 | 28.4 |
| | CV % | | 84.0 | 76.8 | 39.9 | 35.6 | 27.2 | 29.0 | 45.0 | 36.1 | 43.0 |

TABLE 7

Compound I Concentration (ng/mL) Summary for Cohort 6
(100 mg BID of Form B) on Day 1.

| Compound I | | Time (h) | | | | | | | | |
|---|---|---|---|---|---|---|---|---|---|---|
| | | 0.0 | 1.0 | 2.0 | 3.0 | 4.0 | 6.0 | 8.0 | 10.0 | 12.0 |
| Day 1 100 mg BID | N = 6 | Concentration (ng/mL) | | | | | | | | |
| | Mean | 0.00 | 2.80 | 6.21 | 8.72 | 8.98 | 5.70 | 4.07 | 3.29 | 2.93 |
| | SD | 0.00 | 2.09 | 1.68 | 3.07 | 4.14 | 2.97 | 1.90 | 1.43 | 1.63 |
| | Min | 0.00 | 0.00 | 4.90 | 5.87 | 4.31 | 2.97 | 2.27 | 1.92 | 1.49 |
| | Median | 0.00 | 2.60 | 5.71 | 8.09 | 7.47 | 5.12 | 3.71 | 2.91 | 2.20 |
| | Max | 0.00 | 6.42 | 9.57 | 14.7 | 14.5 | 11.0 | 6.93 | 5.26 | 5.26 |
| | CV % | | 74.4 | 27.1 | 35.2 | 46.1 | 52.2 | 46.7 | 43.6 | 55.5 |

TABLE 8

Compound I Concentration (ng/mL) Summary for Cohort 7
(150 mg BID of Form B) on Day 1.

| Compound I | | Time (h) | | | | | | | | |
|---|---|---|---|---|---|---|---|---|---|---|
| | | 0.0 | 1.0 | 2.0 | 3.0 | 4.0 | 6.0 | 8.0 | 10.0 | 12.0 |
| Day 1 150 mg BID | N = 3 | Concentration (ng/mL) | | | | | | | | |
| | Mean | 0.00 | 4.63 | 11.0 | 14.4 | 20.7 | 12.2 | 10.1 | 8.98 | 7.73 |
| | SD | 0.00 | 4.43 | 7.02 | 8.85 | 8.08 | 4.48 | 2.64 | 2.33 | 2.22 |
| | Min | 0.00 | 0.00 | 3.69 | 8.48 | 12.2 | 8.89 | 7.53 | 6.65 | 5.71 |
| | Median | 0.00 | 5.06 | 11.6 | 10.2 | 21.5 | 10.4 | 9.95 | 8.98 | 7.38 |
| | Max | 0.00 | 8.82 | 17.7 | 24.6 | 28.3 | 17.3 | 12.8 | 11.3 | 10.1 |
| | CV % | | 95.7 | 63.9 | 61.4 | 39.1 | 36.8 | 26.1 | 25.9 | 28.7 |

TABLE 9

Compound I Concentration (ng/mL) Summary for Cohort 8
(200 mg BID of Form B) on Day 1.

| Compound I | | Time (h) | | | | | | | | |
|---|---|---|---|---|---|---|---|---|---|---|
| | | 0.0 | 1.0 | 2.0 | 3.0 | 4.0 | 6.0 | 8.0 | 10.0 | 12.0 |
| Day 1 200 mg BID | N = 4 | Concentration (ng/mL) | | | | | | | | |
| | Mean | 0.00 | 5.79 | 9.42 | 12.8 | 15.5 | 15.5 | 8.94 | 6.61 | 5.64 |
| | SD | 0.00 | 4.81 | 5.41 | 6.83 | 10.7 | 8.34 | 3.71 | 3.43 | 2.40 |
| | Min | 0.00 | 0.00 | 1.37 | 3.14 | 3.07 | 5.28 | 4.49 | 2.77 | 3.83 |
| | Median | 0.00 | 6.13 | 11.8 | 14.8 | 14.9 | 17.1 | 9.13 | 6.33 | 4.89 |

TABLE 9-continued

Compound I Concentration (ng/mL) Summary for Cohort 8
(200 mg BID of Form B) on Day 1.

| Compound I | | Time (h) | | | | | | | |
|---|---|---|---|---|---|---|---|---|---|
| | | 0.0 | 1.0 | 2.0 | 3.0 | 4.0 | 6.0 | 8.0 | 10.0 | 12.0 |
| Day 1  200 mg BID  N = 4 | | Concentration (ng/mL) | | | | | | | | |
| | Max | 0.00 | 10.9 | 12.7 | 18.4 | 29.0 | 22.6 | 13.0 | 11.0 | 8.94 |
| | CV % | | 83.1 | 57.5 | 53.5 | 69.2 | 53.8 | 41.5 | 51.9 | 42.6 |

The Day 1 Concentration-Time Data for Metabolite Compound III for all cohorts is provided in Tables 10 to 17.

TABLE 10

Compound III Concentration (ng/mL) Summary for Cohort 1
(200 mg QD of Form B) on Day 1.

| Compound III | | Time (h) | | | | | | | | |
|---|---|---|---|---|---|---|---|---|---|---|
| | | 0.0 | 1.0 | 2.0 | 3.0 | 4.0 | 6.0 | 8.0 | 10.0 | 12.0 | 24.0 |
| Day 1  200 mg QD  N = 6 | | Concentration (ng/mL) | | | | | | | | | |
| | Mean | 0.00 | 1.51 | 2.79 | 3.50 | 4.11 | 2.30 | 1.33 | 0.693 | 0.390 | 0.123 |
| | SD | 0.00 | 2.03 | 2.10 | 2.02 | 2.48 | 1.79 | 0.846 | 0.576 | 0.448 | 0.300 |
| | Min | 0.00 | 0.00 | 0.00 | 0.800 | 1.02 | 0.00 | 0.00 | 0.00 | 0.00 | 0.00 |
| | Median | 0.00 | 0.665 | 2.74 | 3.51 | 3.79 | 2.03 | 1.31 | 0.830 | 0.273 | 0.00 |
| | Max | 0.00 | 5.02 | 6.43 | 6.83 | 7.82 | 5.23 | 2.47 | 1.32 | 0.962 | 0.736 |
| | CV % | | 134.4 | 75.3 | 57.7 | 60.4 | 77.8 | 63.8 | 83.1 | 114.9 | 244.9 |

TABLE 11

Compound III Concentration (ng/mL) Summary for Cohort 2 (300 mg QD of Form
B) on Day 1.

| Compound III | | Time (h) | | | | | | | | |
|---|---|---|---|---|---|---|---|---|---|---|
| | | 0.0 | 1.0 | 2.0 | 3.0 | 4.0 | 6.0 | 8.0 | 10.0 | 12.0 | 24.0 |
| Day 1  300 mg QD  N = 3 | | Concentration (ng/mL) | | | | | | | | | |
| | Mean | 0.00 | 2.41 | 2.52 | 3.40 | 4.00 | 4.04 | 2.80 | 2.27 | 1.30 | 0.455 |
| | SD | 0.00 | 3.33 | 2.37 | 2.35 | 2.15 | 2.64 | 2.36 | 2.21 | 1.47 | 0.432 |
| | Min | 0.00 | 0.00 | 0.974 | 1.78 | 1.82 | 1.19 | 0.643 | 0.517 | 0.00 | 0.00 |
| | Median | 0.00 | 1.01 | 1.33 | 2.33 | 4.08 | 4.53 | 2.44 | 1.54 | 1.01 | 0.506 |
| | Max | 0.00 | 6.21 | 5.25 | 6.09 | 6.11 | 6.40 | 5.33 | 4.75 | 2.89 | 0.859 |
| | CV % | | 138.5 | 94.2 | 69.0 | 53.6 | 65.3 | 84.3 | 97.3 | 112.8 | 94.9 |

TABLE 12

Compound III Concentration (ng/mL) Summary for Cohort 3
(400 mg QD of Form B) on Day 1.

| Compound III | | Time (h) | | | | | | | | |
|---|---|---|---|---|---|---|---|---|---|---|
| | | 0.0 | 1.0 | 2.0 | 3.0 | 4.0 | 6.0 | 8.0 | 10.0 | 12.0 | 24.0 |
| Day 1  400 mg QD  N = 3 | | Concentration (ng/mL) | | | | | | | | | |
| | Mean | 0.00 | 2.61 | 1.33 | 2.46 | 3.02 | 3.83 | 2.33 | 1.13 | 0.668 | 0.00 |
| | SD | 0.00 | 3.72 | 0.548 | 1.20 | 0.922 | 0.820 | 0.522 | 0.345 | 0.138 | 0.00 |
| | Min | 0.00 | 0.00 | 0.719 | 1.15 | 1.96 | 3.02 | 1.79 | 0.728 | 0.546 | 0.00 |
| | Median | 0.00 | 0.960 | 1.49 | 2.70 | 3.51 | 3.81 | 2.38 | 1.31 | 0.640 | 0.00 |
| | Max | 0.00 | 6.87 | 1.78 | 3.52 | 3.60 | 4.66 | 2.83 | 1.34 | 0.818 | 0.00 |
| | CV % | | 142.5 | 41.2 | 49.0 | 30.5 | 21.4 | 22.4 | 30.6 | 20.7 | |

TABLE 13

Compound III Concentration (ng/mL) Summary for Cohort 4 (500 mg QD of Form B) on Day 1.

| Compound III | | Time (h) | | | | | | | | |
|---|---|---|---|---|---|---|---|---|---|---|
| | | 0.0 | 1.0 | 2.0 | 3.0 | 4.0 | 6.0 | 8.0 | 10.0 | 12.0 | 24.0 |
| Day 1 500 mg QD N = 4 | | | | | Concentration (ng/mL) | | | | | | |
| | Mean | 0.00 | 2.76 | 4.47 | 6.14 | 6.86 | 7.69 | 5.62 | 3.71 | 2.49 | 0.806 |
| | SD | 0.00 | 1.10 | 1.57 | 0.751 | 1.34 | 1.50 | 1.59 | 0.836 | 0.702 | 0.211 |
| | Min | 0.00 | 1.31 | 3.12 | 5.22 | 5.12 | 6.00 | 4.11 | 2.59 | 1.62 | 0.611 |
| | Median | 0.00 | 2.97 | 4.26 | 6.15 | 6.99 | 7.86 | 5.31 | 3.83 | 2.57 | 0.787 |
| | Max | 0.00 | 3.81 | 6.24 | 7.03 | 8.36 | 9.03 | 7.77 | 4.58 | 3.21 | 1.04 |
| | CV % | | 39.8 | 35.1 | 12.2 | 19.5 | 19.6 | 28.2 | 22.6 | 28.2 | 26.1 |

TABLE 14

Compound III Concentration (ng/mL) Summary for Cohort 5 (650 mg QD of Form B) on Day 1.

| Compound III | | Time (h) | | | | | | | | |
|---|---|---|---|---|---|---|---|---|---|---|
| | | 0.0 | 1.0 | 2.0 | 3.0 | 4.0 | 6.0 | 8.0 | 10.0 | 12.0 | 24.0 |
| Day 1 650 mg QD N = 6 | | | | | Concentration (ng/mL) | | | | | | |
| | Mean | 0.00 | 2.73 | 4.01 | 6.13 | 8.35 | 9.69 | 10.1 | 6.63 | 5.12 | 2.17 |
| | SD | 0.00 | 1.70 | 1.93 | 2.28 | 2.44 | 2.49 | 3.98 | 3.05 | 2.42 | 1.87 |
| | Min | 0.00 | 0.516 | 1.75 | 2.76 | 3.46 | 5.29 | 5.56 | 4.06 | 2.91 | 0.609 |
| | Median | 0.00 | 2.77 | 3.81 | 6.43 | 9.22 | 10.0 | 8.66 | 5.32 | 4.41 | 1.51 |
| | Max | 0.00 | 5.50 | 6.90 | 9.24 | 9.92 | 12.8 | 16.5 | 11.4 | 8.45 | 5.60 |
| | CV % | | 62.4 | 48.2 | 37.2 | 29.3 | 25.7 | 39.4 | 46.0 | 47.2 | 86.1 |

TABLE 15

Compound III Concentration (ng/mL) Summary for Cohort 6 (100 mg BID of Form B) on Day 1.

| Compound III | | Time (h) | | | | | | | |
|---|---|---|---|---|---|---|---|---|---|
| | | 0.0 | 1.0 | 2.0 | 3.0 | 4.0 | 6.0 | 8.0 | 10.0 | 12.0 |
| Day 1 100 mg BID N = 6 | | | | | Concentration (ng/mL) | | | | | |
| | Mean | 0.00 | 0.248 | 1.04 | 1.41 | 1.25 | 0.471 | 0.219 | 0.00 | 0.0917 |
| | SD | 0.00 | 0.412 | 0.281 | 0.260 | 0.577 | 0.540 | 0.340 | 0.00 | 0.225 |
| | Min | 0.00 | 0.00 | 0.723 | 1.11 | 0.616 | 0.00 | 0.00 | 0.00 | 0.00 |
| | Median | 0.00 | 0.00 | 1.00 | 1.42 | 1.13 | 0.382 | 0.00 | 0.00 | 0.00 |
| | Max | 0.00 | 0.977 | 1.49 | 1.70 | 2.12 | 1.23 | 0.692 | 0.00 | 0.550 |
| | CV % | | 165.9 | 26.9 | 18.4 | 46.2 | 114.7 | 155.3 | | 244.9 |

TABLE 16

Compound III Concentration (ng/mL) Summary for Cohort 7 (150 mg BID of Form B) on Day 1.

| Compound III | | Time (h) | | | | | | | |
|---|---|---|---|---|---|---|---|---|---|
| | | 0.0 | 1.0 | 2.0 | 3.0 | 4.0 | 6.0 | 8.0 | 10.0 | 12.0 |
| Day 1 150 mg BID N = 3 | | | | | Concentration (ng/mL) | | | | | |
| | Mean | 0.00 | 1.03 | 2.33 | 2.60 | 2.47 | 1.59 | 1.02 | 0.730 | 0.503 |
| | SD | 0.00 | 0.892 | 0.687 | 1.02 | 0.669 | 0.313 | 0.137 | 0.169 | 0.453 |
| | Min | 0.00 | 0.00 | 1.58 | 1.63 | 1.72 | 1.24 | 0.870 | 0.543 | 0.00 |

TABLE 16-continued

Compound III Concentration (ng/mL) Summary for Cohort 7 (150 mg BID of Form B) on Day 1.

| Compound III | | Time (h) | | | | | | | |
|---|---|---|---|---|---|---|---|---|---|
| | | 0.0 | 1.0 | 2.0 | 3.0 | 4.0 | 6.0 | 8.0 | 10.0 | 12.0 |
| Day 1 150 mg BID N = 3 | | | | | Concentration (ng/mL) | | | | | |
| | Median | 0.00 | 1.52 | 2.48 | 2.50 | 2.70 | 1.67 | 1.05 | 0.776 | 0.628 |
| | Max | 0.00 | 1.57 | 2.93 | 3.67 | 3.00 | 1.85 | 1.14 | 0.872 | 0.880 |
| | CV % | | 86.6 | 29.5 | 39.4 | 27.1 | 19.8 | 13.5 | 23.2 | 90.2 |

TABLE 17

Compound III Concentration (ng/mL) Summary for Cohort 8 (200 mg BID of Form B) on Day 1.

| Compound III | | Time (h) | | | | | | | |
|---|---|---|---|---|---|---|---|---|---|
| | | 0.0 | 1.0 | 2.0 | 3.0 | 4.0 | 6.0 | 8.0 | 10.0 | 12.0 |
| Day 1 200 mg BID N = 4 | | | | | Concentration (ng/mL) | | | | | |
| | Mean | 0.00 | 1.15 | 1.66 | 2.27 | 2.43 | 2.39 | 1.27 | 0.663 | 0.357 |
| | SD | 0.00 | 0.969 | 1.12 | 0.972 | 1.11 | 1.25 | 0.503 | 0.521 | 0.415 |
| | Min | 0.00 | 0.00 | 0.00 | 0.908 | 1.03 | 1.40 | 0.822 | 0.00 | 0.00 |
| | Median | 0.00 | 1.30 | 2.11 | 2.49 | 2.57 | 2.04 | 1.16 | 0.702 | 0.328 |
| | Max | 0.00 | 2.00 | 2.42 | 3.21 | 3.56 | 4.07 | 1.94 | 1.25 | 0.771 |
| | CV % | | 84.3 | 67.7 | 42.8 | 45.8 | 52.5 | 39.6 | 78.5 | 116.2 |

The Day 29 Concentration-Time Data of Compound I for all Cohorts is provided in Tables 18 to 25.

TABLE 18

Compound I Concentration (ng/mL) Summary for Cohort 1 (200 mg QD of Form B) on Day 29.

| Compound I | | Time (h) | | | | | | | | |
|---|---|---|---|---|---|---|---|---|---|---|
| | | 0.0 | 1.0 | 2.0 | 3.0 | 4.0 | 6.0 | 8.0 | 10.0 | 12.0 | 24.0 |
| Day 29 200 mg QD N = 5 | | | | | | Concentration (ng/mL) | | | | | |
| | N | 5 | 5 | 5 | 5 | 5 | 5 | 5 | 5 | 5 | 3 |
| | Mean | 4.05 | 5.12 | 6.92 | 12.5 | 17.5 | 18.5 | 14.6 | 11.1 | 8.46 | 6.01 |
| | SD | 1.93 | 2.13 | 2.17 | 4.48 | 7.18 | 10.3 | 11.2 | 7.97 | 5.45 | 4.14 |
| | Min | 2.06 | 2.04 | 3.30 | 5.90 | 5.46 | 4.35 | 3.50 | 3.14 | 2.29 | 2.54 |
| | Median | 4.10 | 5.35 | 7.27 | 11.8 | 18.8 | 17.9 | 12.1 | 8.70 | 8.32 | 4.90 |
| | Max | 6.06 | 7.83 | 9.12 | 16.7 | 24.2 | 32.0 | 31.8 | 23.1 | 17.0 | 10.6 |
| | CV % | 47.7 | 41.6 | 31.4 | 35.7 | 41.1 | 55.6 | 76.8 | 71.9 | 64.4 | 68.9 |

TABLE 19

Compound I Concentration (ng/mL) Summary for Cohort 2 (300 mg QD of Form B) on Day 29.

| Compound I | | Time (h) | | | | | | | | |
|---|---|---|---|---|---|---|---|---|---|---|
| | | 0.0 | 1.0 | 2.0 | 3.0 | 4.0 | 6.0 | 8.0 | 10.0 | 12.0 | 24.0 |
| Day 29 300 mg QD N = 3 | | | | | | Concentration(ng/mL) | | | | | |
| | Mean | 13.9 | 16.2 | 22.6 | 31.0 | 44.9 | 35.9 | 31.5 | 25.6 | 26.4 | 14.4 |
| | SD | 10.8 | 8.32 | 15.9 | 21.3 | 24.6 | 10.2 | 9.73 | 12.9 | 11.7 | 8.29 |
| | Min | 7.16 | 8.32 | 8.50 | 12.5 | 27.5 | 24.5 | 21.0 | 17.5 | 18.8 | 8.50 |
| | Median | 8.24 | 15.4 | 19.5 | 26.3 | 34.2 | 39.2 | 33.3 | 18.9 | 20.5 | 10.9 |
| | Max | 26.3 | 24.9 | 39.9 | 54.3 | 73.0 | 44.0 | 40.2 | 40.5 | 39.8 | 23.9 |
| | CV % | 77.4 | 51.3 | 70.4 | 68.6 | 54.7 | 28.3 | 30.9 | 50.3 | 44.2 | 57.4 |

TABLE 20

Compound I Concentration (ng/mL) Summary for Cohort 3 (400 mg QD of Form B) on Day 29.

| Compound I | | | Time (h) | | | | | | | | |
|---|---|---|---|---|---|---|---|---|---|---|---|
| | | | 0.0 | 1.0 | 2.0 | 3.0 | 4.0 | 6.0 | 8.0 | 10.0 | 12.0 | 24.0 |
| Day 29 | 400 mg QD | N = 3 | | | | | Concentration(ng/mL) | | | | | |
| | | Mean | 6.80 | 8.07 | 11.1 | 14.2 | 17.0 | 18.9 | 17.0 | 14.2 | 11.8 | 6.26 |
| | | SD | 4.11 | 4.05 | 5.87 | 6.51 | 9.37 | 10.5 | 9.48 | 6.54 | 6.30 | 2.97 |
| | | Min | 2.37 | 3.43 | 4.38 | 6.69 | 6.24 | 6.94 | 6.25 | 6.66 | 4.84 | 2.98 |
| | | Median | 7.52 | 9.88 | 13.4 | 17.2 | 21.2 | 23.2 | 20.5 | 17.1 | 13.5 | 7.04 |
| | | Max | 10.5 | 10.9 | 15.4 | 18.6 | 23.5 | 26.7 | 24.2 | 18.7 | 17.1 | 8.77 |
| | | CV % | 60.5 | 50.2 | 53.1 | 46.0 | 55.2 | 55.7 | 55.8 | 46.2 | 53.3 | 47.5 |

TABLE 21

Compound I Concentration (ng/mL) Summary for Cohort 4 (500 mg QD of Form B) on Day 29.

| Compound I | | | Time (h) | | | | | | | | |
|---|---|---|---|---|---|---|---|---|---|---|---|
| | | | 0.0 | 1.0 | 2.0 | 3.0 | 4.0 | 6.0 | 8.0 | 10.0 | 12.0 | 24.0 |
| Day 29 | 500 mg QD | N = 3 | | | | | Concentration (ng/mL) | | | | | |
| | | Mean | 14.4 | 21.2 | 34.2 | 40.3 | 41.8 | 41.5 | 34.1 | 26.7 | 24.4 | 12.5 |
| | | SD | 2.14 | 7.15 | 9.16 | 6.86 | 8.45 | 4.54 | 4.43 | 2.17 | 2.08 | 1.90 |
| | | Min | 12.0 | 16.5 | 25.3 | 33.0 | 32.2 | 36.4 | 30.0 | 25.3 | 22.0 | 10.4 |
| | | Median | 15.3 | 17.6 | 33.8 | 41.4 | 44.9 | 43.2 | 33.5 | 25.6 | 25.2 | 13.0 |
| | | Max | 16.0 | 29.4 | 43.6 | 46.6 | 48.2 | 45.0 | 38.8 | 29.2 | 25.9 | 14.1 |
| | | CV % | 14.8 | 33.8 | 26.8 | 17.0 | 20.2 | 10.9 | 13.0 | 8.1 | 8.5 | 15.2 |

TABLE 22

Compound I Concentration (ng/mL) Summary for Cohort 5 (650 mg QD of Form B) on Day 29.

| Compound I | | | Time (h) | | | | | | | | |
|---|---|---|---|---|---|---|---|---|---|---|---|
| | | | 0.0 | 1.0 | 2.0 | 3.0 | 4.0 | 6.0 | 8.0 | 10.0 | 12.0 | 24.0 |
| Day 29 | 650 mg QD | N = 3 | | | | | Concentration (ng/mL) | | | | | |
| | | N= | 3 | 2 | 2 | 2 | 2 | 2 | 2 | 2 | 2 | 2 |
| | | Mean | 20.9 | 20.9 | 25.9 | 28.4 | 33.1 | 58.8 | 66.0 | 58.1 | 46.3 | 24.3 |
| | | SD | 8.85 | 12.4 | 12.8 | 15.8 | 15.2 | 29.1 | 32.2 | 28.5 | 23.9 | 5.02 |
| | | Min | 11.4 | 12.1 | 16.8 | 17.2 | 22.3 | 38.2 | 43.2 | 37.9 | 29.4 | 20.7 |
| | | Median | 22.5 | 20.9 | 25.9 | 28.4 | 33.1 | 58.8 | 66.0 | 58.1 | 46.3 | 24.3 |
| | | Max | 28.9 | 29.6 | 34.9 | 39.5 | 43.8 | 79.3 | 88.7 | 78.2 | 63.2 | 27.8 |
| | | CV % | 42.3 | 59.3 | 49.5 | 55.6 | 46.0 | 49.5 | 48.8 | 49.1 | 51.6 | 20.7 |

TABLE 23

Compound I Concentration (ng/mL) Summary for Cohort 6 (100 mg BID of Form B) on Day 29.

| Compound I | | | Time (h) | | | | | | | | |
|---|---|---|---|---|---|---|---|---|---|---|---|
| | | | 0.0 | 1.0 | 2.0 | 3.0 | 4.0 | 6.0 | 8.0 | 10.0 | 12.0 |
| Day 29 | 100 mg BID | N = 5 | | | | | Concentration (ng/mL) | | | | | |
| | | Mean | 4.35 | 9.25 | 11.0 | 10.5 | 10.5 | 8.82 | 7.45 | 6.23 | 7.16 |
| | | SD | 3.13 | 6.42 | 6.48 | 6.12 | 5.55 | 4.47 | 3.80 | 3.17 | 3.43 |
| | | Min | 1.54 | 1.79 | 2.94 | 4.40 | 5.14 | 4.10 | 3.61 | 2.88 | 2.37 |
| | | Median | 4.13 | 9.34 | 11.8 | 8.31 | 9.26 | 8.11 | 6.57 | 5.44 | 8.36 |
| | | Max | 9.20 | 15.7 | 19.6 | 20.5 | 19.8 | 16.2 | 13.8 | 11.4 | 10.1 |
| | | CV % | 72.0 | 69.4 | 58.9 | 58.4 | 53.0 | 50.7 | 51.0 | 50.9 | 47.9 |

TABLE 24

Compound I Concentration (ng/mL) Summary for Cohort 7 (150 mg BID of Form B) on Day 29.

| Compound I | | | 0.0 | 1.0 | 2.0 | 3.0 | Time (h) 4.0 | 6.0 | 8.0 | 10.0 | 12.0 |
|---|---|---|---|---|---|---|---|---|---|---|---|
| Day 29 | 150 mg BID | N = 3 | | | | | Concentration(ng/mL) | | | | |
| | | Mean | 26.2 | 37.6 | 41.3 | 46.0 | 50.2 | 38.0 | 36.7 | 32.2 | 28.5 |
| | | SD | 22.1 | 16.9 | 21.0 | 27.0 | 28.8 | 25.5 | 27.2 | 24.4 | 25.9 |
| | | Min | 9.03 | 27.0 | 24.6 | 25.7 | 30.5 | 20.3 | 15.8 | 13.0 | 10.2 |
| | | Median | 18.5 | 28.7 | 34.3 | 35.6 | 36.9 | 26.5 | 26.9 | 23.8 | 17.3 |
| | | Max | 51.1 | 57.0 | 64.9 | 76.6 | 83.2 | 67.2 | 67.4 | 59.7 | 58.1 |
| | | CV % | 84.2 | 44.9 | 51.0 | 58.7 | 57.3 | 67.0 | 74.0 | 76.0 | 90.6 |

TABLE 25

Compound I Concentration (ng/mL) Summary for Cohort 8 (200 mg BID of Form B) on Day 29.

| Compound I | | | 0.0 | 1.0 | 2.0 | 3.0 | Time (h) 4.0 | 6.0 | 8.0 | 10.0 | 12.0 |
|---|---|---|---|---|---|---|---|---|---|---|---|
| Day 29 | 200 mg BID | N = 3 | | | | | Concentration (ng/mL) | | | | |
| | | Mean | 9.74 | 9.23 | 12.0 | 15.2 | 21.1 | 19.0 | 14.6 | 18.6 | 19.8 |
| | | SD | 6.49 | 4.10 | 5.84 | 7.51 | 11.9 | 10.4 | 7.17 | 17.6 | 18.4 |
| | | Min | 5.47 | 5.10 | 5.56 | 7.49 | 7.69 | 7.60 | 7.36 | 5.61 | 6.32 |
| | | Median | 6.54 | 9.29 | 13.3 | 15.6 | 25.1 | 21.1 | 14.8 | 11.7 | 12.4 |
| | | Max | 17.2 | 13.3 | 17.0 | 22.5 | 30.5 | 28.1 | 21.7 | 38.6 | 40.8 |
| | | CV % | 66.6 | 44.4 | 48.8 | 49.4 | 56.5 | 55.0 | 49.1 | 94.2 | 92.8 |

The Day 29 Concentration-Time Data for Metabolite Compound III for all cohorts is provided in Tables 26 to 33.

TABLE 26

Compound III Concentration (ng/mL) Summary for Cohort 1 (200 mg QD of Form B) on Day 29.

| Compound III | | | 0.0 | 1.0 | 2.0 | 3.0 | Time (h) 4.0 | 6.0 | 8.0 | 10.0 | 12.0 | 24.0 |
|---|---|---|---|---|---|---|---|---|---|---|---|---|
| Day 29 | 200 mg QD | N = 5 | | | | | Concentration (ng/mL) | | | | | |
| | | N | 5 | 5 | 5 | 5 | 5 | 5 | 5 | 5 | 5 | 3 |
| | | Mean | 0.343 | 0.968 | 1.43 | 2.39 | 2.82 | 2.35 | 1.73 | 1.12 | 0.803 | 0.670 |
| | | SD | 0.511 | 0.868 | 0.624 | 1.06 | 1.47 | 2.26 | 1.90 | 1.07 | 0.903 | 0.708 |
| | | Min | 0.00 | 0.00 | 0.685 | 0.856 | 0.864 | 0.00 | 0.00 | 0.00 | 0.00 | 0.00 |
| | | Median | 0.00 | 0.890 | 1.53 | 2.28 | 2.52 | 1.99 | 1.41 | 0.891 | 0.890 | 0.600 |
| | | Max | 1.14 | 2.34 | 2.30 | 3.80 | 4.84 | 6.11 | 4.96 | 2.85 | 2.20 | 1.41 |
| | | CV % | 148.7 | 89.7 | 43.5 | 44.4 | 51.9 | 96.1 | 110.0 | 96.1 | 112.5 | 105.6 |

TABLE 27

Compound III Concentration (ng/mL) Summary for Cohort 2 (300 mg QD of Form B) on Day 29.

| Compound III | | | 0.0 | 1.0 | 2.0 | 3.0 | Time (h) 4.0 | 6.0 | 8.0 | 10.0 | 12.0 | 24.0 |
|---|---|---|---|---|---|---|---|---|---|---|---|---|
| Day 29 | 300 mg QD | N = 3 | | | | | Concentration (ng/mL) | | | | | |
| | | Mean | 1.66 | 2.01 | 3.28 | 4.08 | 5.23 | 4.39 | 4.00 | 3.06 | 2.47 | 1.45 |
| | | SD | 1.45 | 0.985 | 0.677 | 0.797 | 0.466 | 0.900 | 1.89 | 1.79 | 1.51 | 0.991 |
| | | Min | 0.677 | 1.01 | 2.50 | 3.17 | 4.70 | 3.64 | 2.31 | 1.56 | 1.13 | 0.782 |
| | | Median | 0.976 | 2.03 | 3.63 | 4.44 | 5.44 | 4.15 | 3.65 | 2.58 | 2.18 | 0.983 |
| | | Max | 3.32 | 2.98 | 3.71 | 4.64 | 5.56 | 5.39 | 6.05 | 5.05 | 4.11 | 2.59 |
| | | CV % | 87.3 | 49.1 | 20.6 | 19.5 | 8.9 | 20.5 | 47.3 | 58.6 | 61.1 | 68.3 |

TABLE 28

Compound III Concentration (ng/mL) Summary for Cohort 3 (400 mg QD of Form B) on Day 29.

| Compound III | | | | Time (h) | | | | | | | |
|---|---|---|---|---|---|---|---|---|---|---|---|
| | | | 0.0 | 1.0 | 2.0 | 3.0 | 4.0 | 6.0 | 8.0 | 10.0 | 12.0 | 24.0 |
| Day29 | 400 mg QD | N = 3 | | | | Concentration (ng/mL) | | | | | | |
| | | Mean | 0.914 | 1.67 | 2.23 | 2.77 | 3.05 | 3.31 | 2.48 | 1.98 | 1.59 | 0.815 |
| | | SD | 0.202 | 0.465 | 0.903 | 0.612 | 0.707 | 1.08 | 0.748 | 0.424 | 0.597 | 0.105 |
| | | Min | 0.681 | 1.32 | 1.64 | 2.26 | 2.24 | 2.55 | 1.84 | 1.50 | 1.02 | 0.707 |
| | | Median | 1.02 | 1.50 | 1.78 | 2.61 | 3.40 | 2.84 | 2.29 | 2.12 | 1.54 | 0.821 |
| | | Max | 1.04 | 2.20 | 3.27 | 3.45 | 3.52 | 4.54 | 3.30 | 2.31 | 2.21 | 0.916 |
| | | CV % | 22.1 | 27.8 | 40.5 | 22.1 | 23.2 | 32.5 | 30.2 | 21.4 | 37.5 | 12.8 |

TABLE 29

Compound III Concentration (ng/mL) Summary for Cohort 4 (500 mg QD of Form B) on Day 29.

| Compound III | | | | Time (h) | | | | | | | |
|---|---|---|---|---|---|---|---|---|---|---|---|
| | | | 0.0 | 1.0 | 2.0 | 3.0 | 4.0 | 6.0 | 8.0 | 10.0 | 12.0 | 24.0 |
| Day 29 | 500 mg QD | N = 3 | | | | Concentration (ng/mL) | | | | | | |
| | | Mean | 1.76 | 2.98 | 4.39 | 5.90 | 5.77 | 4.18 | 3.56 | 2.66 | 2.33 | 1.24 |
| | | SD | 0.522 | 0.820 | 0.847 | 1.66 | 1.97 | 0.686 | 0.251 | 0.191 | 0.225 | 0.316 |
| | | Min | 1.41 | 2.06 | 3.61 | 4.66 | 4.04 | 3.55 | 3.30 | 2.52 | 2.10 | 0.959 |
| | | Median | 1.51 | 3.23 | 4.26 | 5.25 | 5.37 | 4.07 | 3.58 | 2.59 | 2.34 | 1.17 |
| | | Max | 2.36 | 3.64 | 5.29 | 7.79 | 7.91 | 4.91 | 3.80 | 2.88 | 2.55 | 1.58 |
| | | CV % | 29.7 | 27.5 | 19.3 | 28.2 | 34.1 | 16.4 | 7.0 | 7.2 | 9.7 | 25.5 |

TABLE 30

Compound III Concentration (ng/mL) Summary for Cohort 5 (650 mg QD of Form B) on Day 29.

| Compound III | | | | Time (h) | | | | | | | |
|---|---|---|---|---|---|---|---|---|---|---|---|
| | | | 0.0 | 1.0 | 2.0 | 3.0 | 4.0 | 6.0 | 8.0 | 10.0 | 12.0 | 24.0 |
| Day 29 | 650 mg QD | N = 3 | | | | Concentration (ng/mL) | | | | | | |
| | | N= | 3 | 2 | 2 | 2 | 2 | 2 | 2 | 2 | 2 | 2 |
| | | Mean | 2.22 | 2.49 | 3.14 | 3.89 | 4.78 | 7.57 | 8.64 | 8.02 | 6.06 | 3.04 |
| | | SD | 1.01 | 1.70 | 1.82 | 1.80 | 1.92 | 3.20 | 4.89 | 4.78 | 3.73 | 0.778 |
| | | Min | 1.30 | 1.28 | 1.85 | 2.61 | 3.42 | 5.30 | 5.18 | 4.64 | 3.42 | 2.49 |
| | | Median | 2.06 | 2.49 | 3.14 | 3.89 | 4.78 | 7.57 | 8.64 | 8.02 | 6.06 | 3.04 |
| | | Max | 3.30 | 3.69 | 4.42 | 5.16 | 6.14 | 9.83 | 12.1 | 11.4 | 8.69 | 3.59 |
| | | CV % | 45.5 | 68.6 | 58.0 | 46.4 | 40.2 | 42.3 | 56.6 | 59.6 | 61.5 | 25.6 |

TABLE 31

Compound III Concentration (ng/mL) Summary for Cohort 6 (100 mg BID of Form B) on Day 29.

| Compound III | | | | Time (h) | | | | | | |
|---|---|---|---|---|---|---|---|---|---|---|
| | | | 0.0 | 1.0 | 2.0 | 3.0 | 4.0 | 6.0 | 8.0 | 10.0 | 12.0 |
| Day 29 | 100 mg BID | N = 5 | | | | Concentration (ng/mL) | | | | | |
| | | Mean | 0.451 | 1.26 | 1.79 | 1.60 | 1.50 | 1.15 | 0.837 | 0.676 | 0.840 |
| | | SD | 0.473 | 1.27 | 1.08 | 0.737 | 0.658 | 0.533 | 0.585 | 0.491 | 0.845 |
| | | Min | 0.00 | 0.00 | 0.740 | 0.838 | 0.855 | 0.608 | 0.00 | 0.00 | 0.00 |
| | | Median | 0.542 | 1.37 | 1.56 | 1.30 | 1.14 | 1.07 | 0.824 | 0.643 | 1.03 |
| | | Max | 1.13 | 2.90 | 3.11 | 2.47 | 2.43 | 1.83 | 1.55 | 1.33 | 1.97 |
| | | CV % | 104.7 | 100.9 | 60.6 | 46.2 | 44.0 | 46.2 | 69.8 | 72.6 | 100.6 |

TABLE 32

Compound III Concentration (ng/mL) Summary for Cohort 7 (150 mg BID of Form B) on Day 29.

| Compound III | | Time (h) | | | | | | | |
|---|---|---|---|---|---|---|---|---|---|
| | | 0.0 | 1.0 | 2.0 | 3.0 | 4.0 | 6.0 | 8.0 | 10.0 | 12.0 |
| Day 29  150 mg BID  N = 3 | | Concentration (ng/mL) | | | | | | | | |
| | Mean | 2.90 | 4.64 | 5.31 | 5.87 | 5.76 | 3.89 | 3.32 | 2.76 | 2.22 |
| | SD | 4.01 | 3.49 | 3.67 | 4.96 | 5.58 | 3.82 | 3.58 | 3.15 | 2.62 |
| | Min | 0.00 | 2.33 | 2.85 | 2.93 | 2.37 | 1.43 | 0.928 | 0.597 | 0.506 |
| | Median | 1.23 | 2.93 | 3.55 | 3.09 | 2.72 | 1.94 | 1.59 | 1.30 | 0.914 |
| | Max | 7.48 | 8.66 | 9.53 | 11.6 | 12.2 | 8.29 | 7.44 | 6.37 | 5.23 |
| | CV % | 138.1 | 75.3 | 69.1 | 84.5 | 96.8 | 98.3 | 108.0 | 114.3 | 118.1 |

TABLE 33

Compound III Concentration (ng/mL) Summary for Cohort 7 (200 mg BID of Form B) on Day 29.

| Compound III | | Time (h) | | | | | | | |
|---|---|---|---|---|---|---|---|---|---|
| | | 0.0 | 1.0 | 2.0 | 3.0 | 4.0 | 6.0 | 8.0 | 10.0 | 12.0 |
| Day 29  200 mg BID  N = 3 | | Concentration (ng/mL) | | | | | | | | |
| | Mean | 0.940 | 1.19 | 1.61 | 1.85 | 2.25 | 2.19 | 1.58 | 2.01 | 2.03 |
| | SD | 0.824 | 0.185 | 0.436 | 0.606 | 0.682 | 0.856 | 0.519 | 1.70 | 1.83 |
| | Min | 0.00 | 1.00 | 1.35 | 1.49 | 1.48 | 1.28 | 1.10 | 0.986 | 0.746 |
| | Median | 1.28 | 1.20 | 1.36 | 1.51 | 2.51 | 2.31 | 1.51 | 1.06 | 1.21 |
| | Max | 1.54 | 1.37 | 2.11 | 2.55 | 2.77 | 2.98 | 2.13 | 3.97 | 4.12 |
| | CV % | 87.7 | 15.6 | 27.1 | 32.8 | 30.3 | 39.1 | 32.8 | 84.9 | 90.3 |

The Day 8, 15, and 22 Trough Concentration Data of Compound I for all cohorts is provided in Tables 34 to 41.

TABLE 34

Trough Compound I Concentration (ng/mL) Summary for Cohort 1 (200 mg QD of Form B).

| 200 mg QD | Analyte = Compound I | N = 6 | Day | | |
|---|---|---|---|---|---|
| | | | 8 | 15 | 22 |
| | | | Concentration (ng/mL) | | |
| | | Mean | 4.93 | 5.56 | 6.24 |
| | | SD | 2.31 | 4.37 | 3.82 |
| | | Min | 2.80 | 1.86 | 2.43 |
| | | Median | 4.22 | 4.59 | 5.32 |
| | | Max | 8.79 | 13.5 | 11.1 |
| | | CV % | 46.8 | 78.6 | 61.2 |

TABLE 35

Trough Compound I Concentration (ng/mL) Summary for Cohort 2 (300 mg QD of Form B).

| 300 mg QD | Analyte = Compound I | N = 3 | Day | | |
|---|---|---|---|---|---|
| | | | 8 | 15 | 22 |
| | | | Concentration (ng/mL) | | |
| | | Mean | 14.0 | 16.7 | 16.4 |
| | | SD | 7.01 | 9.50 | 12.2 |
| | | Min | 5.92 | 5.96 | 7.92 |
| | | Median | 17.3 | 19.9 | 10.9 |
| | | Max | 18.7 | 24.1 | 30.4 |
| | | CV % | 50.2 | 57.0 | 74.4 |

TABLE 36

Trough Compound I Concentration (ng/mL) Summary for Cohort 3 (400 mg QD of Form B).

| 400 mg QD | Analyte = Compound I | N = 3 | Day | | |
|---|---|---|---|---|---|
| | | | 8 | 15 | 22 |
| | | | Concentration (ng/mL) | | |
| | | Mean | 5.63 | 6.66 | 9.34 |
| | | SD | 1.56 | 3.09 | 3.04 |
| | | Min | 3.87 | 4.46 | 5.91 |
| | | Median | 6.16 | 5.33 | 10.4 |
| | | Max | 6.85 | 10.2 | 11.7 |
| | | CV % | 27.7 | 46.4 | 32.5 |

TABLE 37

Trough Compound I Concentration (ng/mL) Summary for Cohort 4 (500 mg QD of Form B).

| 500 mg QD | Analyte = Compound I | N = 4 | Day | | |
|---|---|---|---|---|---|
| | | | 8 | 15 | 22 |
| | | | Concentration (ng/mL) | | |
| | | N | 3 | 4 | 3 |
| | | Mean | 17.1 | 23.8 | 19.8 |
| | | SD | 6.45 | 8.76 | 6.70 |
| | | Min | 10.6 | 14.5 | 14.4 |
| | | Median | 17.2 | 23.9 | 17.7 |
| | | Max | 23.5 | 32.8 | 27.3 |
| | | CV % | 37.7 | 36.8 | 33.8 |

TABLE 38

Trough Compound I Concentration (ng/mL) Summary for Cohort 5 (650 mg QD of Form B).

| 650 mg QD | Analyte = Compound I | N = 6 | Day 8 Concentration (ng/mL) | Day 15 | Day 22 |
|---|---|---|---|---|---|
| | | N= | 6 | 3 | 3 |
| | | Mean | 28.9 | 25.7 | 30.3 |
| | | SD | 10.6 | 5.98 | 11.6 |
| | | Min | 17.0 | 19.1 | 23.3 |
| | | Median | 28.3 | 27.4 | 24.0 |
| | | Max | 43.9 | 30.7 | 43.7 |
| | | CV % | 36.8 | 23.2 | 38.2 |

TABLE 39

Trough Compound I Concentration (ng/mL) Summary for Cohort 6 (100 mg BID of Form B).

| 100 mg BID | Analyte = Compound I | N = 6 | Day 8 Concentration (ng/mL) | Day 15 | Day 22 |
|---|---|---|---|---|---|
| | | Mean | 8.78 | 8.92 | 5.70 |
| | | SD | 7.81 | 7.07 | 3.45 |
| | | Min | 3.29 | 3.31 | 2.34 |
| | | Median | 5.49 | 6.34 | 4.42 |
| | | Max | 23.7 | 22.0 | 10.9 |
| | | CV % | 88.9 | 79.3 | 60.5 |

TABLE 40

Trough Compound I Concentration (ng/mL) Summary for Cohort 7 (150 mg BID of Form B).

| 150 mg BID | Analyte = Compound I | N = 3 | Day 8 Concentration (ng/mL) | Day 15 | Day 22 |
|---|---|---|---|---|---|
| | | Mean | 26.8 | 24.8 | 20.6 |
| | | SD | 13.5 | 10.2 | 8.55 |
| | | Min | 17.4 | 15.5 | 15.5 |
| | | Median | 20.6 | 23.3 | 15.9 |
| | | Max | 42.3 | 35.7 | 30.5 |
| | | CV % | 50.6 | 41.0 | 41.4 |

TABLE 41

Trough Compound I Concentration (ng/mL) Summary for Cohort 8 (200 mg BID of Form B).

| 200 mg BID | Analyte = Compound I | N = 3 | Day 8 Concentration (ng/mL) | Day 15 | Day 22 |
|---|---|---|---|---|---|
| | | N= | 3 | 2 | 3 |
| | | Mean | 9.41 | 11.0 | 7.11 |
| | | SD | 9.27 | 7.49 | 7.83 |
| | | Min | 1.72 | 5.71 | 0.00 |
| | | Median | 6.82 | 11.0 | 5.83 |
| | | Max | 19.7 | 16.3 | 15.5 |
| | | CV % | 98.4 | 68.0 | 110.0 |

The Day 8, 15, and 22 Trough Concentration Data of metabolite Compound III for all cohorts is provided in Tables 42 to 49.

TABLE 42

Trough Compound III Concentration (ng/mL) Summary for Cohort 1 (200 mg QD of Form B).

| 200 mg QD | Analyte = Compound III | N = 6 | Day 8 Concentration (ng/mL) | Day 15 | Day 22 |
|---|---|---|---|---|---|
| | | Mean | 0.453 | 0.554 | 0.628 |
| | | SD | 0.588 | 0.575 | 0.693 |
| | | Min | 0.00 | 0.00 | 0.00 |
| | | Median | 0.285 | 0.572 | 0.555 |
| | | Max | 1.48 | 1.57 | 1.37 |
| | | CV % | 129.9 | 103.8 | 110.4 |

TABLE 43

Trough Compound III Concentration (ng/mL) Summary for Cohort 2 (300 mg QD of Form B).

| 300 mg QD | Analyte = Compound III | N = 3 | Day 8 Concentration (ng/mL) | Day 15 | Day 22 |
|---|---|---|---|---|---|
| | | Mean | 1.19 | 1.80 | 1.72 |
| | | SD | 0.435 | 1.09 | 1.34 |
| | | Min | 0.742 | 0.835 | 0.924 |
| | | Median | 1.22 | 1.57 | 0.975 |
| | | Max | 1.61 | 2.98 | 3.27 |
| | | CV % | 36.5 | 60.7 | 77.8 |

TABLE 44

Trough Compound III Concentration (ng/mL) Summary for Cohort 3 (400 mg QD of Form B).

| 400 mg QD | Analyte = Compound III | N = 3 | Day 8 Concentration (ng/mL) | Day 15 | Day 22 |
|---|---|---|---|---|---|
| | | Mean | 0.406 | 0.435 | 0.729 |
| | | SD | 0.364 | 0.377 | 0.210 |
| | | Min | 0.00 | 0.00 | 0.515 |
| | | Median | 0.515 | 0.640 | 0.736 |
| | | Max | 0.702 | 0.665 | 0.935 |
| | | CV % | 89.6 | 86.7 | 28.8 |

TABLE 45

Trough Compound III Concentration (ng/mL) Summary for Cohort 4 (500 mg QD of Form B).

| 500 mg QD | Analyte = Compound III | N = 4 | Day 8 Concentration (ng/mL) | Day 15 | Day 22 |
|---|---|---|---|---|---|
| | | N | 3 | 4 | 3 |
| | | Mean | 1.71 | 2.07 | 1.73 |
| | | SD | 0.238 | 0.636 | 0.332 |
| | | Min | 1.53 | 1.33 | 1.50 |
| | | Median | 1.62 | 2.15 | 1.58 |

TABLE 45-continued

Trough Compound III Concentration (ng/mL)
Summary for Cohort 4 (500 mg QD of Form B).

| | | | | Day | |
|---|---|---|---|---|---|
| | | | 8 | 15 | 22 |
| 500 mg QD | Analyte = Compound III | N = 4 | | Concentration (ng/mL) | |
| | | Max | 1.98 | 2.66 | 2.11 |
| | | CV % | 13.9 | 30.7 | 19.2 |

TABLE 46

Trough Compound III Concentration (ng/mL)
Summary for Cohort 5 (650 mg QD of Form B).

| | | | | Day | |
|---|---|---|---|---|---|
| | | | 8 | 15 | 22 |
| 650 mg QD | Analyte = Compound III | N = 6 | | Concentration (ng/mL) | |
| | | N= | 6 | 3 | 3 |
| | | Mean | 3.55 | 3.13 | 3.70 |
| | | SD | 1.48 | 0.740 | 1.73 |
| | | Min | 1.65 | 2.28 | 2.34 |
| | | Median | 3.79 | 3.52 | 3.11 |
| | | Max | 4.96 | 3.60 | 5.65 |
| | | CV % | 41.8 | 23.6 | 46.8 |

TABLE 47

Trough Compound III Concentration (ng/mL)
Summary for Cohort 6 (100 mg BID of Form B).

| | | | | Day | |
|---|---|---|---|---|---|
| | | | 8 | 15 | 22 |
| 100 mg BID | Analyte = Compound III | N = 6 | | Concentration (ng/mL) | |
| | | Mean | 1.17 | 0.898 | 0.734 |
| | | SD | 1.94 | 0.849 | 0.883 |
| | | Min | 0.00 | 0.00 | 0.00 |
| | | Median | 0.481 | 0.895 | 0.403 |
| | | Max | 4.99 | 1.98 | 1.83 |
| | | CV % | 165.7 | 94.5 | 120.2 |

TABLE 48

Trough Compound III Concentration (ng/mL) Summary for Cohort 7 (150 mg BID of Form B).

| | | | | Day | |
|---|---|---|---|---|---|
| | | | 8 | 15 | 22 |
| 150 mg BID | Analyte = Compound III | N = 3 | | Concentration (ng/mL) | |
| | | Mean | 2.62 | 2.34 | 2.17 |
| | | SD | 2.08 | 1.66 | 1.81 |
| | | Min | 1.35 | 0.962 | 1.02 |
| | | Median | 1.48 | 1.88 | 1.23 |
| | | Max | 5.02 | 4.18 | 4.26 |
| | | CV % | 79.6 | 70.8 | 83.6 |

TABLE 49

Trough Compound III Concentration (ng/mL)
Summary for Cohort 8 (200 mg BID of Form B).

| | | | | Day | |
|---|---|---|---|---|---|
| | | | 8 | 15 | 22 |
| 200 mg BID | Analyte = Compound III | N = 3 | | Concentration (ng/mL) | |
| | | N= | 3 | 2 | 3 |
| | | Mean | 1.03 | 1.50 | 1.05 |
| | | SD | 1.36 | 0.952 | 1.02 |
| | | Min | 0.00 | 0.823 | 0.00 |
| | | Median | 0.518 | 1.50 | 1.12 |
| | | Max | 2.57 | 2.17 | 2.04 |
| | | CV % | 132.0 | 63.6 | 97.0 |

Example 2. Calculation of Pharmacokinetic Parameters for Compound I in Once a Day (QD) and Twice a Day (BID) Dosing Cohorts of Form B of Compound II The following pharmacokinetic parameters were calculated from the concentration versus time data obtained in Example 1 for each of the above QD (200 mg, 300 mg, 400 mg, 500 mg, or 650 mg dosed) and BID (100 mg, 150 mg, or 200 mg doses) Form B of Compound II dosage cohorts:

$C_{max}$— the observed peak plasma concentration determined from the plasma concentration versus time data obtained on Day 1 and Day 29, as applicable;

$T_{max}$—the time to reach the observed peak plasma concentration from the plasma concentration versus time data obtained on Day 1 and Day 29, as applicable;

AUC—area under the plasma concentration versus time curve during a dosing interval on Day 1 and Day 29, as applicable; and $R_{acc}$—accumulation ratio calculated as $AUC_{Day\ 29}$/$AUC_{Day\ 1}$.

The Day 1 pharmacokinetic parameters for Compound I for all cohorts is provided in Tables 50 to 57.

TABLE 50

Noncompartmental Pharmacokinetic Parameters of Compound I for Cohort 1 (200 mg QD of Form B) on Day 1.

| Compound I | Day 1 | 200 mg QD | N = 6 | $C_{max}$ (ng/mL) | $T_{max}$ (h) | $AUC_{last}$ (h * ng/mL) |
|---|---|---|---|---|---|---|
| | | | Mean | 25.5 | 4.17 | 215 |
| | | | SD | 10.8 | 0.983 | 91.5 |
| | | | Min | 8.26 | 3.00 | 98.9 |
| | | | Median | 27.0 | 4.00 | 232 |
| | | | Max | 40.0 | 6.00 | 355 |
| | | | CV % | 42.5 | 23.6 | 42.5 |

TABLE 51

Noncompartmental Pharmacokinetic Parameters of Compound I for Cohort 2 (300 mg QD of Form B) on Day 1.

| Compound I | Day 1 | 300 mg QD | N = 3 | $C_{max}$ (ng/mL) | $T_{max}$ (h) | $AUC_{last}$ (h * ng/mL) |
|---|---|---|---|---|---|---|
| | | | Mean | 40.2[a] | 4.67 | 413[a] |
| | | | SD | 28.1 | 1.15 | 266 |
| | | | Min | 10.2 | 4.00 | 106 |
| | | | Median | 44.3 | 4.00 | 554 |

TABLE 51-continued

Noncompartmental Pharmacokinetic Parameters of Compound I for Cohort 2 (300 mg QD of Form B) on Day 1.

| Compound I | Day 1 | 300 mg QD | N = 3 | $C_{max}$ (ng/mL) | $T_{max}$ (h) | $AUC_{last}$ (h * ng/mL) |
|---|---|---|---|---|---|---|
|  |  |  | Max | 66.0 | 6.00 | 580 |
|  |  |  | CV % | 70.0 | 24.7 | 64.4 |

[a] $C_{max}$ of 55.2 and $AUC_{last}$ of 567 obtained upon exclusion of data for patient that vomited immediately after dosing.

TABLE 52

Noncompartmental Pharmacokinetic Parameters of Compound I for Cohort 3 (400 mg QD of Form B) on Day 1.

| Compound I | Day 1 | 400 mg QD | N = 3 | $C_{max}$ (ng/mL) | $T_{max}$ (h) | $AUC_{last}$ (h * ng/mL) |
|---|---|---|---|---|---|---|
|  |  |  | Mean | 20.1 | 6.00 | 202 |
|  |  |  | SD | 5.16 | 0.00 | 39.2 |
|  |  |  | Min | 14.4 | 6.00 | 177 |
|  |  |  | Median | 21.6 | 6.00 | 183 |
|  |  |  | Max | 24.4 | 6.00 | 248 |
|  |  |  | CV % | 25.6 | 0.0 | 19.4 |

TABLE 53

Noncompartmental Pharmacokinetic Parameters of Compound I for Cohort 4 (500 mg QD of Form B) on Day 1.

| Compound I | Day 1 | 500 mg QD | N = 4 | $C_{max}$ (ng/mL) | $T_{max}$ (h) | $AUC_{last}$ (h * ng/mL) |
|---|---|---|---|---|---|---|
|  |  |  | Mean | 48.9 | 5.75 | 577 |
|  |  |  | SD | 16.7 | 2.06 | 121 |
|  |  |  | Min | 27.8 | 3.00 | 403 |
|  |  |  | Median | 49.6 | 6.00 | 611 |
|  |  |  | Max | 68.7 | 8.00 | 684 |
|  |  |  | CV % | 34.2 | 35.9 | 21.0 |

TABLE 54

Noncompartmental Pharmacokinetic Parameters of Compound I for Cohort 5 (650 mg QD of Form B) on Day 1.

| Compound I | Day 1 | 650 mg QD | N = 6 | $C_{max}$ (ng/mL) | $T_{max}$ (h) | $AUC_{last}$ (h * ng/mL) |
|---|---|---|---|---|---|---|
|  |  |  | Mean | 62.5 | 7.67 | 799 |
|  |  |  | SD | 17.8 | 1.97 | 224 |
|  |  |  | Min | 38.2 | 4.00 | 482 |
|  |  |  | Median | 67.0 | 8.00 | 805 |
|  |  |  | Max | 80.7 | 10.0 | 1040 |
|  |  |  | CV % | 28.5 | 25.6 | 28.0 |

TABLE 55

Noncompartmental Pharmacokinetic Data of Compound I for Cohort 6 (100 mg BID of Form B) on Day 1.

| Compound I | Day 1 | 100 mg BID | N = 6 | $C_{max}$ (ng/mL) | $T_{max}$ (h) | $AUC_{last}$ (h * ng/mL) |
|---|---|---|---|---|---|---|
|  |  |  | Mean | 10.2 | 3.17 | 59.7 |
|  |  |  | SD | 3.15 | 0.753 | 20.1 |
|  |  |  | Min | 7.25 | 2.00 | 42.8 |
|  |  |  | Median | 8.95 | 3.00 | 53.1 |
|  |  |  | Max | 14.7 | 4.00 | 92.6 |
|  |  |  | CV % | 30.8 | 23.8 | 33.6 |

TABLE 56

Noncompartmental Pharmacokinetic Data of Compound I for Cohort 7 (150 mg BID of Form B) on Day 1.

| Compound I | Day 1 | 150 mg BID | N = 3 | $C_{max}$ (ng/mL) | $T_{max}$ (h) | $AUC_{last}$ (h * ng/mL) |
|---|---|---|---|---|---|---|
|  |  |  | Mean | 21.7 | 3.67 | 130 |
|  |  |  | SD | 8.43 | 0.577 | 23.7 |
|  |  |  | Min | 12.2 | 3.00 | 103 |
|  |  |  | Median | 24.6 | 4.00 | 141 |
|  |  |  | Max | 28.3 | 4.00 | 146 |
|  |  |  | CV % | 38.9 | 15.7 | 18.2 |

TABLE 57

Noncompartmental Pharmacokinetic Data of Compound I for Cohort 7 (200 mg BID of Form B) on Day 1.

| Compound I | Day 1 | 200 mg BID | N = 4 | $C_{max}$ (ng/mL) | $T_{max}$ (h) | $AUC_{last}$ (h * ng/mL) |
|---|---|---|---|---|---|---|
|  |  |  | Mean | 17.3 | 5.00 | 118 |
|  |  |  | SD | 10.3 | 1.15 | 62.1 |
|  |  |  | Min | 5.28 | 4.00 | 37.9 |
|  |  |  | Median | 17.6 | 5.00 | 125 |
|  |  |  | Max | 29.0 | 6.00 | 185 |
|  |  |  | CV % | 59.6 | 23.1 | 52.6 |

The Day 29 pharmacokinetic parameters for compound I for all cohorts is provided in Tables 58 to 65.

TABLE 58

Noncompartmental Pharmacokinetic Data of Compound I for Cohort 1 (200 mg QD of Form B) on Day 29.

| 200 mg QD | N = 5 |  | $C_{max}$ (ng/mL) | $T_{max}$ (h) | $AUC_{last}$ (h * ng/mL) | $R_{acc}$ ((h * ng/mL)/(h * ng/mL)) |
|---|---|---|---|---|---|---|
|  |  | Mean | 20.4 | 4.20 | 229 | 1.17 |
|  |  | SD | 9.52 | 1.10 | 126 | 0.362 |
|  |  | Min | 5.90 | 3.00 | 73.2 | 0.740 |
|  |  | Median | 21.3 | 4.00 | 227 | 1.15 |
|  |  | Max | 32.0 | 6.00 | 407 | 1.72 |
|  |  | CV % | 46.6 | 26.1 | 55.0 | 31.1 |

TABLE 59

Noncompartmental Pharmacokinetic Data of Compound I for Cohort 2 (300 mg QD of Form B) on Day 29.

| 300 mg QD | N = 3 |  | $C_{max}$ (ng/mL) | $T_{max}$ (h) | $AUC_{last}$ (h * ng/mL) | $R_{acc}$ ((h * ng/mL)/(h * ng/mL)) |
|---|---|---|---|---|---|---|
|  |  | Mean | 47.0[a] | 6.00 | 592 | 2.03 |
|  |  | SD | 23.4 | 3.46 | 203 | 1.39 |
|  |  | Min | 27.5 | 4.00 | 384 | 1.04 |
|  |  | Median | 40.5 | 4.00 | 604 | 1.42 |
|  |  | Max | 73.0 | 10.0 | 789 | 3.62 |
|  |  | CV % | 49.9 | 57.7 | 34.2 | 68.6 |

TABLE 60

Noncompartmental Pharmacokinetic Data of Compound I for Cohort 3 (400 mg QD of Form B) on Day 29.

| 400 mg QD | N = 3 | $C_{max}$ (ng/mL) | $T_{max}$ (h) | $AUC_{last}$ (h * ng/mL) | $R_{acc}$ ((h * ng/mL)/(h * ng/mL)) |
|---|---|---|---|---|---|
| Mean | | 19.0 | 5.33 | 278 | 1.35 |
| SD | | 10.6 | 1.15 | 142 | 0.639 |
| Min | | 6.94 | 4.00 | 115 | 0.653 |
| Median | | 23.5 | 6.00 | 348 | 1.50 |
| Max | | 26.7 | 6.00 | 371 | 1.90 |
| CV % | | 55.7 | 21.7 | 50.9 | 47.2 |

TABLE 61

Noncompartmental Pharmacokinetic Data of Compound I for Cohort 4 (500 mg QD of Form B) on Day 29.

| 500 mg QD | N = 3 | $C_{max}$ (ng/mL) | $T_{max}$ (h) | $AUC_{last}$ (h * ng/mL) | $R_{acc}$ ((h * ng/mL)/(h * ng/mL)) |
|---|---|---|---|---|---|
| Mean | | 43.2 | 5.33 | 607 | 1.12 |
| SD | | 6.10 | 1.15 | 47.3 | 0.300 |
| Min | | 36.4 | 4.00 | 570 | 0.932 |
| Median | | 45.0 | 6.00 | 591 | 0.965 |
| Max | | 48.2 | 6.00 | 660 | 1.47 |
| CV % | | 14.1 | 21.7 | 7.8 | 26.7 |

TABLE 62

Noncompartmental Pharmacokinetic Data of Compound I for Cohort 5 (650 mg QD of Form B) on Day 29.

| 650 mg QD | N = 2 | $C_{max}$ (ng/mL) | $T_{max}$ (h) | $AUC_{last}$ (h * ng/mL) | $R_{acc}$ ((h * ng/mL)/(h * ng/mL)) |
|---|---|---|---|---|---|
| Mean | | 43.2 | 5.33 | 607 | 1.12 |
| SD | | 6.10 | 1.15 | 47.3 | 0.300 |
| Min | | 36.4 | 4.00 | 570 | 0.932 |
| Median | | 45.0 | 6.00 | 591 | 0.965 |
| Max | | 48.2 | 6.00 | 660 | 1.47 |
| CV % | | 14.1 | 21.7 | 7.8 | 26.7 |

TABLE 63

Noncompartmental Pharmacokinetic Data of Compound I for Cohort 6 (100 mg BID of Form B) on Day 29.

| 100 mg BID | N = 5 | $C_{max}$ (ng/mL) | $T_{max}$ (h) | $AUC_{last}$ (h * ng/mL) | $R_{acc}$ ((h * ng/mL)/(h * ng/mL)) |
|---|---|---|---|---|---|
| Mean | | 12.3 | 4.40 | 101 | 1.90 |
| SD | | 6.01 | 4.39 | 51.8 | 0.851 |
| Min | | 5.14 | 1.00 | 41.1 | 0.931 |
| Median | | 11.8 | 3.00 | 88.2 | 2.06 |
| Max | | 20.5 | 12.0 | 183 | 2.96 |
| CV % | | 49.0 | 99.8 | 51.5 | 44.7 |

TABLE 64

Noncompartmental Pharmacokinetic Data of Compound I for Cohort 7 (150 mg BID of Form B) on Day 29.

| 150 mg BID | N = 3 | $C_{max}$ (ng/mL) | $T_{max}$ (h) | $AUC_{last}$ (h * ng/mL) | $R_{acc}$ ((h * ng/mL)/(h * ng/mL)) |
|---|---|---|---|---|---|
| Mean | | 50.2 | 4.00 | 455 | 3.88 |
| SD | | 28.8 | 0.00 | 299 | 3.33 |
| Min | | 30.5 | 4.00 | 235 | 1.66 |
| Median | | 36.9 | 4.00 | 334 | 2.28 |
| Max | | 83.2 | 4.00 | 795 | 7.71 |
| CV % | | 57.3 | 0.0 | 65.7 | 85.7 |

TABLE 65

Noncompartmental Pharmacokinetic Data of Compound I for Cohort 8 (200 mg BID of Form B) on Day 29.

| 200 mg BID | N = 3 | $C_{max}$ (ng/mL) | $T_{max}$ (h) | $AUC_{last}$ (h * ng/mL) | $R_{acc}$ ((h * ng/mL)/(h * ng/mL)) |
|---|---|---|---|---|---|
| Mean | | 26.3 | 6.67 | 197 | 2.06 |
| SD | | 16.9 | 4.62 | 113 | 0.128 |
| Min | | 7.69 | 4.00 | 79.8 | 1.91 |
| Median | | 30.5 | 4.00 | 205 | 2.11 |
| Max | | 40.8 | 12.0 | 306 | 2.15 |
| CV % | | 64.4 | 69.3 | 57.5 | 6.2 |

The Day 1 pharmacokinetic parameters for Compound III for all cohorts is provided in Tables 66 to 73.

TABLE 66

Noncompartmental Pharmacokinetic Data of Compound III for Cohort 1 (200 mg QD of Form B) on Day 1.

| Compound III | Day 1 | 200 mg QD | N = 6 | $C_{max}$ (ng/mL) | $T_{max}$ (h) | $AUC_{last}$ (h * ng/mL) |
|---|---|---|---|---|---|---|
| | | | Mean | 4.18 | 4.17 | 23.7 |
| | | | SD | 2.41 | 0.983 | 19.6 |
| | | | Min | 1.27 | 3.00 | 5.29 |
| | | | Median | 3.88 | 4.00 | 21.3 |
| | | | Max | 7.82 | 6.00 | 58.5 |
| | | | CV % | 57.6 | 23.6 | 82.7 |

TABLE 67

Noncompartmental Pharmacokinetic Data of Compound III for Cohort 2 (300 mg QD of Form B) on Day 1.

| Compound III | Day 1 | 300 mg QD | N = 3 | $C_{max}$ (ng/mL) | $T_{max}$ (h) | $AUC_{last}$ (h * ng/mL) |
|---|---|---|---|---|---|---|
| | | | Mean | 4.81 | 3.67 | 43.1 |
| | | | SD | 2.59 | 2.52 | 28.5 |
| | | | Min | 1.82 | 1.00 | 10.9 |
| | | | Median | 6.21 | 4.00 | 53.1 |
| | | | Max | 6.40 | 6.00 | 65.2 |
| | | | CV % | 53.9 | 68.6 | 66.1 |

TABLE 68

Noncompartmental Pharmacokinetic Data of Compound III for Cohort 3 (400 mg QD of Form B) on Day 1.

| Compound III | Day 1 | 400 mg QD | N = 3 | | $C_{max}$ (ng/mL) | $T_{max}$ (h) | $AUC_{last}$ (h * ng/mL) |
|---|---|---|---|---|---|---|---|
| | | | | Mean | 4.85 | 4.33 | 25.6 |
| | | | | SD | 1.93 | 2.89 | 6.81 |
| | | | | Min | 3.02 | 1.00 | 17.8 |
| | | | | Median | 4.66 | 6.00 | 29.2 |
| | | | | Max | 6.87 | 6.00 | 29.8 |
| | | | | CV % | 39.8 | 66.6 | 26.6 |

TABLE 69

Noncompartmental Pharmacokinetic Data of Compound III for Cohort 4 (500 mg QD of Form B) on Day 1.

| Compound III | Day 1 | 500 mg QD | N = 4 | | $C_{max}$ (ng/mL) | $T_{max}$ (h) | $AUC_{last}$ (h * ng/mL) |
|---|---|---|---|---|---|---|---|
| | | | | Mean | 7.98 | 5.50 | 77.7 |
| | | | | SD | 1.13 | 1.00 | 12.9 |
| | | | | Min | 6.84 | 4.00 | 61.6 |
| | | | | Median | 8.03 | 6.00 | 79.0 |
| | | | | Max | 9.03 | 6.00 | 91.4 |
| | | | | CV % | 14.2 | 18.2 | 16.7 |

TABLE 70

Noncompartmental Pharmacokinetic Data of Compound III for Cohort 5 (650 mg QD of Form B) on Day 1.

| Compound III | Day 1 | 650 mg QD | N = 6 | | $C_{max}$ (ng/mL) | $T_{max}$ (h) | $AUC_{last}$ (h * ng/mL) |
|---|---|---|---|---|---|---|---|
| | | | | Mean | 10.9 | 6.67 | 123 |
| | | | | SD | 3.71 | 1.63 | 40.1 |
| | | | | Min | 5.56 | 4.00 | 61.8 |
| | | | | Median | 10.4 | 7.00 | 125 |
| | | | | Max | 16.5 | 8.00 | 174 |
| | | | | CV % | 34.2 | 24.5 | 32.6 |

TABLE 71

Noncompartmental Pharmacokinetic Data of Compound III for Cohort 6 (100 mg BID of Form B) on Day 1.

| Compound III | Day 1 | 100 mg BID | N = 6 | | $C_{max}$ (ng/mL) | $T_{max}$ (h) | $AUC_{last}$ (h * ng/mL) |
|---|---|---|---|---|---|---|---|
| | | | | Mean | 1.59 | 3.17 | 5.37 |
| | | | | SD | 0.343 | 0.753 | 2.32 |
| | | | | Min | 1.11 | 2.00 | 2.87 |
| | | | | Median | 1.60 | 3.00 | 5.18 |
| | | | | Max | 2.12 | 4.00 | 8.61 |
| | | | | CV % | 21.6 | 23.8 | 43.3 |

TABLE 72

Noncompartmental Pharmacokinetic Data of Compound III for Cohort 7 (150 mg BID of Form B) on Day 1.

| Compound III | Day 1 | 150 mg BID | N = 3 | | $C_{max}$ (ng/mL) | $T_{max}$ (h) | $AUC_{last}$ (h * ng/mL) |
|---|---|---|---|---|---|---|---|
| | | | | Mean | 3.20 | 3.00 | 16.5 |
| | | | | SD | 0.409 | 1.00 | 0.929 |
| | | | | Min | 2.93 | 2.00 | 15.7 |
| | | | | Median | 3.00 | 3.00 | 16.3 |
| | | | | Max | 3.67 | 4.00 | 17.5 |
| | | | | CV % | 12.8 | 33.3 | 5.6 |

TABLE 73

Noncompartmental Pharmacokinetic Data of Compound III for Cohort 8 (200 mg BID of Form B) on Day 1.

| Compound III | Day 1 | 200 mg BID | N = 4 | | $C_{max}$ (ng/mL) | $T_{max}$ (h) | $AUC_{last}$ (h * ng/mL) |
|---|---|---|---|---|---|---|---|
| | | | | Mean | 2.87 | 4.75 | 17.2 |
| | | | | SD | 1.19 | 1.50 | 8.49 |
| | | | | Min | 1.40 | 3.00 | 6.18 |
| | | | | Median | 3.00 | 5.00 | 18.6 |
| | | | | Max | 4.07 | 6.00 | 25.4 |
| | | | | CV % | 41.6 | 31.6 | 49.5 |

The Day 29 pharmacokinetic parameters for Compound III for all cohorts is provided in Tables 74 to 81.

TABLE 74

Noncompartmental Pharmacokinetic Data of Compound III for Cohort 1 (200 mg QD of Form B) on Day 29.

| Compound III | Day 29 | 200 mg QD | N = 5 | | $C_{max}$ (ng/mL) | $T_{max}$ (h) | $AUC_{last}$ (h * ng/mL) |
|---|---|---|---|---|---|---|---|
| | | | | Mean | 3.14 | 4.20 | 27.9 |
| | | | | SD | 1.96 | 1.10 | 23.5 |
| | | | | Min | 0.864 | 3.00 | 1.97 |
| | | | | Median | 2.52 | 4.00 | 25.4 |
| | | | | Max | 6.11 | 6.00 | 64.2 |
| | | | | CV % | 62.3 | 26.1 | 84.3 |

TABLE 75

Noncompartmental Pharmacokinetic Data of Compound III for Cohort 2 (300 mg QD of Form B) on Day 29.

| Compound III | Day 29 | 300 mg QD | N = 3 | | $C_{max}$ (ng/mL) | $T_{max}$ (h) | $AUC_{last}$ (h * ng/mL) |
|---|---|---|---|---|---|---|---|
| | | | | Mean | 5.44 | 5.33 | 66.2 |
| | | | | SD | 0.683 | 2.31 | 27.6 |
| | | | | Min | 4.70 | 4.00 | 45.1 |
| | | | | Median | 5.56 | 4.00 | 56.1 |
| | | | | Max | 6.05 | 8.00 | 97.5 |
| | | | | CV % | 12.6 | 43.3 | 41.7 |

TABLE 76

Noncompartmental Pharmacokinetic Data of Compound III for Cohort 3 (400 mg QD of Form B) on Day 29.

| Compound III | Day 29 | 400 mg QD | N = 3 | | $C_{max}$ (ng/mL) | $T_{max}$ (h) | $AUC_{last}$ (h * ng/mL) |
|---|---|---|---|---|---|---|---|
| | | | | Mean | 3.50 | 5.33 | 42.6 |
| | | | | SD | 0.999 | 1.15 | 11.4 |
| | | | | Min | 2.55 | 4.00 | 32.2 |
| | | | | Median | 3.40 | 6.00 | 40.9 |
| | | | | Max | 4.54 | 6.00 | 54.7 |
| | | | | CV % | 28.6 | 21.7 | 26.7 |

TABLE 77

Noncompartmental Pharmacokinetic Data of Compound III for Cohort 4 (500 mg QD of Form B) on Day 29.

| Compound III | Day 29 | 500 mg QD | N = 3 | | $C_{max}$ (ng/mL) | $T_{max}$ (h) | $AUC_{last}$ (h * ng/mL) |
|---|---|---|---|---|---|---|---|
| | | | | Mean | 5.98 | 3.67 | 66.4 |
| | | | | SD | 1.71 | 0.577 | 5.73 |
| | | | | Min | 4.66 | 3.00 | 59.8 |
| | | | | Median | 5.37 | 4.00 | 69.6 |
| | | | | Max | 7.91 | 4.00 | 69.8 |
| | | | | CV % | 28.6 | 15.7 | 8.6 |

TABLE 78

Noncompartmental Pharmacokinetic Data of Compound III for Cohort 5 (650 mg QD of Form B) on Day 29.

| Compound III | Day 29 | 650 mg QD | N = 2 | | $C_{max}$ (ng/mL) | $T_{max}$ (h) | $AUC_{last}$ (h * ng/mL) |
|---|---|---|---|---|---|---|---|
| | | | | Mean | 8.70 | 7.00 | 125 |
| | | | | SD | 4.81 | 1.41 | 62.2 |
| | | | | Min | 5.30 | 6.00 | 80.6 |
| | | | | Median | 8.70 | 7.00 | 125 |
| | | | | Max | 12.1 | 8.00 | 169 |
| | | | | CV % | 55.3 | 20.2 | 49.9 |

TABLE 79

Noncompartmental Pharmacokinetic Data of Compound III for Cohort 6 (100 mg BID of Form B) on Day 29.

| Compound III | Day 29 | 100 mg BID | N = 5 | | $C_{max}$ (ng/mL) | $T_{max}$ (h) | $AUC_{last}$ (h * ng/mL) |
|---|---|---|---|---|---|---|---|
| | | | | Mean | 1.89 | 4.40 | 13.0 |
| | | | | SD | 0.977 | 4.34 | 7.91 |
| | | | | Min | 0.855 | 2.00 | 3.45 |
| | | | | Median | 1.56 | 2.00 | 9.86 |
| | | | | Max | 3.11 | 12.0 | 21.6 |
| | | | | CV % | 51.8 | 98.5 | 60.8 |

TABLE 80

Noncompartmental Pharmacokinetic Data of Compound III for Cohort 7 (150 mg BID of Form B) on Day 29.

| Compound III | Day 29 | 150 mg BID | N = 3 | | $C_{max}$ (ng/mL) | $T_{max}$ (h) | $AUC_{last}$ (h * ng/mL) |
|---|---|---|---|---|---|---|---|
| | | | | Mean | 6.23 | 3.00 | 47.9 |
| | | | | SD | 5.18 | 1.00 | 46.0 |
| | | | | Min | 2.93 | 2.00 | 19.4 |
| | | | | Median | 3.55 | 3.00 | 23.3 |
| | | | | Max | 12.2 | 4.00 | 101 |
| | | | | CV % | 83.2 | 33.3 | 96.1 |

TABLE 81

Noncompartmental Pharmacokinetic Data of Compound III for Cohort 8 (200 mg BID of Form B) on Day 29.

| Compound III | Day 29 | 200 mg BID | N = 3 | | $C_{max}$ (ng/mL) | $T_{max}$ (h) | $AUC_{last}$ (h * ng/mL) |
|---|---|---|---|---|---|---|---|
| | | | | Mean | 2.79 | 6.33 | 22.0 |
| | | | | SD | 1.32 | 4.93 | 8.01 |
| | | | | Min | 1.49 | 3.00 | 15.2 |
| | | | | Median | 2.77 | 4.00 | 20.1 |
| | | | | Max | 4.12 | 12.0 | 30.8 |
| | | | | CV % | 47.1 | 77.9 | 36.4 |

Tables 82A, 82B, and 82C provide baseline characteristics and patient disposition for all dosage cohorts studied.

TABLE 82A

Baseline Characteristics

| | Age, median years (range) | ECOG PS, n (%) 0 | ECOG PS, n (%) 1 | Menopausal status, n (%) Pre/peri meno-pausal | Menopausal status, n (%) post-meno-pausal | Visceral metastasis, n (%) |
|---|---|---|---|---|---|---|
| Dose (mg) | | | | | | |
| 200 QD (n = 6) | 58 (44, 69) | 4 (67) | 2 (33) | 1 (17) | 5 (83) | 4 (67) |
| 300 QD (n = 3) | 46 (45, 72) | 1 (33) | 2 (67) | 0 | 3 (100) | 3 (100) |
| 400 QD (n = 3) | 55 (50, 59) | 3 (100) | 0 | 1 (33) | 2 (67) | 3 (100) |
| 500 QD (n = 3) | 54 (25, 63) | 3 (100) | 0 | 1 (33) | 2 (67) | 3 (100) |
| 650 QD (n = 6) | 63 (56, 65) | 5 (83) | 1 (17) | 0 | 6 (100) | 6 (100) |
| 100 BID (n = 6) | 61 (47, 67) | 5 (83) | 1 (17) | 1 (17) | 5 (83) | 5 (83) |
| 150 BID (n = 3) | 55 (40, 59) | 2 (67) | 1 (33) | 1 (33) | 2 (67) | 2 (67) |
| 200 BID (n = 3) | 53 (47, 63) | 3 (100) | 0 | 1 (33) | 2 (67) | 2 (67) |
| All cohorts (n = 33) | 59 (25, 72) | 26 (79) | 7 (21) | 6 (18) | 27 (82) | 25 (76) |

TABLE 82B

Baseline Characteristics, Continued

Prior Lines of Therapy, median (range)

| Dose (mg) | Total | Endocrine | Chemo-therapy | Prior Aromatase Inhibitor Therapy, n (%) |
|---|---|---|---|---|
| 200 QD (n = 6) | 2 (2-4) | 2 (1-2) | 0.5 (0-2) | 5 (83) |
| 300 QD (n = 3) | 3 (1-3) | 1 (1-3) | 2 (0-2) | 1 (33) |
| 400 QD (n = 3) | 3 (3-4) | 2 (1-3) | 1 (1-2) | 3 (100) |
| 500 QD (n = 3) | 3 (2-3) | 2 (1-2) | 1 (1-1) | 2 (67) |
| 650 QD (n = 6) | 3.5 (3-8) | 2 (1-5) | 2 (1-3) | 3 (75) |
| 100 BID (n = 6) | 2 (1-3) | 1 (0-2) | 1 (1-3) | 2 (33) |
| 150 BID (n = 3) | 5 (5-6) | 3 (3-3) | 2 (2-3) | 3 (100) |

TABLE 82B-continued

| Baseline Characteristics, Continued | | | | |
|---|---|---|---|---|
| | Prior Lines of Therapy, median (range) | | | |
| Dose (mg) | Total | Endocrine | Chemo-therapy | Prior Aromatase Inhibitor Therapy, n (%) |
| 200 BID (n = 3) | 5.5 (3-8) | 3.5 (2-5) | 1.5 (1-2) | 1 (50) |
| All cohorts (n = 33) | 3 (1-8) | 2 (0-5) | 1 (1-3) | 20 (67) |

TABLE 82C

| Patient Disposition | | | | | |
|---|---|---|---|---|---|
| | | | Discontinued | | |
| Dose (mg) | Ongoing Treatment | Total | Adverse Event | Disease Progression | Patient Decision |
| 200 QD (n = 6) | 3 (50) | 3 (50) | 0 | 2 | 1 |
| 300 QD (n = 3) | 2 (67) | 1 (33) | 0 | 1 | 0 |
| 400 QD (n = 3) | 2 (67) | 1 (33) | 0 | 1 | 0 |
| 500 QD (n = 3) | 2 (67) | 1 (33) | 0 | 1 | 0 |
| 650 QD (n = 6) | 6 (100) | 0 | 0 | 0 | 0 |
| 100 BID (n = 6) | 3 (50) | 3 (50) | 0 | 2 | 1 |
| 150 BID (n = 3) | 3 (50) | 3 (50) | 0 | 2 | 1 |
| 200 BID (n = 3) | 3 (50) | 3 (50) | 0 | 0 | 0 |
| All cohorts (n = 33) | 22 (67) | 11 (33) | 0 | 10 | 1 |

Table 83 provides a summary of adverse events for all dosing cohorts by CTCAE grade and frequency.

TABLE 83

| Adverse Events by CTCAE Grade and Frequency | | | | | | | | | |
|---|---|---|---|---|---|---|---|---|---|
| Dose (mg) | Neutropenia | Leukopenia | Nausea | Diarrhea | Vomiting | Anemia | Fatigue | Thrombocytopenia | Hematuria |
| 200 QD | 4 | 4 | 0 | 1 | 0 | 3 | 0 | 0 | 1 |
| 300 QD | 3 | 2 | 2 | 2 | 2 | 1 | 1 | 1 | 1 |
| 400 QD | 3 | 0 | 3 | 2 | 3 | 2 | 2 | 1 | 1 |
| 500 QD | 3 | 1 | 3 | 1 | 1 | 2 | 1 | 3 | 0 |
| 650 QD | 2 | 2 | 3 | 4 | 5 | 0 | 1 | 0 | 0 |
| 100 BID | 4 | 3 | 2 | 1 | 0 | 2 | 1 | 1 | 1 |
| 150 BID | 3 | 3 | 1 | 2 | 1 | 1 | 1 | 1 | 1 |
| 200 BID | 2 | 1 | 1 | 1 | 0 | 0 | 1 | 0 | 0 |
| Total | | | | | | | | | |
| Grade 1 | 6 | 4 | 8 | 6 | 5 | 3 | 5 | 5 | 5 |
| Grade 2 | 7 | 9 | 7 | 8 | 3 | 2 | 3 | 2 | 0 |
| Grade 3 | 9 | 3 | 0 | 0 | 0 | 1 | 0 | 0 | 0 |
| Grade 4 | 2 | 0 | 0 | 0 | 0 | 0 | 0 | 0 | 0 |
| All Grades | 24 | 16 | 15 | 14 | 12 | 11 | 8 | 7 | 5 |

| Dose (mg) | ALT increase | SCr increased | BUN increased | AST increased | Febrile neutropenia | GGT increased | Lymphopenia | Metrorrhagia | Stomatitis |
|---|---|---|---|---|---|---|---|---|---|
| 200 QD | 0 | 0 | 1 | 0 | 0 | 0 | 1 | 0 | 0 |
| 300 QD | 0 | 0 | 1 | 0 | 0 | 0 | 0 | 0 | 0 |
| 400 QD | 1 | 0 | 0 | 1 | 0 | 1 | 0 | 0 | 0 |
| 500 QD | 1 | 1 | 0 | 0 | 0 | 0 | 0 | 0 | 0 |
| 650 QD | 0 | 0 | 0 | 0 | 0 | 0 | 0 | 0 | 0 |
| 100 BID | 0 | 1 | 0 | 0 | 0 | 0 | 0 | 0 | 0 |
| 150 BID | 0 | 0 | 0 | 0 | 1 | 0 | 0 | 1 | 1 |
| 200 BID | 0 | 0 | 0 | 0 | 0 | 0 | 0 | 0 | 0 |
| Total | | | | | | | | | |
| Grade 1 | 1 | 2 | 2 | 0 | 0 | 0 | 0 | 0 | 0 |
| Grade 2 | 1 | 0 | 0 | 1 | 0 | 1 | 1 | 1 | 1 |
| Grade 3 | 0 | 0 | 0 | 0 | 1 | 0 | 0 | 0 | 0 |
| Grade 4 | 0 | 0 | 0 | 0 | 0 | 0 | 0 | 0 | 0 |
| All Grades | 2 | 2 | 2 | 1 | 1 | 1 | 1 | 1 | 1 |

Example 3. Calculation of Pharmacokinetic Parameters for Compound I for Administration of a Single Dose of Form B of Compound II in Healthy Volunteers Table 84 provides the pharmacokinetic parameters of Compound I upon administration of a single dose of Form B of Compound II (48, 100, 200, 300, 400, or 600 mg) in healthy volunteers. Blood samples for analysis of Compound I were collected pre-dose and 0.25, 0.5, 1, 1.5, 2, 3, 4, 6, 8, 12, 24, 36, 48, 72, and 96 hours post-dose.

TABLE 84

Pharmacokinetics of Compound I in Healthy Volunteers After a Single Dose of Form B of Compound II

| Dose (mg) | n | $T_{max}$, h (min, max) | $C_{max}$, ng/mL (CV %) | $AUC_{0-inf}$, ng * h/mL (CV %) | $T_{1/2}$, h (CV %) | CL/F, L/h (CV %) | $V_z/F$, (CV %) |
|---|---|---|---|---|---|---|---|
| 48 | 3 | 2.0 (1.97, 3.0) | 3.65 (64.6) | 20.4 (116.1) | 3.07 (57.5) | 2354 (116.1) | 10427 (40.6) |
| 100 | 3 | 2.0 (2.0, 4.0) | 9.23 (51.0) | 60.2 (18.8) | 4.71 (10.8) | 1660 (18.8) | 11277 (27.8) |
| 200 | 6 | 3.0 (2.0, 3.0) | 29.3 (21.6) | 275 (19.7) | 13.8 (17.5) | 727 (19.7) | 14514 (23.1) |
| 300 | 6 | 3.5 (3.0, 6.0) | 27.0 (38.6) | 349 (51.2) | 15.4 (24.3) | 861 (51.2) | 19130 (47.0) |
| 400 | 6 | 5.0 (1.5, 6.0) | 26.3 (70.6) | 432 (92.0) | 14.9 (36.3) | 926 (92.0) | 19915 (63.8) |
| 600 | 4 | 6.0 (6.0, 8.0) | 59.0 (49.5) | 886 (43.4) | 17.2 (27.2) | 677 (43.4) | 16822 (45.1) |

Example 4. Comparison of Steady-State Pharmacokinetic Parameters of Compound I, Palbociclib, and Ribociclib The mean steady-state AUC ($AUC_{0-24,ss}$) and (mean $AUC_{0-24,ss}$)/dose (mg) was determined for compound I from Day 29 concentration versus time data obtained in Example 1 and compared to published steady state AUC data for palbociclib (see Flaherty et al. Clin. Cancer Res. 2012, 18, 568-576; FDA Clin. Pharm. Review, Appl. No. 207103Orig1s000, submitted Aug. 13, 2014), ribociclib (see FDA Multi-Discipline Review, Appl. No. 209092Orig1s000, submitted Aug. 29, 2016), and abemaciclib (see Patnaik et al., Cancer Discov. 2016, 7, 740-53). The time to reach steady state was defined as five half-lives (97% steady state achieved). A summary of time to steady-state for Compound I, palbociclib, and ribociclib is provided in Table 85.

TABLE 85

Mean Half-Life and Time to Steady-State for Compound I, Palbociclib, and Ribociclib.

| Compound | Mean Half-Life (hr) | Time to Steady-State (hr) | Time to Steady State (days) |
|---|---|---|---|
| Compound I 200 mg QD of Form B of Compound II | 15.2 | 76 | 3.2 |
| Palbociclib 125 mg[a] QD | 26.5 | 132.5 | 5.5 |
| Ribociclib 600 mg[a] QD | 32.5 | 162.5 | 6.8 |

[a]FDA labeled doses of each drug.

The (mean $AUC_{0-24,ss}$)/dose was calculated for Compound I from Day 29 pharmacokinetic parameters for QD dosing of 200 mg, 300 mg, 400 mg, 500 mg, and 650 mg of Form B of Compound II as summarized in Table 86.

TABLE 86

Steady State Pharmacokinetic Parameters of Compound I for QD Dosing of Form B of Compound II.

| QD Dose (mg) | N= | Mean $C_{max}$ (ng/mL) | Mean $AUC_{0-24,ss}$ (h * ng/mL) | (Mean $AUC_{0-24,ss}$)/ Dose (mg) |
|---|---|---|---|---|
| 200 | 5 | 20.4 | 229 | 1.15 |
| 300 | 3 | 47.0 | 592 | 1.97 |
| 400 | 3 | 19.0 | 278 | 0.695 |
| 500 | 3 | 43.2 | 607 | 1.21 |
| 650 | 2 | 66.0 | 956 | 1.47 |

The steady-state $AUC_{0-24}$ for various doses of palbociclib provided in Table 87 was extrapolated from the above provided $AUC_{0-10}$ data from previous published studies by the following formula: $AUC_{0-24} = (AUC_{0-10}) * 2.49655$. The AUC data are presented as the arithmetic mean.

TABLE 87

Steady State AUC of Palbociclib for QD Dosing.

| QD Dose (mg) | N= | $AUC_{0-10,ss}$ (ng * h/mL) | Extrapolated $AUC_{0-24,ss}$ (ng * h/mL) | Extrapolated $(AUC_{0-24,ss})/$ dose (mg) |
|---|---|---|---|---|
| 25 | 3 | 119 | 297 | 11.88 |
| 50 | 3 | 274 | 684 | 13.68 |
| 75 | 7 | 492 | 1228 | 16.37 |
| 100 | 3 | 592 | 1478 | 14.78 |
| 125 | 22 | 724 | 1807 | 14.46 |
| 150 | 3 | 1084 | 2706 | 18.04 |

The steady-state $AUC_{0-24}$ for various doses of ribociclib provided in Table 88 was obtained from the above cited prior published studies. The AUC data are presented as the geometric mean.

TABLE 88

Steady-State AUC of Ribociclib for QD Dosing.

| QD Dose (mg) | N= | $AUC_{0-24,ss}$ (h * ng/mL) | $(AUC_{0-24,ss})/$ dose (mg) |
|---|---|---|---|
| 50 | 2-3 | 770 | 15.40 |
| 70 | 2 | 1000 | 14.29 |
| 140 | 3 | 2490 | 17.79 |
| 260 | 4 | 5990 | 23.04 |
| 280 | 3 | 6600 | 23.57 |
| 350 | 4 | 15300 | 43.71 |
| 400 | 4 | 14700 | 36.75 |
| 600 | 12-14 | 26600 | 44.33 |
| 750 | 4-6 | 22300 | 29.73 |
| 900 | 10-11 | 43500 | 48.33 |
| 1200 | 1 | 51800 | 43.17 |

The steady-state $AUC_{0-24}$ for various BID doses of abemaciclib provided in Table 89 was obtained from the above cited prior published studies. The AUC data are presented as the geometric mean.

TABLE 89

Steady-State AUC for Abemaciclib for BID Dosing.

| BID Dose (mg) | N= | $AUC_{0-24,ss}$ (h * ng/mL) | $(AUC_{0-24,ss})$/Dose (mg) |
|---|---|---|---|
| 75 | 3 | 1300 | 17.33 |
| 100 | 8 | 3910 | 39.10 |
| 150 | 72 | 4280 | 28.53 |
| 200 | 52 | 5520 | 27.60 |

Compound I consistently had $(AUC_{0-24,ss})$/Dose values not greater than 5, while those reported for palbociclib, ribociclib, and abemaciclib are consistently above 5.

The apparent volume of distribution ($V_d/F$) was calculated from the terminal rate constant ($k_e$) derived from the plasma concentration-versus-time data provided for Compound I in Example 1 when dosed with 200 mg QD of Form B of Compound II. A comparison of apparent volume of distribution ($V_d/F$) for Compound I, palbociclib, and ribociclib is provided in Table 90.

TABLE 90

Apparent Volume of Distribution ($V_d/F$) for Compound I, Palbociclib, and Ribociclib.

| Drug | Mean $V_d/F$ (L) |
|---|---|
| Compound I, (200 mg QD of compound II) | 15200 |
| Palbociclib, (125 mg QD) | 2583 |
| Ribociclib, (600 mg QD) | 1090 |

Example 5. Calculation of $(AUC_{0-24,ss})$/ANC of Compound I for QD Dosing of Form B of Compound II and Analysis of Mean Percent Change in ANC Absolute neutrophil count (ANC) was determined from the blood sample obtained from subjects described in Example 1 on day 22 using standard methods. The steady-state AUC ($AUC_{0-24,ss}$) was calculated as described in Example 3 for 200 mg, 300 mg, 400 mg, and 500 mg once a day (QD) doses of Form B of Compound II. As shown in Table 91, $(AUC_{0-24,ss})$/ANC was consistently less than 1.25 for all the doses examined. The Mean ANC ($10^9$ cells/L) combined for all dosing cohorts over 89 weeks of dosing showed vary little variation as provided in Table 92.

TABLE 91

$(AUC_{0-24,ss})$/ANC Ratio of Compound I for QD Dosing of Form B of Compound II.

| QD Dose (mg) | N= | Mean $AUC_{0-24,ss}$ (h * ng/mL) | Day 22 ANC, Mean (cells/mm³) | $(AUC_{0-24,ss})$/ANC |
|---|---|---|---|---|
| 200 | 5 | 229 | 2260 | 0.10 |
| 300 | 3 | 592 | 1267 | 0.47 |
| 400 | 6/3* | 278 | 1802 | 0.15 |
| 500 | 6/3* | 607 | 1338 | 0.45 |
| 650 | 6/3* | 956 | 1077 | 0.89 |

*number of patients with available ANC data/number of patients with available AUC data

TABLE 92

Mean ANC Over Time for All Dosing Cohorts of Form B of Compound II.

| Week | N= | Mean ANC ($10^9$ cells/L) |
|---|---|---|
| 4 (Day 22) | 72 | 1.53 |
| 8 | 63 | 1.79 |
| 12 | 44 | 1.87 |
| 17 | 36 | 1.87 |
| 21 | 31 | 1.53 |
| 25 | 27 | 1.55 |
| 29 | 24 | 1.62 |
| 33 | 20 | 1.72 |
| 37 | 19 | 1.77 |
| 41 | 18 | 1.88 |
| 45 | 16 | 1.99 |
| 49 | 14 | 1.72 |
| 53 | 13 | 1.82 |
| 57 | 12 | 1.76 |
| 61 | 10 | 1.63 |
| 65 | 9 | 1.86 |
| 69 | 8 | 1.80 |
| 73 | 5 | 1.96 |
| 77 | 5 | 1.84 |
| 81 | 3 | 1.91 |
| 85 | 3 | 2.00 |
| 89 | 3 | 2.52 |

Figure 2:
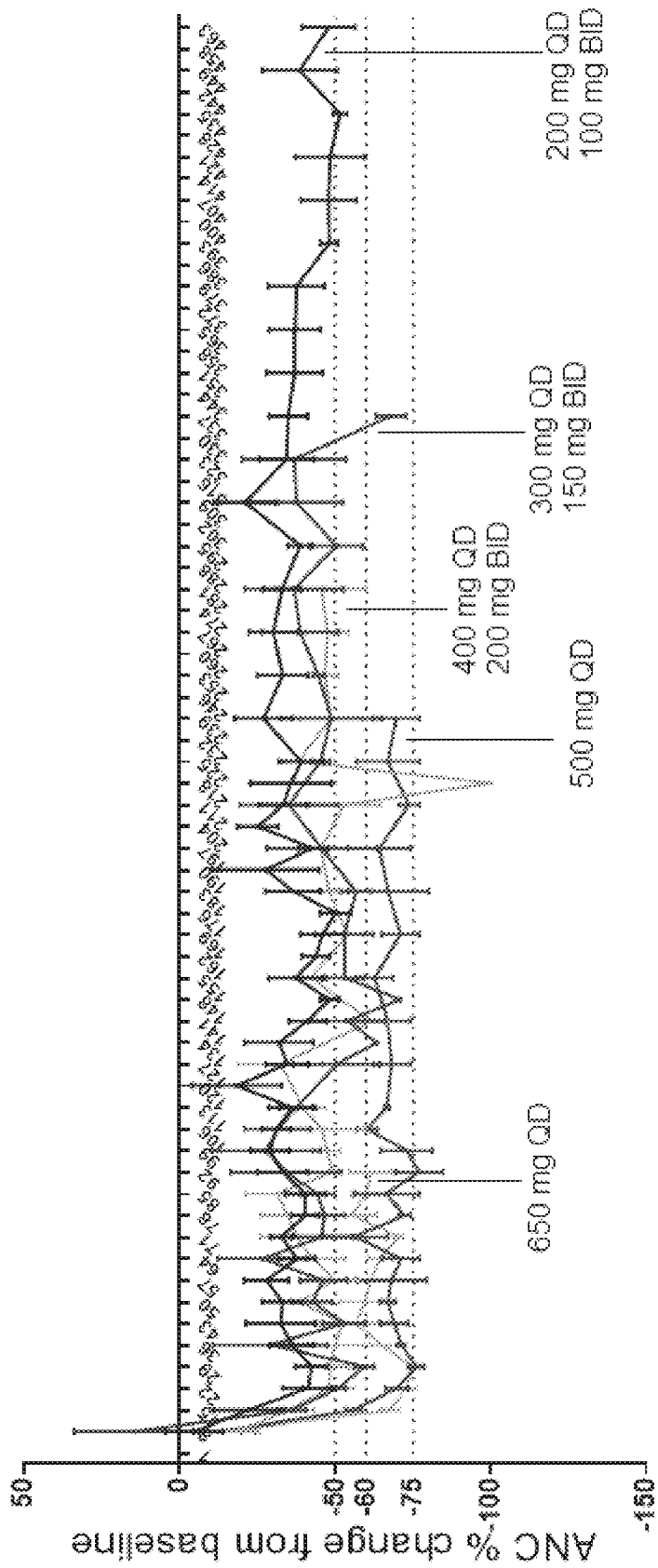
FIG. 2 is a graph of the mean absolute neutrophil count (ANC) percent change for cohorts dosed at 200 mg once a day (QD), 100 mg twice a day (BID), 300 mg QD, 150 mg BID, 400 mg QD, 200 mg BID, 500 mg QD, and 650 mg QD as measured on selected days of the study (Example 5). Cohorts that were dosed at 200 mg QD and 100 mg BID were combined in the graph. Cohorts that were dosed at 300 QD and 150 mg BID were combined in the graph. Cohorts that were dosed as 400 QD and 200 BID were combined in the graph. The x axis is time measured in days and the y axis is ANC change in baseline measured percent.

Absolute neutrophil count (ANC) was also determined for blood samples obtained from subjects in all dosing cohorts (200 mg QD, 300 mg QD, 400 mg QD, 500 mg QD, 100 mg BID, and 150 mg BID dosage of Form B of Compound II). The mean ANC results over time for the different dosing cohorts is shown in FIG. 1. The mean ANC percent change for different dosing cohorts is shown in FIG. 2. Table 93 shows the mean ANC percentage change on Day 29 for all QD dosing cohorts.

TABLE 93

Day 29 Mean ANC Percentage Change from Baseline by QD Dose of Form B of Compound II.

| QD Dose (mg) | N= | Day 29 Mean ANC % Change |
|---|---|---|
| 200 | 6 | −48% |
| 300 | 3 | −66% |
| 400 | 3 | −50% |
| 500 | 3 | −74% |

Example 6. Evaluation of Efficacy of Combination of Form B of Compound II and Fulvestrant in Patients with HR+, HER2− Locally Advanced or Metastatic Breast Cancer Target lesions in subjects from Example 1 were evaluated every 8 weeks using the RECIST, Version 1.1 criteria (Eisenhower 2009) as follows:

Complete Response (CR): Disappearance of all target lesions. Any pathological lymph nodes (whether target or nontarget) must have reduction in short axis to <10 mm.

Partial Response (PR): At least a 30% decrease in the sum of diameters of target lesions, taking as reference the baseline sum of diameters.

Progressive Disease (PD): At least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. The appearance of one or more new lesions was also considered progression.

Stable Disease (SD): Neither sufficient shrinkage to qualify for PR nor sufficient increase to qualify for PD, taking as reference the smallest sum of diameters while on study.

A response category of not evaluable (NE) was used when there was inadequate information to otherwise categorize the response status.

Non-target lesions were evaluated using the following criteria:

Complete Response (CR): Disappearance of all nontarget lesions and normalization of tumor marker level. All lymph nodes must be <10 mm short axis.

Non-CR/Non-PD: Persistence of 1 or more nontarget lesions and/or maintenance of tumor marker level above the normal limits.

Progressive Disease (PD): Unequivocal progression of existing nontarget lesions or the appearance of at least one new lesion.

The overall response (OR) was determined by evaluation of the combination of target and nontarget lesion responses as outlined in Table 94.

TABLE 94

Evaluation of Overall Response at Each Time Point

| Target Lesions | Nontarget Lesions | New Lesions | Overall Response |
| --- | --- | --- | --- |
| CR | CR | No | CR |
| CR | Non-CR/Non-PD | No | PR |
| CR | Not evaluated | No | PR |
| PR | Non-PD/not evaluated | No | PR |
| SD | Non-PD/not evaluated | No | SD |
| NE | Non-PD | NO | NE |
| PD | Any | Yes or No | PD |
| Any | PD | Yes or No | PD |
| Any | Any | Yes | PD |

The clinical efficacy of the combination of Form B of Compound II and fulvestrant for QD dosing for the subjects from Example 1 was evaluated using the above criteria. The clinical efficacy results are outlined in Table 95. The clinical benefit rate (CBR) was determined by evaluating the sum of patients with an overall response of CR, PR, and SD after more than 24 weeks of continuous treatment. The median time to response was 12 weeks.

TABLE 95

Clinical Efficacy of a Combination of Form B of Compound II and Fulvestrant

| Overall Response (OR) | Response Level (%) |
| --- | --- |
| PR | 4/20 (20%) |
| SD | 13/20 (65%) |
| PD | 3/20 (15%) |
| CBR (≥24 weeks) | 8/14 (57%) |

Figure 3:
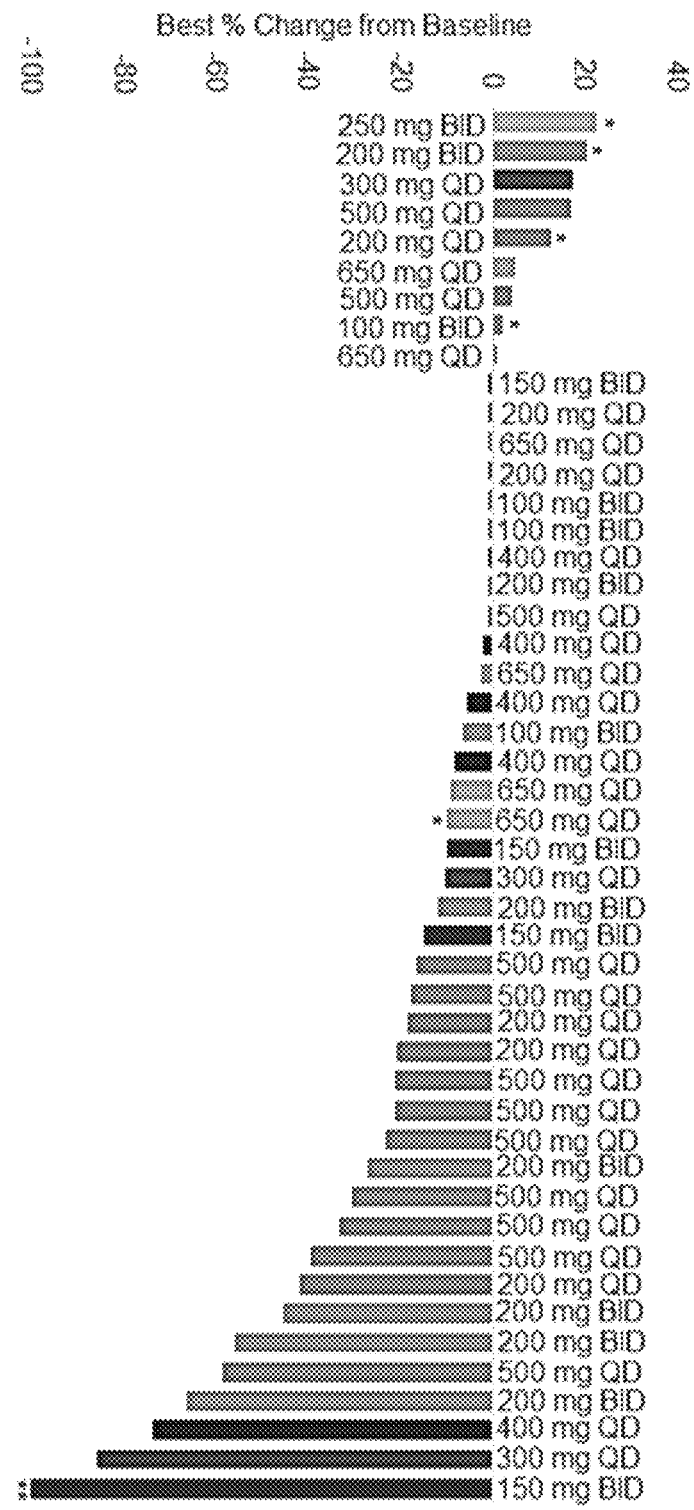
FIG. 3 is a waterfall plot of the best percentage change from baseline for target lesions per patient (Example 6). Each bar is labeled with the dose amount and schedule given to each patient. The x axis labeled with the dose amount and dose schedule and the y axis is change from baseline measured in percent.
Figure 4:
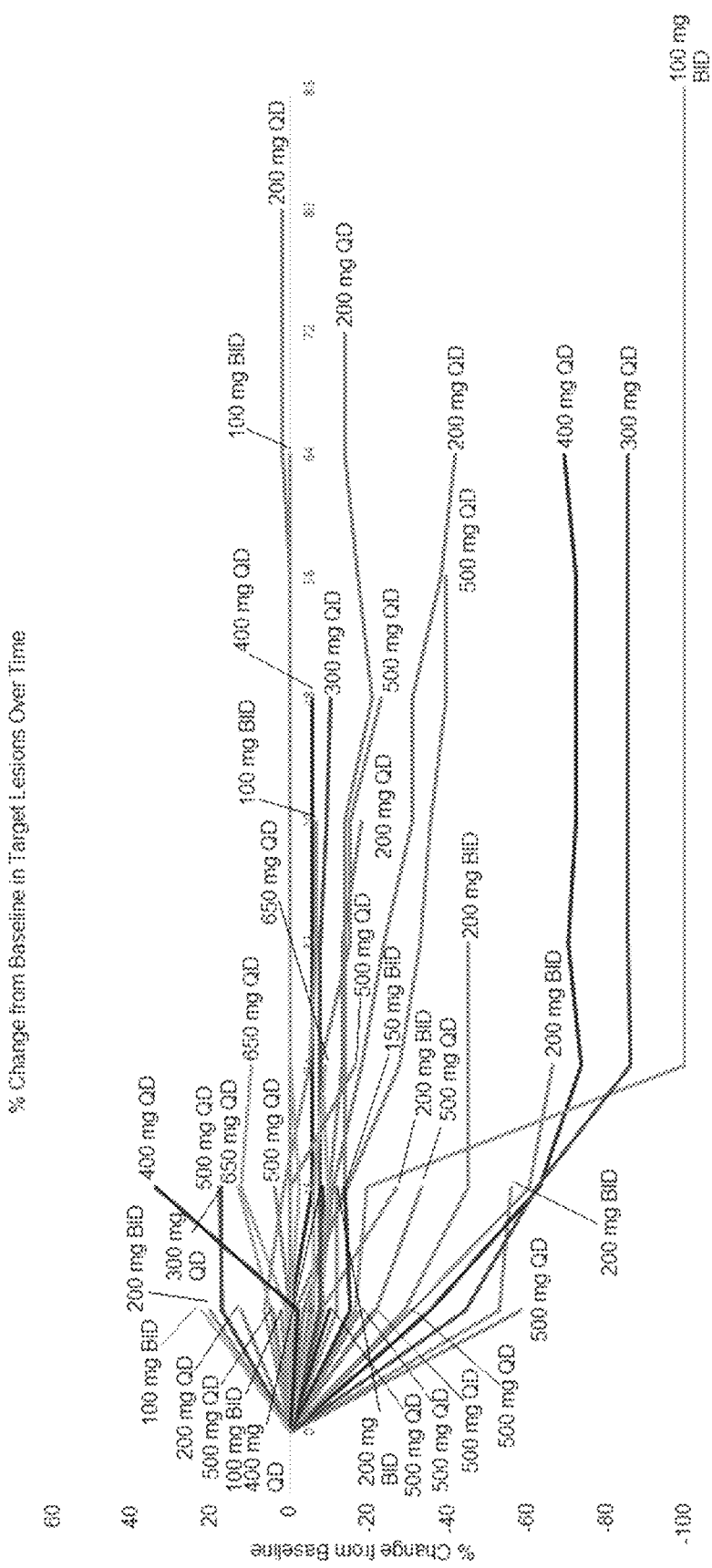
FIG. 4 is a spider plot of the percent change from baseline over time for target lesions by patient every 8 weeks (Example 6). Each line is labeled with the dose amount and schedule given to each patient. The x axis is the time measured in days and the y axis is change from baseline measured in percent.

A waterfall plot of the best percentage change from baseline for target lesions per patient is provided in FIG. 3. A spider plot of the percent change from baseline over time for target lesions by patient every 8 weeks is provided in FIG. 4. Both of these plots demonstrate the effective anti-tumor activity of Form B.

Figure 5:
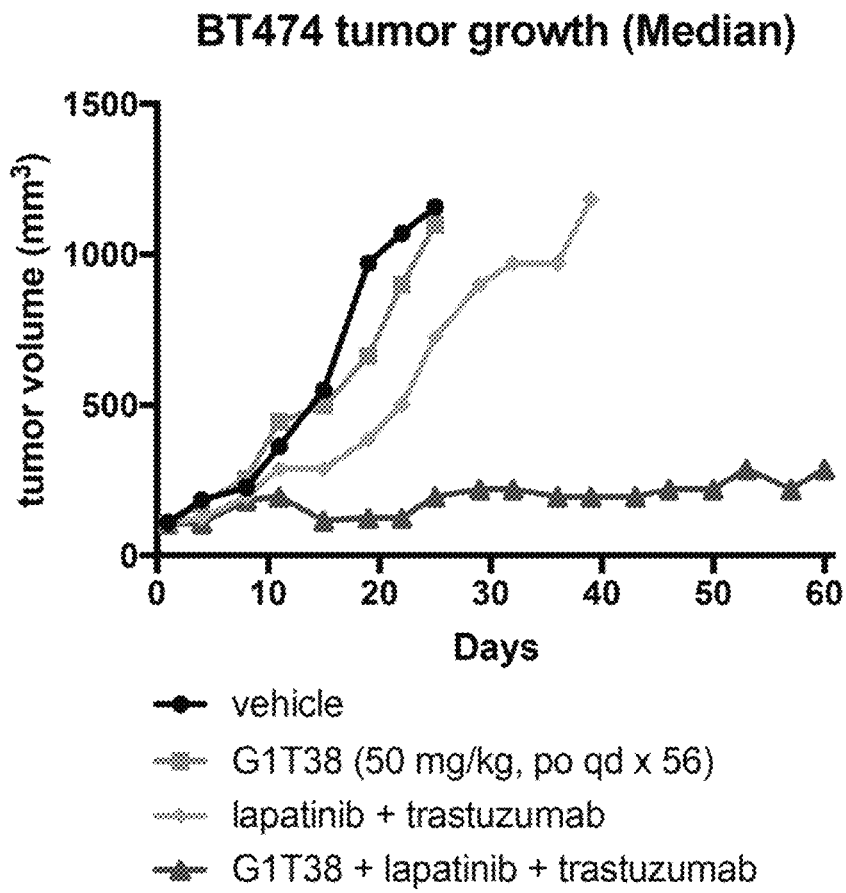
FIG. 5 is a line graph showing the level of BT474 median tumor growth in a murine HER2$^+$ ER$^+$ CBX model when treated with vehicle, Compound I (50 mg/kg po qd×56), lapatinib+trastuzumab, and Compound I+lapatinib+trastuzumab (Example 7). The y axis is tumor volume measured in mm$^3$. The x axis is time measured in days.
Figure 6:
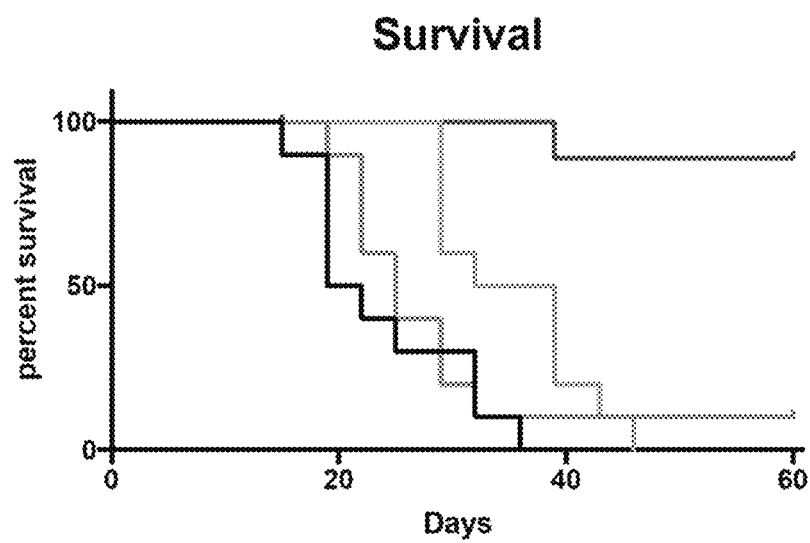
FIG. 6 is a line graph showing the percent survival of a murine HER2$^+$ ER$^+$ CBX model when treated with vehicle, Compound I (50 mg/kg po qd×56), lapatinib+trastuzumab, and Compound I+lapatinib+trastuzumab (Example 7). The y axis is survival measured in percent. The x axis is time measured in days.

Example 7. Compound I Enhances the Efficacy of Lapatanib and Trastuzumab Combination in a Murine HER$^+$ ER$^+$ CBX Model Mice containing a BT474 tumor were treated with vehicle, Compound I (50 mg/kg by mouth once a day for 56 days), lapatinib+trastuzumab, or Compound I+lapatinib+trastuzumab. As shown in FIG. 5, tumor growth was abated by the combination of Compound I+trastuzumab+lapatinib compared to Compound I or lapatinib+trastuzumab alone. As shown in FIG. 6, overall survival was significantly enhanced for the combination of Compound1+lapatinib+trastuzumab compared to either alone. The median overall survival (OS) days for each cohort is provided in Table 96.

TABLE 96

Median Overall Survival of BT474 Tumor-Containing Mice with Combinations of Compound I and Lapatinib + Trastuzumab.

| Cohort | Median OS (days) |
| --- | --- |
| Vehicle | 20.5 |
| Compound I | 25 |
| Lapatanib + Trastuzumab | 35.5 |
| Compound I + Lapatanib + Trastuzumab | Not reached |

Figure 7:
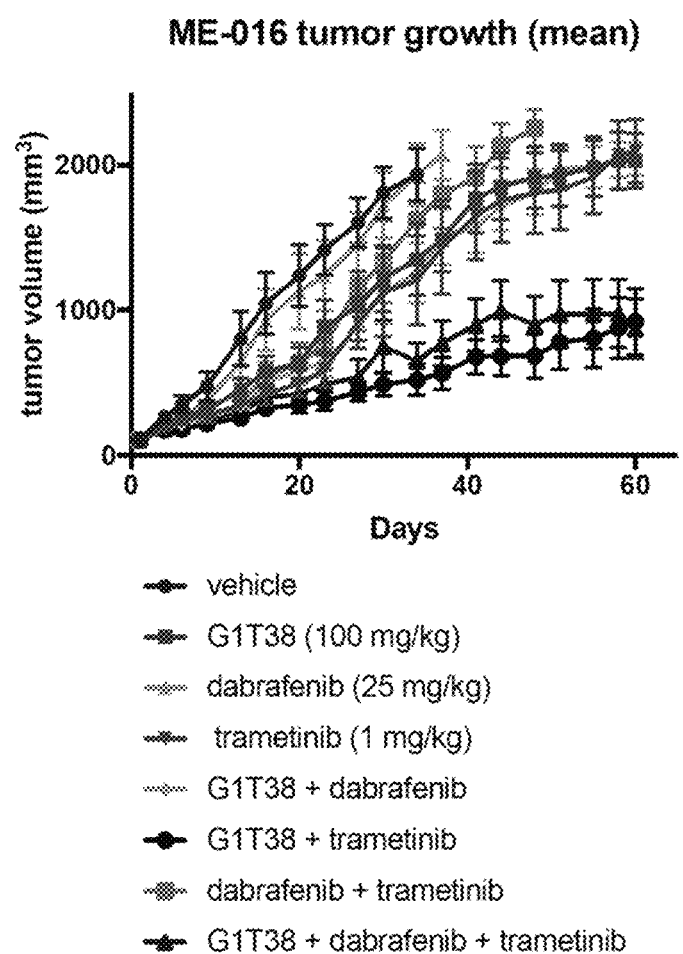
FIG. 7 is a line graph showing the level of ME-016 mean tumor growth in a murine BRAF$^{mut}$ melanoma PDX model when treated with vehicle, Compound I (100 mg/kg), dabrafenib (25 mg/kg), trametinib (1 mg/kg), Compound I+dabrafenib, Compound I+trametinib, dabrefinib+trametinib, and Compound I+dabrefinib+trametinib (Example 8). The y axis is tumor volume measured in mm$^3$. The x axis is time measured in days.
Figure 8:
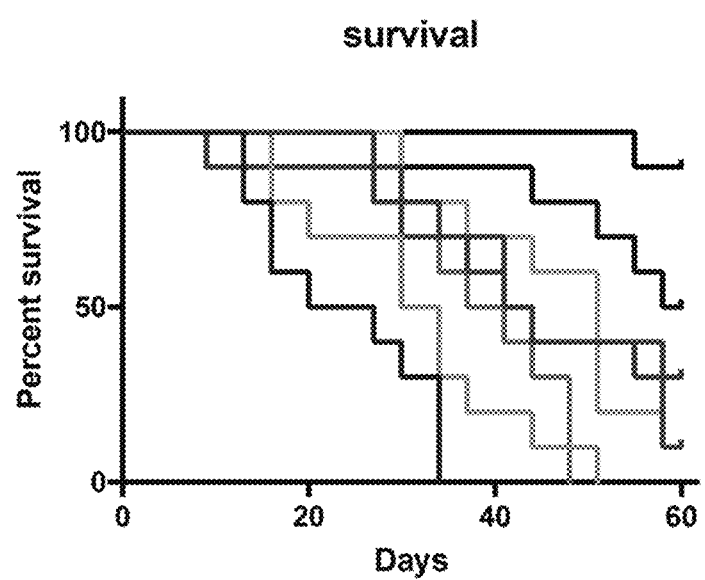
FIG. 8 is a line graph showing the percent survival of a murine BRAF$^{mut}$ melanoma PDX model when treated with vehicle, Compound I (100 mg/kg), dabrafenib (25 mg/kg), trametinib (1 mg/kg), Compound I+dabrafenib, Compound I+trametinib, dabrefinib+trametinib, and Compound I+dabrefinib+trametinib (Example 8). The y axis is survival measured in percent. The x axis is time measured in days.

Example 8. Compound I Enhances the Efficacy of Dabrafenib in a Murine BRAF$^{mut}$ Melanoma PDX Model Mice containing a ME-016 tumor were treated with vehicle, Compound I (100 mg/kg), dabrafenib (25 mg/kg), trametinib (1 mg/kg), Compound I+dabrafenib, Compound I+trametinib, dabrafenib+trametinib, and Compound I+dabrafenib+trametinib. As shown in FIG. 7, tumor growth for Compound I+dabrefinib+trametinib and Compound I+trametinib was lowered compared to other cohorts. As Shown in FIG. 8, overall survival was improved for Compound I+dabrafenib (51 days) and Compound I+dabrafenib+tramtinib (54 days). The median overall survival (OS) days for each cohort are provided in Table 97.

TABLE 97

Median Overall Survival of ME-016 Tumor-Containing Mice with Combinations of Compound I, Dabrefinib, and Trametinib.

| Cohort | Median OS (days) |
| --- | --- |
| Vehicle | 23.5 |
| Compound I (100 mg/kg) | 42.5 |
| Dabrefinib (25 mg/kg) | 32 |
| Trametinib (1 mg/kg) | 42.5 |
| Compound I + Dabrefinib | 51 |
| Compound I + Trametinib | Undefined |
| Dabrefinib + Trametinib | 39 |
| Compound I + Dabrefinib + Trametinib | 54 |

Example 9. Conversion of Compound I to its HCl Counterpart, Compound II

A representative synthesis of Compound II is provided in Scheme 1.

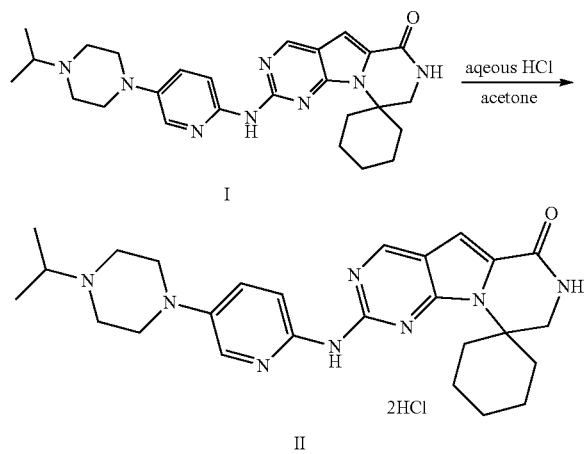

Scheme 1

Compound I (0.9 kg. 1.9 moles, 1 eq) was charged to a 22 L flask and dissolved in aqueous, 2 M hydrochloric acid solution (3.78 L). The solution was heated to 50±5° C., stirred for 30 minutes, and the resulting mixture filtered over Celite (alternatively the solution may be filtered through a 0.45 micron in-line filter) to afford Compound II. The flask was rinsed with 0.1 M hydrochloric acid solution to collect any additional Compound II. Compound II was then heated to 50±5° C. while acetone (6.44 L) was slowly added. The solution was stirred at 50±5° C. for 30 minutes, the temperature was decreased to 20±5° C., and stirring continued for 2 hours. The solids were collected by filtration, washed with acetone, and dried to afford 820.90 g of Compound II (82.1% yield). In one embodiment instead of acetone, ethanol is used.

Example 10. Morphic Forms of Compound II

Figure 9:
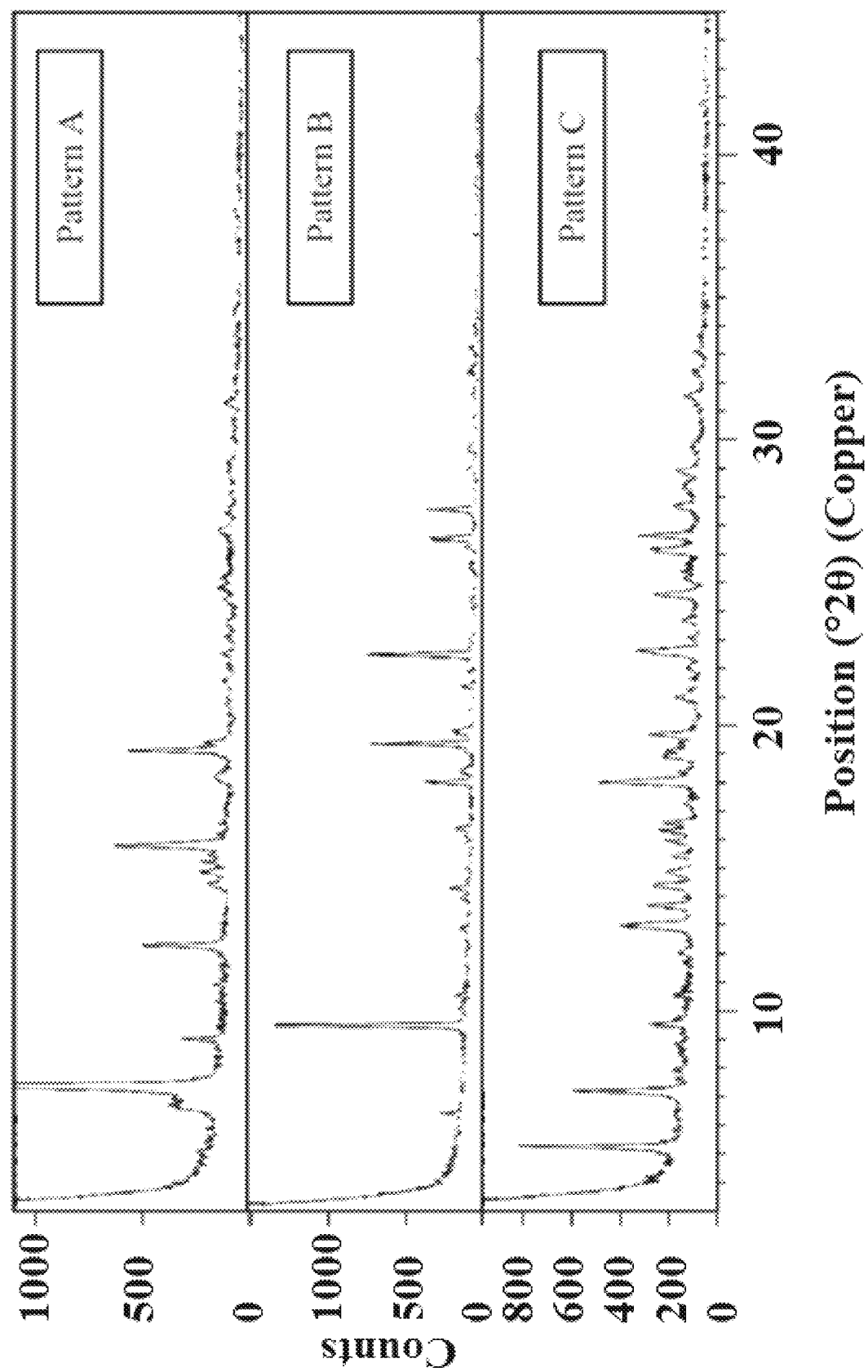
FIG. 9 is a comparison of XRPD patterns of Form A, Form B, and Form C. These three forms were obtained from crystallization and slurry experiments as described in Examples 9 and 10 and shown in Tables 98-101. The x-axis is 2Theta measured in degrees and the y-axis is intensity measured in counts.
Figure 10:
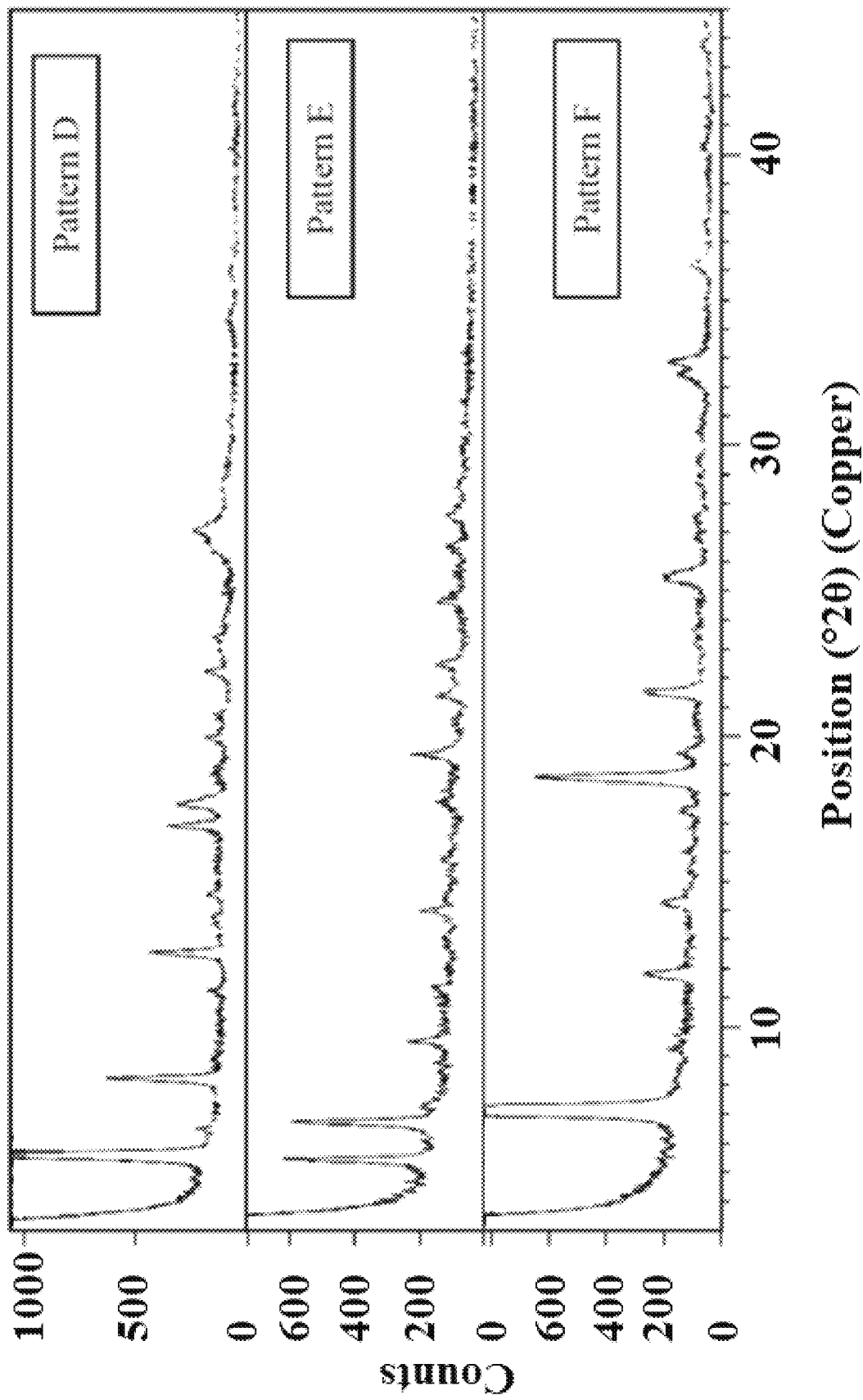
FIG. 10 is a comparison of XRPD patterns of Form D, Form E, and Form F. These three forms were obtained from crystallization and slurry experiments as described in Examples 9 and 10 and shown in Tables 98-101. The x-axis is 2Theta measured in degrees and the y-axis is intensity measured in counts.
Figure 11:
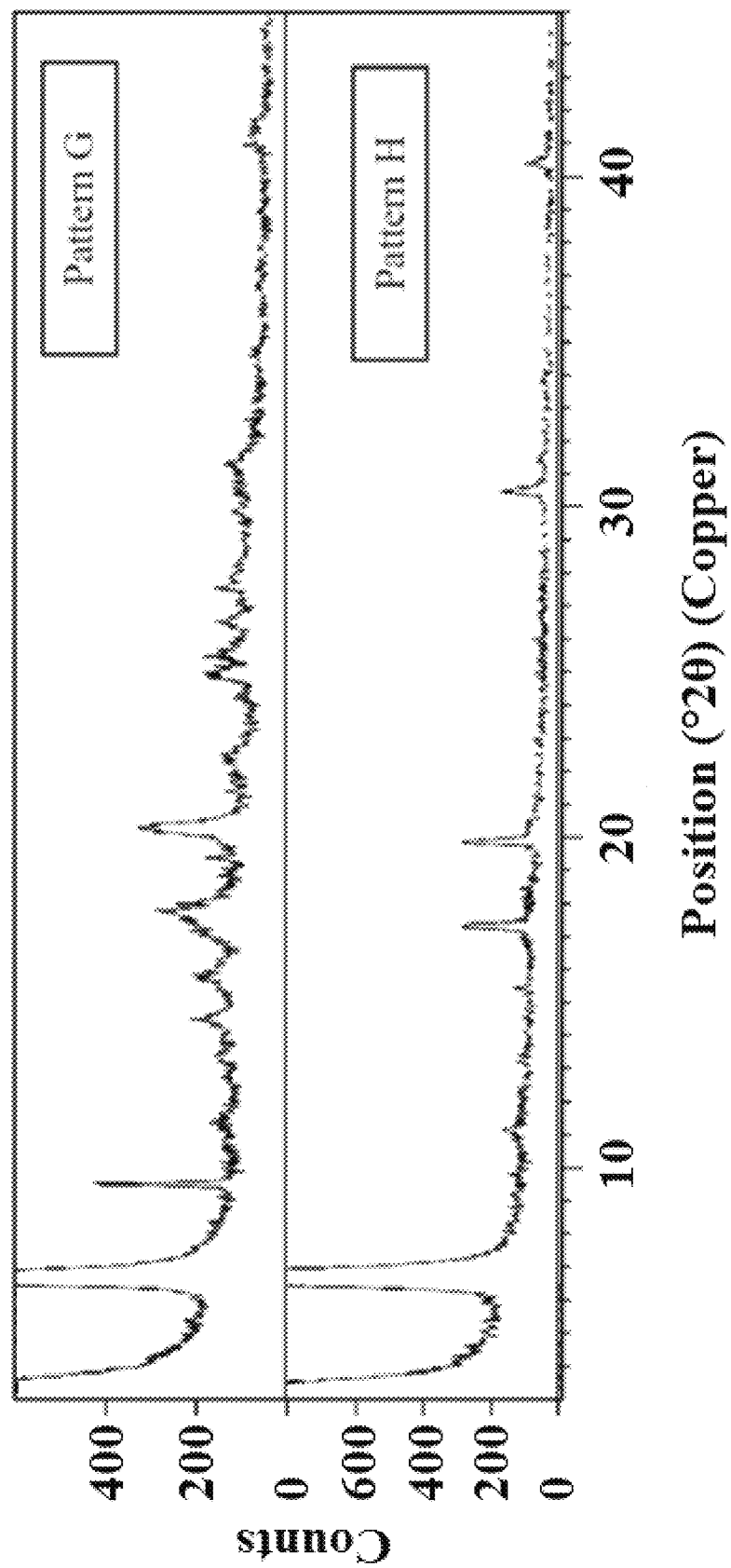
FIG. 11 is a comparison of XRPD patterns of Form G and Form H. These two forms were obtained from crystallization and slurry experiments as described in Examples 9 and 10 and shown in Tables 98-101. Form G is an anhydrate and Form H is an n-PrOH solvate. The x-axis is 2Theta measured in degrees and the y-axis is intensity measured in counts.

Eleven unique XRPD patterns (Form A-Form K) of Compound II were obtained from crystallization and slurry experiments using various solvents. The conditions and XRPD results for these crystallization experiments are given in Tables 98-101. Single solvent crystallizations (Table 98) resulted in weak crystalline forms or Form A. Binary solvent crystallizations using water (Table 99) and MeOH (Table 100) as the primary solvent resulted in weak crystalline forms and Form A, Form B, Form F, Form G, and Form H. Solids recovered from slurry experiments after one and seven days of equilibration (Table 101) were analyzed by XRPD to determine the crystalline form, and after seven days, Form A, Form B, Form C, Form D, and Form E were observed. FIG. 9 shows the XRPD patterns of Form A, Form B, and Form C. FIG. 10 shows the XRPD patterns of Form D, Form E, and Form F. FIG. 11 shows the XRPD patterns of Form G and Form H.

TABLE 98

Single Solvent Crystallization Conditions and Results

| Solvent | Volume (mL) | Temp. (° C.) | Cooling | Precipitation/ Isolation | XRPD |
|---|---|---|---|---|---|
| Water | 2.0 | 60 | Slow (20° C./hr) | Turbid/ Evap. | Weak crystalline |
| MeOH | 0.5 | 60 | Slow (20° C./hr) | ppt/filter | A |
| EtOH | 4.0 | 60 | Slow (20° C./hr) | ppt/filter | A |
| 1-PrOH | 4.0 | 60 | Slow (20° C./hr) | ppt/filter | Weak crystalline |
| 1-BuOH | 4.0 | 60 | Slow (20° C./hr) | ppt/filter | A |
| Water | 2.0 | 60 | Fast Cooling (4° C.) | Turbid/ Evap. | Weak crystalline |
| MeOH | 0.5 | 60 | Fast Cooling (4° C.) | ppt/filter | Weak crystalline |
| EtOH | 4.0 | 60 | Fast Cooling (4° C.) | ppt/filter | A |
| 1-PrOH | 4.0 | 60 | Fast Cooling (4° C.) | ppt/filter | Weak crystalline |
| 1-BuOH | 4.0 | 60 | Fast Cooling (4° C.) | ppt/filter | Weak crystalline |

TABLE 99

Binary Solvent Crystallizations using water as Primary Solvent

| Primary Solvent/ Vol.(mL) | Temp. (° C.) | Cooling | Anti Solvent/ Vol. (mL) | Precipitation/ Isolation | XRPD |
|---|---|---|---|---|---|
| Water/0.5 | 60.0 | Fast Cooling (4° C.) | EtOH/5.0 | Clear/Evap. | Weak crystalline |
| Water/0.5 | 60.0 | Fast Cooling (4° C.) | n-PrOH/5.0 | Clear/Evap. | Weak crystalline |
| Water/0.5 | 60.0 | Fast Cooling (4° C.) | IPA/5.0 | ppt/filter | G |
| Water/0.5 | 60.0 | Fast Cooling (4° C.) | MeCN/5.0 | ppt/filter | Weak crystalline |
| Water/0.5 | 60.0 | Fast Cooling (4° C.) | THF/3.0 | ppt/filter | Weak crystalline |
| Water/0.5 | 60.0 | Fast Cooling (4° C.) | Acetone/3.5 | ppt/filter | G |
| Water/0.5 | 60.0 | Slow Cooling (20° C./hr) | EtOH/5.0 | Clear/Evap. | Weak crystalline |
| Water/0.5 | 60.0 | Slow Cooling (20° C./hr) | n-PrOH/5.0 | Clear/Evap. | H |
| Water/0.5 | 60.0 | Slow Cooling (20° C./hr) | IPA/5.0 | ppt/filter | B |
| Water/0.5 | 60.0 | Slow Cooling (20° C./hr) | MeCN/5.0 | ppt/filter | A |

TABLE 99-continued

Binary Solvent Crystallizations using water as Primary Solvent

| Primary Solvent/ Vol.(mL) | Temp. (° C.) | Cooling | Anti Solvent/ Vol. (mL) | Precipitation/ Isolation | XRPD |
|---|---|---|---|---|---|
| Water/0.5 | 60.0 | Slow Cooling (20° C./hr) | THF/3.0 | ppt/filter | G |
| Water/0.5 | 60.0 | Slow Cooling (20° C./hr) | Acetone/3.5 | ppt/filter | B |

TABLE 100

Binary Solvent Crystallizations using MeOH as Primary Solvent

| Primary Solvent/ Vol. (mL) | Temp. (° C.) | Cooling | Anti Solvent/ Vol. (mL) | Precipitation/ Isolation | XRPD |
|---|---|---|---|---|---|
| MeOH/0.5 | 60.0 | Fast Cooling (4° C.) | EtOH/5.0 | ppt/filter | A |
| MeOH/0.5 | 60.0 | Fast Cooling (4° C.) | n-PrOH/5.0 | ppt/filter | Weak crystalline |
| MeOH/0.5 | 60.0 | Fast Cooling (4° C.) | IPA/2.5 | ppt/filter | F |
| MeOH/0.5 | 60.0 | Fast Cooling (4° C.) | n-BuOH/5.0 | ppt/filter | Weak crystalline |
| MeOH/0.5 | 60.0 | Fast Cooling (4° C.) | MeCN/2.5 | ppt/filter | A |
| MeOH/0.5 | 60.0 | Fast Cooling (4° C.) | THF/0.5 | ppt/filter | A |
| MeOH/0.5 | 60.0 | Fast Cooling (4° C.) | 2-MeTHF/0.1 | ppt/filter | A |
| MeOH/0.5 | 60.0 | Fast Cooling (4° C.) | EtOAc/0.2 | ppt/filter | Weak crystalline |
| MeOH/0.5 | 60.0 | Fast Cooling (4° C.) | IPAc/0.1 | ppt/filter | A |
| MeOH/0.5 | 60.0 | Fast Cooling (4° C.) | Acetone/0.5 | ppt/filter | A |
| MeOH/0.5 | 60.0 | Slow Cooling (20° C./hr) | MEK/0.2 | ppt/filter | A |
| MeOH/0.5 | 60.0 | Slow Cooling (20° C./hr) | MIBK/0.1 | ppt/filter | Weak crystalline |
| MeOH/0.5 | 60.0 | Slow Cooling (20° C./hr) | DCM/5.0 | Clear/Evap. | A |
| MeOH/0.5 | 60.0 | Slow Cooling (20° C./hr) | Toluene/1.5 | ppt/filter | A |
| MeOH/0.5 | 60.0 | Slow Cooling (20° C./hr) | MTBE/0.1 | ppt/filter | A |
| MeOH/0.5 | 60.0 | Slow Cooling (20° C./hr) | EtOH/5.0 | ppt/filter | Weak crystalline |
| MeOH/0.5 | 60.0 | Slow Cooling (20° C./hr) | n-PrOH/5.0 | ppt/filter | Weak crystalline |
| MeOH/0.5 | 60.0 | Slow Cooling (20° C./hr) | IPA/2.5 | ppt/filter | A |
| MeOH/0.5 | 60.0 | Slow Cooling (20° C./hr) | n-BuOH/5.0 | ppt/filter | Weak crystalline |
| MeOH/0.5 | 60.0 | Slow Cooling (20° C./hr) | MeCN/2.5 | ppt/filter | Weak crystalline |
| MeOH/0.5 | 60.0 | Slow Cooling (20° C./hr) | THF/0.5 | ppt/filter | Weak crystalline |
| MeOH/0.5 | 60.0 | Slow Cooling (20° C./hr) | 2-MeTHF/0.1 | ppt/filter | A |
| MeOH/0.5 | 60.0 | Slow Cooling (20° C./hr) | EtOAc/0.2 | ppt/filter | A |
| MeOH/0.5 | 60.0 | Slow Cooling (20° C./hr) | IPAc/0.1 | ppt/filter | A |
| MeOH/0.5 | 60.0 | Slow Cooling (20° C./hr) | Acetone/0.5 | ppt/filter | Weak crystalline |
| MeOH/0.5 | 60.0 | Slow Cooling (20° C./hr) | MEK/0.2 | ppt/filter | A |
| MeOH/0.5 | 60.0 | Slow Cooling (20° C./hr) | MIBK/0.1 | ppt/filter | A |
| MeOH/0.5 | 60.0 | Slow Cooling (20° C./hr) | DCM/5.0 | Clear/Evap. | A |
| MeOH/0.5 | 60.0 | Slow Cooling (20° C./hr) | Toluene/1.5 | ppt/filter | Weak crystalline |
| MeOH/0.5 | 60.0 | Slow Cooling (20° C./hr) | MTBE/0.1 | ppt/filter | A |

TABLE 101

Slurry Experiments of Compound II

| Solvent | Solvent Vol. (mL) | Method | Time point (1 day) XRPD | Time point (7 days) XRPD |
|---|---|---|---|---|
| IPA | 1.0 | Stirring at RT | A | F |
| MeCN | 1.0 | Stirring at RT | D | D |
| THF | 1.0 | Stirring at RT | Weak Crystalline | E |
| 2-MeTHF | 1.0 | Stirring at RT | Weak Crystalline | B |
| EtOAc | 1.0 | Stirring at RT | A | C |
| IPAc | 1.0 | Stirring at RT | A with extra peak | B |
| Acetone | 1.0 | Stirring at RT | E | B |
| MEK | 1.0 | Stirring at RT | Weak Crystalline | B |
| MIBK | 1.0 | Stirring at RT | E | B |
| Toluene | 1.0 | Stirring at RT | E | B |
| MTBE | 1.0 | Stirring at RT | A | B |
| n-Heptane | 1.0 | Stirring at RT | A | A |
| c-Hexane | 1.0 | Stirring at RT | A | A |

Characterization of Compound II Morphic Forms

A summary of characterization data of all isolated forms of Compound II is given in Table 102. Forms A, B, and D were evaluated as solid state forms.

TABLE 102

Characterization Data of Morphic Forms of Compound II

| XRPD Pattern | Possible Form | DSC (° C.) | TGA (wt loss) | 1H NMR (DMSO-d$_6$) | % Cl (API:HCl) |
|---|---|---|---|---|---|
| A | Hydrate | Endotherms at 110.3, 275.6, 344.8 | Onset 5.7 wt % loss at 66.0° C., Onset 5.4 wt % loss at 215.5° C., Onset 6.2 wt % loss at 314.0° C. | Contains water | 11.1% (1:1.67)* |
| B | Hydrate | Endotherms at 105.2, 220.8, 265.6, 350.6 | Onset 5.1 wt % loss at 60.9° C., Onset 7.2 wt % loss at 198.3° C., Onset 7.8 wt % loss at 319.6° C. | Contains water and residual solvent | 11.90% (1:1.81) |
| C | EtOAc solvate | Endotherms at 95.1, 235.6, 257.8, 344.6 | Onset 1.6 wt % loss at 72.9° C., Onset 5.1 wt % loss at 192.0° C., Onset 0.9 wt % loss at 223.4° C., Onset 6.9 wt % loss at 306.7° C. | Contains water and EtOAc as residual solvent | Not determined |
| D | Hydrate | Endotherms at 108.3, 266.1, 347.0 | Onset 6.0 wt % loss at 68.8° C., Onset 6.0 wt % loss at 207.6° C., Onset 3.6 wt % loss at 304.9° C., Onset 6.6 wt % loss at 324.7° C. | Contains water and residual solvent | 12.23% (1:1.87) |
| E | Acetone solvate | Endotherms at 70.3, 275.2, 345.9 Exotherm at 220.0 | Onset 1.0 wt % loss at 41.9° C., Onset 1.1 wt % loss at 61.5° C., Onset 1.0 wt % loss at 93.2° C., Onset 5.0 wt % loss at 211.6° C., Onset 5.6 wt % loss at 308.5° C. | Contains water and acetone as residual solvent | Not determined |
| F | Unstable hydrate | Endotherms at 73.2, 214.5, 303.4, 329.7 Exotherm at 277.8 | Onset 8.0 wt % loss at 43.7° C., Onset 2.1 wt % loss at 190.7° C., Onset 7.6 wt % loss at 308.8° C. | Contains water | Not determined |
| G | Anhydrate | Endotherms at 81.8, 120.8, 268.2, 347.9 | Onset 4.5 wt % loss at 47.2° C., Onset 3.1 wt % loss at 86.6° C., Onset 4.5 wt % loss at 213.3° C., Onset 4.6 wt % loss at 311.2° C. | Contains water | Not determined |
| H | n-PrOH solvate | Endotherms at 110.5, 225.6, 274.5, 346.3 | Onset 1.9 wt % loss at 45.6° C., Onset 4.6 wt % loss at 71.9° C., Onset 1.8 wt % loss at 187.9° C., Onset 2.2 wt % loss at 222.1° C., Onset 3.0 wt % loss at 303.0° C., Onset 2.2 wt % loss at 325.2° C. | Contains water and n-PrOH as residual solvent | Not determined |

In one embodiment Form A is characterized by at least one XRPD peaks at 7.4±0.2°, 9.0±0.2°, or 12.3±0.2° 2theta. In one embodiment Form B is characterized by at least one XRPD peaks at 6.4±0.2°, or 9.5±0.2° 2theta. In one embodiment Form C is characterized by at least one XRPD peaks at 5.3±0.2°, or 7.2±0.2° 2theta. In one embodiment Form D is characterized by at least one XRPD peaks at 5.6±0.2°, or 8.2±0.2° 2theta. In one embodiment Form E is characterized by at least one XRPD peak at 5.5±0.2°, or 6.7±0.2° 2theta. In one embodiment Form E is characterized by at least one XRPD peak at 5.5±0.2°, or 6.7±0.2° 2theta. In one embodiment Form F is characterized by a XRPD peak at 7.2±0.2° 2theta. In one embodiment Form G is characterized by a XRPD peak at 6.7±0.2° 2theta. In one embodiment Form H is characterized by a XRPD peak at 6.6±0.2° 2theta.

Example 11. Dynamic Vapor Sorption Experiments of Form A, Form B, and Form D

Dynamic vapor sorption experiments were performed on Form A, Form B, and Form D. Table 103 provides the results of the DVS experiment.

TABLE 103

Moisture Sorption Data of Forms A, B, and D

| XRPD (pre DVS) | % wt change at 60% RH | % wt change at 90% RH | XRPD (post DVS) |
|---|---|---|---|
| Form A | 14.9 | 15.8 | Form K |
| Form B | 5.8 | 5.9 | Form B |
| Form D | 4.4 | 17.0 | Form K |

Figure 12A:
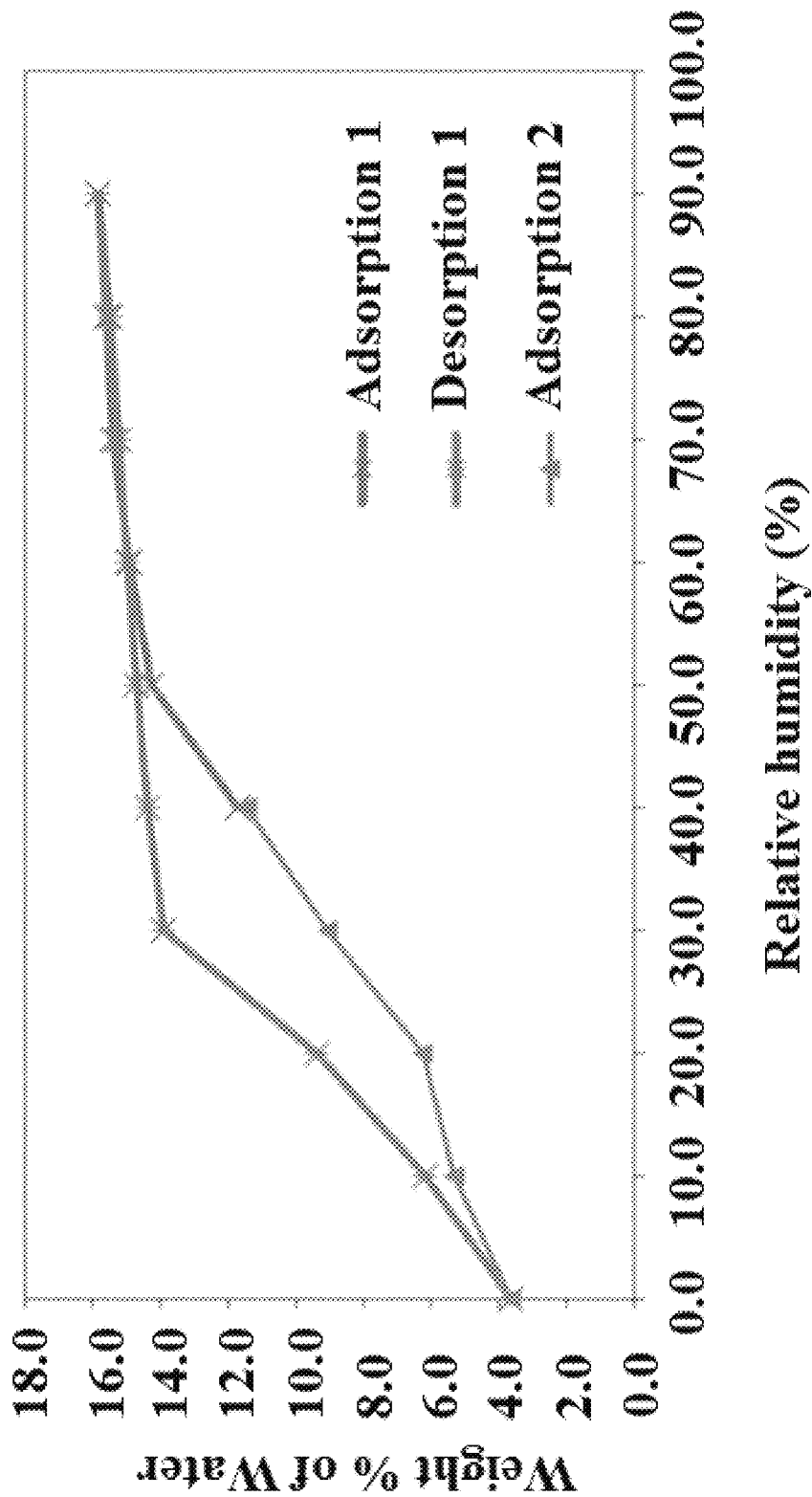
FIG. 12A is a dynamic vapor sorption analysis showing the results from a moisture sorption experiment of Form A (Example 11). The material was found to be unstable and the XRPD analysis of dried sample at the conclusion of the experiment revealed a new Form, Form K. Form A adsorbed 14.9 wt % at 60% RH (relative humidity) and 15.8 wt % at 90% RH. The x-axis is relative humidity measured as a percent and the y-axis is weight of water of the material measured as a percent.
Figure 12B:
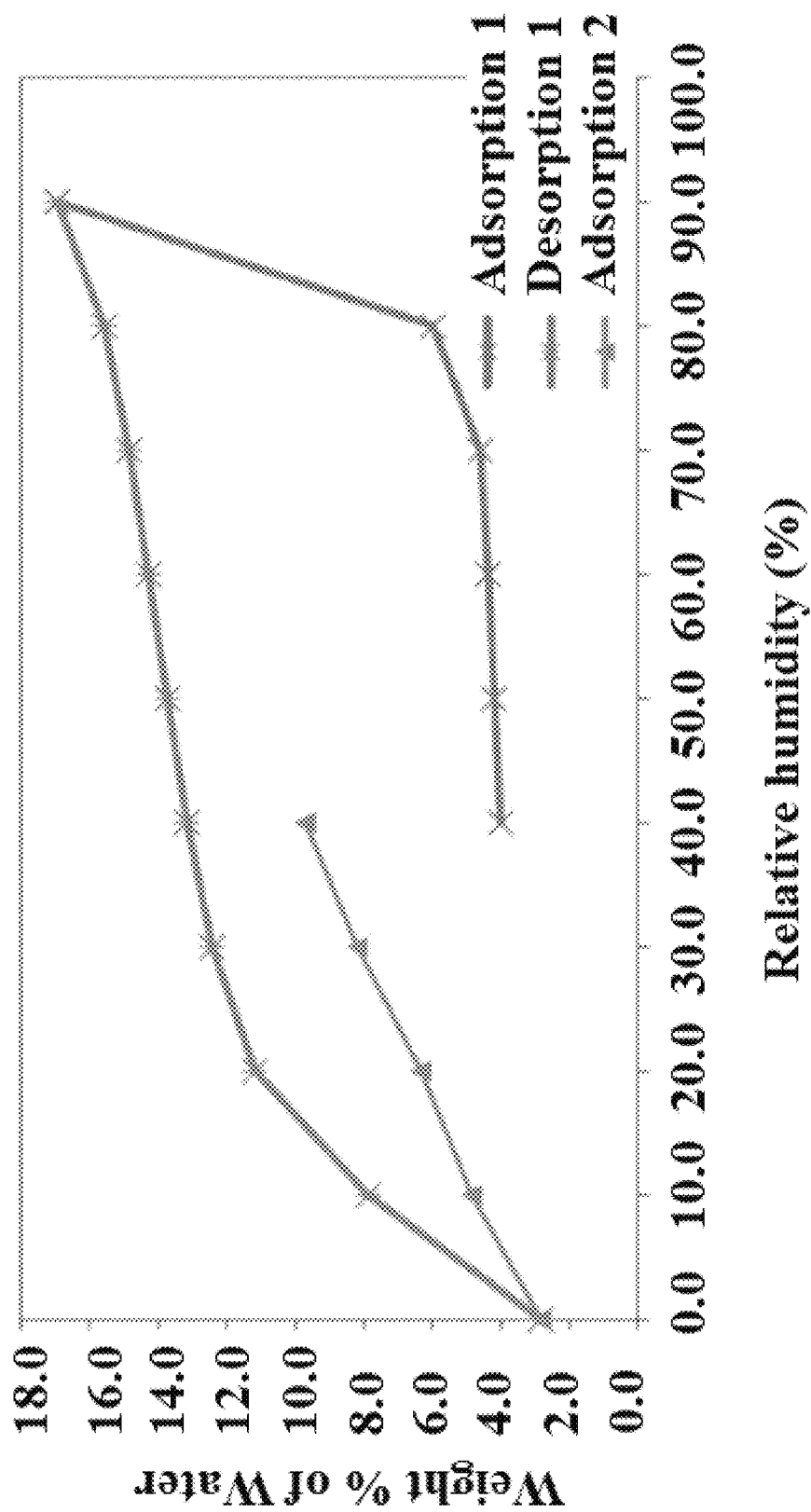
FIG. 12B is a dynamic vapor sorption analysis showing the results from a moisture sorption experiment of Form D (Example 11). The material was found to be unstable and the XRPD analysis of dried sample at the conclusion of the experiment revealed a new Form, Form K. Form D adsorbed 4.4 wt % at 60% RH (relative humidity) and 4.4 wt % at 90% RH. The x-axis is relative humidity measured as a percent and the y-axis is weight of water of the material measured as a percent.

Form A was found to be unstable in the moisture sorption experiment. The material adsorbed 14.9 wt % moisture at 60% RH and 15.8 wt % at 90% RH. After the moisture sorption experiment, the sample was dried at 60° C. and 0% RH and the result of the XRPD analysis of dried sample showed a new Form (Form K). The DVS analysis of Form A is shown in FIG. 12A. Form D was also found to be unstable in the moisture sorption experiment. The material adsorbed 4.4 wt % moisture at 60% RH and 17.0 wt % at 90% RH. After the moisture sorption experiment, the sample was dried at 60° C. and 0% RH and the result of the XRPD analysis of dried sample showed Form K. The DVS analysis of Form D is shown in FIG. 12B.

Figure 12C:
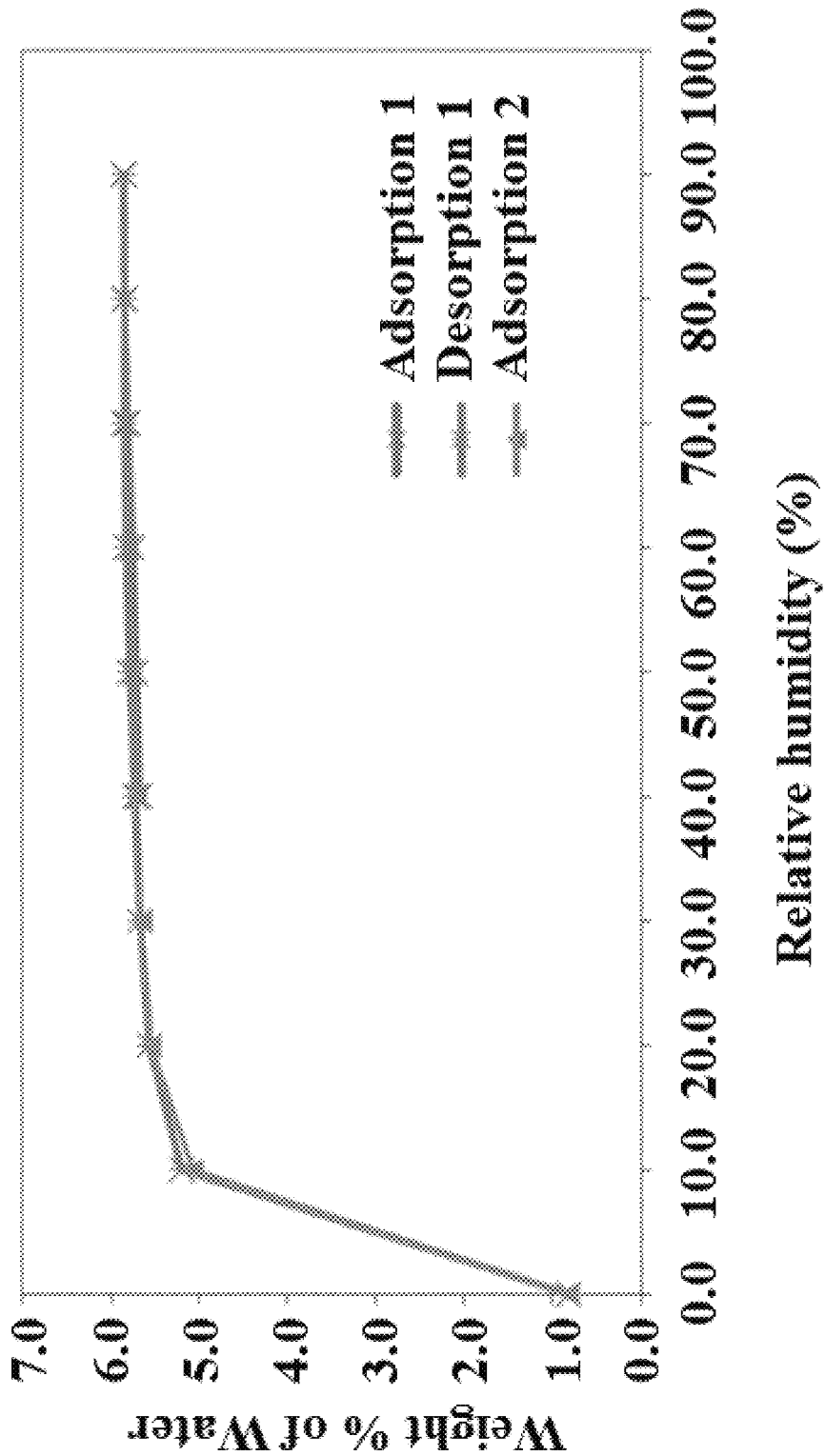
FIG. 12C is a dynamic vapor sorption analysis showing the results from a moisture sorption experiment of Form B (Example 11). The material is stable and the XRPD analysis of a dried sample at the conclusion of the experiment confirmed Form B. Form B adsorbed 5.8 wt % at 60% RH (relative humidity), and 5.9 wt % at 90% RH. The x-axis is relative humidity measured as a percent and the y-axis is weight of water of the material measured as a percent.

Unlike Form A and Form D, Form B was stable in the moisture sorption experiment. The material adsorbed 5.8 wt % moisture at 60% RH and 5.9 wt % at 90% RH. After drying at 60° C. and 0% RH for two hours, the XRPD pattern remained unchanged as Form B. The DVS analysis of Form B is shown in FIG. 12C.

Figure 13A:
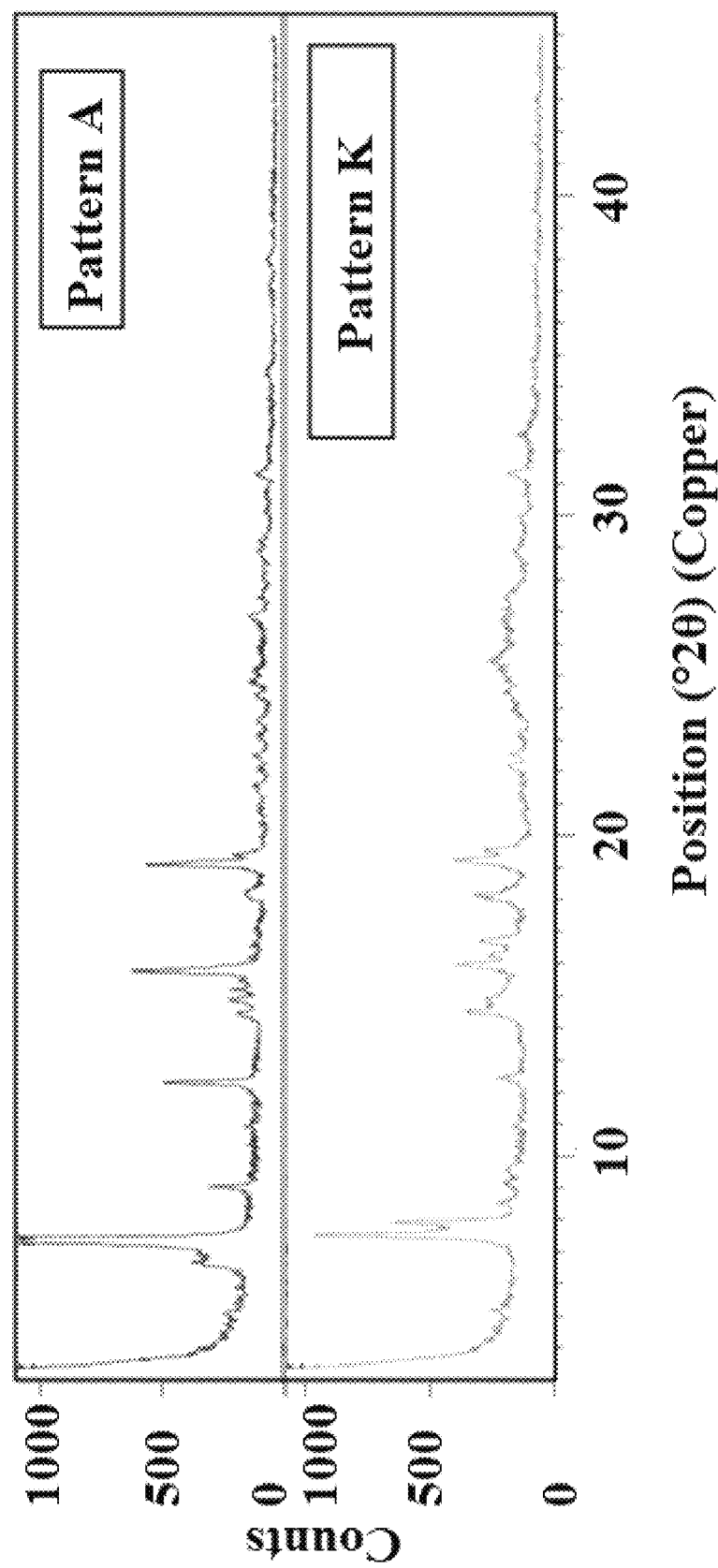
FIG. 13A is a comparison of XRPD patterns of Form A before the moisture sorption experiment (top) and after the moisture sorption experiment (bottom). After the moisture sorption experiment, XRPD analysis revealed that Form A is not stable and had converted to a new Form, Form K (Example 11). The x-axis is 2Theta measured in degrees and the y-axis is intensity measured in counts.
Figure 13B:
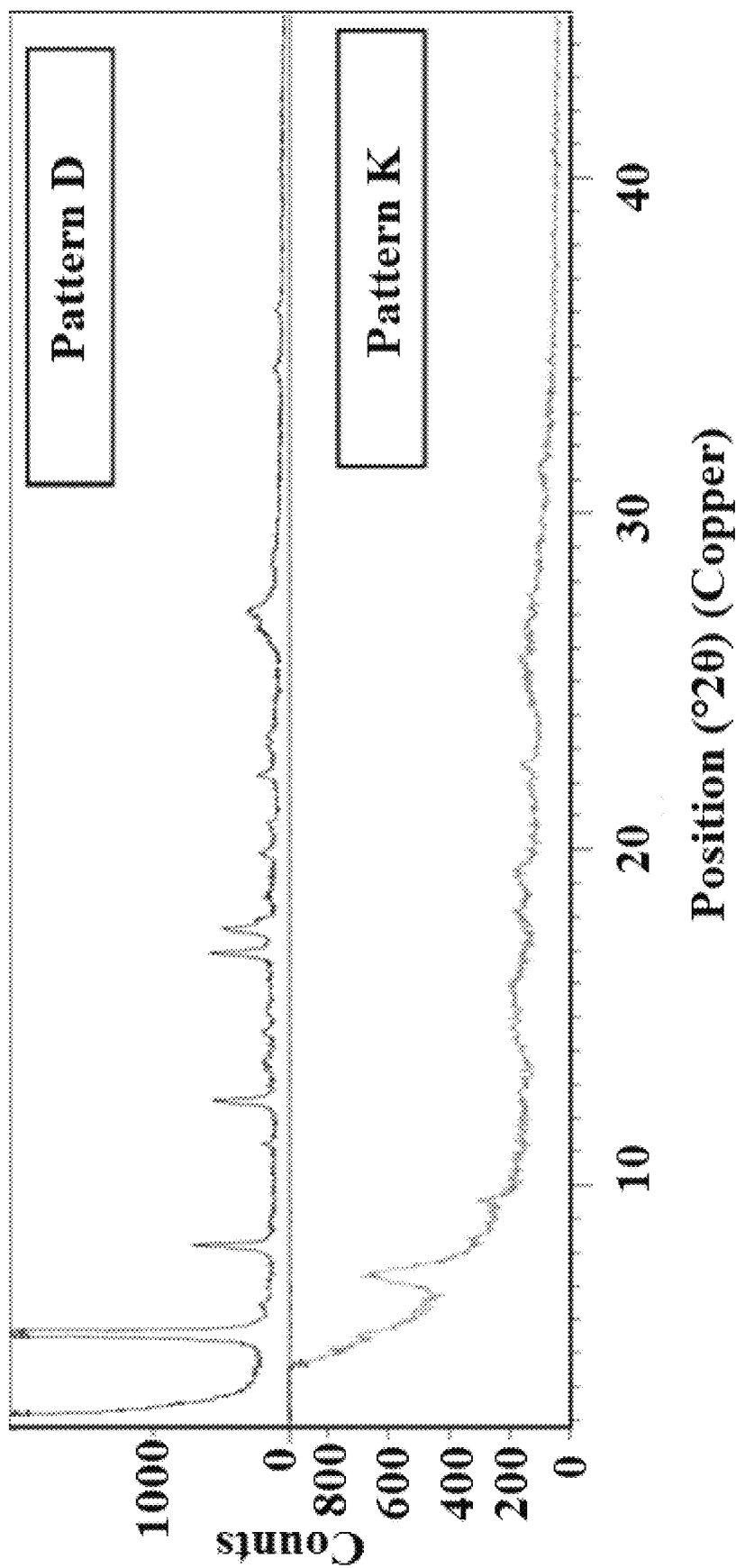
FIG. 13B is a comparison of XRPD patterns of Form D before the moisture sorption experiment (top) and after the moisture sorption experiment (bottom). After the moisture sorption experiment, XRPD analysis revealed that Form D is not stable and had converted to a new Form, Form K (Example 11). The x-axis is 2Theta measured in degrees and the y-axis is intensity measured in counts.

FIG. 13A is a comparison of the XRPD pattern of Form A before DVS analysis and the new pattern (Form K) that resulted from DVS. FIG. 13B is a comparison of the XRPD pattern of Form D before DVS and the pattern (Form K) that resulted after DVS.

Example 12. Stability Study of Forms A, B, and D Under Thermal Stress

Figure 14:
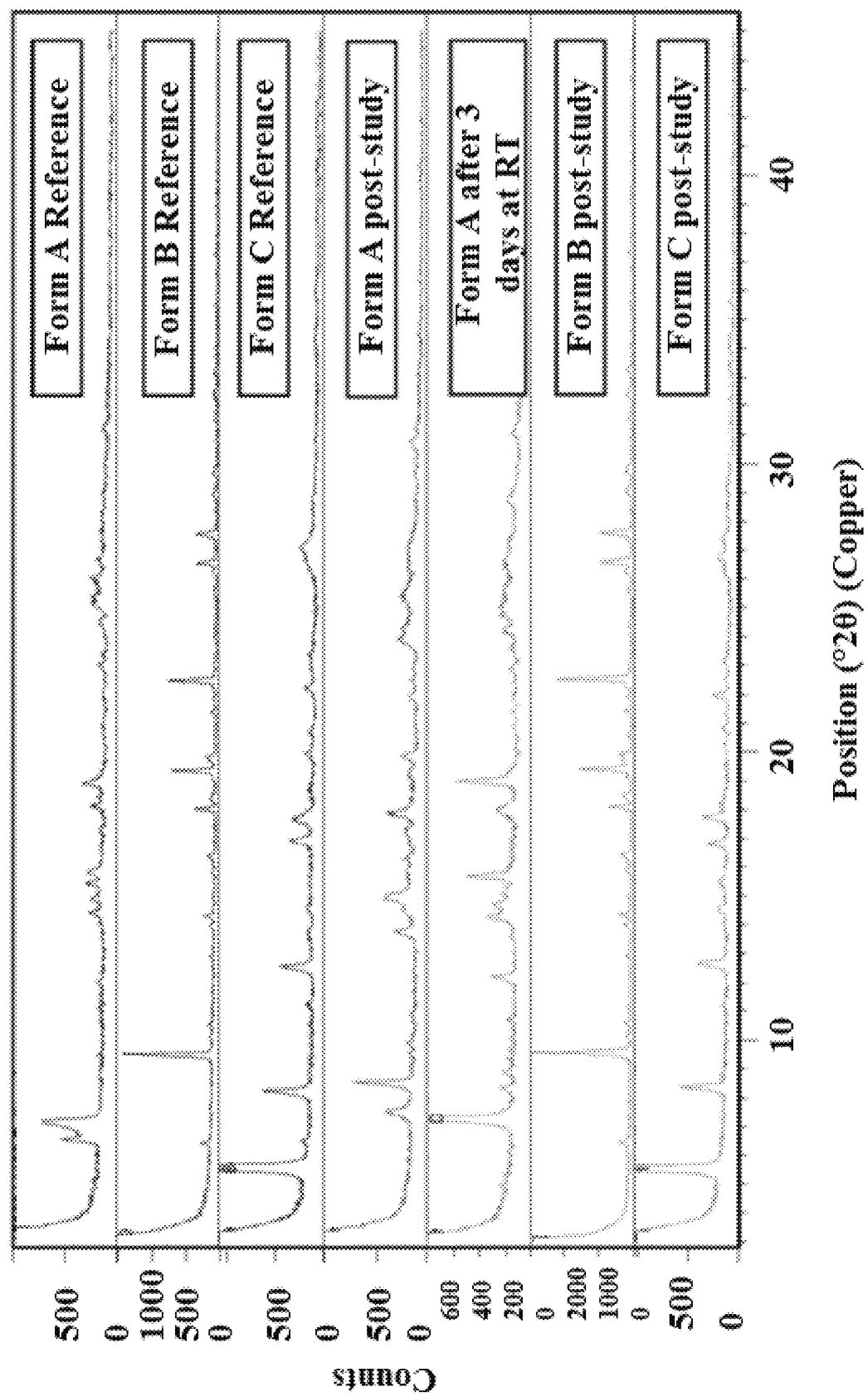
FIG. 14 is a comparison of the XRPD patterns of Form A, Form B, and Form C after the stability study (Example 12) to reference Form A, Form B and Form C. The top three patterns are reference forms of Form A, Form B, and Form C. After the seven-day stability study, Form A converted to a new Form (Form A post-study), but after equilibrium at room temperature for 3 days, the new form changed back to Form A (Form A after 3 days). Form B and Form C remained unchanged during the stability study. The x-axis is 2Theta measured in degrees and the y-axis is intensity measured in counts.

Forms A, B, and D were stored in an oven maintained at 60° C. for 7 days. No change in the XRPD pattern was observed for Form B or Form D. A new pattern was found for Form A at the conclusion of the stability study, however after equilibrium for three days at room temperature, the XRPD of the new Form revealed that it had converted back to Form A. FIG. 14 compares the XRPD patterns of Form A, Form B, and Form D to reference material. FIG. 14 also shows the new pattern that resulted from exposing Form A to thermal stress along with the Form A pattern that resulted after three additional days at room temperature.

Example 13. Recrystallization Procedures to Produce Form B from Compound II

Recrystallization studies were conducted to define a procedure to improve chromatographic purity. All recrystallization procedures in Table 104 involved dissolving Compound II in concentrated HCl and then adding the antisolvent, acetone. The differences in the processes are subtle but important in terms of their results.

Recrystallization Process 1: Compound I was charged to an appropriately sized flask or reactor, dissolved in aqueous hydrochloric acid solution and heated to at least 55±10° C. The solution was stirred for about 45 minutes and the resulting mixture was filtered through an in-line filter. Acetone was added at 55±10° C. over the course of an hour and the solution was stirred for about an additional hour. The temperature was decreased to about 25±5° C., and the solution was stirred for at least 2 hours. The solids were collected by filtration, washed with acetone, and dried to afford Compound II form B.

Recrystallization Process 2: Compound I was charged to an appropriately sized flask or reactor, dissolved in aqueous hydrochloric acid solution and heated to at least 55±10° C. The solution was stirred for about 45 minutes and the resulting mixture was filtered through an in-line filter. The temperature was decreased to about 25±5° C., and the solution was stirred for at least 2 hours. Acetone was added at 25±5° C. over the course of an hour and the solution was stirred for an additional two hours. The solids were collected by filtration, washed with acetone, and dried to afford Compound II form D.

Recrystallization Process 3: Compound I was charged to an appropriately sized flask or reactor, dissolved in aqueous hydrochloric acid solution and heated to at least 55±10° C. The solution was stirred for about 45 minutes and the resulting mixture was filtered through an in-line filter. The temperature was decreased to about 25±5° C. and the solution was stirred for at least 2 hours. The solids were collected by filtration, washed with acetone, and dried to afford Compound II form D.

TABLE 104

Effect of crystallization procedures on purging of chromatographic impurities from Compound I

| RRT | % area | Recrys Process 1% area | Recrys Process 2% area | Recrys Process 3% area |
|---|---|---|---|---|
| 1.11 | 1.13 | 1.11 | 0.87 | 0.27 |
| 1.37 | 0.14 | 0.15 | 0.13 | ND |
| 1.62 | 0.14 | ND | 0.13 | ND |

While conducting the experiments presented in Table 104, it was discovered that not all recrystallization processes resulted in the preferred solid state form, Form B. Specifically, Recrystallization Processes 2 and 3 result in a different solid state form (putative Form D) whereas Recrystallization 1 reproducibly provides Form B. In one embodiment, Compound II is converted to Form D by Recrystallization Procedure 2 and 3 and Form D is converted to Form B by Recrystallization Process 1.

Example 14. XRPD Analysis of Compound II, Morphic Form B

The XRPD pattern of Form B was collected with a PANalytical X'Pert PRO MPD diffractometer using an incident beam of Cu radiation produced using an Optix long, fine-focus source. An elliptically graded multilayer mirror was used to focus Cu Kα X-rays through the specimens and onto the detector. Prior to the analysis, a silicon specimen (NIST SRM 640e) was analyzed to verify the observed position of the Si 111 peak is consistent with the NIST-certified position. The sample was sandwiched between 3-μm-thick films and analyzed in transmission geometry. A beamstop, short anti-scatter extension and an anti-scatter knife edge were used to minimize the background generated by air. Soller slits for the incident and diffracted beams were used to minimize broadening from axial divergence. The diffraction patterns were collected using a scanning position-sensitive detector (X'Celerator) located 240 mm from the specimens and Data Collector software v. 2.2b. Data acquisition parameters for each pattern are displayed above the image in the Data section of this report including the divergence slit (DS) before the mirror.

Figure 15:
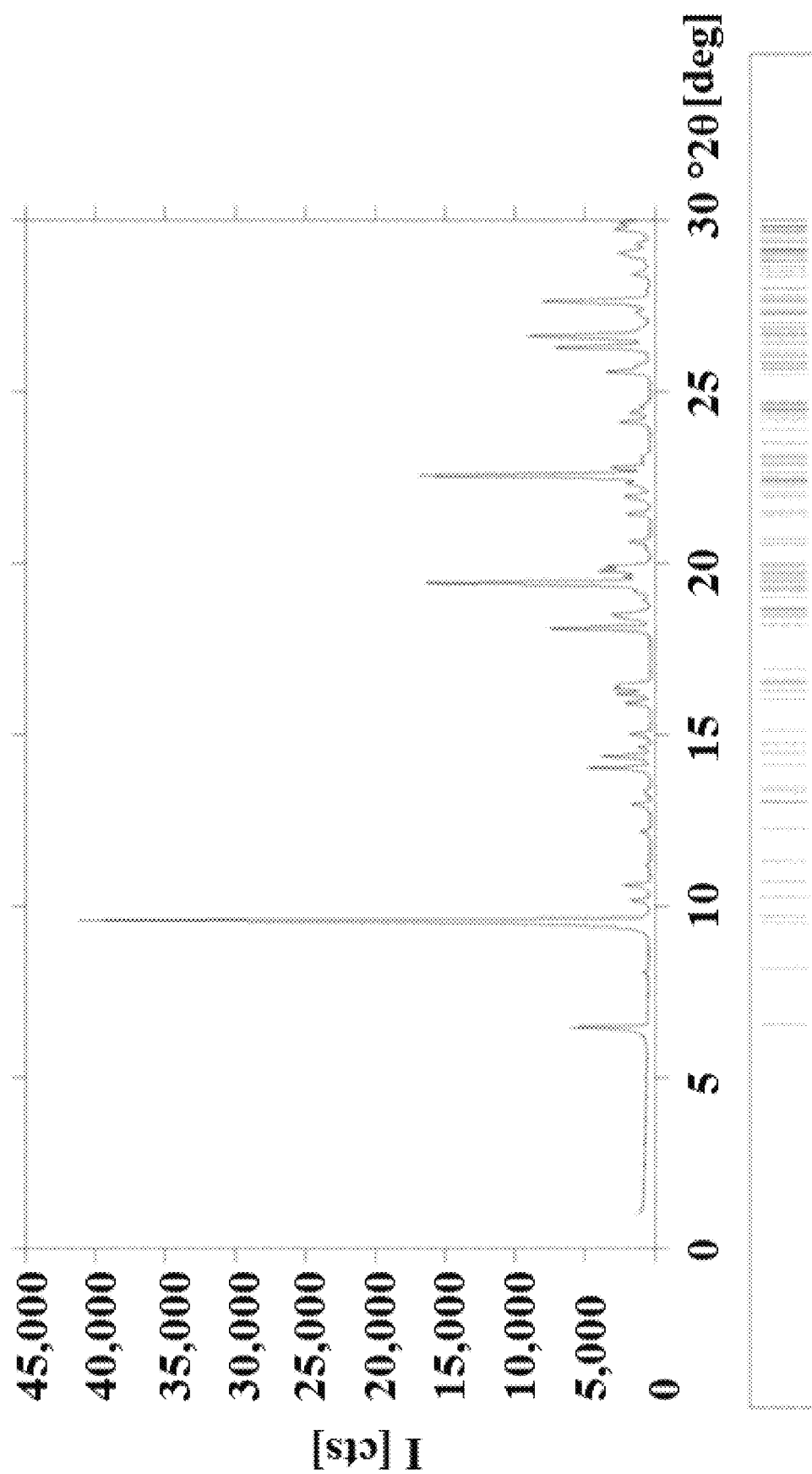
FIG. 15 is the XRPD pattern for pure Form B. The peaks, marked with bars, are listed in Example 14. The x-axis is 2Theta measured in degrees and the y-axis is intensity measured in counts.

The XRPD pattern of pure Form B along with the indexing solution is shown in FIG. 15. The pure Form B XRPD pattern exhibited sharp peaks, indicating the sample was composed of crystalline material. The allowed peak positions from the XRPD indexing solution are 6.5, 8.1, 9.4, 9.6, 10.2, 10.6, 11.2, 12.2, 12.9, 13.0, 13.3, 13.4, 14.0, 14.4, 14.6, 15.0, 15.9, 16.2, 16.4, 16.5, 16.8, 18.1, 18.4, 18.5, 18.6, 18.6, 18.9, 19.1, 19.2, 19.3, 19.4, 19.5, 19.6, 19.7, 19.8, 19.9, 20.4, 20.6, 21.3, 21.4, 21.8, 22.0, 22.2, 22.3, 22.4, 22.5, 22.8, 23.0, 23.1, 23.4, 23.8, 24.1, 24.2, 24.3, 24.4, 24.5, 24.6, 25.4, 25.6, 25.7, 25.9, 26.0, 26.1, 26.3, 26.4, 26.5, 26.6, 26.7, 26.8, 26.9, 27.2, 27.3, 27.5, 27.6, 27.7, 27.9, 28.3, 28.4, 28.5, 28.7, 28.9, 29.0, 29.1, 29.3, 29.4, 29.5, 29.6, 29.7, 29.8, 29.9, 30.0, 30.3, 30.4, 30.5, 30.6, 30.7, 30.9, 31.2, 31.5, 31.6, 31.7, 31.8, 31.9, 32.0, 32.2, 32.3, 32.4, 32.5, 32.6, 32.7, 32.8, 33.1, 33.2, 33.3, 33.6, 33.7, 33.8, 34.0, 34.1, 34.2, 34.3, 34.6, 34.7, 34.8, 35.0 35.2, 35.3, 35.5, 35.6, 35.9, 36.0, 36.2, 36.5, 36.6, 36.7, 36.8, 36.9, 37.1, 37.2, 37.3, 37.4, 37.5, 37.6, 37.7, 37.8, 37.9, 38.2, 38.3, 38.4, 38.5, 38.6, 38.7, 38.8, 38.9, 39.0, 39.1, 39.2, 39.3, 39.4, 39.5, 39.6, 39.7, 39.8, 39.9, and 40.0° 2θ.

For example, Form B's XRPD may be indexed as follows 6.47, 8.08, 9.42, 9.59, 10.18, 10.62, 11.22, 12.17, 12.91, 12.97, 13.27, 13.37, 14.03, 14.37, 14.63, 15.02, 15.93, 16.20, 16.35, 16.43, 16.47, 16.81, 18.10, 18.35, 18.41, 18.50, 18.55, 18.60, 18.91, 19.11, 19.15, 19.24, 19.34, 19.43, 19.51, 19.61, 19.65, 19.76, 19.85, 19.90, 20.44, 20.61, 21.34, 21.43, 21.84, 21.95, 22.17, 22.28, 22.30, 22.33, 22.44, 22.54, 22.76, 22.81, 22.97, 23.00, 23.11, 23.42, 23.80, 24.11, 24.22, 24.34, 24.38, 24.40, 24.48, 24.56, 24.57, 25.40, 25.56, 25.57, 25.59, 25.72, 25.74, 25.94, 25.99, 26.11, 26.28, 26.29, 26.37, 26.51, 26.58, 26.61, 26.73, 26.81, 26.92, 27.15, 27.19, 27.23, 27.31, 27.49, 27.57, 27.61, 27.71, 27.88, 27.94, 28.27, 28.41, 28.53, 28.71, 28.74 28.86, 28.94, 28.98, 29.03, 29.06, 29.08, 29.25, 29.30, 29.38, 29.51, 29.57, 29.61, 29.70, 29.73, 29.75, 29.90, 29.95, 30.31, 30.38, 30.42, 30.54, 30.55, 30.66, 30.73, 30.85, 30.87, 30.89, 31.23, 31.51, 31.55, 31.61, 31.70, 31.76, 31.77, 31.80, 31.81, 31.82, 31.82, 31.90, 31.91, 31.95, 32.17, 32.21, 32.23, 32.25, 32.36, 32.37, 32.43, 32.53, 32.54, 32.56, 32.61, 32.73, 32.80, 32.82, 33.05, 33.13, 33.17, 33.22, 33.28, 33.30, 33.60, 33.65, 33.71, 33.76, 33.77, 33.99, 34.01, 34.01, 34.05, 34.10, 34.17, 34.29, 34.55, 34.60, 34.62, 34.63, 34.68, 34.75, 34.76, 35.03, 35.16, 35.19, 35.21, 35.25, 35.31, 35.46, 35.61, 35.63, 35.85, 35.86, 35.90, 35.97, 36.19, 36.45, 36.56, 36.58, 36.67, 36.68, 36.70, 36.71, 36.77, 36.85, 36.87, 36.90, 37.09, 37.19, 37.27, 37.28, 37.29, 37.32, 37.33, 37.37, 37.38, 37.48, 37.48, 37.50, 37.51, 37.54, 37.61, 37.64, 37.65, 37.68, 37.69, 37.71, 37.74, 37.74, 37.76, 37.81, 37.83, 37.93, 37.94, 38.15, 38.19, 38.32, 38.36, 38.39, 38.46, 38.59, 38.63, 38.69, 38.76, 38.79, 38.85, 38.87, 38.88, 38.96, 38.98, 39.02, 39.05, 39.19, 39.27, 39.33, 39.36, 39.39, 39.43, 39.44, 39.53, 39.53, 39.6, 39.61, 39.70, 39.71, 39.72, 39.82, 39.87, 39.9, and 39.98 °2θ.

Observed peaks for Form B include 9.5±0.2, 18.1±0.2, 19.3±0.2, 22.4±0.2, 26.6±0.2, and 27.7±0.2, °2θ.

Agreement between the allowed peak positions, marked with bars, and the observed peaks indicated a consistent unit cell determination. Successful indexing of the pattern indicated that the sample was composed primarily of a single crystalline phase. Space groups consistent with the assigned extinction symbol, unit cell parameters, and derived quantities are given in Table 105.

TABLE 105

Parameters of the XRPD of Compound II, Form B

| Bravais Type | C-centered Monoclinic |
| --- | --- |
| a [Å] | 27.719 |
| b [Å] | 9.796 |
| c [Å] | 22.221 |
| α [deg] | 90 |
| β [deg] | 100.16 |
| γ [deg] | 90 |
| Volume [Å$^3$/cell] | 5,939.0 |
| Chiral contents | Not specified |
| Extinction Symbol | C 1 c 1 |
| Space Group(s) | Cc (9), C2/c (15) |

In one embodiment, Form B is characterized by an XRPD pattern comprising at least two 2theta values selected from 6.5±0.2°, 9.5±0.2°, 14.0±0.2°, 14.4±0.2°, 18.1±0.2°, 19.9±0.2°, and 22.4±0.2°. In one embodiment, Form B is characterized by an XRPD pattern comprising at least three 2theta values selected from 6.5±0.2°, 9.5±0.2°, 14.0±0.2°, 14.4±0.2°, 18.1±0.2°, 19.9±0.2°, and 22.4±0.2°. In one embodiment, Form B is characterized by an XRPD pattern comprising at least four 2theta values selected from 6.5±0.2°, 9.5±0.2°, 14.0±0.2°, 14.4±0.2°, 18.1±0.2°, 19.9±0.2°, and 22.4±0.2°. In one embodiment, Form B is characterized by an XRPD pattern comprising at least five 2theta values selected from 6.5±0.2°, 9.5±0.2°, 14.0±0.2°, 14.4±0.2°, 18.1±0.2°, 19.9±0.2°, and 22.4±0.2°. In one embodiment, Form B is characterized by an XRPD pattern comprising at least six 2theta values selected from 6.5±0.2°, 9.5±0.2°, 14.0±0.2°, 14.4±0.2°, 18.1±0.2°, 19.9±0.2°, and 22.4±0.2°. In one embodiment, Form B is characterized by an XRPD pattern comprising the 2theta values selected from 6.5±0.2°, 9.5±0.2°, 14.0±0.2°, 14.4±0.2°, 18.1±0.2°, 19.9±0.2°, and 22.4±0.2°. In one embodiment, Form B is characterized by an XRPD pattern comprising at least the 2theta value of 9.5±0.4°.

Example 15. Six- and Twelve-Month Stability Study of Form B at 25° C./60% RH and at 40° C./75% RH Conditions Form B was stored at 25° C./60% RH for twelve months and at 40° C./75% RH for six months.

Table 106 shows the results from the 25° C./60% RH storage conditions and Table 107 shows the results at the 40° C./75% RH. In both conditions, Form B was 99.5% pure and the XRPD spectrum conformed to the reference spectrum at the longest time point studied.

TABLE 106

Twelve-month Stability Study at the 25° C./60% RH Conditions

| Test | Storage Time | | | | |
|---|---|---|---|---|---|
| | 0 M | 3 M | 6 M | 9 M | 12 M |
| Appearance | Yellow solid | Yellow solid | Yellow solid | Yellow solid | Yellow solid |
| Moisture (%) | 4.9% | 4.07% | 7.53% | 7.29% | 7.48% |
| XRPD | Form B | N/A | N/A | N/A | Form B |
| HPLC Purity | 99.5% | 99.5% | 99.5% | 99.6% | 99.5% |

TABLE 107

Six-month Stability Study at the 40° C./75% RH Conditions

| Test | Storage Time | | | |
|---|---|---|---|---|
| | 0 M | 1 M | 3 M | 6 M |
| Appearance | Yellow solid | Yellow solid | Yellow solid | Yellow solid |
| Moisture (%) | 4.9% | 2.75% | 7.47% | 7.53% |
| XRPD | Form B | N/A | Form B | Form B |
| HPLC Purity | 99.5% | 99.5% | 99.5% | 99.5% |

Example 16. Conversion of Impure Form B Material to Pure Form B Material

Figure 16:
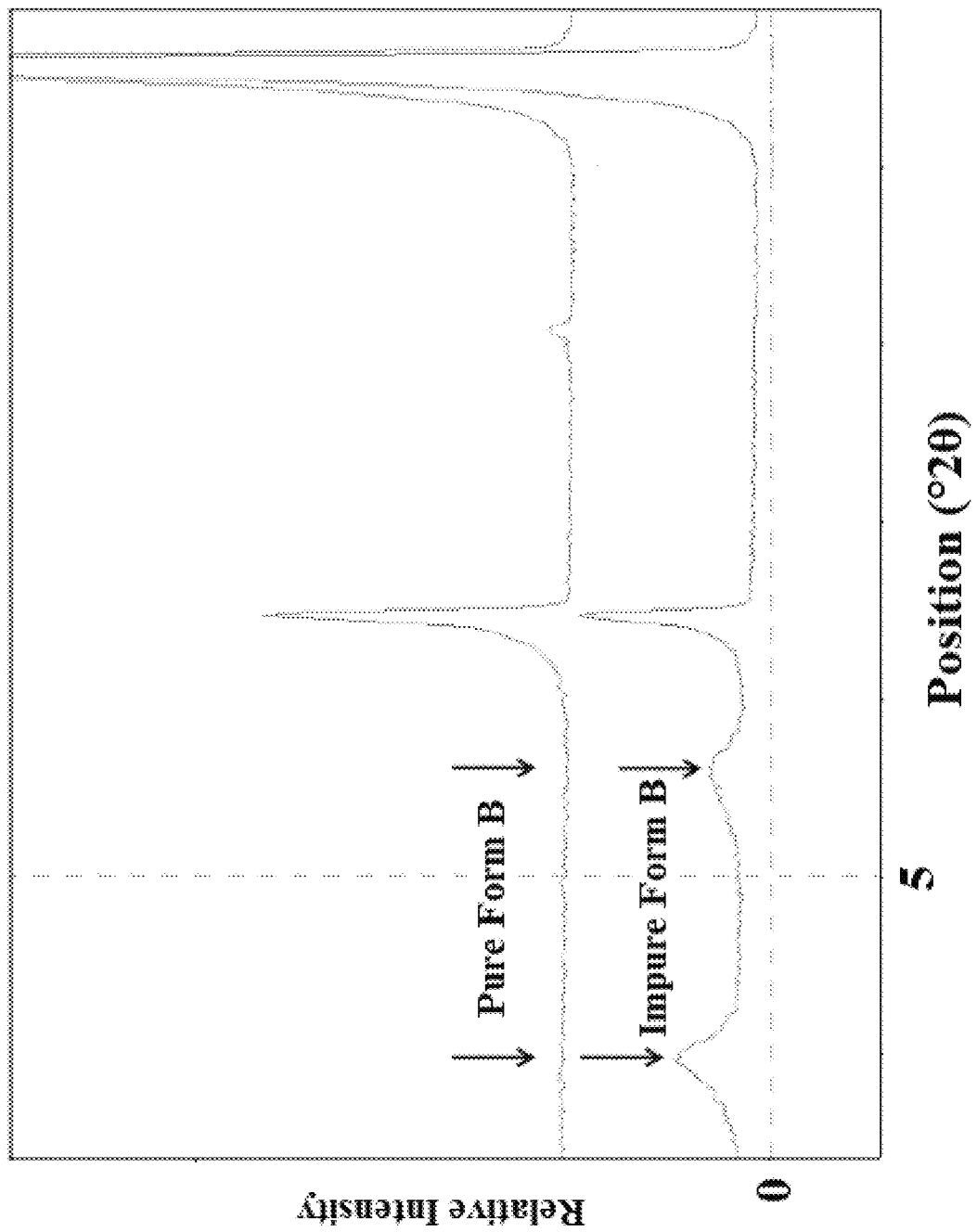
FIG. 16 is a comparison of the XRPD patterns of impure Form B material and pure Form B material as characterized in Example 16. Impure Form B material has two peaks at approximately 4.0 and 5.6 degrees that are missing in the pure Form B material. The x-axis is 2Theta measured in degrees and the y-axis is relative intensity as a means to compare the two Form B materials.
Figure 17:
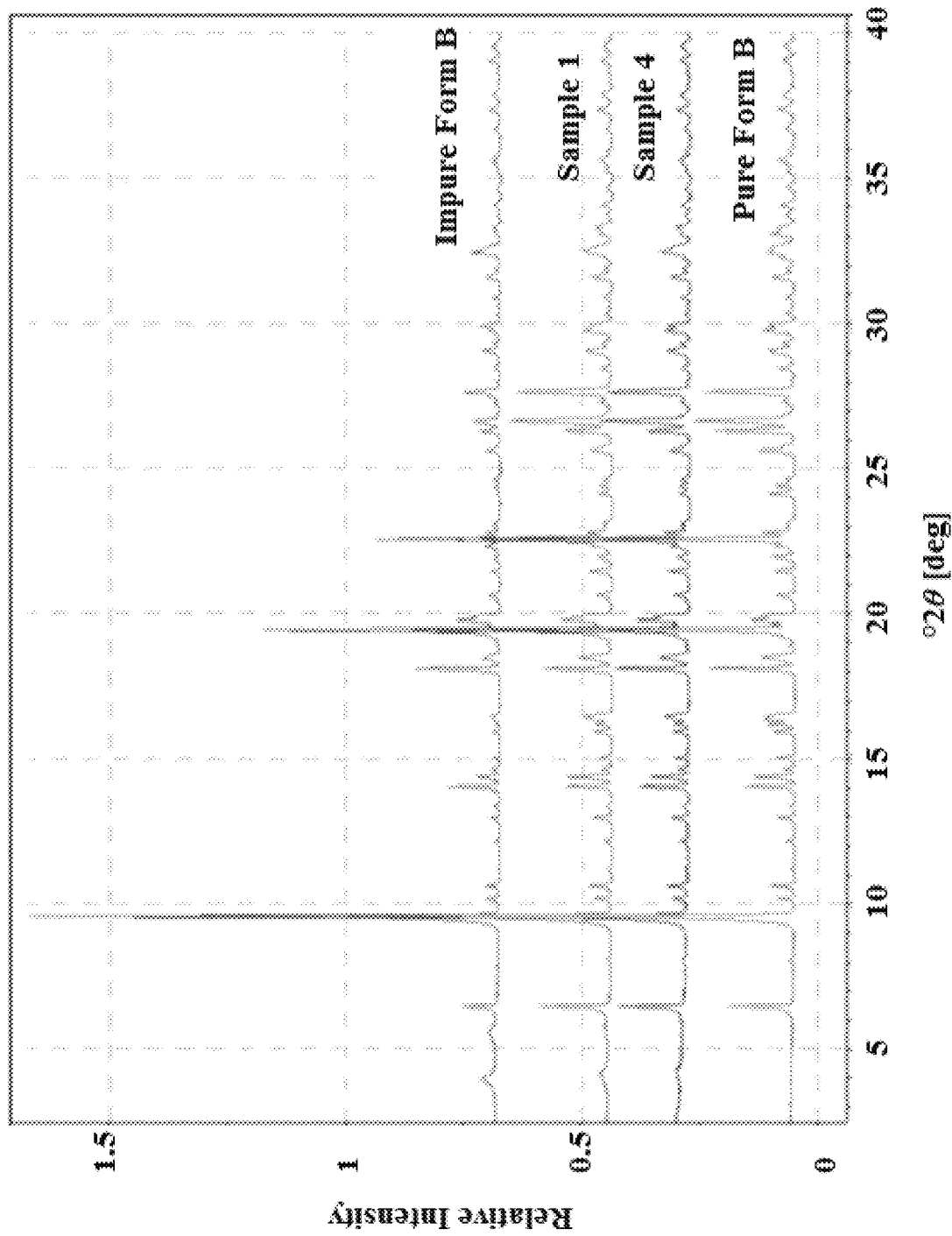
FIG. 17 is a comparison of impure Form B, Samples 1 and 4 from the slurry experiment described in Example 16, and pure Form B. Pure Form B is the Form B characterized in Example 13. A number of experiments were conducted to convert impure Form B to pure Form B material, including a slurry experiment with 1:1 (v/v) 0.1 M HCl:acetone (Sample 1) and 1:2 (v/v) 0.5 M HCl:acetone (Sample 4). The acidic aqueous acetone mixtures failed to convert impure material to pure material. The XRPD patterns of Sample 1 and 4 were not consistent with the XRPD pattern of pure Form B since a peak at approximately 4.0 degrees was still present. The x-axis is relative humidity measured as a percent and the y-axis is weight of water of the material measured as a percent.

Pure Form B was isolated from impure Form B, material that was characterized as containing a residual amount of an unknown form in addition to Form B. The difference in the XRPD patterns of impure Form B and pure Form B is shown in FIG. 16. (In the following experiments described below, pure Form B is the Form B as characterized in Example 14). The pattern of pure Form B is visually similar to the pattern of impure Form B, with the exception of the absence of peaks at 2-theta angles of approximately 4.0 and 5.6°. As is common in XRPD analysis, there are also differences in relative peak intensities that are likely due to preferred orientation and/or particle statistics effects.

Solubility studies, small scouting experiments, and experiments with drying conditions were first performed to confirm the conditions suitable for the conversion to pure Form B. TG-IR Characterization was performed on a number of isolated samples of Form B. Once conditions were confirmed, the conversion from impure material to pure material was conducted in water:acetone 1:2 (v/v) slurry at 125 mg/mL concentration and 30° C. for 43 hours as described in more detail below.

Solubility Estimate Experiments for the Development of Conditions Suitable for Recrystallization Solubility estimates of impure Form B were attempted in various predominantly HCl acidic aqueous acetone solvent mixtures using an aliquot addition method that involved visual observation. Aliquots of various solvents or diluent/organic solvent mixtures were added to measured amounts of impure Form B with agitation (typically sonication) at ambient temperature until complete dissolution was achieved, as judged by visual observation. Solubilities were calculated based on the total solvent used to give a solution; actual solubilities may be greater because of the volume of solvent portions utilized or a slow rate of dissolution. If dissolution did not occur as determined by visual assessment, the value was reported as "<". If dissolution occurred at the first aliquot, the value was reported as ">". Due to the haziness of the obtained samples, effective solubility estimates were difficult to discern. In general, impure Form B showed very limited solubility (3-7 mg/mL) in the tested solvent mixtures (Table 108).

TABLE 108

Approximate Solubility of Impure Form B

| Solvent/Solvent System | Temperature (° C.) | Solubility$^a$ (mg/mL) | Observation |
|---|---|---|---|
| 1M HCl:acetone 20:80 | ambient | <1 | solids remained |
| 0.5M HCl:acetone 20:80 | ambient | <1 | solids remained |
| 0.1M HCl:acetone 20:80 | ambient | <1 | solids remained |
| 1M HCl:acetone 10:90 | ambient | <1 | solids remained |
| 0.5M HCl:acetone 10:90 | ambient | <1 | solids remained |
| 1M HCl:acetone 5:95 | ambient | <1 | solids remained |
| 1M HCl:acetone 33:67 | ambient | 2 | hazy solution |
| 1M HCl:acetone 50:50 | ambient | 4 | hazy solution |
| 1M HCl:acetone 60:40 | ambient | 4 | hazy solution |
| 1M HCl:acetone 67:33 | ambient | 6 | hazy solution |
| 1.0 M HCl:acetone 75:25 | ambient | 7 | hazy solution |
| 2.0M HCl | ambient | 4 | hazy solution |
| 5.0M HCl | ambient | 3 | hazy solution |
| Water | ambient | <7 | solids remained |
| Water:acetone 1:2 | ambient | 3 | hazy solution |
| Water:acetone 3:1 | ambient | <3 | solids remained |
| 5.0M HCl:water 1:2 | ambient | 7 | clear solution |

$^a$Solubilities were calculated based on the total solvent used to give a solution; actual solubilities may be greater because of the volume of the solvent portions used or a slow rate of dissolution. Values are rounded to whole number. If dissolution did not occur as determined by visual assessment, the value is reported as "<". If dissolution occurred as determined by the visual assessment after the addition of the first aliquot, the value is reported as ">".

Figure 18:
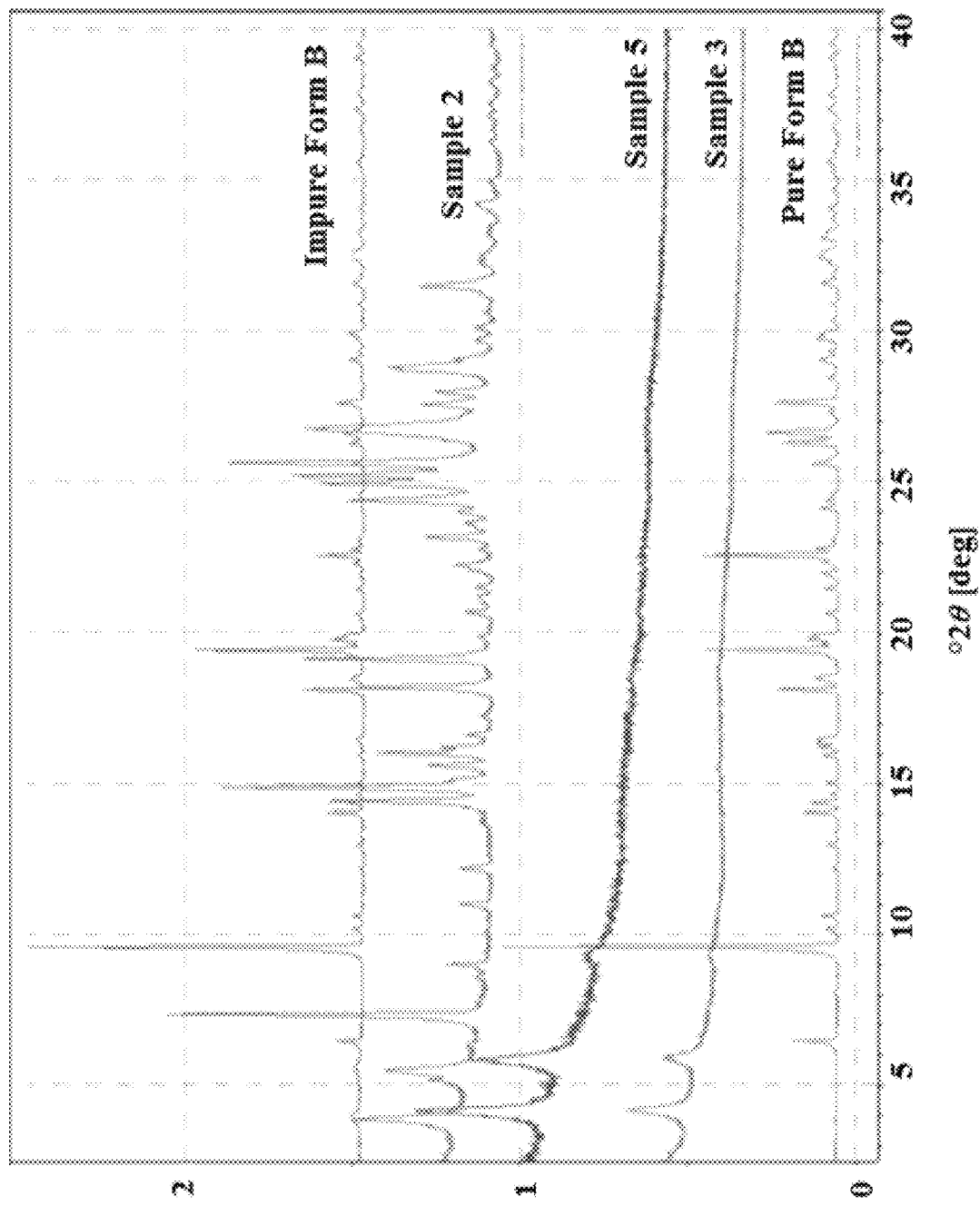
FIG. 18 is a comparison of impure samples of Form B, Samples 3 and 5 from the slurry experiment described in Example 16, and pure Form B. A number of experiments were conducted to convert impure Form B to pure Form B material, including a slurry experiment with 75:25 (v/v) 0.1 M HCl:acetone (Sample 3) and 50:50 (v/v) 0.5 M HCl:acetone (Sample 5). The acidic aqueous acetone mixtures failed to convert impure material to pure material. Pure Form B is the Form B characterized in Example 14. Impure Form B is the material used as starting material in the slurry experiments and impure Form B Sample 2 is a second impure form used as a reference. The x-axis is relative humidity measured as a percent and the y-axis is weight of water of the material measured as a percent.

Small-Scale Scouting Experiments Towards the Development of Conditions Suitable for Recrystallization Approximately 16 small scale slurry experiments were carried out by varying the slurry concentration, temperature, HCl acid molar concentration, and content in the aqueous acetone mixtures as well as the water content. Slurries of impure Form B were performed in a given solvent system at targeted calculated concentration at ambient or elevated temperatures for various time/durations. The solids were isolated by vacuum filtration and submitted for XRPD analysis. The specific experimental conditions are detailed in Table 109 where solvent system ratios are by volume. The slurries in acidic aqueous acetone mixtures (Samples 1, 2, and 4) at ambient temperature failed to convert impure Form B to pure Form B. FIG. 18 compares the XRPD patterns of Samples 1 and 4 to the XRPD pattern of the starting material of the experiments, impure Form B. FIG. 18 also compares Samples 1 and 4 to pure Form B material previously characterized in Example 14.

Figure 19:
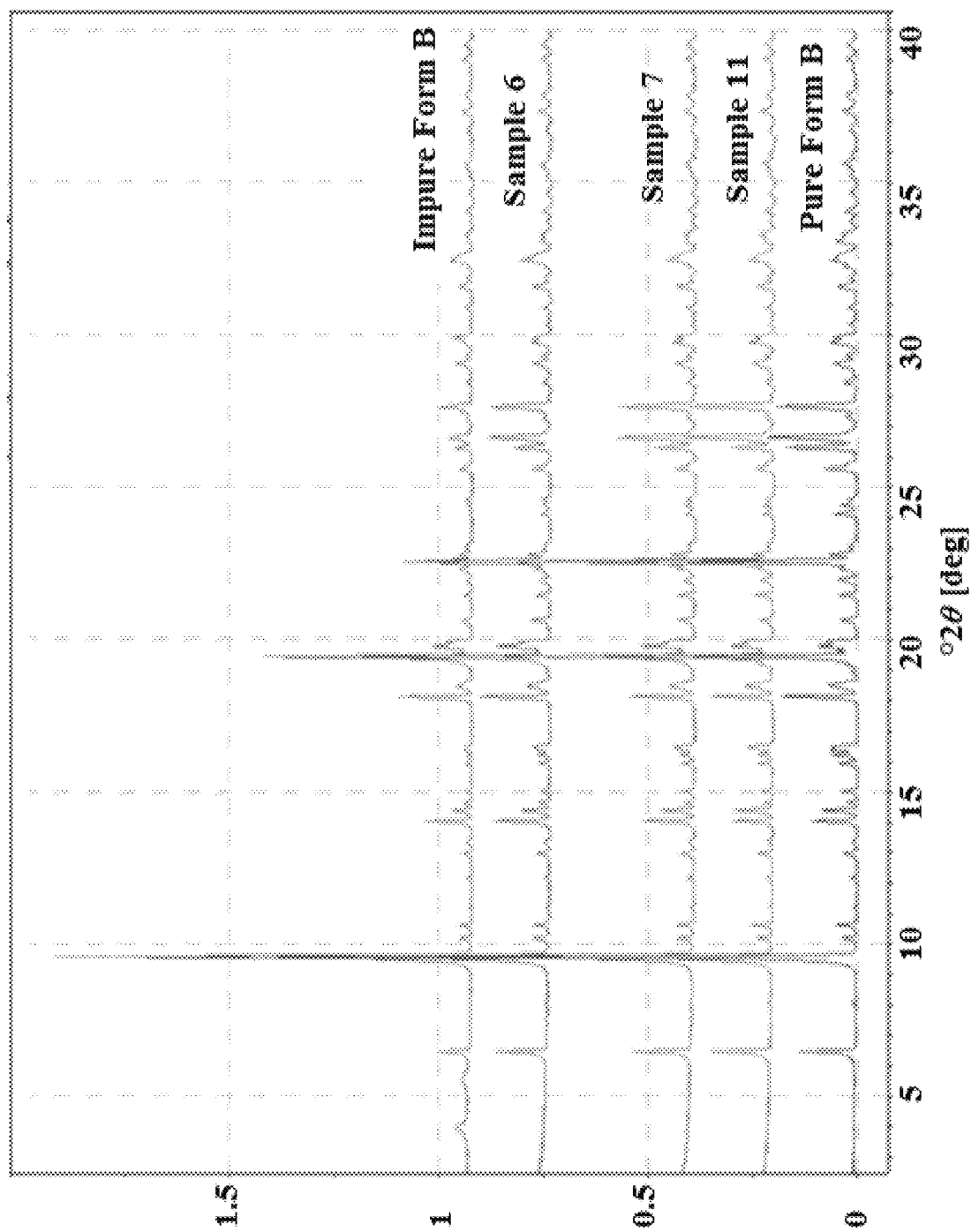
FIG. 19 is a comparison of impure Form B, Samples 6, 7, and 11 from the slurry experiment described in Example 16, and pure Form B. A number of experiments were conducted to convert impure Form B to pure Form B material, including slurry experiments with 1:2 (v/v) water:acetone that stirred at room temperature. Samples 6, 7, and 11 varied in the concentration of impure Form B and the length of time that the samples stirred (details are given in Table 98). All three conditions converted impure Form B to pure Form B since the XRPD patterns from Samples 6, 7, and 11 matched the pure Form B XRPD pattern. Pure Form B is the Form B characterized in Example 14 and impure Form B is the material used as staring material in the slurry experiments. The x-axis is relative humidity measured as a percent and the y-axis is weight of water of the material measured as a percent.

The slurries in acidic aqueous acetone mixtures at an elevated temperature of 50° C. (Samples 3 and 5) produced a disordered material with two broad low angle peaks material suggestive of a potential mesophase. FIG. 19 compares XRPD patterns of Sample 3 and 5 to the starting material of the experiments, impure Form B and to pure Form B. For comparison purposes, the samples were also compared to a second impure sample of Form B, (Impure Form B Sample 2 in FIG. 19). This second impure Form B contained larger amounts of the unknown Form than the impure Form B previously described in Example 8. When increasing the molar concentration of HCl from 0.1 M (Sample 3) to 0.5 M (Sample 5), the intensity of these two peaks also increased.

Figure 20:
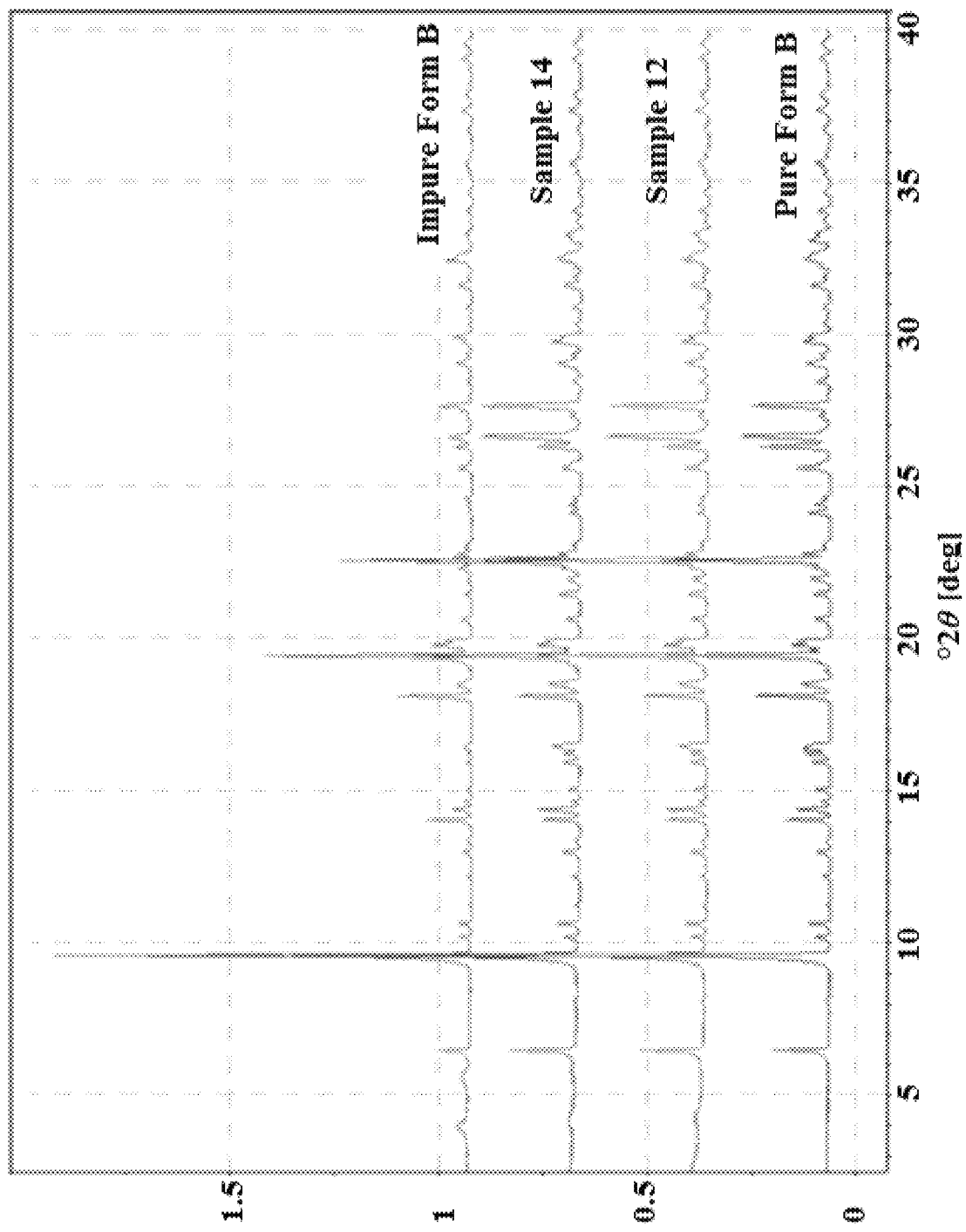
FIG. 20 is a comparison of impure Form B, Samples 12 and 14 from the slurry experiment described in Example 16, and pure Form B. Slurry experiments with 1:3 (v/v) water:acetone (Sample 14) and 1:2 water:acetone followed by additional acetone (Sample 12) were conducted in an effort to improve the yield of the recrystallization process. The XRPD patterns of Samples 12 and 14 were not consistent with the XRPD pattern of Form B since a peak at approximately 4.0 degrees was still present. Pure Form B is the Form B characterized in Example 13 and impure Form B is the material used as staring material in the slurry experiments. The x-axis is relative humidity measured as a percent and the y-axis is weight of water of the material measured as a percent.

Several slurry experiments were performed in water:acetone solvent systems starting with impure Form B and varying the water:acetone ratio, slurry concentration, and time. Based on the initial slurry results, experiments in 1:2 (v/v) water:acetone at ambient temperature were performed with aliquots taken after 16 hours (Sample 6) and 20.5 hours (Sample 7). The slurry in this solvent system was conducted at a concentration of 100-125 mg/mL and ambient temperature. The XRPD patterns of the resulting materials were consistent with pure Form B (FIG. 20). Using a water:acetone (1:2) solvent system resulted in a low yield of 5 that was calculated for solids isolated by vacuum filtration without drying.

Figure 21:
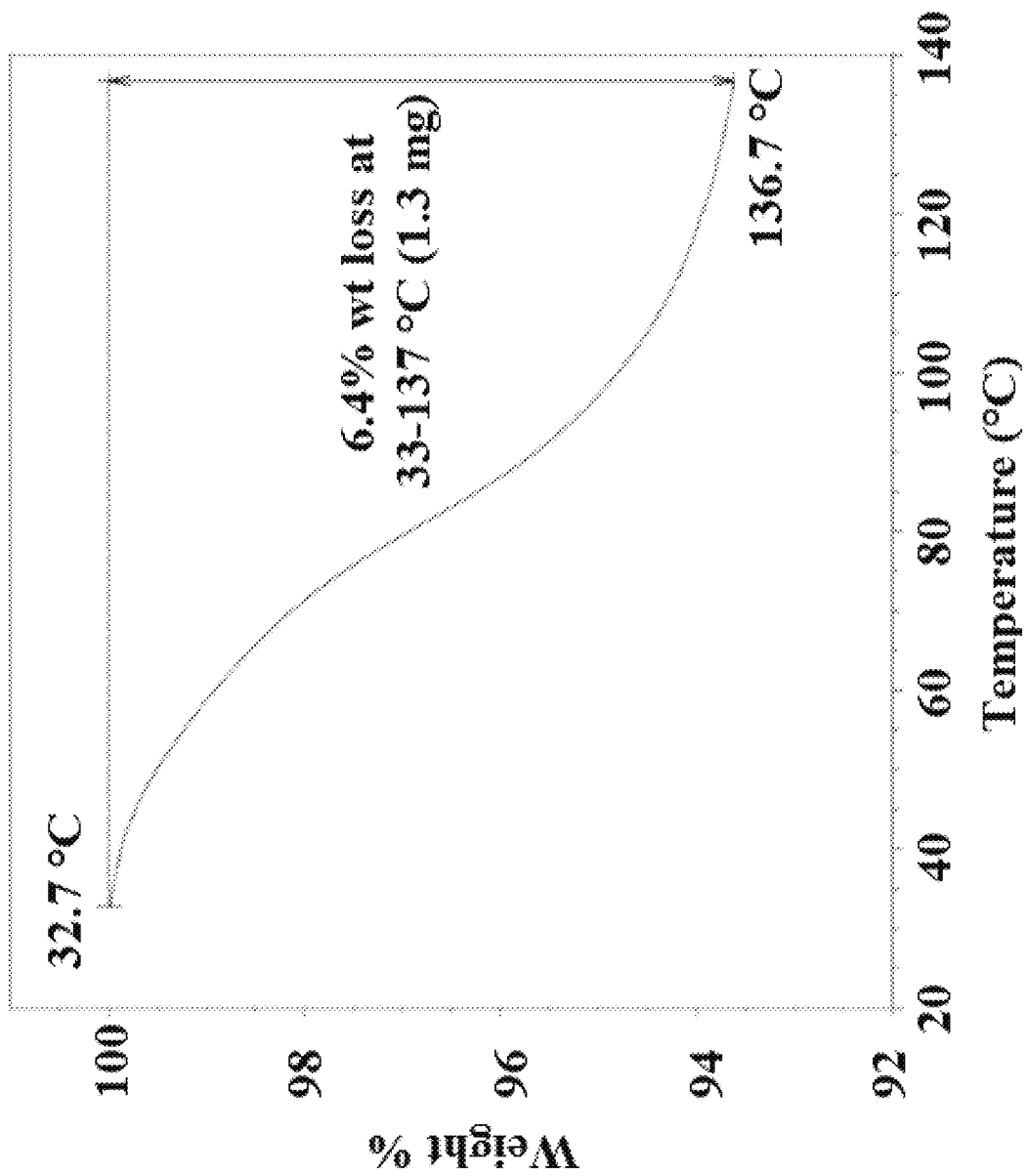
FIG. 21 is a graph from the TG-IR experiment of pure Form B, Sample 11 (Example 16). The TG data showed a 6.4% wt loss at 33-137° C. The x-axis is temperature measured in degrees Celsius and the y-axis is weight of the material measured as a percent.

In an effort to improve the yield, water:acetone 1:3 (v/v) was used at 150 mg/mL concentration (Samples 13 and 14) however, the conversion was not completed even after 4 days (FIG. 21). Therefore, one experiment was performed using water:acetone 1:2 (v/v) slurry for 18 hours and then adding acetone to reach ratio water:acetone 1:4 (v/v) followed by slurry for 4 hours (Sample 12). The XRPD pattern of the resulting material was consistent with Form B, however, one of the undesired peaks reappeared shifted from 3.95 °2θ to 4.2 °2θ (FIG. 21).

TABLE 109

Small-scale Slurry Experiment Conditions and Results

| Sample ID | Solvent System[a] | Conditions | Observation | XRPD Result |
|---|---|---|---|---|
| 1 | 0.5M HCl:acetone 1:1 | 100 mg/mL Slurry, RT, 3 days | Dark yellow solids | B + broad peaks at 3.95° 2θ and 5.55° 2θ |
| 2 | 2.0M HCl | 150 mg/mL Slurry, RT, 3 days | Light yellow solids | B + A |
| 3 | 0.1M HCl:acetone 75:25 | 100 mg/mL | Yellow orange mobile suspension | Two low angle peaks in disordered material |
| 4 | 0.1M HCl:acetone 1:2 | Slurry, 50° C., 15 h | Bright yellow mobile suspension | Form B + broad peak at 3.95° 2θ |
| 5 | 0.5M HCl:acetone 50:50 | 100 mg/mL Slurry, RT, 16 h | Dark orange mobile suspension | Two low angle peaks in disordered material |
| 6 | water:acetone 1:2 | 100 mg/mL Slurry, RT, 16 h | Bright yellow mobile suspension | Form B |
| 7 | | 100 mg/mL Slurry, RT, 20.5 h | Bright yellow mobile suspension | Form B |
| 8 | | 100 mg/mL Slurry, RT, 5 days | Bright yellow mobile suspension | Not analyzed |
| 9 | water:acetone 1:2 | 150 mg/mL Slurry, RT, 20 h | | Form B + broad smaller peak at 4.2° 2θ |
| 10 | | 150 mg/mL Slurry, RT, 4 days | Bright yellow suspension with ribbon of orange solids below solvent line | Not analyzed |
| 11 | water:acetone 1:2 | 125 mg/mL Slurry, RT, 20 h | Bright yellow mobile suspension | Form B |
| 12 | 1. water:acetone 1:2 2. water:acetone 1:4 | 1. 125 mg/mL, slurry, RT, 18 h 2. Acetone added to reach H2O:acetone 1:4 3. Slurry, RT, 4 h | 1. Bright yellow mobile suspension 2. No observation 3. Bright yellow mobile suspension | Form B + small broad peak at 4.27° 2θ |

TABLE 109-continued

Small-scale Slurry Experiment Conditions and Results

| Sample ID | Solvent System[a] | Conditions | Observation | XRPD Result |
|---|---|---|---|---|
| 13 | water:acetone 1:3 | 150 mg/mL Slurry, RT, 20 h | | Form B + broad peaks at 4.2° 2θ and 5.9° 2θ |
| 14 | | 150 mg/mL Slurry, RT, 4 days | Bright yellow suspension with tiny ring of orange solids below solvent line | Form B + broad peaks at 4.2° 2θ and 5.7° 2θ |
| 15 | 0.1M HCl:EtOH 1:9 | 100 mg/mL Slurry, RT, 16 h | Bright yellow mobile suspension | Form B + broad peak at 3.95° 2θ |
| 16 | | 100 mg/mL Slurry, RT, 20.5 h | Bright yellow mobile suspension | Form B + broad peak at 3.95° 2θ |

Lara Controlled Laboratory Reactor Slurry Experiments

Several scale up experiments were carried out in efforts to demonstrate applicable conditions for the conversion of impure Form B to pure Form B. The slurry conversion experiment was performed using a 1 L round-bottomed controlled laboratory reactor (Radleys Lara CLR) equipped with a Teflon anchor impeller, Julabo temperature control unit, and temperature probe for monitoring of the reactor temperature throughout the experiment. The Julabo FP50 temperature control unit contained Julabo Thermal C10 fluid and the reactor temperature was measured with a K-type PTFE temperature probe. The experiments were carried out with Lara Control software version 2.3.5.0. The software tracked circulator temperature, vessel temperature, and stir rate, recording readings every tenth of a second throughout the experiment.

The reactor vessel was charged with the solids of impure Form B (58.86 g) in 471 mL of a water:acetone 1:2 (v/v) solvent system achieving 125 mg/mL slurry concentration (Samples 20-23). The resulting slurry was stirred at 30° C. for up to 43 hours with stirring speed of 400 rpm. The slurry was cooled to 25° C. over 30 minutes, discharged from the reactor vessel, and immediately slowly filtered (drop by drop) to dry land. A water:acetone 1:2 (v/v) wash solution was prepared in advance and used to wash the filter cake in one portion.

Pulls were taken usually at the 20th hour and if needed at later time points (Table 110). The scale up experiments showed that longer times and slightly elevated temperature (from ambient temperature to 30° C.) were needed at larger scale to convert impure Form B completely to pure Form B. Sample 22 was converted to pure Form B, while Samples 21 and 23 were not analyzed. Sample 20 resulted in Form B, but a broad peak was also observed at 4.2 °2θ.

TABLE 110

Scale-up Slurry Experimental Conditions and XRPD Results

| Sample ID | Solvent System (v/v) | Conditions | XRPD Result |
|---|---|---|---|
| 17 | water:acetone 30:70 | 125 mg/mL Slurry, RT, 18 h | B + broad peaks at 4.2° 2θ and 5.8° 2θ |
| 18 | | 125 mg/mL Slurry, RT, 23 h | B + broad peak at 4.2° 2θ |
| 19 | | 125 mg/mL Slurry, RT, 30 h | B + broad peaks at 4.2° 2θ and 5.8° 2θ |
| 20 | water:acetone 1:2 | 125 mg/mL Slurry, RT, 20 h | B + broad peak at 4.2° 2θ |
| 21 | | 125 mg/mL Slurry, RT, 45 h | Not analyzed |
| 22 | | 125 mg/mL Slurry, 30° C., 20 h | Form B |
| 23 | | 125 mg/mL Slurry, 30° C., 20.5 h | Not analyzed |

TG-IR Characterization of Compound II, Form B

The TG analyses were performed using a TA Instrument Q5000 thermogravimetric analyzer. Temperature calibration was performed using nickel and Alumel. The sample was placed in a platinum pan and inserted into the TG furnace. The furnace was heated under a nitrogen purge to 350° C. at a rate of 10° C./min.

Thermogravimetric infrared (TG-IR) analysis was performed on a TA Instruments Q5000 IR thermogravimetric (TG) analyzer interfaced to a Magna-IR 560® Fourier transform infrared (FT-IR) spectrophotometer (Thermo Nicolet) equipped with an Ever-Glo mid/far IR source, a potassium bromide (KBr) beamsplitter, and a mercury cadmium telluride (MCT-A) detector. The FT-IR wavelength verification was performed using polystyrene, and the TG calibration standards were nickel and Alumel™. The sample was placed in a platinum sample pan and the pan was inserted into the TG furnace. The TG instrument was started first, immediately followed by the FT-IR instrument. The TG instrument was operated under a flow of helium at 90 and 10 cc/minute for the purge and balance, respectively. The furnace was heated under helium at a rate of 20° C./minute to a final temperature of approximately 140° C. IR spectra were collected approximately every 32 seconds for approximately 7.5 minutes. Each IR spectrum represents 32 co-added scans collected at a spectral resolution of 4 cm-1. Volatiles were identified from a search of the High Resolution Nicolet Vapor Phase spectral library.

A TG-IR experiment was carried out on pure Form B (Sample 11 from the small-scale slurry experiments) at ambient temperature for 20 hours in an effort to investigate the stability of Form B at elevated temperature by monitoring potential release of hydrogen chloride.

Figure 22:
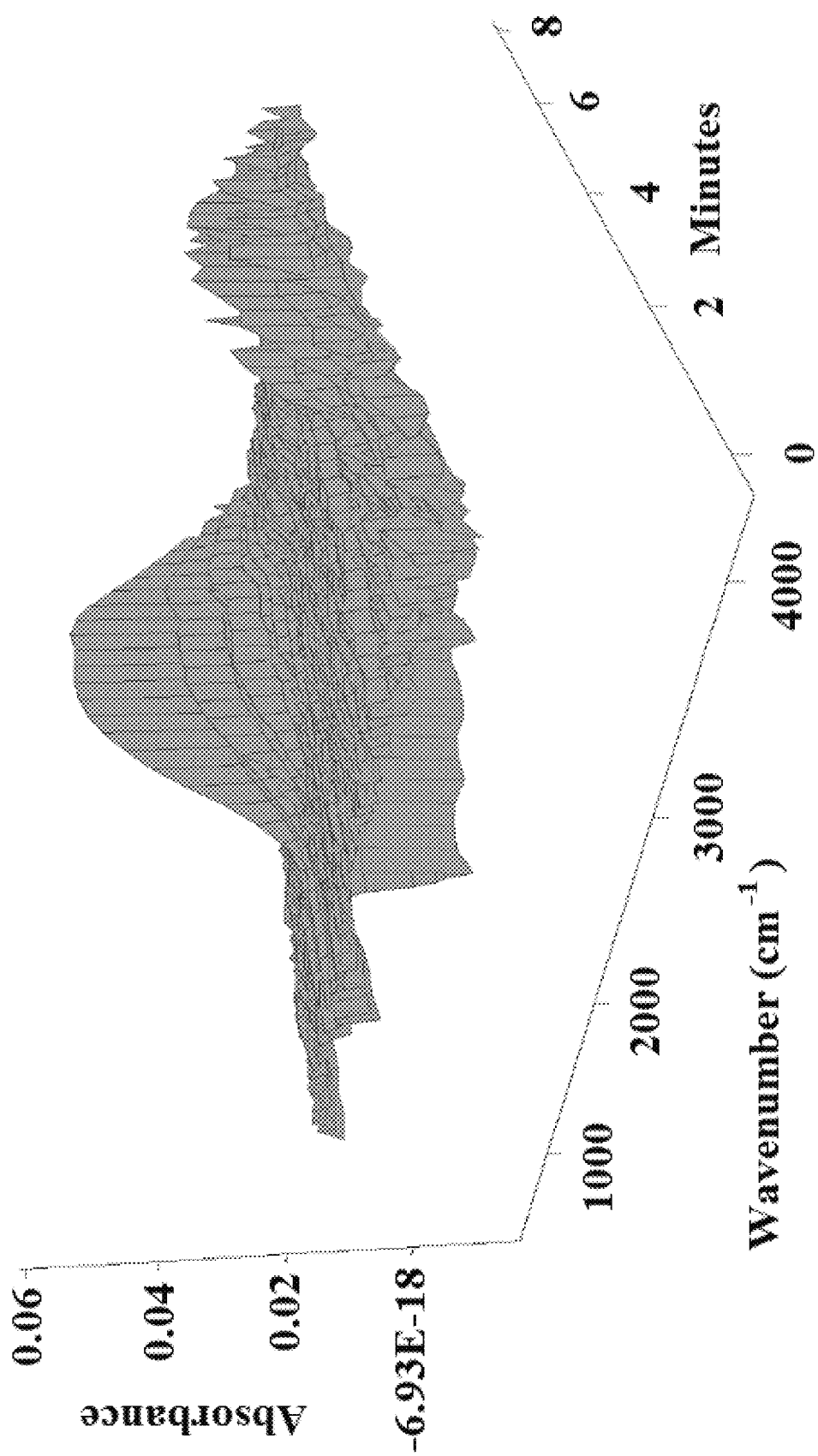
FIG. 22 is IR data from the TG-IR experiment of pure Form B, Sample 11 (Example 16). The x-axes are wavenumber measured in $cm^{-1}$ and time measured in minutes. The y-axis is absorbance.
Figure 23:
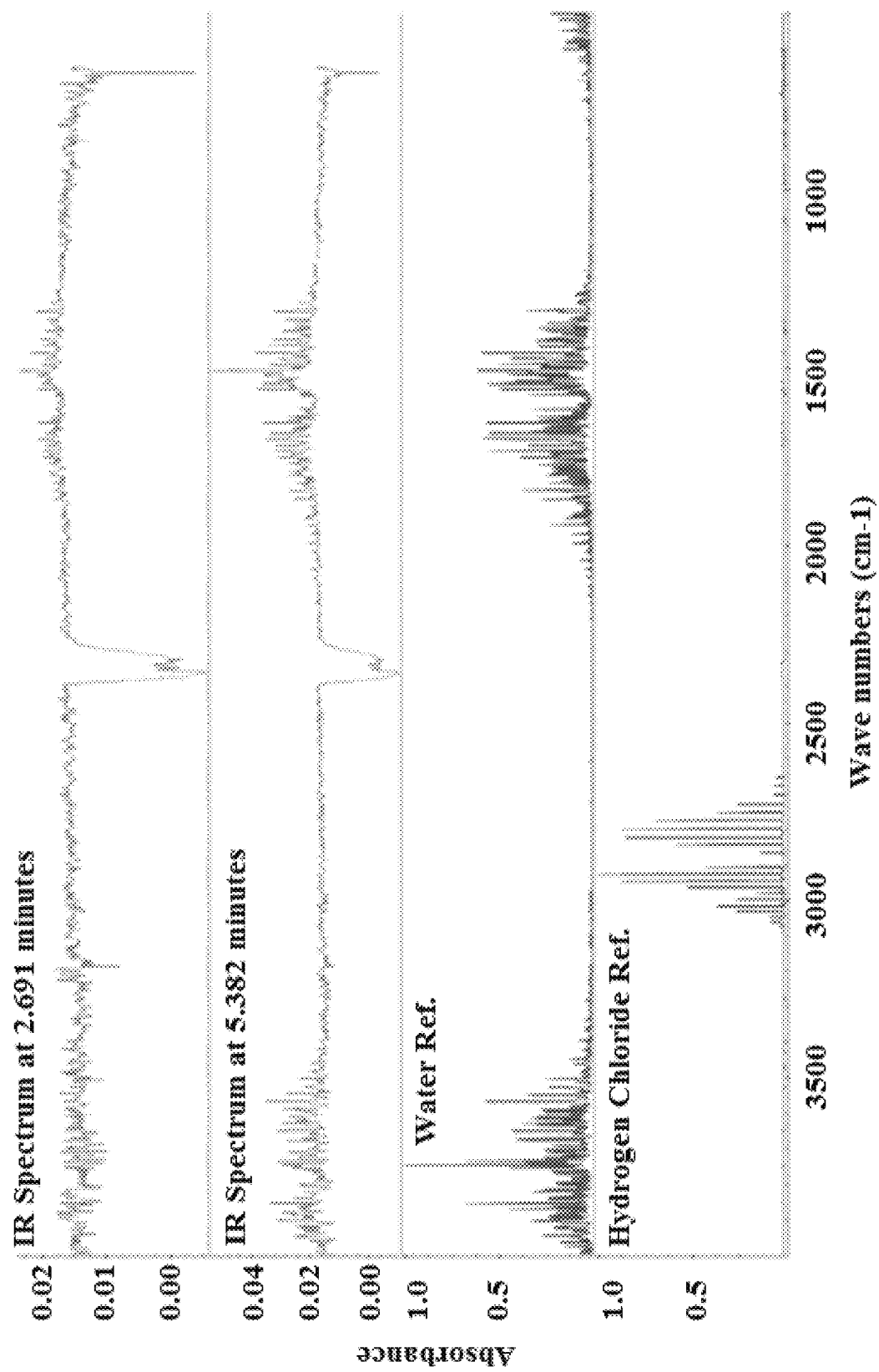
FIG. 23 compares IR spectra of pure Form B, Sample 11 obtained at 2.691 minutes and 5.382 minutes in the TG-IR experiment to IR spectra of water and hydrogen chloride. During the TG-IR experiment, only water, and no hydrogen chloride, was released as a volatile. The x-axis is wavenumber measured in $cm^{-1}$ and the y-axis is absorbance.
Figure 24:
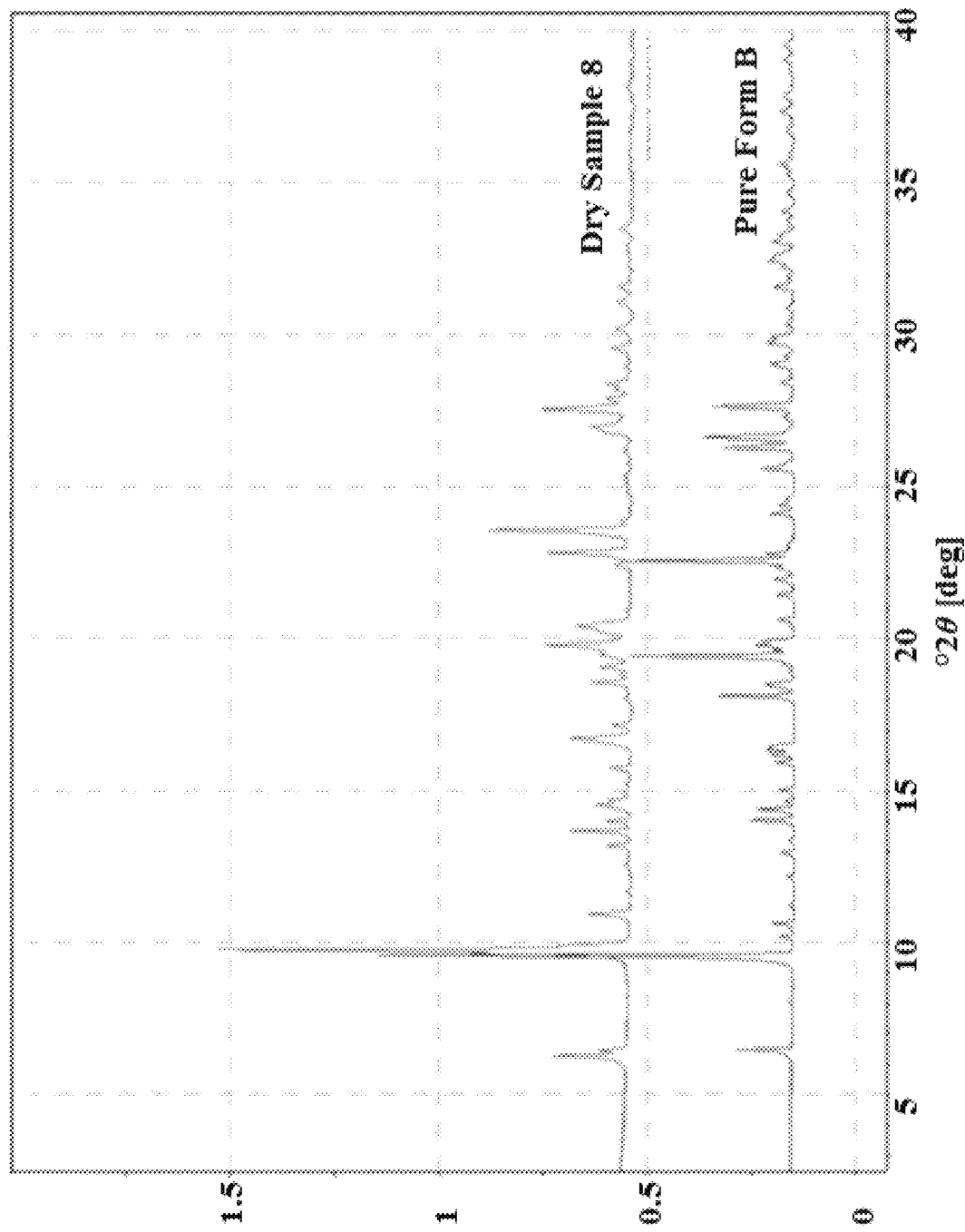
FIG. 24 is a comparison of Sample 8 dried in a vacuum oven for 15 hours at approximately 40° C. (Example 16, Table 112). The XRPD following the vacuum procedure did not correlate with the XRPD pattern of pure Form B. Dry sample 8 is a new crystalline Form. The x-axis is 2Theta measured in degrees and the y-axis is intensity measured in counts.

The TG data showed 6.4% weight loss at 33-137° C. (FIG. 22). The correlation between the time and temperature is presented in Table 111. The series of IR spectra collected during the TG-IR experiment are presented in FIG. 23 and FIG. 24. The spectra demonstrated that only water was detected as a volatile and that no hydrogen chloride was released.

TABLE 111

Correlation between Time and Temperature for TG-IR of Compound II, Form B

| Time (min) | Temperature (° C.) | Weight (%) |
|---|---|---|
| 0.13 | 33.00 | 99.98 |
| 0.38 | 36.60 | 99.93 |
| 0.55 | 40.20 | 99.87 |
| 0.73 | 43.80 | 99.77 |
| 0.90 | 47.40 | 99.63 |
| 1.08 | 51.00 | 99.46 |
| 1.25 | 54.60 | 99.26 |
| 1.43 | 58.20 | 99.03 |
| 1.61 | 61.80 | 98.79 |
| 1.78 | 65.40 | 98.52 |
| 1.96 | 69.00 | 98.22 |
| 2.14 | 72.60 | 97.86 |
| 2.32 | 76.20 | 97.44 |
| 2.50 | 79.80 | 96.95 |
| 2.68 | 83.40 | 96.45 |
| 2.86 | 87.00 | 95.97 |
| 3.04 | 90.60 | 95.57 |
| 3.23 | 94.20 | 95.23 |
| 3.41 | 97.80 | 94.95 |
| 3.59 | 101.40 | 94.71 |
| 3.77 | 105.00 | 94.50 |
| 3.95 | 108.60 | 94.32 |
| 4.13 | 112.20 | 94.18 |
| 4.31 | 115.80 | 94.06 |
| 4.50 | 119.40 | 93.96 |
| 4.68 | 123.00 | 93.86 |
| 4.86 | 126.60 | 93.78 |
| 5.04 | 130.20 | 93.71 |
| 5.22 | 133.80 | 93.65 |

Drying Experiments of Compound II, Form B

Weighted amounts of impure Form B and pure Form B samples from the previous experiments (Samples 14, 8, 11, 19, 21, and 23) were vacuum dried at ambient or elevated temperatures using various vacuum levels from approximately 14 in Hg up 27-28 in Hg. The resulting materials were weighted out prior to submission for XRPD analysis.

Figure 25:
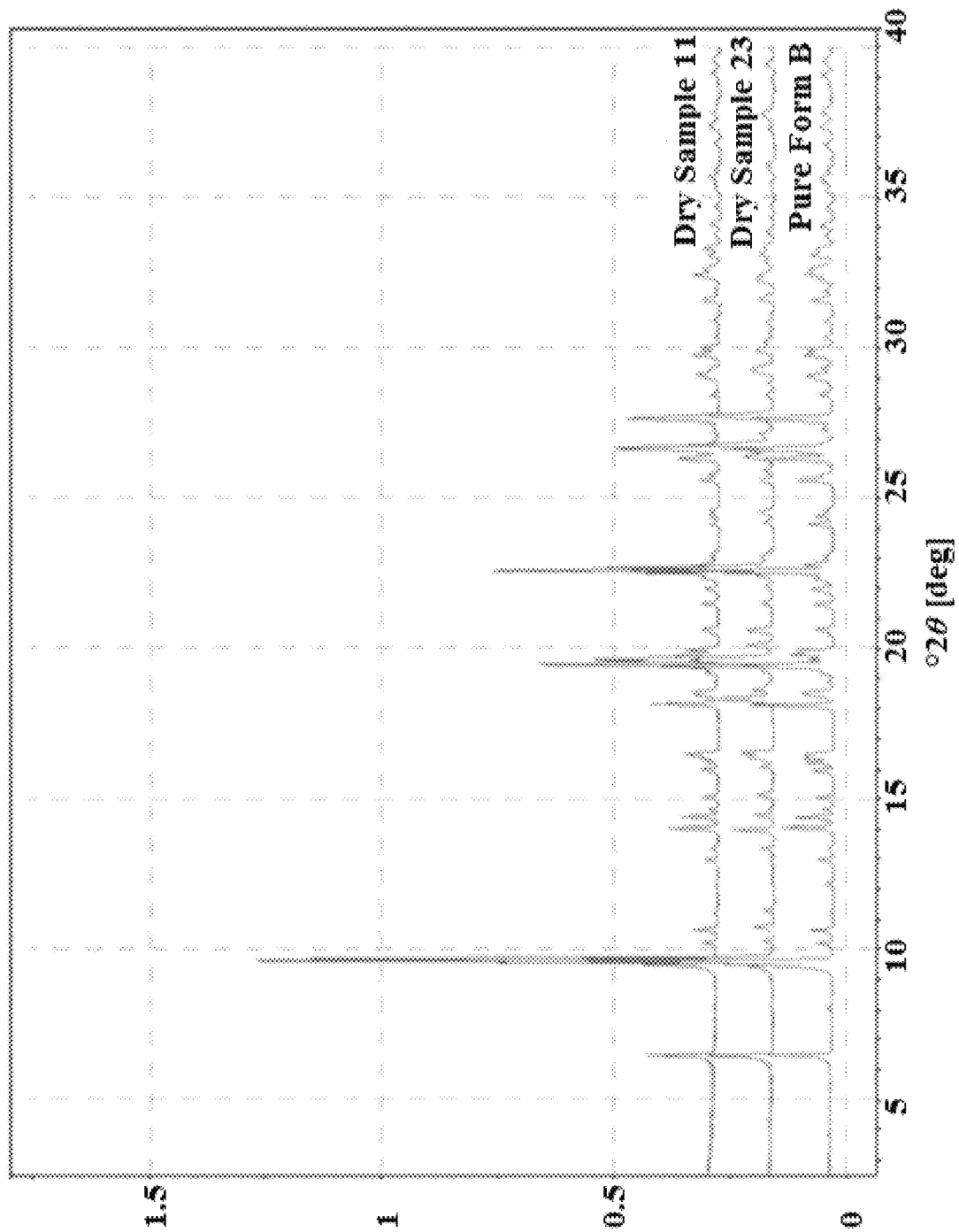
FIG. 25 are the XRPD patterns of Sample 11 and Sample 23 that were both dried in a vacuum oven, but under different conditions (Example 16, Table 112) compared to the XRPD pattern of pure Form B. Both Sample 11 and 23 exhibited XRPD patterns of Form B. The x-axis is 2Theta measured in degrees and the y-axis is intensity measured in counts.

Two samples (Sample 14 and 8) were vacuum dried at 40° C. for 15 hours (approximately 29 in Hg) and demonstrated approximately 7.4% weight loss. One of the samples (Sample 8) was analyzed by XRPD and a new crystalline XRPD pattern was obtained (FIG. 25) that was not consistent with Form B.

Figure 26:
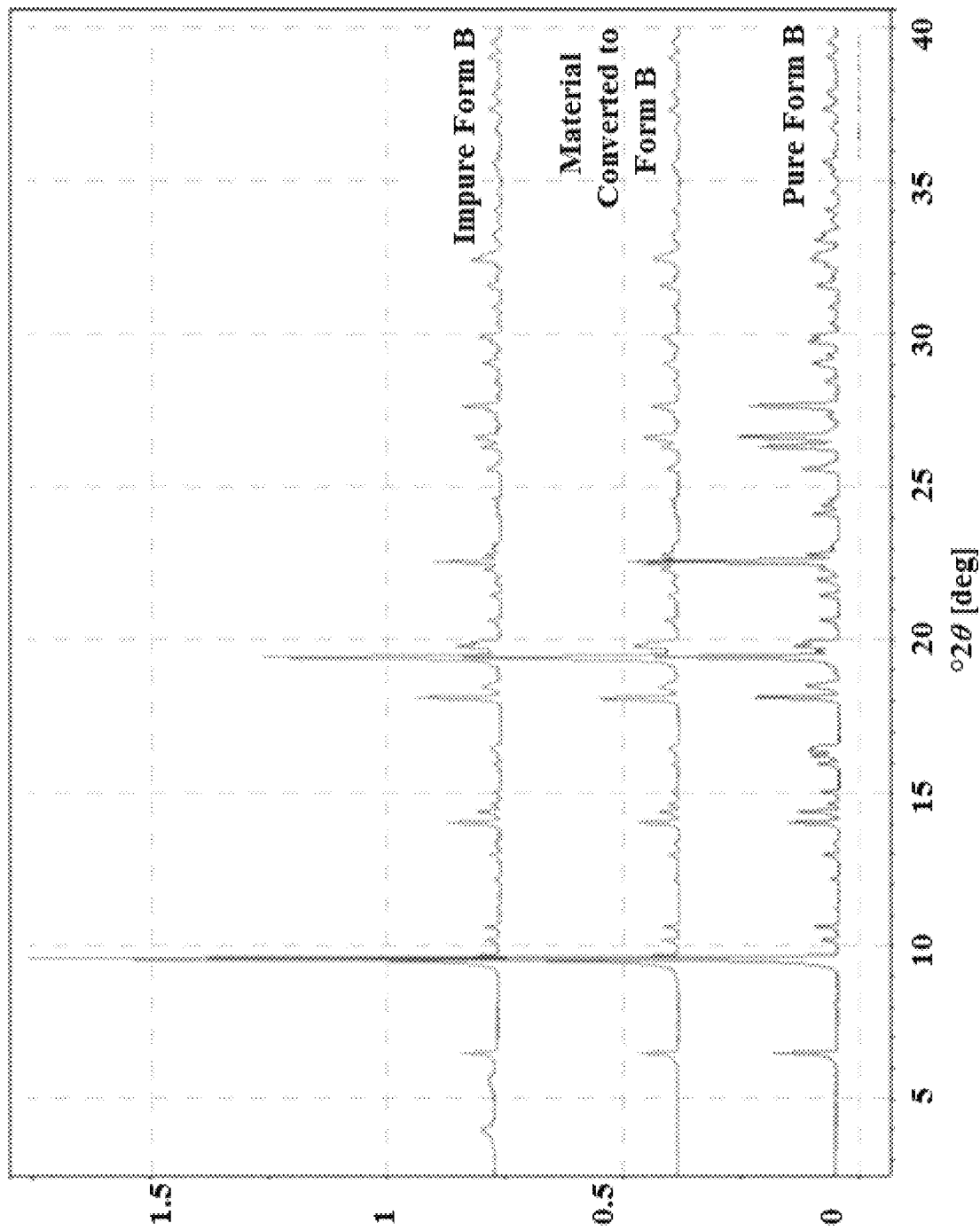
FIG. 26 is a comparison of XRPD patterns from impure Form B, pure Form B, and the material that was converted from impure Form B as described in Example 16. The XRPD pattern of the converted material aligned with the pure Form B material. Pure Form B is the Form B characterized in Example 14 and impure Form B is the material used as staring material in the conversion procedure. The x-axis is 2Theta measured in degrees and the y-axis is intensity measured in counts.

Sample 11 was vacuum dried at ambient temperature for 0.5 hour (approximately 14 in Hg) demonstrating a 1.8% weight loss (calculated from weighing the sample before and after drying). The XRPD pattern of the resulting material was consistent with Form B, however, tiny shifting in a few peak positions in the XRPD pattern was observed (FIG. 26). Significant peak shifting was observed in the XRPD pattern of Sample 23 (FIG. 26) that was vacuum dried at ambient temperature for 1 h (approximately 27-28 in Hg) demonstrating an 4.7% weight loss (calculated from weighing the sample before and after drying).

TABLE 112

Drying Conditions and Results for Compound II, Form B

| Sample Source | Conditions | Weight Loss (calculated by weight before and after drying) | XRPD Result |
|---|---|---|---|
| Sample 14 | Vacuum oven, ~40° C., 15 h (~29.5 in Hg) | Weight loss: 7.5% | Not analyzed |
| Sample 8 | Vacuum oven, ~40° C., 15 h (~29.5 in Hg) | Weight loss: 7.4% | New crystalline material, not indexable |
| Sample 14 | Vacuum oven, 23° C., 2 h (~29.5 in Hg) | Weight loss: 6.8% | Not analyzed |

TABLE 112-continued

Drying Conditions and Results for Compound II, Form B

| Sample Source | Conditions | Weight Loss (calculated by weight before and after drying) | XRPD Result |
|---|---|---|---|
| Sample 11 | Vacuum oven, 22° C., 0.5 h (~14 in Hg) | Weight loss: 1.8% | Form B tiny peak shifting |
| Sample 19 | Vacuum oven, RT, 1.0 h (~27-28 in Hg) | Weight loss: 9.7% | Form B + broad peaks at 4.3° 2θ |
| Sample 21 | Vacuum oven, 22° C., 0.5 h (~28 in Hg) | Weight loss: 30.6% | B + broad peaks at 4.2° 2θ and 5.8° 2θ |
| Sample 23 | Vacuum oven, 22° C., 1.0 h (~27-28 in Hg) | Weight loss: 4.7% | Most likely Form B shifted |

Conversion of Impure Form B to Pure Form B

The conversion of impure Form B to pure Form B was conducted in water:acetone 1:2 (v/v) slurry at 125 mg/mL concentration and 30° C. for 43 hours. Very slow filtration was observed and the wet cake was air-dried at ambient conditions for 3.5 hours followed by vacuum drying at ambient temperature and 15 in Hg for 0.5 hour and then at ~27 in Hg for 3.5 hours yielding 49.26 g (840%).

An XRPD pattern was obtained at different points in the conversion as shown in Table 113. After 42 hours of heating, XRPD analysis showed that impure Form B had completely converted to pure Form B. Once the material was filtered and dried, TG analysis was performed in addition to XRPD analysis.

Figure 27:
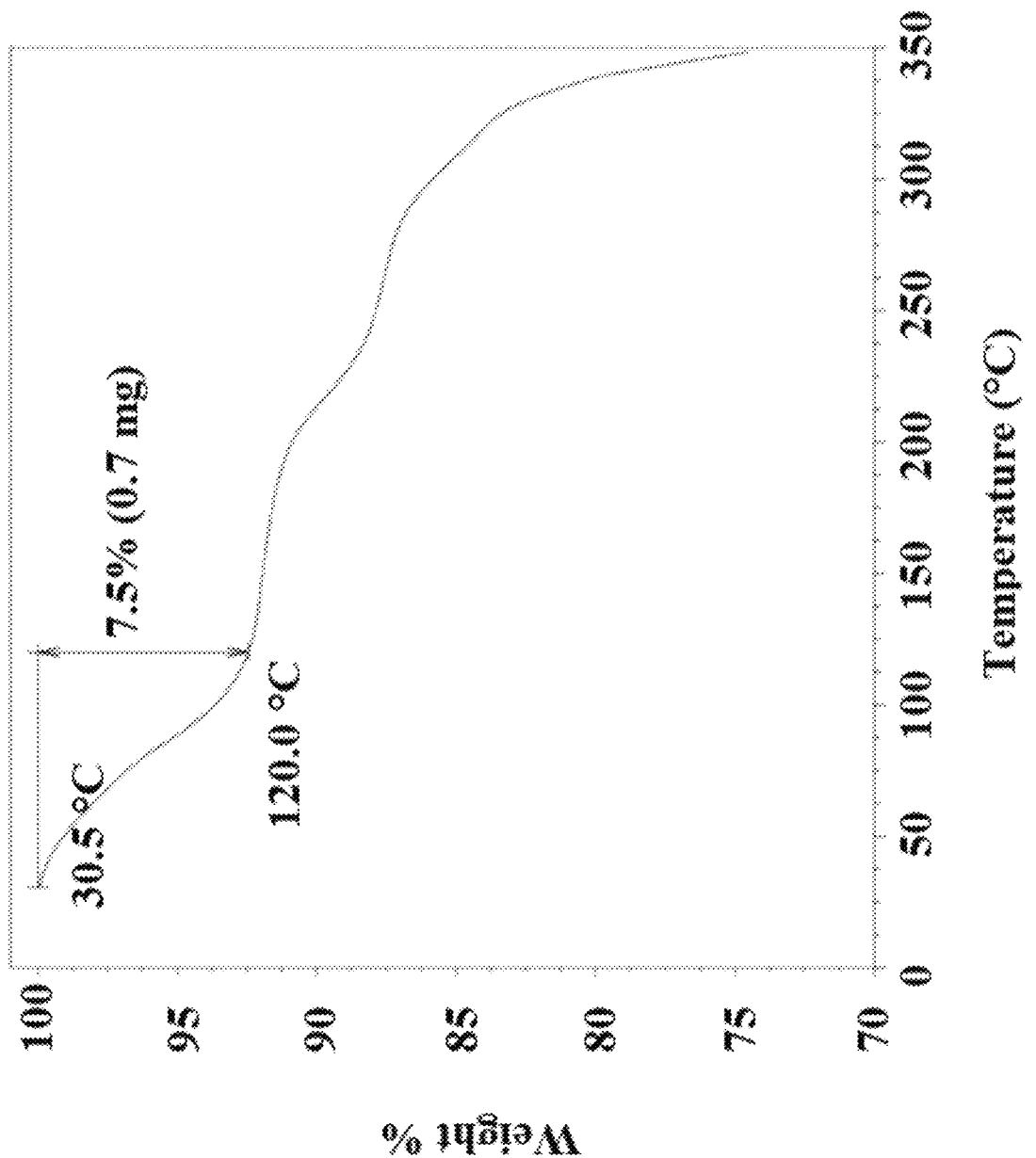
FIG. 27 is the TGA data from the batch converted to pure Form B material from impure Form B as described in Example 16. The TGA data showed a 7.6% weight loss at 31-120° C. it also showed an approximately 20% weight loss from 120-350° C. The x-axis is temperature measured in degrees Celsius and the y-axis is weight of the material measured as a percent.

The XRPD pattern exhibited by the converted batch after drying was consistent with the XRPD pattern in FIG. 16 of pure Form B and its peaks aligned with the allowed peak positions from the pattern shown in FIG. 16. FIG. 27 compares the patterns of impure Form B, pure Form B as characterized in Example 6, and the pure Form B converted from impure Form B as described in Example 15.

Figure 28:
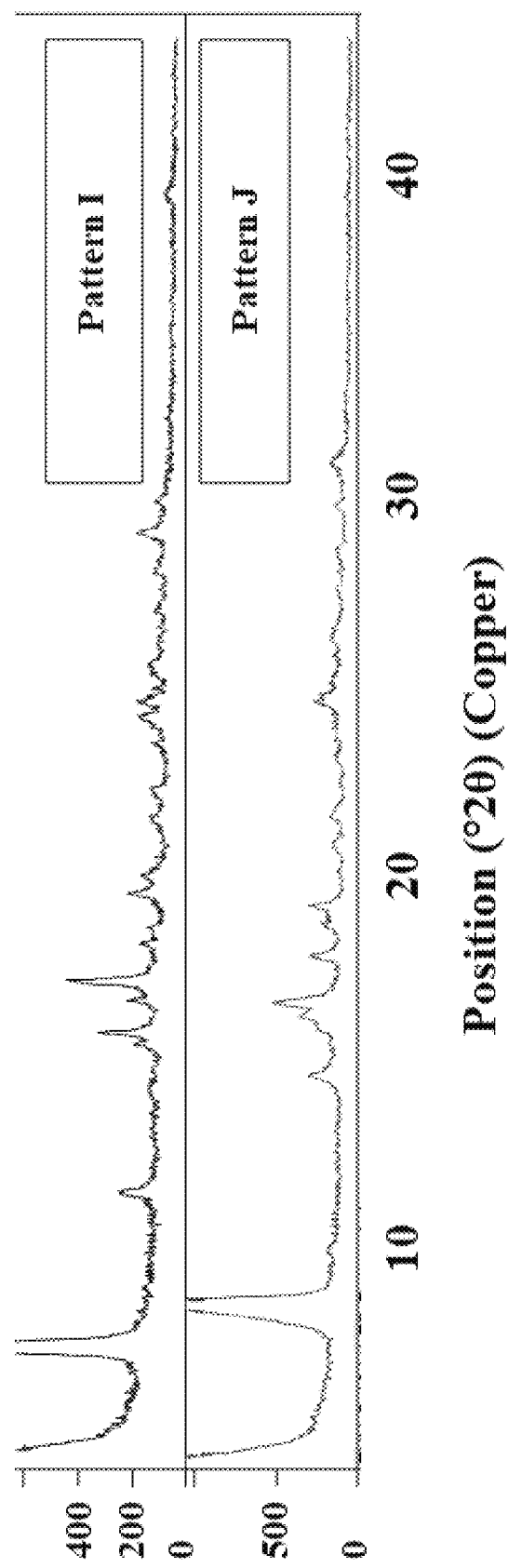
FIG. 28 are XRPD patterns of Form I and Form J. The x-axis is 2Theta measured in degrees and the y-axis is intensity measured in counts.
Figure 29:
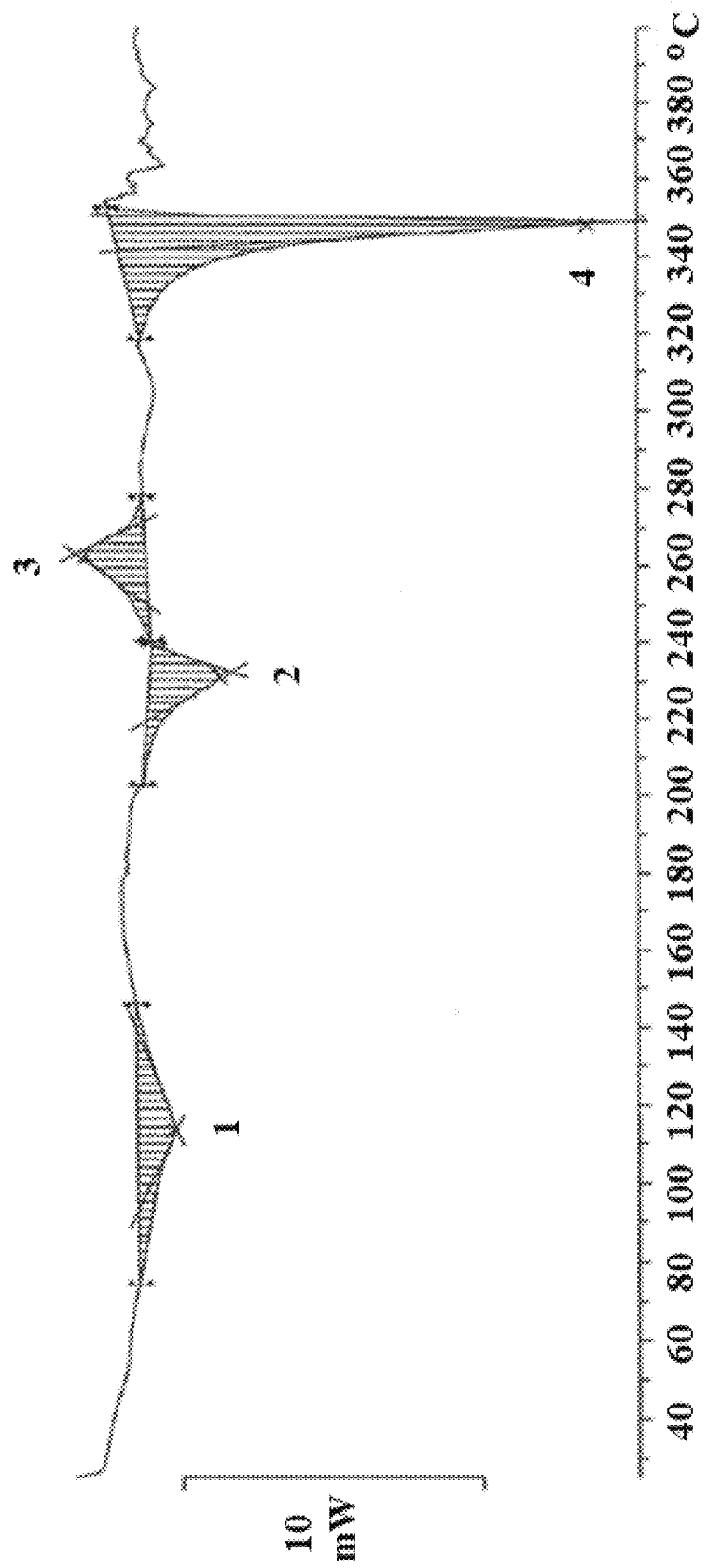
FIG. 29 is the DSC data from a representative batch of Form B material. The DSC data was collected by increasing the temperature of the sample (3.9 mg) from 25-400° C. at a rate of 10° C./minute. Endotherms were observed at 113° C. (1), 231° C. (2), 262° C. (3), and 348° C. (4). Endotherm 1 (integral=−237 mJ; normalized=−60 J/g) exhibited an onset of 113° C. and an endset of 140° C. Endotherm 2 (integral=−182 mJ; normalized=−46 J/g) exhibited an onset of 219° C. and an endset of 239° C. Endotherm 3 (integral=177 mJ; normalized=45 J/g) exhibited an onset of 250° C. and an endset of 271° C. Endotherm 4 (integral=−728 mJ; normalized=−186 J/g) exhibited an onset of 341° C. and an endset of 350° C. The x-axis is temperature measured in Celsius and the y-axis the heat flow measured in milli Watts (mW).
Figure 30:
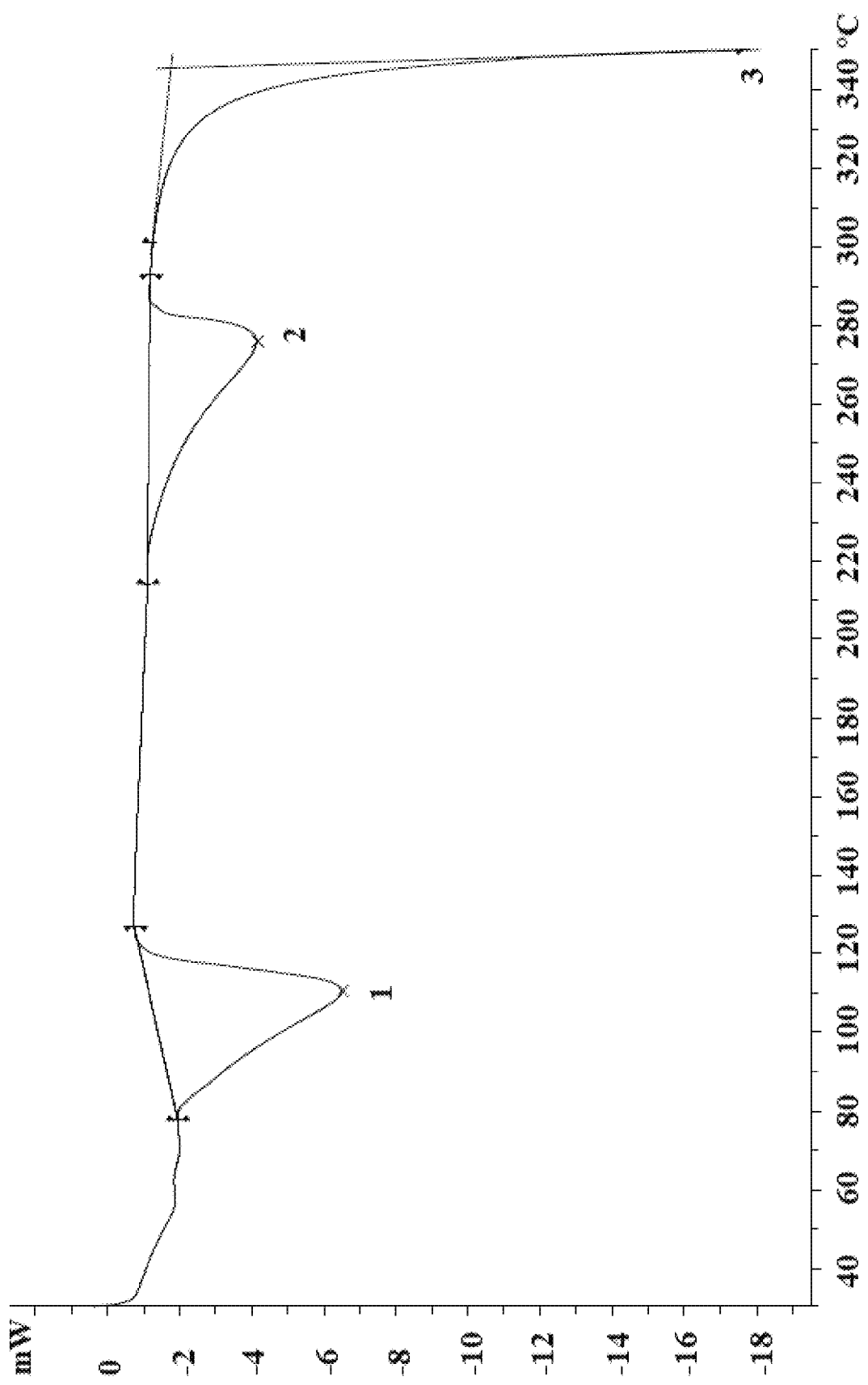
FIG. 30 is the DSC data from a representative batch of Form A. The DSC data was collected by increasing the temperature of the sample (4.4 mg) from 30-350° C. at a rate of 10° C./minute. Endotherms were observed at 110° C. (1), 275° C. (2), and 344° C. (3). Endotherm 1 (integral=−670 mJ; normalized=−151 J/g) exhibited an onset of 84° C. Endotherm 2 (integral=−480 mJ; normalized=−108 J/g) exhibited an onset of 242° C. Endotherm 3 exhibited an onset of 344° C. The x-axis is temperature measured in Celsius and the y-axis the heat flow measured in milli Watts (mW).
Figure 31:
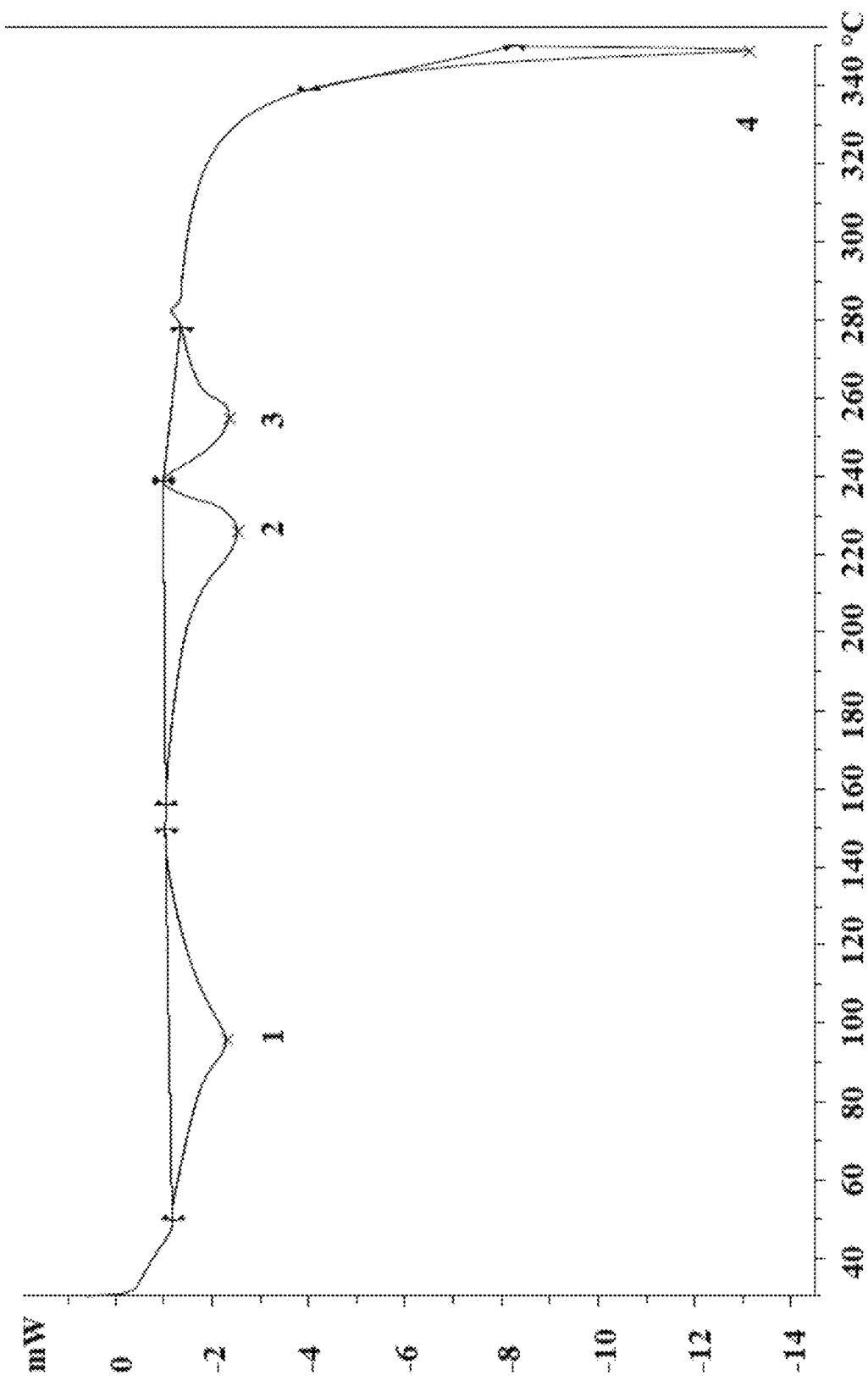
FIG. 31 is the DSC data from a representative batch of Form B. The DSC data was collected by increasing the temperature of the sample (2.6 mg) from 30-350° C. at a rate of 10° C./minute. Endotherms were observed at 95° C. (1), 225° C. (2), 254° C. (3), and 348° C. (4). Endotherm 1 (integral=−256 mJ; normalized=−97 J/g) exhibited an onset of 75° C. Endotherm 2 (integral=−265 mJ; normalized=−101 J/g) exhibited an onset of 199° C. Endotherm 3 (integral=−140 mJ; normalized=−53 J/g) exhibited an onset of 239° C. Endotherm 4 (integral=−94 mJ; normalized=−36 J/g) exhibited an onset of 344° C. The x-axis is temperature measured in Celsius and the y-axis the heat flow measured in milli Watts (mW).
Figure 32:
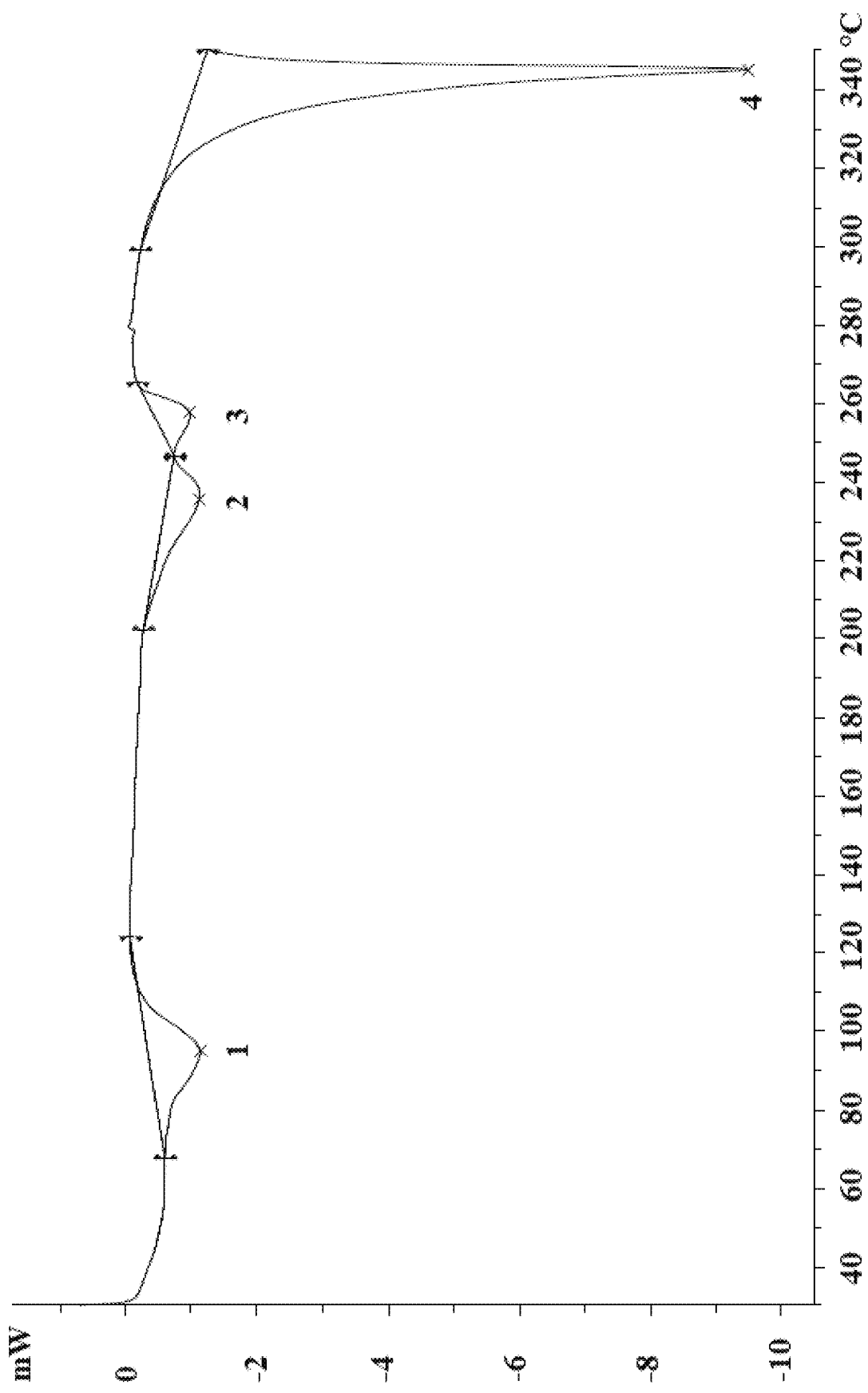
FIG. 32 is the DSC data from a representative batch of Form C. The DSC data was collected by increasing the temperature of the sample (2.5 mg) from 30-350° C. at a rate of 10° C./minute. Endotherms were observed at 95° C. (1), 235° C. (2), 257° C. (3), and 344° C. (4). Endotherm 1 (integral=−88 mJ; normalized=−36 J/g) exhibited an onset of 77° C. Endotherm 2 (integral=−58 mJ; normalized=−23 J/g) exhibited an onset of 216° C. Endotherm 3 (integral=−31 mJ; normalized=−12 J/g) exhibited an onset of 247° C. Endotherm 4 (integral=−379 mJ; normalized=−154 J/g) exhibited an onset of 338° C. The x-axis is temperature measured in Celsius and the y-axis the heat flow measured in milli Watts (mW).
Figure 33:
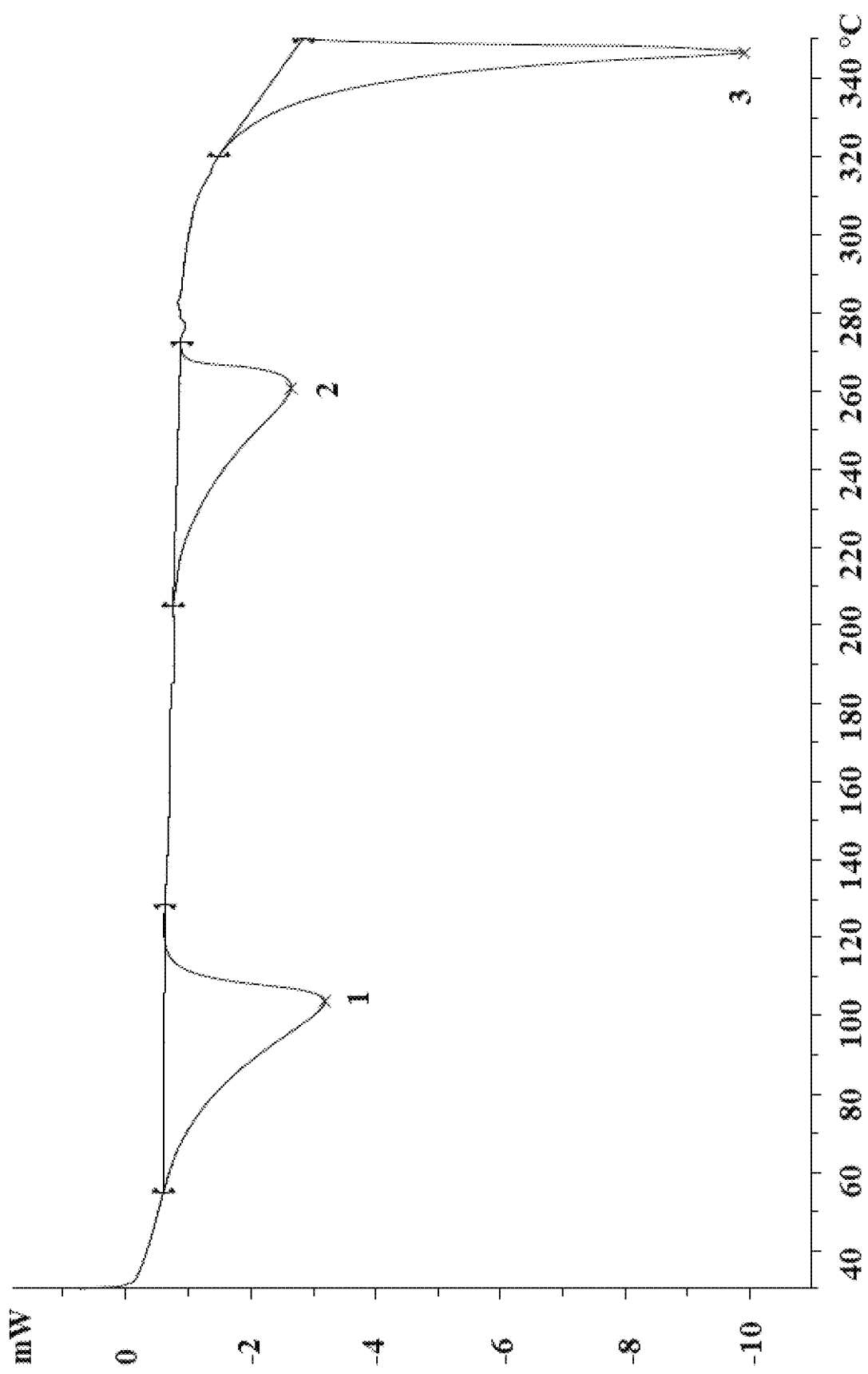
FIG. 33 is the DSC data from a representative batch of Form D. The DSC data was collected by increasing the temperature of the sample (2.5 mg) from 30-350° C. at a rate of 10° C./minute. Endotherms were observed at 103° C. (1), 260° C. (2) and 345° C. (3). Endotherm 1 (integral=−370 mJ; normalized=−149 J/g) exhibited an onset of 73° C. Endotherm 2 (integral=−271 mJ; normalized=−109 J/g) exhibited an onset of 228° C. Endotherm 3 (integral=−321 mJ; normalized=−129 J/g) exhibited an onset of 340° C. The x-axis is temperature measured in Celsius and the y-axis the heat flow measured in milli Watts (mW).
Figure 34:
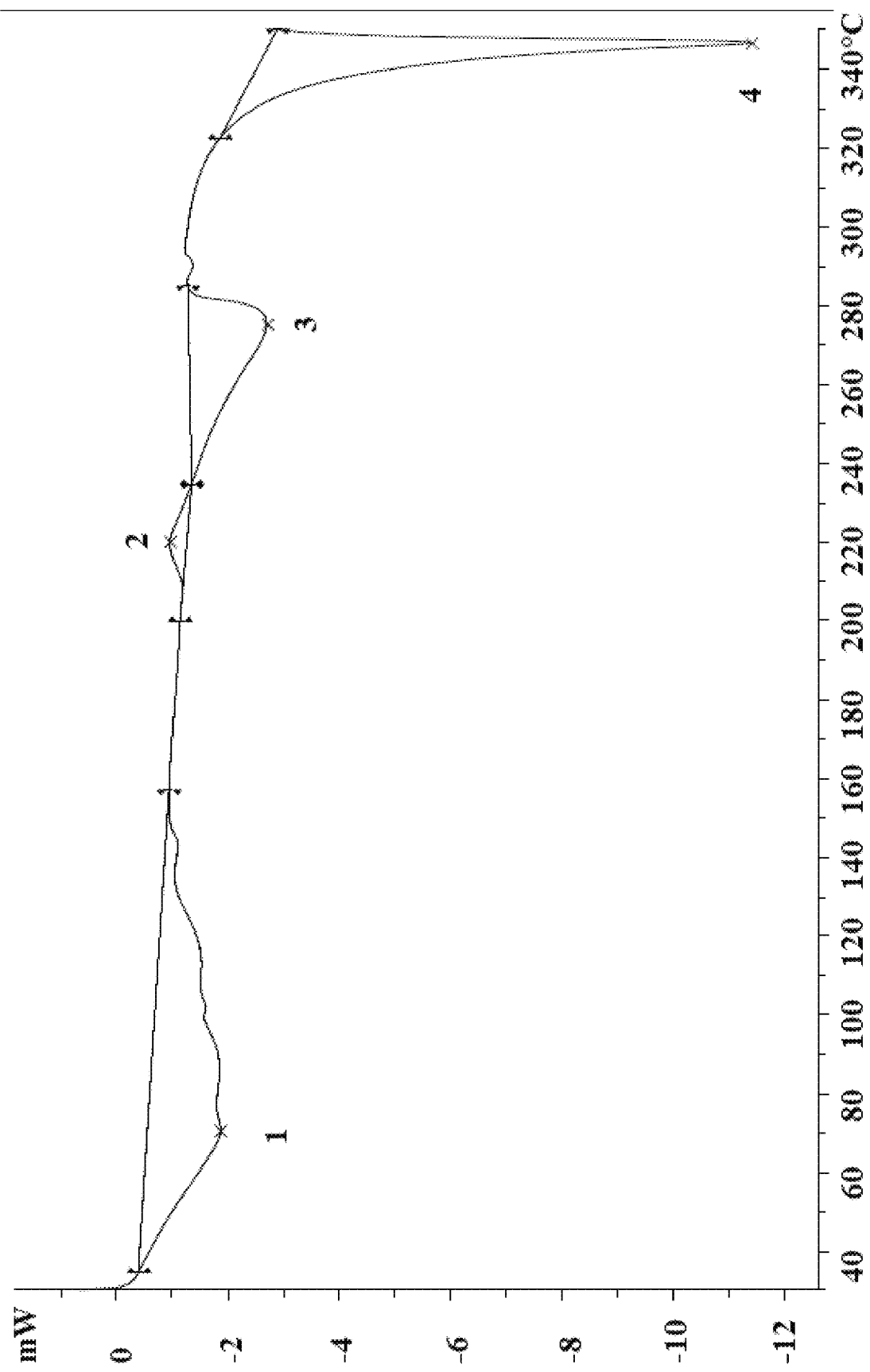
FIG. 34 is the DSC data from a representative batch of Form E. The DSC data was collected by increasing the temperature of the sample (2.5 mg) from 30-350° C. at a rate of 10° C./minute. Endotherms were observed at 70° C. (1), 219° C. (2), 275° C. (3), and 345° C. (4). Endotherm 1 (integral=−495 mJ; normalized=−194 J/g) exhibited an onset of 38° C. Endotherm 2 (integral=25 mJ; normalized=10 J/g) exhibited an onset of 209° C. Endotherm 3 (integral=−208 mJ; normalized=−81 J/g) exhibited an onset of 242° C. Endotherm 4 (integral=−339 mJ; normalized=−133 J/g) exhibited an onset of 340° C. The x-axis is temperature measured in Celsius and the y-axis the heat flow measured in milli Watts (mW).
Figure 35:
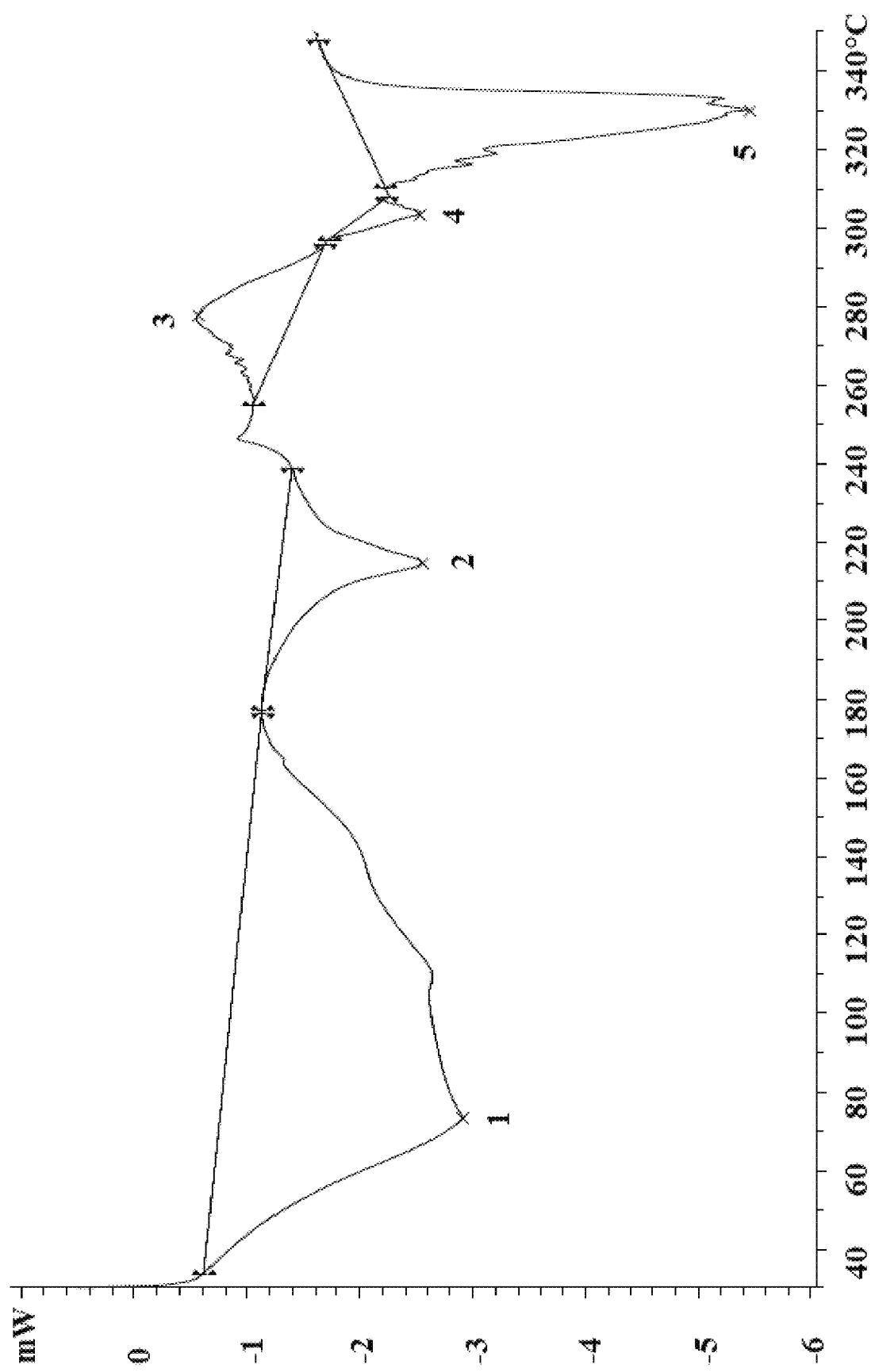
FIG. 35 is the DSC data from a representative batch of Form F. The DSC data was collected by increasing the temperature of the sample (3.0 mg) from 30-350° C. at a rate of 10° C./minute. Endotherms were observed at 73° C. (1), 214° C. (2), 277° C. (3), 303° C. (4), and 329° C. (5). Endotherm 1 (integral=−991 mJ; normalized=−323 J/g) exhibited an onset of 43° C. Endotherm 2 (integral=−121 mJ; normalized=−39 J/g) exhibited an onset of 205° C. Endotherm 3 (integral=98 mJ; normalized=32 J/g) exhibited an onset of 265° C. Endotherm 4 (integral=−15 mJ; normalized=−5 J/g) exhibited an onset of 297° C. Endotherm 5 (integral=−283 mJ; normalized=−92 J/g) exhibited an onset of 318° C. The x-axis is temperature measured in Celsius and the y-axis the heat flow measured in milli Watts (mW).
Figure 36:
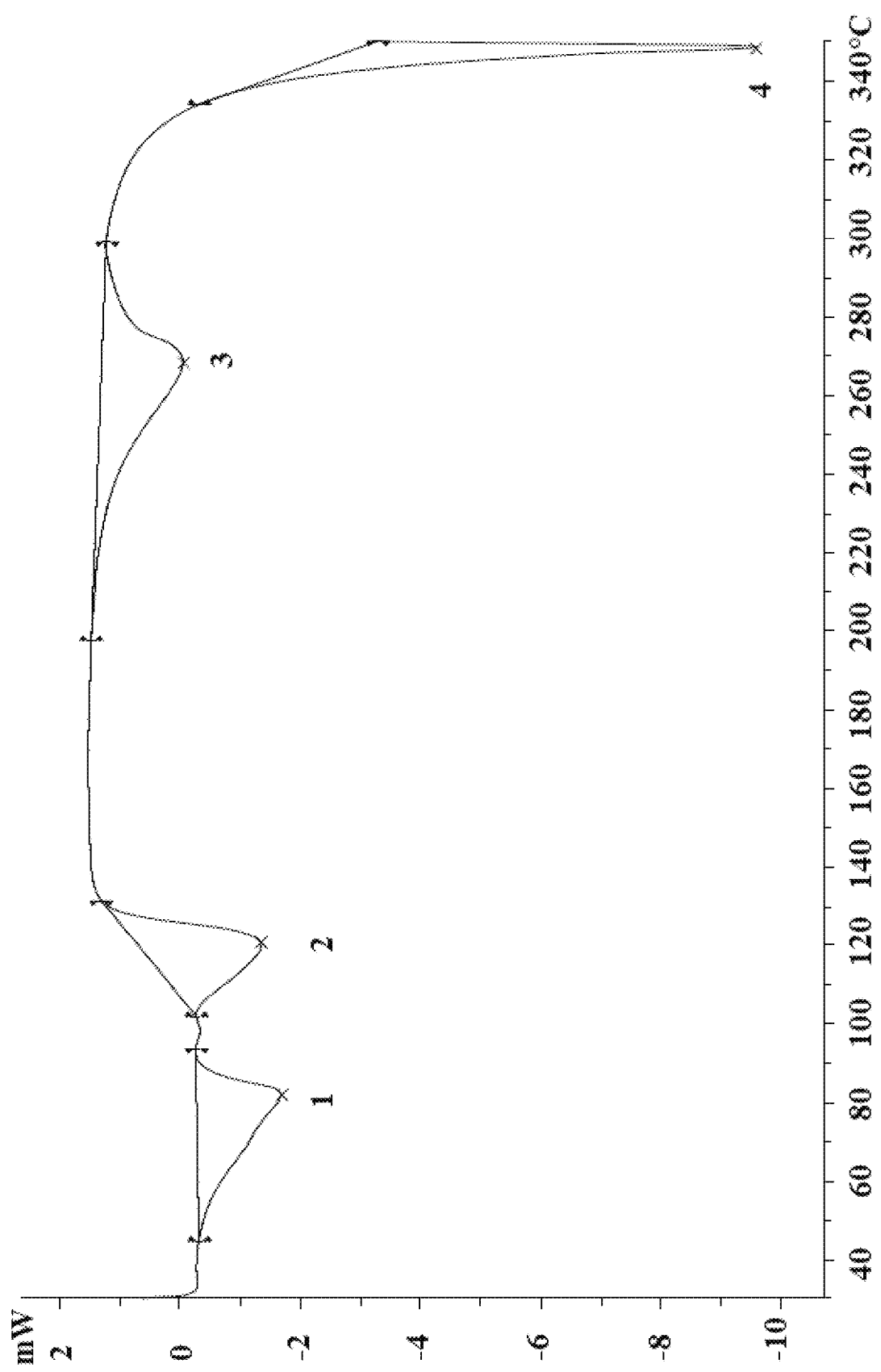
FIG. 36 is the DSC data from a representative batch of Form G. The DSC data was collected by increasing the temperature of the sample (2.8 mg) from 30-350° C. at a rate of 10° C./minute. Endotherms were observed at 81° C. (1), 120° C. (2), 260° C. (3), and 347° C. (4). Endotherm 1 (integral=−167 mJ; normalized=−59 J/g) exhibited an onset of 56° C. Endotherm 2 (integral=−183 mJ; normalized=−65 J/g) exhibited an onset of 103° C. Endotherm 3 (integral=−251 mJ; normalized=−89 J/g) exhibited an onset of 235° C. Endotherm 4 (integral=−164 mJ; normalized=−58 J/g) exhibited an onset of 344° C. The x-axis is temperature measured in Celsius and the y-axis the heat flow measured in milli Watts (mW).
Figure 37:
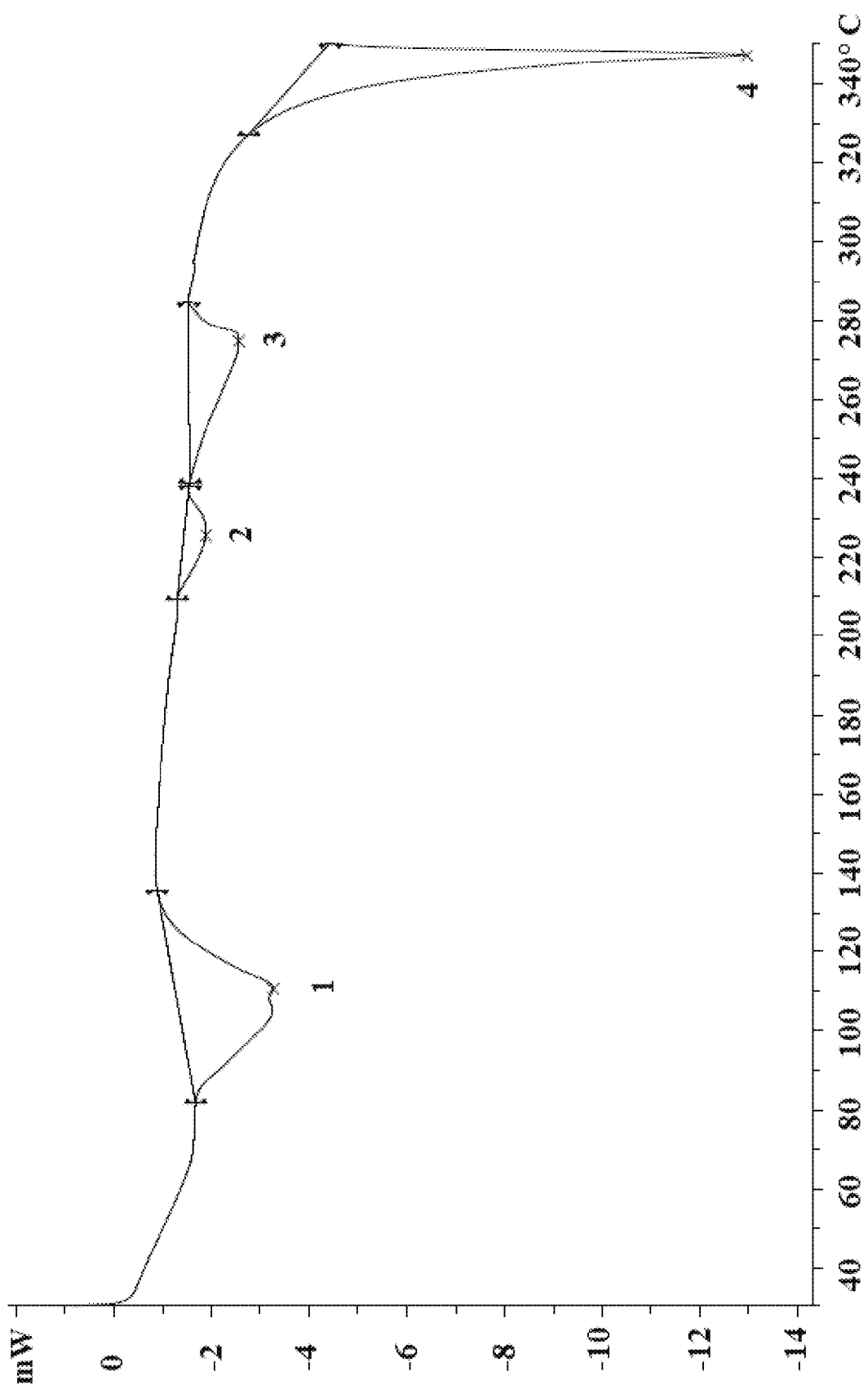
FIG. 37 is the DSC data from a representative batch of Form H. The DSC data was collected by increasing the temperature of the sample (2.7 mg) from 30-350° C. at a rate of 10° C./minute. Endotherms were observed at 110° C. (1), 225° C. (2), 274° C. (3), and 346° C. (4). Endotherm 1 (integral=−300 mJ; normalized=−110 J/g) exhibited an onset of 109° C. Endotherm 2 (integral=−41 mJ; normalized=−15 J/g) exhibited an onset of 210° C. Endotherm 3 (integral=−138 mJ; normalized=−50 J/g) exhibited an onset of 242° C. Endotherm 4 (integral=−301 mJ; normalized=−110 J/g) exhibited an onset of 346° C. The x-axis is temperature measured in Celsius and the y-axis the heat flow measured in milli Watts (mW).
Figure 38:
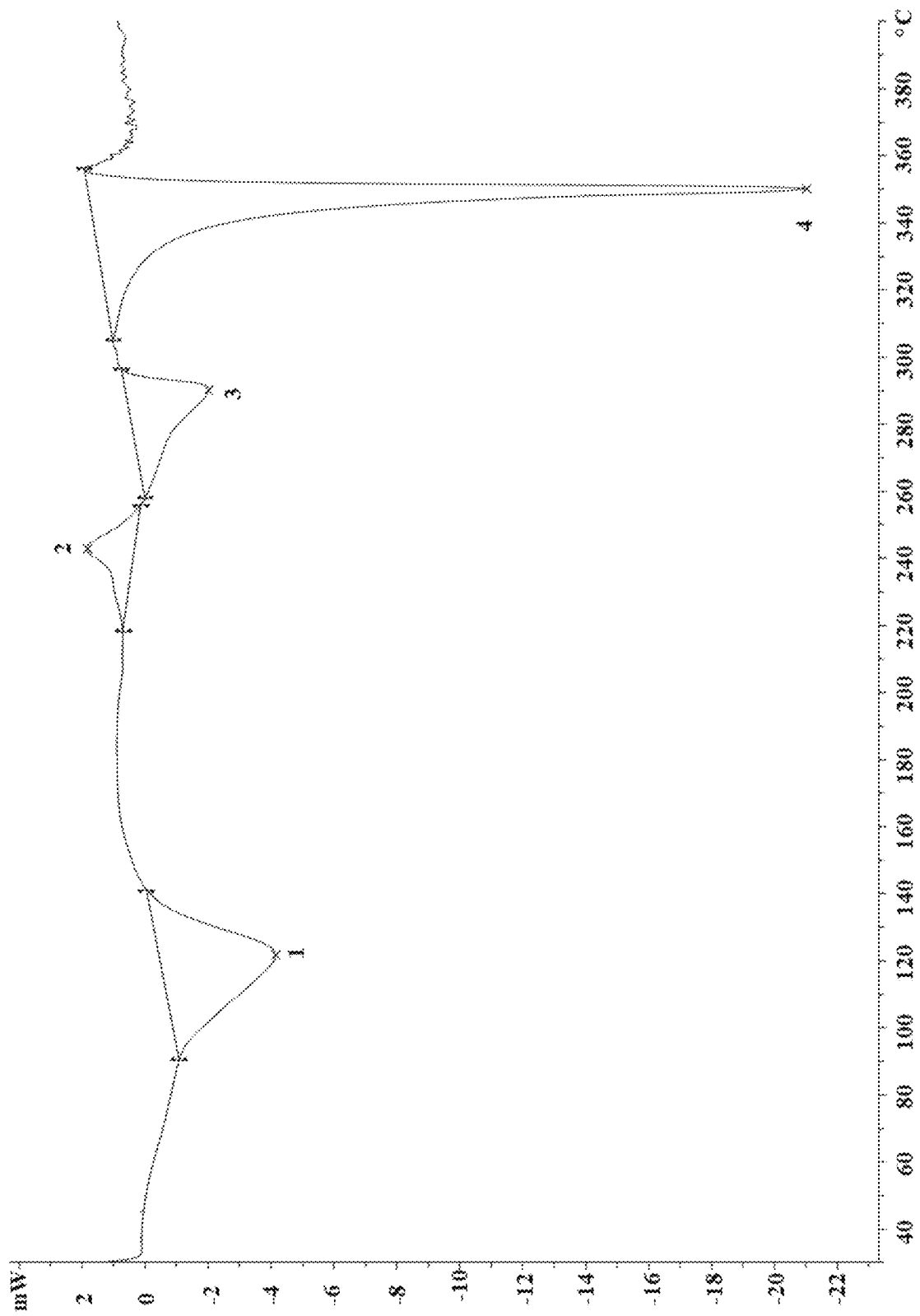
FIG. 38 is the DSC data from a representative batch of Form A. The DSC data was collected by increasing the temperature of the sample (6.0 mg) from 30-350° C. at a rate of 10° C./minute. Endotherms were observed at 121° C. (1), 242° C. (2), 290° C. (3), and 348° C. (4). Endotherm 1 (integral=−541 mJ; normalized=−90 J/g) exhibited an onset of 93° C. Endotherm 2 (integral=133 mJ; normalized=22 J/g) exhibited an onset of 233° C. Endotherm 3 (integral=−272 mJ; normalized=−45 J/g) exhibited an onset of 268° C. Endotherm 4 (integral=−1131 mJ; normalized=−198 J/g) exhibited an onset of 344° C. The x-axis is temperature measured in Celsius and the y-axis the heat flow measured in milli Watts (mW).
Figure 39:
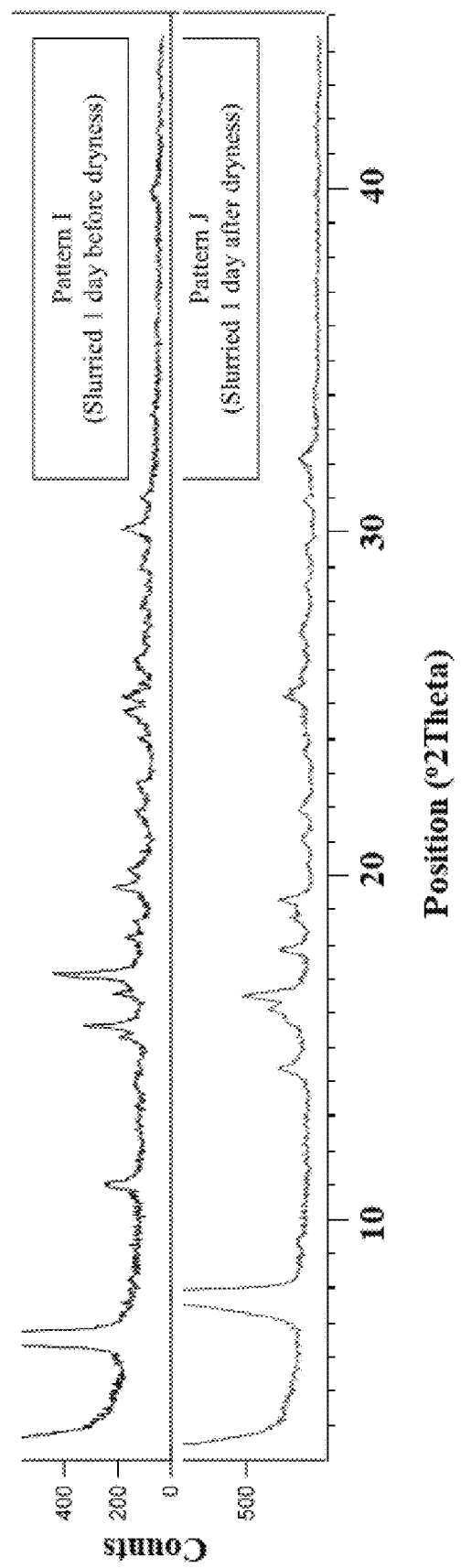
FIG. 39 is the XRPD pattern for Form I and Form J. The x-axis is 2Theta measured in degrees and the y-axis is intensity measured in counts.

The TGA data of the converted batch, Form B showed 7.5% weight loss between 31 and 120° C. (FIG. 28).

TABLE 113

Results of XRPD Analysis and TG Analysis during Conversion of Compound II to Form B

| Point in Conversion | Analytical Technique | Result |
|---|---|---|
| 125 mg/mL Slurry, 30° C., 20 h | XRPD | Form B + small broad peak at 4.0° 2θ |
| 125 mg/mL Slurry, 30° C., 24 h | XRPD | B + broad peaks at 4.2° 2θ and 5.7° 2θ |
| 125 mg/mL Slurry, 30° C., 42 h | XRPD | Form B |
| 125 mg/mL | XRPD | Form B |
| Slurry, 30° C., 43 h VF, washed with 50 mL of H₂O:acetone 1:2 Air-dried for 3.5 h | TGA | 10% weight loss at 26-120° C. |
| Vacuum drying, 22° C., 0.5 h, 15 in Hg Vacuum drying, 22° C. 1.5 h, 27-28 in Hg | XRPD TGA | Form B 9.9% weight loss at 26-120° C. |
| Vacuum drying, 22° C., 2.0 h, 27 in Hg | XRPD TGA | Form B 7.5% weight loss at 31-120° C. |

This specification has been described with reference to embodiments of the invention. However, one of ordinary skill in the art appreciates that various modification and changes can be made without departing from the scope of the invention as set forth in the claims below. Accordingly, the specification is to be regarded in an illustrative rather than a restrictive sense, and all such modifications are intended to be included within the scope of the invention.

What is claimed is:

1. A dosing regime for treating a human with cancer, the dosing regime comprising oral administration of a solid dosage form comprising a cyclin-dependent kinase 4/6 (CDK4/6) inhibitor compound of structure:

(Compound II)

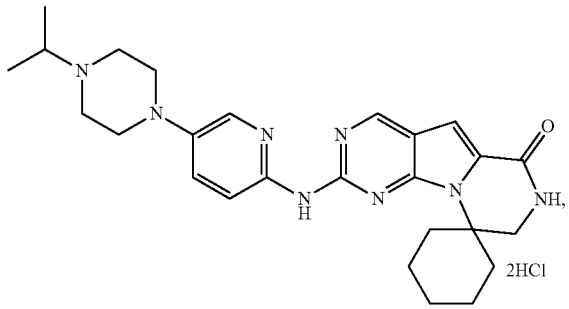

wherein the dosing regime provides a (mean $AUC_{(0-24)ss}$ (h*ng/mL))/(Absolute Neutrophil Count (cells/mm³)) ratio in humans of less than 1.25 on day 22 of dosing, and wherein the solid dosage form is administered twice daily at a concentration of about 150 mg spaced about 12 hours apart.

2. The dosing regime of claim 1, wherein the dosing regime provides a mean $AUC_{(0-24)ss}$ (h*ng/mL))/(Absolute Neutrophil Count (cells/mm³)) ratio in humans of less than 1.0.

3. The dosing regime of claim 1, further comprising the administration of one or more additional therapeutic agents.

4. The dosing regime of claim 3, wherein the cancer is HR+/HER2− breast cancer and the additional therapeutic agent is an anti-estrogen compound.

5. The dosing regime of claim 4, wherein the anti-estrogen compound is selected from the group consisting of tamoxifen, raloxifene, fulvestrant, letrozole, anastrozole, and exemestane.

6. The dosing regime of claim 1, wherein the dosing regime is administered for at least 24 weeks.

7. The dosing regime of claim 1, wherein the cancer is a CDK4/6 replication dependent cancer.

8. The dosing regime of claim 1, wherein the cancer is selected from the group consisting of breast cancer, non-small cell lung carcinoma, liver cancer, prostate cancer, hematological cancer, melanoma, colon cancer, pancreatic cancer, liposarcoma, and gastrointestinal stromal tumor (GIST).

9. The dosing regime of claim 1, wherein the cancer is selected from the group consisting of HR+/HER2− breast cancer, HR−/HER2+ breast cancer, EGFR mutant non-small cell carcinoma, KRAS mutant non-small cell lung carcinoma, hepatocellular carcinoma, uterine cancer, castrate resistant prostate cancer, mantle cell lymphoma, marginal zone lymphoma, chronic lymphocytic leukemia, follicular lymphoma, diffuse large B-cell lymphoma, BRAF mutant melanoma, RAS mutant colorectal cancer, RAS mutant pancreatic cancer, and RAS mutant cholangiocarcinoma.

10. The dosing regime of claim 4, wherein Compound II and the anti-estrogen compound are administered after endocrine therapy failure.

11. The dosing regime of claim 5, wherein the anti-estrogen compound is fulvestrant.

12. The dosing regime of claim 5, wherein the anti-estrogen compound is letrozole.

13. The dosing regime of claim 8, wherein the cancer is liver cancer.

14. The dosing regime of claim 9, wherein the cancer is hepatocellular carcinoma.

15. The dosing regime of claim 8, wherein the cancer is a hematological cancer.

16. The dosing regime of claim 9, wherein the cancer is diffuse large B-cell lymphoma.

17. The dosing regime of claim 8, wherein the cancer is non-small cell lung carcinoma.

18. The dosing regime of claim 1, wherein the solid dosage form is administered twice daily at a concentration of 150 mg spaced 12 hours apart.

* * * * *